US012479816B2

(12) United States Patent
McDermott et al.

(10) Patent No.: US 12,479,816 B2
(45) Date of Patent: Nov. 25, 2025

(54) 20-HETE FORMATION INHIBITORS

(71) Applicant: UNIVERSITY OF PITTSBURGH—OF THE COMMONWEALTH SYSTEM OF HIGHER EDUCATION, Pittsburgh, PA (US)

(72) Inventors: Lee Apostle McDermott, Pittsburgh, PA (US); David Koes, Pittsburgh, PA (US); Samuel M. Poloyac, Pittsburgh, PA (US); Shabber Mohammed, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1055 days.

(21) Appl. No.: 17/429,289

(22) PCT Filed: Feb. 7, 2020

(86) PCT No.: PCT/US2020/017170

§ 371 (c)(1),
(2) Date: Aug. 6, 2021

(87) PCT Pub. No.: WO2020/163689

PCT Pub. Date: Aug. 13, 2020

(65) Prior Publication Data

US 2022/0144797 A1 May 12, 2022

Related U.S. Application Data

(60) Provisional application No. 62/803,398, filed on Feb. 8, 2019.

(51) Int. Cl.

| | |
|---|---|
| ***C07D 401/04*** | (2006.01) |
| ***C07D 231/38*** | (2006.01) |
| ***C07D 401/14*** | (2006.01) |
| ***C07D 403/12*** | (2006.01) |
| ***C07D 409/14*** | (2006.01) |
| ***C07D 413/14*** | (2006.01) |

(52) U.S. Cl.

CPC ......... *C07D 401/04* (2013.01); *C07D 231/38* (2013.01); *C07D 401/14* (2013.01); *C07D 403/12* (2013.01); *C07D 409/14* (2013.01); *C07D 413/14* (2013.01)

(58) Field of Classification Search

CPC ....... A61P 9/00; C07D 231/38; C07D 401/04; C07D 401/14; C07D 403/12; C07D 409/14; C07D 413/14; C07D 417/14

See application file for complete search history.

(56) References Cited

U.S. PATENT DOCUMENTS

| | | | |
|---|---|---|---|
| 2,969,374 | A | 1/1961 | Bernard et al. |
| 2,989,538 | A | 6/1961 | Flores et al. |
| 2,992,163 | A | 7/1961 | Easton |
| 3,236,893 | A | 2/1966 | Blout et al. |
| 3,254,093 | A | 5/1966 | Huisgen |
| 3,534,058 | A | 10/1970 | Santilli et al. |
| 3,647,351 | A | 3/1972 | Lange |
| 3,839,336 | A | 10/1974 | Borck et al. |
| 3,920,693 | A | 11/1975 | Ege |
| 3,926,999 | A | 12/1975 | Poetsch |
| 3,944,551 | A | 3/1976 | Regnier et al. |
| 3,984,431 | A | 10/1976 | Gueremy |
| 3,988,348 | A | 10/1976 | Cross et al. |
| 4,008,049 | A | 2/1977 | Clemmer et al. |
| 4,062,858 | A | 12/1977 | Hoehn et al. |
| 4,166,817 | A | 9/1979 | Ferres et al. |
| 4,178,449 | A | 12/1979 | Dusza et al. |
| 4,281,000 | A | 7/1981 | Dusza et al. |
| 4,314,809 | A | 2/1982 | Rose et al. |
| 4,371,370 | A | 2/1983 | Rose et al. |
| 4,410,537 | A | 10/1983 | Kneen |
| 4,421,753 | A | 12/1983 | Tomcufeik et al. |
| 4,451,473 | A | 5/1984 | Nador et al. |
| 4,478,834 | A | 10/1984 | Shroff et al. |
| 4,535,183 | A | 8/1985 | Kneen |
| 4,562,189 | A | 12/1985 | Tomcufelk et al. |
| 4,576,943 | A | 3/1986 | Tomcufcik et al. |
| 4,629,466 | A | 12/1986 | Rose et al. |

(Continued)

FOREIGN PATENT DOCUMENTS

| | | | |
|---|---|---|---|
| DE | 2238628 | A | 8/1972 |
| DE | 2238734 | A | 8/1972 |

(Continued)

OTHER PUBLICATIONS

Abbaszade, et al., "Cloning and Characterization of ADAMTS11, an Aggrecanase from the ADAMTS Family," J Biol Chem., vol. 274, 23443-23450 (1999).

(Continued)

*Primary Examiner* — Sarah Pihonak
*Assistant Examiner* — Padmaja S Rao
(74) *Attorney, Agent, or Firm* — Foley & Lardner LLP

(57) ABSTRACT

This disclosure provides novel heterocyclic compounds and methods for inhibiting the enzyme CYP4. Further disclosed methods include: a method of inhibiting the biosynthesis of 20-hydroxyeicosatetraenoic acid (20-HETE) in a subject in need thereof and a method of producing neuroprotection and decreased brain damage by preventing cerebral microvascular blood flow impairment and anti-oxidant mechanisms in a subject experiencing or having experienced an ischemic event.

19 Claims, No Drawings

(56) References Cited

U.S. PATENT DOCUMENTS 4,745,652 A 5/1988 Rose et al.
4,801,600 A 1/1989 Wang et al.
4,803,215 A 2/1989 Jensen-Korte et al.
4,826,866 A 5/1989 Taylor et al.
4,910,204 A 3/1990 Walker et al.
4,918,074 A 4/1990 Tsuda et al.
4,921,869 A 5/1990 Wang et al.
4,931,444 A 6/1990 Van Wauwe et al.
4,948,801 A 8/1990 Carlson et al.
4,963,575 A 10/1990 Buntain et al.
4,977,173 A 12/1990 Brittelli et al.
4,985,063 A 1/1991 Fischer et al.
4,992,442 A 2/1991 Tsujitani et al.
5,051,518 A 9/1991 Murray et al.
5,134,142 A 7/1992 Matsuo et al.
5,185,251 A 2/1993 Chen et al.
5,202,243 A 4/1993 Balani
5,254,577 A 10/1993 Carlson et al.
5,290,941 A 3/1994 Volante et al.
5,344,464 A 9/1994 Madrange et al.
5,356,897 A 10/1994 Oku et al.
5,430,159 A 7/1995 Neunhoeffer et al.
5,478,838 A 12/1995 Arita et al.
5,486,534 A 1/1996 Lee et al.
5,559,137 A 9/1996 Adams et al.
5,571,815 A 11/1996 Schaper et al.
5,580,843 A 12/1996 Stetter et al.
5,589,439 A 12/1996 Goto et al.
5,652,238 A 7/1997 Brickner et al.
5,658,903 A 8/1997 Adams et al.
5,679,678 A 10/1997 Binder et al.
5,681,567 A 10/1997 Martinez et al.
5,723,450 A 3/1998 Reuschling et al.
5,736,545 A 4/1998 Gadwood et al.
5,739,143 A 4/1998 Adams et al.
5,756,529 A 5/1998 Isakson et al.
5,760,232 A 6/1998 Chen et al.
5,840,900 A 11/1998 Greenwald et al.
5,865,855 A 2/1999 Doehling et al.
5,880,131 A 3/1999 Greenwald et al.
5,912,254 A 6/1999 Bishop et al.
5,965,566 A 10/1999 Greenwald et al.
5,965,572 A 10/1999 Ellis et al.
5,968,947 A 10/1999 Urch et al.
5,972,972 A 10/1999 Mihelich et al.
5,994,353 A 11/1999 Breault
5,998,425 A 12/1999 Adams et al.
6,011,042 A 1/2000 Greenwald et al.
6,066,646 A 5/2000 Bishop et al.
6,096,753 A 8/2000 Spohr et al.
6,111,107 A 8/2000 Greenwald et al.
6,127,355 A 10/2000 Greenwald et al.
6,153,655 A 11/2000 Martinez et al.
6,194,580 B1 2/2001 Greenwald et al.
6,200,980 B1 3/2001 Piazza et al.
6,214,817 B1 4/2001 Riley et al.
6,228,869 B1 5/2001 Levin et al.
6,229,011 B1 5/2001 Chen et al.
6,232,320 B1 5/2001 Stewart et al.
6,239,176 B1 5/2001 Nudelman et al.
6,242,644 B1 6/2001 Ackermann et al.
6,355,661 B1 3/2002 Lai et al.
6,395,266 B1 5/2002 Martinez et al.
6,403,816 B1 6/2002 Jaggi et al.
6,420,385 B1 7/2002 Spohr et al.
6,423,713 B1 7/2002 Anantanarayan et al.
6,498,167 B2 12/2002 Levin et al.
6,514,977 B1 2/2003 Anantanarayan et al.
6,518,267 B1 2/2003 Bondinell et al.
6,525,059 B1 2/2003 Anantanarayan et al.
6,541,473 B2 4/2003 Bradley et al.
6,548,524 B2 4/2003 Levin et al.
6,593,472 B2 7/2003 Hoffman et al.
6,608,076 B1 8/2003 Greenwald et al.
6,617,324 B1 9/2003 Naraian et al.
6,627,646 B2 9/2003 Bakale et al.
6,630,496 B1 10/2003 Seehra et al.
6,649,604 B2 11/2003 Spohr et al.
6,706,707 B2 3/2004 Mutel et al.
6,927,232 B2 8/2005 Mutel et al.
6,972,299 B2 12/2005 Mutel et al.
7,160,910 B2 1/2007 Safo et al.
7,411,083 B2 8/2008 Gopalsamy et al.
7,429,594 B2 9/2008 Liu et al.
7,456,162 B2 11/2008 Ohkawa et al.
7,485,727 B2 2/2009 Hamamoto et al.
7,750,037 B2 7/2010 Ohkawa et al.
8,003,649 B2 8/2011 Bradbury et al.
8,883,826 B2 11/2014 Bessis et al.
8,952,171 B2 2/2015 Xu et al.
8,980,937 B2 3/2015 Mihara et al.
9,012,450 B2 4/2015 Metcalf et al.
9,018,210 B2 4/2015 Metcalf et al.
9,248,199 B2 2/2016 Metcalf
9,422,279 B2 8/2016 Metcalf et al.
9,447,071 B2 9/2016 Li et al.
9,458,139 B2 10/2016 Xu et al.
9,604,999 B2 3/2017 Harris et al.
9,776,960 B2 10/2017 Xu et al.
9,802,900 B2 10/2017 Li et al.
10,034,879 B2 7/2018 Metcalf et al.
10,806,733 B2 10/2020 Metcalf et al.
2001/0025047 A1 9/2001 Levin et al.
2001/0046989 A1 11/2001 Levin et al.
2001/0046997 A1 11/2001 Abraham et al.
2002/0040031 A1 4/2002 Glasky et al.
2002/0095035 A1 7/2002 Warshawsky et al.
2002/0128263 A1 9/2002 Mutel et al.
2002/0132826 A1 9/2002 Levin et al.
2002/0137961 A1 9/2002 Bradley et al.
2002/0142995 A1 10/2002 Nicolau et al.
2002/0147138 A1 10/2002 Firestone et al.
2003/0022923 A1 1/2003 Lai et al.
2003/0036652 A1 2/2003 Bakthavatchalam et al.
2003/0060425 A1 3/2003 Ahlem et al.
2003/0073712 A1 4/2003 Wang et al.
2003/0165714 A1 9/2003 Lee et al.
2003/0187026 A1 10/2003 Li et al.
2003/0190333 A1 10/2003 Mossman et al.
2003/0199511 A1 10/2003 Li et al.
2003/0208082 A1 11/2003 Mutel et al.
2003/0225070 A1 12/2003 Mutel et al.
2004/0072796 A1 4/2004 Embury et al.
2004/0167171 A1 8/2004 Ohkawa et al.
2004/0186077 A1 9/2004 Diakur et al.
2004/0209921 A1 10/2004 Bridger et al.
2005/0038010 A1 2/2005 Cao et al.
2005/0065178 A1 3/2005 Basha et al.
2005/0085484 A1 4/2005 Mitchell et al.
2005/0096337 A1 5/2005 Ackermann et al.
2005/0131043 A1 6/2005 Mutel et al.
2005/0143420 A1 6/2005 Moutouh-de Parseval et al.
2005/0159605 A1 7/2005 Tarur et al.
2005/0228018 A1 10/2005 Astles et al.
2006/0094761 A1 5/2006 Haque et al.
2007/0099933 A1 5/2007 Heinrich et al.
2007/0213323 A1 9/2007 Imogai et al.
2007/0293698 A1 12/2007 Quick et al.
2008/0021011 A1 1/2008 Planken et al.
2008/0045506 A1 2/2008 Bruton et al.
2008/0114167 A1 5/2008 Castro et al.
2009/0023709 A1 1/2009 Gillespie et al.
2009/0054490 A1 2/2009 Jaeschke et al.
2009/0124625 A1 5/2009 Bessis et al.
2009/0143371 A1 6/2009 Buettelmann et al.
2009/0163512 A1 6/2009 Chen et al.
2009/0215801 A9 8/2009 Albert et al.
2009/0312315 A1 12/2009 Yamaguchi et al.
2010/0204235 A1 8/2010 Lizos et al.
2010/0210651 A1 8/2010 Hernandez et al.
2010/0311748 A1 12/2010 Dakin et al.
2012/0028243 A1 2/2012 Peyrefitte et al.
2012/0220569 A1 8/2012 Ohashi et al.
2012/0245344 A1 9/2012 Endo et al.

(56) References Cited

U.S. PATENT DOCUMENTS

| | | | |
|---|---|---|---|
| 2013/0045251 A1 | 2/2013 | Cen et al. | |
| 2013/0072472 A1 | 3/2013 | Gless, Jr. et al. | |
| 2013/0190315 A1 | 7/2013 | Metcalf et al. | |
| 2013/0190316 A1 | 7/2013 | Metcalf et al. | |
| 2013/0190375 A1 | 7/2013 | Dunkel et al. | |
| 2014/0271591 A1 | 9/2014 | Sinha et al. | |
| 2014/0274961 A1 | 9/2014 | Metcalf et al. | |
| 2014/0275152 A1 | 9/2014 | Metcalf et al. | |
| 2014/0275176 A1 | 9/2014 | Xu et al. | |
| 2014/0275181 A1 | 9/2014 | Harris et al. | |
| 2014/0329811 A1 | 11/2014 | Sweeney et al. | |
| 2015/0057251 A1 | 2/2015 | Harris | |
| 2015/0133430 A1 | 5/2015 | Xu et al. | |
| 2015/0141465 A1 | 5/2015 | Yee et al. | |
| 2015/0152102 A1 | 6/2015 | Kobayashi et al. | |
| 2015/0259296 A1 | 9/2015 | Li et al. | |
| 2015/0344472 A1 | 12/2015 | Metcalf et al. | |
| 2015/0344483 A1 | 12/2015 | Metcalf et al. | |
| 2016/0024127 A1 | 1/2016 | Harris et al. | |
| 2016/0031865 A1 | 2/2016 | Li et al. | |
| 2016/0031904 A1 | 2/2016 | Li et al. | |
| 2016/0038474 A1 | 2/2016 | Sinha et al. | |
| 2016/0039801 A1 | 2/2016 | Metcalf et al. | |
| 2016/0083343 A1 | 3/2016 | Xu et al. | |
| 2016/0152602 A1 | 6/2016 | Xu et al. | |
| 2016/0185785 A1 | 6/2016 | Ioannidis et al. | |
| 2016/0206604 A1 | 7/2016 | Metcalf | |
| 2016/0206614 A1 | 7/2016 | Metcalf et al. | |
| 2016/0207904 A1 | 7/2016 | Li | |
| 2016/0303099 A1 | 10/2016 | Dufu et al. | |
| 2016/0332984 A1 | 11/2016 | Metcalf et al. | |
| 2016/0346263 A1 | 12/2016 | Li et al. | |
| 2017/0066763 A1* | 3/2017 | Masse | A61P 35/00 |
| 2017/0107199 A1 | 4/2017 | Metcalf et al. | |
| 2017/0157101 A1 | 6/2017 | Ramos et al. | |
| 2017/0174654 A1 | 6/2017 | Metcalf et al. | |

FOREIGN PATENT DOCUMENTS

| | | | | |
|---|---|---|---|---|
| DE | 2853765 A | 6/1980 | | |
| DE | 29 04 829 | 8/1980 | | |
| DE | 32 26 921 A1 | 2/1983 | | |
| DE | 3503435 A | 8/1985 | | |
| EP | 0 807 9 A1 | 2/1980 | | |
| EP | 0 195 363 A2 | 9/1986 | | |
| EP | 0 355 599 B1 | 2/1990 | | |
| EP | 0 918 051 A1 | 5/1999 | | |
| EP | 1 347 982 B1 | 11/2005 | | |
| GB | 2 102 801 A | 2/1983 | | |
| OA | 13049 A | 11/2006 | | |
| WO | WO-89/00423 | 1/1989 | | |
| WO | WO-91/07963 | 6/1991 | | |
| WO | WO 93/19050 A1 | 9/1993 | | |
| WO | WO-95/07271 | 3/1995 | | |
| WO | WO 95/07891 | 3/1995 | | |
| WO | WO-98/01418 | 1/1998 | | |
| WO | WO-98/01434 | 1/1998 | | |
| WO | WO 98/22462 | 5/1998 | | |
| WO | WO 98/25924 | 6/1998 | | |
| WO | WO-98/52940 | 11/1998 | | |
| WO | WO-99/18076 | 4/1999 | | |
| WO | WO-01/90101 | 11/2001 | | |
| WO | WO-02/18346 | 3/2002 | | |
| WO | WO 02/48152 A2 | 6/2002 | | |
| WO | WO-02/056882 | 7/2002 | | |
| WO | WO-2004/002490 A1 | 1/2004 | | |
| WO | WO-2004/011436 A1 | 2/2004 | | |
| WO | WO 2004/037809 A1 | 5/2004 | | |
| WO | WO-2005/014578 A1 | 2/2005 | | |
| WO | WO 2005/095380 A1 | 10/2005 | | |
| WO | WO-2005/123703 A1 | 12/2005 | | |
| WO | WO-2006/061147 A1 | 6/2006 | | |
| WO | WO 2008/110611 A1 | 9/2008 | | |
| WO | WO-2008/128711 A1 | 10/2008 | | |
| WO | WO 2009/012125 A1 | 1/2009 | | |
| WO | WO-2009/081197 A1 | 7/2009 | | |
| WO | WO 2009/144555 A1 | 12/2009 | | |
| WO | WO-2012/028243 A1 | 3/2012 | | |
| WO | WO 2012/087520 A1 | 6/2012 | | |
| WO | WO 2012/087521 A1 | 6/2012 | | |
| WO | WO 2013/007387 A1 | 1/2013 | | |
| WO | WO-2017144633 A1 * | 8/2017 | | A61K 31/4427 |

OTHER PUBLICATIONS

Ghozlan, "Discrepancies in the reactivity pattern of azaenamines towards cinnamonitriles ," Tetrahedron, vol. 71, 1413-1418 (2015).

Ghozlan, "Studies on Enaminonitriles: a New Synthesis of 1,3-Substituted Pyrazole-4-carbonitrile Said Ahmed Soliman Ghozlan1, Ismail Abdelshafy Abdelhamid1, Hatem Moustafa Gaber2 and Mohamed Hilmy Elnagdi*1," J Heterocycl Chem, vol. 42, 1185-1189 (2005).

Ghozlan, et al., "Synthesis of pyridazines and fused pyridazines via [3 3] atom combination using Chitosan as a green catalyst," Arkivoc pp. 302-311 (2009).

Ghozlan, et al., Chemistry of Azaenamines, Curr Org Chem., vol. 15, pp. 3098-3119 (2011).

Hoepping, "Synthesis of fluorine substituted pyrazolopyrimidines as potential leads for the development of PET-imaging agents for the GABAA receptors ," Bioorg Med Chem 2008, 16, 1184 Bioorganic & Medicinal Chemistry, vol. 16, Issue 3, pp. 1184-1194 (Feb. 2008).

Jadidi, et al., "Spirooxindoles: reaction of 2,6-diaminopyrimidin-4(3H)-one and isatins," Tetrahedron, vol. 65, 2005-2009 (2009).

Ghozlan, et al., "Cytotoxic and Antimicrobial Evaluations of Novel Apoptotic and Anti-Angiogenic Spiro Cyclic 2-Oxindole Derivatives of 2-Amino-tetrahydroquinolin-5-one," Arch Pharm (Weinheim) 348, 113-124 (2015).

Abdulmalik et al, "Sickle cell disease: current therapeutic approaches," Expert Opinion Ther Patents, 15(11):1497-1506 (2005).

Abraham et al, "Vanillin, a potential agent for the treatment of sickle cell anemia," Blood, 77(6): 1334-1341 (1991).

Adhikary et al, "A new antisickling agent: In vitro studies of its effect on S/S erythrocytes and on hemoglobin S," Experientia, 34(6):804-806 (1978).

Bacsa et al, "Novel products from Baylis-Hillman reactions of salicylaldehydes," South African Journal of Chemistry, 51(1): 47-54 (1998).

Ballerini et al, High pressure Diels-Alder approach to hydroxy-substituted 6a-cyano-tetahydro-6Hbenzo[c]chromen-6-ones: A route to D6-Cis-Cannabidiol, J Org Chem, 74(11):4511-4317 (2009).

Ballet et al, "Novel selective human melanocortin-3 receptor ligands: Use of the 4-amino-1,2,4,5-tetrahydro-2-benzazepin-3-one (Aba) scaffold," Bioorganic & Medicinal Chemistry Letters, 17(9): 2492-2498 (2007).

Baxter et al, "Reductive aminations of carbonyl compounds with borohydride and borane reducing agents," Organic Reactions (Hoboken, NJ, United States), 59, including pp. 1-57 and 660-727, 125 pages (2002).

Beaumont et al, Design of ester prodrugs to enhance oral absorption of poorly permeable compounds: challenges to the discovery scientist Curr Drug Metab 2003, 4:461-85 2003.

Beddell, "Substituted benzaldehydes designed to increase the oxygen affinity of human haemoglobin and inhibit the sickling of sickle erythrocytes," Br J Pharmac, 82:397-407 (1984).

Beena et al, "Synthesis and antibacterial activity evaluation of metronidazole-triazole conjugates," Bioorg Med Chem Lett, 19(5):1396-1398 (2009).

Berge et al, "Pharmaceutical Salts," Journal of Pharmaceutical Science, 66:1-19 (1977).

Bode et al, "Novel synthesis and x-ray crystal structure of a coumarin derivative," South African Journal of Chemistry, 45(1):25-27 (1992).

Bradbury et al, "New nonpeptide angiotensin II receptor antagonists", Journal of Medicinal Chemistry, 1993, vol. 36, pp. 1245-1254 1993.

(56) References Cited

OTHER PUBLICATIONS

Britton et al, “Structure-activity relationships of a series of benzothiophene-derived NPY Y1 antagonists: optimization of the C-2 side chain,” Bioorganic & Medicinal Chemistry Letters 9(3):475-480 (1999).
Brown et al, “1,2-Dihydroisoquinolines-III Dimerization,” Tetrahedron, 22(8):2437-2443 (1966).
Chemical Abstract Registry No <collkey context=“embedded” form= “n-2-1” fkey=“y” coll=“registry”>1142191-55-6, Indexed in the Registry File on STN CAS Online May 4, 2009, 1 page (2009).
Cherian et al, “Structure-activity relationships of antitubercula nitroimidazoles 3, exploration of the linker and lipophilic tail of ((S)-2-nitro-6,7-dihydro-5H-imidazol[2, 1b] [1,3]oxazin-6-yl)-(4-trifluoromethoxy-benzyl)amine (6-Amino PA-824),” J Med Ch 2011.
Ciganek, “The catalyzed alpha-hydroxyalkylation and alpha-aminoalkylation of activated olefins (the Morita-Baylis-Hillman reaction,” Organic Reactions (Hoboken, NJ, United States), 51:201-267 and 342-350, 76 pages (1997).
Cos et al, “Structure-activity relationship and classification of flavonoids as inhibitors of xanthineoxidease and superoxide scavengers,” J Nat Prod, 61:71-76 (1998).
Database Espacenet, Bibliographic data: CN102952062 (A), Li et al., “Substituted-benzoheterocycle derivatives, preparation, and application for preparation of antiviral or antineoplastic drugs,” XP002726578 retrieved from STN Database accession No. 2013:36677 2013.
Desideri et al, “Guanylhydrazones of 3-substituted 2-pyridinecarboxaldehyde and of (2-substituted 3-pyridinyloxy) acetaldehyde as prostanoid biosynthesis and platelet aggregation inhibitors”, European Journal of Medicinal Chemistry, Editions Scientifique E 1991.
Ding et al, “Crystal structure of bis(m3-oxo)-bis[m2-2-(2-formylphenoxy)acetato-O,O']-bis[m2-2-(2-formylphenoxy)acetato-O,O']-octakis(n-butyl)tetratin(IV), Sn4O2(C9H7O4)4(C4H9)8,” Zeitschrift fuer Kristallographie—New Crystal Structures, 226(1):31-32 (2011).
Elwahy, “Synthesis of new benzo-substituted macrocyclic ligands containing quinoxaline subunits,” Tetrahedron, 56(6): 897-907 (2000).
Epsztajn et al, “Application of organolithium”, Tetrahedron, Elsevier Science Publishers, Amsterdam, NL, 1991, vol. 47, No. 9, pp. 1697-1706 (1991).
Gadaginamath et al, “Synthesis and antibacterial activity of novel 1-butyl-2-phenoxy/2-phenylthio/2-aminomethyl-5-methoxyindole derivatives,” Polish Journal of Chemistry, 71(7):923-928 (1997).
Gao et al, “A novel one-pot three-step synthesis of 2-(1-benzofuran-2-yl)quinoline-3-carboxylic acid derivatives,” Journal of the Brazilian Chemical Society, 21(5):806-812 (2010).
Ghate et al, “Synthesis of vanillin ethers from 4-(bromomethyl) coumarins as anti-inflammatory agents,” European Journal of Medicinal Chemistry, 38(3):297-302 (2003).
Gibson et al, “Novel small molecule bradykinin B2 receptor antagonists”, Journal of Medicinal Chemistry, 2009, vol. 52, pp. 4370-4379 (2009).
Grashey, “The nitro group as a 1,3-dipole in cycloadditions,” Angewandte Chemie, 74:155 (1962).
Gunter et al, “Structural control of co-receptor binding in porphyrin-bipyridinium supramolecular assemblies,” Journal of the Chemical Society, Perkin Transactions 1: Organic and Bio-Organic Chemistry, (1: 1945-1958 (1998).
Hanmantgad et al, “Synthesis and pharmacological properties of some 4-(2'-benzo[b]furanyl) coumarins,” Indian Journal of Chemistry, Section B: Organic Chemistry Including Medicinal Chemistry, 25B(7):779-781 (1986).
He et al, “Prodrugs of phosphonates, phosphinates, and phosphates”, Prodrugs: Challenges and Rewards, Part 2, edited by Stella et al, pp. 223-264 (2007).
Heimbach et al, “2.2.1: Over-coming poor aqueous solubility of drugs for oral delivery,” from Prodrugs: Challenges and Rewards, Part I, New York NY, Singer: AAPS Press, pp. 157-215 (2007).
Heimbach et al, “Enzyme-mediated precipitation of parent drugs from their phosphate prodrugs,” International Journal of Pharmaceutics 261:81-92 (2002).
Heimgartner et al, “Stereoselective synthesis of swainsonines from pyridines”, Tetrahedron, Elsevier Science Publishers, Amsterdam, NL, 2005, vol. 61, No. 3, pp. 643-655 (2005).
Hong et al, “Potential Anticancer Agents VI:5-Substituted Pyrimidine-6-Carboxaldehydes”, Journal of Pharmaceutical Sciences, American Pharmaceutical Association, Washington, US, 1970, vol. 59, No. 11, pp. 1637-1645 (1970).
Ito et at, “A medium-term rat liver bioassay for rapid in vivo detection of carcinogenic potential of chemicals,” Cancer Science, 94(1):3-8 (2003) 2003 non; Ivanisevic, et al Uses of x-ray powder diffraction in the pharmaceutical industry Pharm Sci Encycl 2010; 1-42 (2010).
Jarvest et al, “Discovery and optimisation of potent, selective, ethanolamine inhibitors of bacterial phenylalanyl tRNA synthetase,” Bioorganic & Medicinal Chemistry Letters, 15(9):2305-2309 (2005).
Karche et al, “Electronic effects in migratory groups [1,4]-versus [1,2]-rearrangement in rhodium carbenoid generated bicyclic oxonium ylides,” Journal of Organic Chemistry, 66(19):6323-6332 (2001).
Katritzky et al, “Synthesis of 3-hydroxymethyl-2,3-dihydrobenzofurans and 3-hydroxymethylbenzofurans,” Arkivoc (Gainesville, FL, United States), (6):49-61 (2003).
Kaye et al “DABCO-catalyzed reactions of salicylaldehydes with acrylate derivatives,” Synthetic Communications: An International Journal for Rapid Communication of Synthetic Organic Chemistry, 26(11):2085-97 (1996).
Kaye et al, “Does the DABCO-catalysed reaction of 2-hydroxybenzaldehydes with methyl acrylate follow a Baylis-Hillman pathway?,” Organic & Biomolecular Chemistry, 1(7):1133-1138 (2003).
Kessar et al, “An interesting application of photocyclisation in aporhoeadane alkaloid synthesis”, Tetrahedron Letters, 28(44):5323-5326 (1987).
Kessar et al, “Synthesis of isoindolobenzazepines via photocyclization of N-(2-formylphenethyl)phthalimide derivatives,” Indian Journal of Chemistry, 30B(11):999-1005 (1991).
Kise et al, “Electroreductive intramolecular coupling of phthalimides with aromatic aldehydes: application to the synthesis of lennoxamine,” Journal of Organic Chemistry, 76(23):9856-9860 (2011).
Krow, Grant R, “Chapter 3, The Baeyer-Villiger oxidation of ketones and aldehydes,” Organic Reactions, 43:251-353 and 775-808 (1993).
Lakkannavar et al, “4-[2'-Benzylideneanilino aryloxymethyl] coumarins E and Z isomers,” Indian Journal of Heterocyclic Chemistry, 4(4):303-304 (1995).
Lin et al, “Potential Antitumor Agents.8 Derivatives of 3- and 5-Benzyloxy-2-formylpyridine Thiosemicarbazone”, Journal of Medicinal Chemistry, American Chemical Society, US, 1972, vol. 15, No. 6, pp. 615-618 (1972).
Liu et al, “Synthesis of Double-Armed Benzo-15-crown-5 and Their Complexation Thermodynamics with Alkali Cations,” Journal of Inclusion Phenomena and Macrocyclic Chemistry, 52(3-4):229-235 (2005).
Mahoney et al, “Functionalization of Csp3-H bond-Sc(OTf)3-catalyzed domino 1,5-hydride shift/cyclization/Friedel-Crafts acylation reaction of benzylidene Meldrum's acids,” Tetrahedron Letters, 50(33):4706-4709 (2009).
Majhi et al, “An efficient synthesis of novel dibenzo-fused nine-membered oxacycles using a sequential Baylis-Hillman reaction and radical cyclization,” Synthesis, (1):94-100 (2008).
Manna et al, Synthesis and beta-adrenoreceptor blocking activity of [[3-(alkylamine)-2-hydroxypropyl]oximino]pyridines and 0[3-(alkylamine)-2-hydroxypropyl]methylpyridine ketone oximes derivatives, IL Farmaco, 1996, vol. 51, No. 8, 9, pp. 579-587(1996).
Mantyla et al, Synthesis, in vitro evaluation and antileishmanial activity of water-soluble prodrugs of buparvaquone J Med Chem 2004, 47:188-195 (2004).
Marchetti et al, “Synthesis and biological evaluation of 5-substituted O4-alkylpyrimidines as CDK2 inhibitors,” Org Biomol Chem, 8:2397-2407 (2010).

(56) References Cited

OTHER PUBLICATIONS

McKay et al, "7,11,15,28-Tetrakis[(2-formylphenoxy)-methyl]-1,21,23,25-tetramethyl-resorcin[4]arene cavitand ethyl acetate clathrate at 173 K," Acta Crystallographica, Section E: Structure Reports Online, E65(4):o692-o693 (2009).
McKay et al, "Microwave-assisted synthesis of a new series of resorcin[4]arene cavitand-capped porphyrin capsules," Organic & Biomolecular Chemistry, 7(19):3958-3968 (2009).
Merlino et al, "Development of second generation amidinohydrazones, thio- and semicarbazones as Trypanosoma cruzi-inhibitors bearing benzofuroxan and benzimidazole 1,3-dioxide core scaffolds," Med Chem Commun, 1(3):216-228 (2010).
Mesguiche et al, "4-Alkoxy-2,6-diaminopyrimidine derivatives: inhibitors of cyclin dependent kinases 1 and 2," Bioorganic & Medicinal Chemistry Letters, 13:217-222 (2003).
Mitra et al, "Synthesis and biological evaluation of dibenz[b,f][1,5]oxazocine derivatives for agonist activity at k-opioid receptor," European Journal of Medicinal Chemistry, 46(5):1713-1720 (2011).
Mulwad et al, "Synthesis and antimicrobial activity of [6'-methyl-4'-methoxy-2-oxo-2H-[1]-benzopyran)-2",4"—dihydro-[1",2",4"]-triazol-3"-one and 3"-phenylthiazolidin-4"-one-phenoxymethyl derivatives of dipyranoquinoline," Pharmaceutical Chemistry 2011.
Nagy et al, Selective coupling of methotrexate to peptide hormone carriers through a y-carboxamide linkage of its glutamic acid moiety: Benzotriazol-1-yloxytris(dimethylamino)phosphonium hexafluorophosphate activation in salt coupling Proc Natl Acad Sci USA 1993.
Neelima et al, "A novel annelation reaction: synthesis of 6H-[1]benzopyrano[4,3-b]quinolines," Chemistry & Industry (London, United Kingdom), (4):141-2 (1986).
Nnamani et al, "Pyridyl derivatives of benzaldehyde as potential antisickling agents", Chemistry & Biodiversity, 5:1762-1769 (2008).
Nogrady, Medicinal Chemistry A Biochemical Approach, Oxford University Press, New York, pp. 388-392 (1985).
Nonoyama et al, "Cyclometallation of 2-(2-pyridyl)benzo[b]furan and 1-(2-pyridyl and 2-pyrimidyl)indole with palladium(II) and rhodium(III) Structures of unexpectedly formed nitro palladium(II) complexes," Polyhedron, 18:533-543 (1999).
Nyerges et al, "Synthesis of indazole N-oxides via the 1,7-electrocyclization of azomethine ylides," Tetrahedron Letters, 42(30):5081-5083 (2001).
Nyerges et al, "Synthesis of indazole-N-oxides via the 1,7-electrocyclization of azomethine ylides," Tetrahedron, 60(44):9937-9944 (2004).
OECD SIDS, "Potassium Hydroxide, SIDS Initial Assessment Report for SIAM 13, CAS No. 1310-58-3," UNEP Publications, pp. 1-96 (2002).
O'Reilly et al, "Metal-phenoxyalkanoic acid interactions XXV The crystal structures of (2-formyl-6-methoxyphenoxy)acetic acid and its zinc(II) complex and the lithium, zinc(II) and cadmium(II) complexes of (2-chlorophenoxy)acetic acid," Australian Journal 1987.
Perez et al, "Preparation of new 1,2-disubstituted ferrocenyl stibine derivatives containing ether/thioether pendant arm from a quaternary ferrocenyl ammonium salt," Polyhedron, 28(14):3115-3119 (2009).
Perkins et al, "Manganese(II), iron(II), cobalt(II), and copper(II) complexes of an extended inherently chiral trisbipyridyl cage," Proceedings of the National Academy of Sciences of the United States of America, 103(3):532-537 (2006).
Pubchem CID 54009805, create date: Dec. 4, 2011, 3 pages, (2011) 2011.
Pubchem CID 54883281, create date: Jan. 24, 2012, 3 pages, (2012) 2012.
Rooseboom et al, Enzyme-catalyzed activation of anticancer prodrugs Pharmacol Rev 2004, 56:53-102 (2004).
Ruchirawat et al, "A novel synthesis of aporhoeadanes," Tetrahedron Letters, 25(32):3485-3488 (1984).
Sahakitpichan et al, "A practical and highly efficient synthesis of lennoxamine and related isoindolobenzazepines," Tetrahedron, 60(19):4169-4172 (2004).
Sahm et al, "Synthesis of 2-arylbenzofurans," Justus Liebigs Annalen der Chemie, (4):523-38, includes English language abstract, (1974).
Sainsbury et al, "1,2-Dihydroisoquinolines IV Acylation," Tetrahedron, 22(8):2445-2452 (1966).
Sarodnick et al, "Quinoxalines XV Convenient synthesis and structural study of pyrazolo[1,5-a]quinoxalines," Journal of Organic Chemistry, 74(3):1282-1287 (2009).
Siddiqui et al, "The presence of substitutents on the aryl moiety of the aryl phosphoramidate derivatives of d4T enhances anti-HIV efficacy in cell culture: a structure-activity relationship," J Med Chem, 42:393-399 (1999).
Silva et al, "Advances in proddrug design," Mini-Rev Med Chem, 5(10):893-914, 2005.
Singh et al, "Reductive-cyclization-mediated synthesis of fused polycyclic quinolines from Baylis-Hillman adducts of acrylonitrile: scope and limitations," European Journal of Organic Chemistry, (20):3454-3466 (2009).
Sobolev et al, Effect of acyl chain length and branching on the enantioselectivity of Candida rugosa lipase in the kinetic resolution of 4-(2-difluoromethoxyphenyl)-substituted 1,4-dihydropyridine 3,5-diesters J Org Chem 2002, 67:401-410 (2002).
Srivastava et al, "Synthesis and biological evaluation of 4-substituted tetrazolo[4,5-a]quinolines and 2,3-disubstituted quinoline derivatives," Indian Journal of Chemistry, Section B: Organic Chemistry Including Medicinal Chemistry, 28B(7):562-573 (1989).
Starke et al, "Quinoxalines Part 13: Synthesis and mass spectrometric study of aryloxymethylquinoxalines and benzo[b]furylquinoxalines," Tetrahedron, 60(29):6063-6078 (2004).
Swann et al, "Rates of reductive elimination of substituted nitrophenols from the (indo1-3-yl)methyl position of indolequinones," Journal of the Chemical Society, Perkin Transactions 2, (8):1340-1345 (2001).
Testa et al, Hydrolysis in Drug and Prodrug Metabolism, Jun. 2003, Wiley-VCH, Zurich, 419-534 (2003).
Tome, A.C, "13.13, Product class 13:1,2,3-triazoles," Science of Synthesis: Houben-Weyl Methods of Molecular Transformations, Georg Thieme Verlag publishers, Stuttgart, Germany, pp. 415-601, (2003).
Van Rompaey et al, "A versatile synthesis of 2-substituted 4-amino-1,2,4,5-tetrahydro-2-benzazepine-3-ones," Tetrahedron, 59(24):4421-4432 (2003).
Van Rompaey et al, "Synthesis and evaluation of the b-turn properties of 4-amino-1,2,4,5-tetrahydro-2-benzazepin-3-ones and of their spirocyclic derivative," European Journal of Organic Chemistry, (13):2899-2911 (2006).
Vicente et al, "Carbopalladation of maleate and fumarate esters and 1,1-dimethylallene with ortho-substituted aryl palladium complexes," Organometallics, 29(2):409-416 (2010).
Wang et al, "Studies of benzothiophene template as potent factor IXa (FIXa) inhibitors in thrombosis," Journal of Medicinal Chemistry, 53(4):1465-1472 (2010).
Warshawsky et al, "The synthesis of aminobenzazepinones as anti-phenylalanine dipeptide mimics and their use in NEP inhibition," Bioorganic & Medicinal Chemistry Letters, 6(8):957-962 (1996).
Wendt et al, "Synthesis and SAR of 2-aryl pyrido[2,3-d]pyrimidines as potent mGlu5 receptor antagonists," Bioorganic & Medicinal Chemistry Letters, 17:5396-5399 (2007).
Wermuth, Camille G, "Molecular Variations Based on Isosteric Replacements", The Practice of Medicinal Chemistry, 1996, pp. 203-232 (1996).
Yan et al, "Synthesis, crystal structure and antibacterial activity of di-n-butyltin carboxylate," Huaxue Tongbao, 70(4):313-316, includes English language abstract, (2007).
Yan et al, "Synthesis, crystal structure and antibacterial activity of di-n-butyltin di-2-(2-formylphenoxy)acetic ester," Yingyong Huaxue, 24(6):660-664, includes English language abstract, (2007).
Yoon et al, "The chirality conversion reagent for amino acids based on salicyl aldehyde," Bull Korean Chem Soc, 33(5), pp. 1715-1718 (2012).

(56) References Cited

OTHER PUBLICATIONS

Zhang et al, "DFT study on RuII-catalyzed cyclization of terminal alkynals to cycloalkenes," International Journal of Quantum Chemistry, 109(4), pp. 679-687 (2009).
Zhu et al, "Isoquinoline-pyridine-based protein kinase B/Akt antagonists: SAR and in vivo antitumor activity", Bioorganic & Medicinal Chemistry Letters, Pergamon, Amsterdam, NL, 2006, vol. 16, No. 12, pp. 3150-3155 (2006).
Zwaagstra et at, "Synthesis and structure-activity relationships of carboxylated chalcones: a novel series of Cys-LT1 (LTD4) Receptor Antagonists", Journal of Medicinal Chemistry, 40(7), pp. 1075-1089 (1997).
Boehm, et al., "New inhibitors of p38 kinase," J; Exp. Opin. Ther., vol. 10, pp. 25-37 (Feb. 2005).
Brickner, et al., "Synthesis and antibacterial activity of U-100592 and U-100766, two oxazolidinone antibacterial agents for the potential treatment of multidrug-resistant gram-positive bacterial infections," J. Med. Chem., vol. 39, No. 3, pp. 673-679 (1996).
Carotti, A; "Synthesis and Monoamine Oxidase Inhibitory Activity of New Pyridazine-, Pyrimidine- and 1,2,4-Triazine-Containing Tricyclic Derivatives," J. Med. Chem., vol. 50, No. 22, pp. 5364-5371 (2007).
Catalan, et al., "New Ultraviolet Stabilizers: 3- and 5-(2'-Hydroxyphenyl)pyrazoles," J. Am. Chem. Soc., vol. 114, No. 13 pp. 5039-5048 (1992).
Chebanov, et al., "Tuning of Chemo- and Regioselectivities in Multicomponent Condensations of 5-Aminopyrazoles, Dimedone, and Aldehydes," J. Org. Chem., vol. 73, pp. 5110-5118 (2008).
Deng, et al., "Regioselective Synthesis of 1,3,5-Tri- and 1,3,4,5-Tetrasubstituted Pyrazoles from N-Arylhydrazones and Nitroolefins," J. Org. Chem., vol. 73, pp. 2412-2415 (2008).
Ewen, et al., "Chiral Ansa Metallocenes with Cp Ring-Fused to Thiophenes and Pyrroles: Syntheses, Crystal Structures, and Isotactic Polypropylene Catalysts," J. Am. Chem. Soc., vol. 123, No. 28, p. 6964 (2001).
Fustero, et al., "Improved Regioselectivity in Pyrazole Formation through the Use of Fluorinated Alcohols as Solvents: Synthesis and Biological Activity of Fluorinated Tebufenpyrad Analogs," J. Org. Chem., vol. 73, pp. 3523-3529 (2008).
Gilbert, A., M. Bursavich, et al., "5-((1H-Pyrazol-4-yl)methylene)-2-thioxothiazolidin-4-one inhibitors of ADAMTS-5," Bioorg Med Chem Lett, vol. 17, No. 5, pp. 1189-1192 (Mar. 2007).
Mahata, et al., "Reaction of r-Oxoketene-N,S-arylaminoacetals with Vilsmeier Reagents: An Efficient Route to Highly Functionalized Quinolines and Their Benzo/Hetero-Fused Analogues," J. Org. Chem., vol. 68, pp. 3966-3975 (2003).
Mandal, et al., "Studies in sulfur heterocycles. Part 15.1 Condensed heterocycles derived from thieno [2,3-c]- and thieno[3,2-c]-thiopyrans," J. Chem. Soc., Perkin Trans., 1, pp. 2639-2644 (1999).
Misra, et al., "An Efficient Highly Regioselective Synthesis of 2,3,4-Trisubstituted Pyrroles by Cycloaddition of Polarized Ketene S,S- and N,S-Acetals with Activated Methylene Isocyanides," J. Org. Chem., vol. 72, pp. 1246-1251 (2007).
Moerck, et al., "Pyrazole Addition to Δ1-Azirines. Structure of Purported 2:1 Adducts of Δ1-Azirines with sym-Tetrazines," J.C.S. Chem. Comm., pp. 782-783 (1974).
Molina, et al., "Fused Pyrimidines by a Tandem Aza-Wittig/Electrocyclic Ring Closure Strategy: Synthesis of Pyrazolo[3,4-d]pyrimidine, [I,2,3]Triazolo[4,5-d ]pyrimidine, and Thiazolo[4,5-d ]pyrimidine Derivatives," J. Org. Chem., vol. 53, pp. 4654-4663 (1988).
Nandi, et al., "Biginelli and Hantzsch-Type Reactions Leading to Highly Functionalized Dihydropyrimidinone, Thiocoumarin, and Pyridopyrimidinone Frameworks via Ring Annulation with β-Oxodithioesters," J. Org. Chem., vol. 75, pp. 7785-7795 (2010).
Nandi, et al., One-Pot Two-Component [3 2] Cycloaddition/Annulation Protocol for the Synthesis of Highly Functionalized Thiophene Derivatives, J. Org. Chem., vol. 76, pp. 8009-8014 (2011).
Peruncheralathan, et al., "Highly Regioselective Synthesis of 1-Aryl-3 (or 5)-alkyl/aryl-5 (or 3)-(N-cycloamino)pyrazoles," J. Org. Chem., vol. 70, pp. 9644-9647 (2005).
Peruncheralathan, et al., Regioselective Synthesis of 1-Aryl-3,4-substituted/annulated-5-(methylthio)pyrazoles and 1-Aryl-3-(methylthio)-4,5-substituted/annulated Pyrazoles, J. Org. Chem., vol. 70, pp. 10030-10035 (2005).
Potts, et al., "Ketene Dithioacetals as Synthetic Intermediates. Synthesis of Unsaturated 1,5-Diketones," J. Am. Chem. Soc., vol. 103, pp. 3585-3586 (1981).
Rastogi, et al, "Keten SS-Acetals.S Part 9.1a Reaction of a-Oxo- and a-Cyano-keten SS-Acetals with Cyanoacetamide: a New General Method for Substituted and Fused 4-Alkylthio-3-cyano-2(1H)-pyridones and Formation of Novel Pyridones through Base-induced Rearrangements," Medicinal Chemistry Division, Central Drug Research Institute, pp. 549-553 (1978).
Singh et al., "Application of B-Oxodithioesters in Domino and Multicomponent Reactions: Facile Route to Dihydropyrimidines and Coumarins," J. Org. Chem., vol. 74, pp. 3141-3144 (2009).
Singh, et al., "Novel Route to 2,3-Substituted Benzo[b]thiophenes via Intramolecular Radical Cyclization," J. Org. Chem., vol. 74, pp. 5496-5501 (2009).
Surmont, et al., "Synthesis of 3-Amino-4-fluoropyrazoles," J. Org. Chem., vol. 76, pp. 4105-4111 (2011).
Svenstrup, et al., "A Pyrazole to Furan Rearrangement. Thermolysis of 5-Azido-4-formylpyrazoles," J. Org. Chem., vol. 64, pp. 2814-2820 (1999).
Chauhan, et al., "The Reactions of α-Keto and α-Cyanoketene-S,S-Acetals with Guanidine and Thiourea: A New General Synthesis of Alkoxy-Pyrimidines," *Tetrahedron*, vol. 32, pp. 1779-1787 (1976).
Cherney, et al., "Potent and Selective Aggrecanase Inhibitors Containing Cyclic P1 Substituents," *Bioorganic & Medicinal Chemistry Letters*, vol. 13, pp. 1297-1300 (2003).
Das et al., "5-Amino-pyrazoles as potent and selective p38α inhibitors," Bioorganic & Medicinal Chemistry Letters, vol. 20, pp. 6886-6889 (2010).
Deng, et al., "Base-Mediated Reaction of Hydrazones and Nitroolefins with a Reversed Regioselectivity: A Novel Synthesis of 1,3,4-Trisubstituted Pyrazoles," *Organic Letters*, vol. 10, No. 6, pp. 1307-1310 (2008).
Fossa, et al., "Synthesis and Pharmacological Characterization of Functionalized 2-Pyridones Structurally Related to the Cardiotonic Agent Milrinone," Bioorganic & Medicinal Chemistry, vol. 11, pp. 4749-4759 (2003).
Gallagher, et al., "Regulation of Stress-Induced Cytokine Production by Pyridinylimidazoles; Inhibition of CSBP Kinase," Bioorganic & Medicinal Chemistry, vol. 5, No. 1, pp. 49-64 (1997).
Gerstenberger, et al., "One-Pot Synthesis of N-Arylpyrazoles from Arylhalides," Organic Letters, vol. 11, No. 10, pp. 2097-2100 (2009).
Graneto, et al., "Synthesis, Crystal Structure, and Activity of Pyrazole-Based Inhibitors of p38 Kinase," J. Med. Chem., vol. 50, pp. 5712-5719 (2007).
Hoepping, et al., "Synthesis of fluorine substituted pyrazolopyrimidines as potential leads for the development of PET-imaging agents for the GABAA receptors," Bioorganic & Medicinal Chemistry, vol. 16, pp. 1184-1194 (2008).
Junjappa, et al., "α-Oxoketene-S,S-, N,S- and N,N-Acetals: Versatile Intermediates in Organic Synthesis," Tetrahedron Report Number 278, Tetrahedron, vol. 46, No. 16, pp. 5423-5506 (1990).
Karatsu, et al., "Photoinduced Electron Transfer Reactions of 3H-Pyrazole Derivatives, Formation of Solvent Adduct by Specific Sensitizer," Bull. Chem. Soc. Japan, vol. 76, pp. 1227-1231 (2003).
Kawano, et al., "Synthesis of indenothiophenone derivatives by cycloaromatization of non-conjugated thienyl tetraynes," Tetrahedron Letters, vol. 46, pp. 1233-1236 (2005).
Khan, et al., "Hetarylpyrazoles. IV (1). Synthesis and Reactions of 1,5'-Bipyrazoles," J. Heterocyclic Chem., vol. 20, pp. 277-279 (1983).
Kuettel, et al., "Synthesis and Evaluation of Antiparasitic Activities of New 4-[5-(4-Phenoxyphenyl)-2H-pyrazol-3-yl]morpholine Derivatives," J. Med. Chem. vol. 50, pp. 5833-5839 (2007).

(56) References Cited

OTHER PUBLICATIONS

Kumar, et al., "Heteroaromatic annulation studies on 10,11-dihydro-11-[bis(methylthio)methylene]dibenzoxepin-10-one: a facile access to novel dibenzoxepino[4,5]-fused heterocycles," Tetrahedron, vol. 63, pp. 10067-10076 (2007).
De Laszlo, et al., "Pyrroles and Other Heterocycles as Inhibitors of P38 Kinase," Bioorganic & Medicinal Chemistry Letters 8, pp. 2689-2694 (1998).
Lau et al., "Synthesis and Biological Evaluation of 3-Heteroaryloxy-4-Phenyl-2(5H)-Furanones as Selective Cox-2 Inhibitors," Bioorganic & Medicinal Chemistry Letters 9, pp. 3187-3192 (1999).
Leblanc, et al., "Sar in the Alkoxy Lactone Series: The Discovery of DFP, a Potent and Orally Active Cox-2 Inhibitor," Bioorganic & Medicinal Chemistry Letters 9, pp. 2207-2212 (1999).
Lee, et al., "Regioselective Synthesis of 1,3,4,5-tetrasubstituted pyrazoles from Baylis-Hillman Adducts," Tetrahedron Letters 44, pp. 6737-6740 (2003).
Li et al., "A New Structural Variation on the Methanesulfonylphenyl Class of Selective Cyclooxygenase-2 Inhibitors," Bioorganic & Medicinal Chemistry Letters 9, pp. 3181-3186 (1999).
Li, et al., "Synthesis of Di-heterocclic Compounds; Pyrazolylimidazoles and Isoxazolylimidazoles," Heteroatom Chemistry, vol. 9, No. 3, pp. 317-320 (1998).
Liverton, et al., "Design and Synthesis of Potent, Selective, and Orally Bioavailable Tetrasubstituted Imidazole Inhibitors of p38 Mitogen-Activated Protein Kinase," J. Med. Chem., vol. 42, pp. 2180-2190 (1999).
Maeda, et al., Dipyrrolylpyrazoles: anion receptors in protonated form and efficient building blocks for organized structures, Chem. Commun., pp. 1136-1138 (2007).
Cativiela, et al., "On the Synthesis of 3(5)-Carbomethoxy-4-hetarylpyrazoles," *J. Heterocyclic Chem.*, vol. 25, pp. 851-855 (May-Jun. 1988).
Chauhan, et al., "A Novel One Step Synthesis of 5(3)-Methylthio-Alkoxy-, Amino- and Hydroxypyrazoles using α-Ketoketene-S,S-Diacetals," *Synthesis*, pp. 798-801 (1975).
Chauhan, et al., "The Use of α-Ketoketene-S,S-Diacetals for a Novel Pyrimidine Synthesis," *Synthesis*, pp. 880-882 (Dec. 1974).
Dannhardt, et al., "Transformations of Pyrrolidine Enaminones Yielding (ω-Aminopropyl)-pyrazoles," *Arch. Pharm.* (Weinheim), vol. 321, pp. 17-19 (1988). Eng. Abstract.
Dodd, et al., "One-pot synthesis of 5-(substituted-amino) pyrazoles," *Tetrahedron Letters*, vol. 45, pp. 4265-4267 (2004).
Dolzhenko, et al., "Pyrazolo[1,5-α-][1,3,5]Triazines (5-AZA-9-Deazapurines): Synthesis and Biological Activity," Heterocycles, vol. 75, No. 7, 1575-1622 (2008).
Dorlars, et al., "Heterocycles as Structural Units in New Optical Brighteners," Angew. Chem., vol. 14, No. 10 pp. 665-679 (1975).
Dorlars, et al., "Heterocycles as building blocks for new optical brighteners," Angew. Chem., vol. 87, No. 19, pp. 693-707 (1975).
Elguero, et al., "Pyrazoles as Drugs: Facts and Fantasies," Targets in Heterocyclic Systems, pp. 52-98 (2002). Eng. Abstract.
Elmaati, "New Trends in the Chemistry of 5-Aminopyrazoles," J. Heterocyclic Chem., vol. 41, pp. 109-134 (2004).
Von Ulf Fischer, et al., "180. 1,3-Dipolare Additionen an 7-Methylthieno [2,3-c]pyridine-1, 1-dioxid," Helvetica Chimica ACTA, vol. 63, No. 6, pp. 1719-1727 (1980).
Glasson, et al., "Characterization of and Osteoarthritis Susceptibility in ADAMTS-4-Knockout Mice," Arthritis & Rheumatism, vol. 50, No. 8, pp. 2547-2558 (Aug. 2004).
Hansen, et al., "Synthesis of Enantioenriched 4-Thiazolidinone (−)-LY213829 by Chemoselective Benzylamide Cleavage in the Presence of a C—S Bond," Tetrahedron: Asymmetry, vol. 7, No. 9, pp. 2515-2518 (1996).
Henry, et al., "p38 Mitogen-activated protein kinase as a target for drug discovery," Drugs of the Future, vol. 24(12), pp. 1345-1354 (1999).
Jachak, et al., "Synthesis of Pyrazolo[3,4-b]pyridines Using Ammonium Acetate as Green Reagent in Multi-component Reactions," J. Heterocyclic Chem., vol. 45, pp. 1221-1224 (2008).
Kumar, et al., "A Novel and Convenient Synthesis of 2-Amino-4-(N-alkyl-N-arylamino)-pyrimidines using Polarized Ketene S,S- and S,N-Acetals," Synthesis, pp. 748-751 (1980).
Kupferberg, "Strategies for Identifying and Developing New Anticonvulsant Drugs," Pharmaceutisch Weekblad Scientific edition, vol. 14(3A), pp. 132-138 (1992).
Lamberth, Pyrazole Chemistry in Crop Protection, Heterocycles, vol. 71, pp. 1467-1502 (2007).
Martin, et al., "Domino Cu-Catalyzed C—N Coupling/Hydroamidation: A Highly Efficient Synthesis of Nitrogen Heterocycles," Angew. Chem. Int. Ed., vol. 45, pp. 7079-7082 (2006).
Mashraqui, et al., "Application of Commercially Available Anhydrous Potassium Fluoride for a Convenient Synthesis of Ketene Dithioacetals," J. Chem. Research, pp. 492-493 (1999).
Matasi, et al., "The Discovery and Synthesis of Novel Adenosine Receptor (A2A) Antagonists," Bioorganic & Medicinal Chemistry Letters, vol. 15, pp. 1333-1336 (2005).
Mukherjee, "Coordination Chemistry with Pyrazole-based Chelating Ligands: Molecular Structural Aspects," Coordination Chemistry Reviews, vol. 203, pp. 151-218 (2000).
Nugiel, et al., "Synthesis and Evaluation of Indenopyrazoles as Cyclin-Dependent Kinase Inhibitors. 2. Probing the Indeno Ring Substitute Pattern," J. Med. Chem., vol. 45, pp. 5224-5232 (2002).
Nugiel, et al., "Indenopryazoles as Novel Cyclin Dependent Kinase (CDK) Inhiitors," J. Med. Chem., vol. 44, pp. 1334-1336 (2001).
Penning, et al., Synthesis and Biological Evaluation of the 1,5-Diarylpyrazole Class of Cyclooxygenase-2 Inhibitors: Identification of 4-[5-(4-Methylphenyl)-3-(trifluoromethyl)-1 H-pyrazol-1-yl] benzenesulfonamide (SC-58635, Celecoxib), J. Med. Chem., vol. 40, pp. 1347-1365 (1997).
Purkayasha, et al., "Regioselective Synthesis of 5-Alkylthio- and 3-Alkylthioisoxazoles from Acylketene Dithioacetals," Synthesis, pp. 20-24 (1988).
Reddy, et al., "A Clean and Rapid Synthesis of 5-Amino and 5-Alkoxycarbonylpyrazoles using Montomorillonite under Acid Free Conditions," Organic Preparations and Procedures International, vol. 36, No. 5, pp. 494-498 (2004).
Ried, et al., "Synthese von Indeno[1,2-c][1,2$\lambda^4$,6]thiadiazinen aus S,S-Dialkylschwefeldiimiden," Chem. Ber., vol. 121, pp. 805-808 (1988).
Roy, et al., "An Expedient Route to 2,3-Substituted and Fused Benzo[a]quinolizine-4-thione Framework via Ring Annulation with β-Oxodithioesters," Organic Letters, vol. 3, No. 2, pp. 229-232 (2001).
Ryckebusch, et al., "Synthesis, Cytotoxicity, DNA Interaction, and Topoisomerase II Inhibition Properties of Novel Indeno[2,1-c]quinoline-7-one and Indeno[1,2-c]isoquinolin-5, 11-dione Derivatives," J. Med. Chem., vol. 51, pp. 3617-3629 (2008).
Sakya, et al., "5-Heteroatom substituted pyrazoles as canine COX-2 inhibitors. Part III: Molecular modeling studies on binding contribution of 1-(5-methylsulfonyl)pyrid-2-yl and 4-nitrile." Bioorganic & Medicinal Chemistry Letters, vol. 17, pp. 1067-1072 (2007).
Samuel, et al., "A facile method for the synthesis of substitute 2-ylidene-1,3-oxathioles from acetophenones," Tetrahedron Letters 48, pp. 8376-8378 (2007).
Singh, et al., "A Facile One-Step Synthesis of Methyl B-Oxodithiocarboxylates," Communications, p. 693 (Aug. 1982).
Stanovik, et al., "Synthesis of Heterocycles from Alkyl 3-(Dimethylamino)propenoates and Related Enaminones," Chem. Rev., vol. 104, pp. 2433-2480 (2004).
Stanton, et al., "ADAMTS5 is the major aggrecanase in mouse cartilage in vivo and in vitro," Nature, vol. 434, pp. 648-652 (2005).
Tang, et al., "Anilinopyrazole as Selective CDK2 Inhibitors: Design, Synthesis, Biological Evaluation, and X-ray Crystallographic Analysis," Bioorganic & Medicinal Chemistry Letters, vol. 13, pp. 2985-2988 (2003).
Tao, et al., "Discovery of 40-(1,4-dihydro-indeno[1,2-c]pyrazol-3-yl)-benzonitriles and 40-(1,4-dihydro-indeno[1,2-c]pyrazol-3-yl)-pyridine-20-carbonitriles as potent checkpoint kinase 1 (Chkl) inhibitors," Bioorganic & Medicinal Chemistry Letters, vol. 17, pp. 5944-5951 (2007).

(56) References Cited

OTHER PUBLICATIONS

Tao et al., "A facile synthesis of antitumoral indeno [1,2-c]pyrazole-4-one by mild oxidation with molecular oxygen," Tetrahedron Letters 46, pp. 7615-7618 (2005).
Teng, et al., "Structure-Based Design of (5-Arylamino-2H-pyrazol-3-yl)-biphenyl-2',4'-idiols as Novel and Potent Human CHK1 Inhibitors," J. Med. Chem, vol. 50, pp. 5253-5256 (2007).
Terrett, et al., "Sildenafil (ViagraTm), a Potent and Selective Inhibitor of Type 5 CGMP Phosphodiesterase with utility for the treatment of male erectile dysfunction," Bioorganic & Medicinal Chemistry Letters, vol. 6, No. 15, pp. 1819-1824 (1996).
Pubchem CID 126655306, pp. 1-9 (Apr. 22, 2017).
Pubchem CID 133279368, pp. 1-7 (May 25, 2018).
Pubchem CID 103078000, pp. 1-8 (Jan. 12, 2016).
Pubchem CID 133316087, pp. 1-7 (May 25, 2018).
Pubchem CID 53015280, pp. 1-8 (Jun. 21, 2011).
Pubchem CID 135280901, pp. 1-9 (Dec. 15, 2018).
Pubchem CID 127940724, pp. 1-7 (Jun. 18, 2017).
Pubchem CID 133464874, pp. 1-7 (May 25, 2018).
Pubchem CID 133465554, pp. 1-8 (May 25, 2018).
Pubchem CID 53588362, pp. 1-8 (Dec. 3, 2011).
International Search Report and Written Opinion issued in International Patent Application No. PCT/US2020/017170, dated Apr. 27, 2020.
Edson, et al., "CYP4 Enzymes as Potential Drug Targets: Focus on Enzyme Multiplicity, Inducers and Inhibitors, and Therapeutic Modulation of 20-hydroxy-eicosatetraenoic acid (20-HETEC) Synthase and Fatty Acid Omega-Hydroxylase Activities," *Current Topics in Medicinal Chemistry*, vol. 13(12), pp. 1-24 (2013).
International Preliminary Report on Patentability issued in International Patent Application No. PCT/US2020/017170, Aug. 19, 2021.
Babu, et al., "Regioselective synthesis and structural elucidation of 1,4-disubstituted 1,2,3-triazole derivatives using 1D and 2D NMR spectral techniques" Magn. Reson. Chem., vol. 49, pp. 824-829 (2011).
Chebanov, et al., "Aminoazoles as Key Reagents in Multicomponent Heterocyclizations," Top Heterocycl Chem, vol. 23 pp. 41 (2010).
Chebanov, et al., "Cyclocondensation reactions of 5-aminopyrazoles, pyruvic acids and aldehydes. Multicomponent approaches to pyrazolopyridines and related products," Tetrahedron, vol. 63 pp. 1229 (2007).
Chebanov, et al., "High regioselective ultrasonic-assisted synthesis of 2,7-diaryl-4,7-dihydropyrazolo[1,5-a]pyrimidine-5-carboxylic acids," Ultrason Sonochem, vol. 19, pp. 707 (2012).
Chebanov, et al., "Microwave-Assisted Three-Component Synthesis of 7-Aryl-2-alkylthio-4,7-dihydro-1,2,4-triazolo[1,5-a]-pyrimidine-6-carboxamides and Their Selective Reduction," Comb Chem., vol. 8 pp. 427 (2006).
Chebanov, et al., "One-Pot, Multicomponent Route to Pyrazoloquinolizinones," Org Lett, vol. 9 pp. 1691 (2007).
Chebanov, et al., "Tuning of Chemo- and Regioselectivities in Multicomponent Condensations of 5-Aminopyrazoles, Dimedone, and Aldehydes," Org Chem, vol. 73 pp. 5110 (2008).
Chebanov, et. al., "Synthesis and Rotamerism of 9,10-Diaryl-substituted 1,2,3,4,5,6,7,8,9,10-Decahydo-Acridine- 1,8-Diones," Chem Heterocycl Compd., vol. 40 pp. 475 (2004).
Desenko, et al., "Formation of Derivatives of 1,2,4-Triazoloquinazolines in the Reactions of 3-Amino-1,2,4-Triazoles with Cyclohexanone," Chem. Heterocycl. Compound, vol. 26, pp. 839 (1990).
Desenko, et al., "Three Component Condensation of 3-Amino-1,2,4-Triazole with Carbonyl Compounds. A New Synthesis of 1,2,4-Triazolo [1,5-a] Pyrimidines," Chem Heterocycl Compound, vol. 29, pp. 406 (1993).
Elmaati, et al, "New Trends in the Chemistry of 5-Aminopyrazoles," Heterocycl Chem., vol. 41, pp. 109 (2004).
Ghorab, et al., "Docking study, in vitro anticancer screening and radiosensitizing evaluation of some new fuorine-containing quinoline and pyrimidoquinoline derivatives bearing a sulfonamide moiety," Med Chem Res, vol. 20, pp. 388 (2010).
Luan, et al., "Tops-mode model of multiplexing neuroprotective effects of drugs and experimental-theoretic study of new 1,3-rasagiline derivatives potentially useful in neurodegenerative diseases," Bioorganic & Medicinal Chemistry, vol. 21, pp. 1870-1879 (2013).
Ram, et al., "Synthesis of Functionalized Pyrazoles and Pyrazolo[3,4-d]Pyrimidines as Potential Leishmanicides," Indian Journ. of Chemistry, vol. 34B, pp. 521-524 (Jun. 1995).
Rolan, et al., "The pharmacokinetics, tolerability and pharmacodynamics of tucaresol (589C80; 4[2-formyl-3-hydroxyphenoxymethyl] benzoic acid), a potential anti-sickling agent, following oral administration to healthy subjects," Br. J. clin. Pharmac. vol. 35 pp. 419-425 (1993).
Tominaga, et al., "Pyrimidine and Fused Pyrimidine Derivatives. 3. Syntheis of s—Triazolo [1,5-a] pyrimidine Derivatives by Using Ketene Dithioacetals," Chem. Pharm. Bull. vol 33(3), pp. 962-970 (1985).
Usui, et al., "Discovery of indenopyrazoles as EGFR and VEGFR-2 tyrosine kinase inhibitors by in silico high-throughput screening" Elsevier Bioorganic & Medicinal Chemistry Letter, vol. 18, pp. 285-288 (2008).
Vichinsky, et al., "Emerging 'A' therapies in hemoglobinopathies: agonists, antagonists, antioxidants, and arginine," Hemoglobinopathies, pp. 271-275 (2012).
Wang, et al., "IRAK-4 Inhibitors for Inflammation," Current Topics in Medicinal Chemistry, vol. 9, pp. 724-737 (2009).
Wieland, et al., "Osteoarthritis—an Untreatable Disease?" Nat Rev Drug Disc, vol. 4 pp. 331 (2005).
Wommack, et al., "Journal of Medicinal Chemistry," Journal of Medicinal Chemistry, vol. 12, pp. 1228 (1971).
Yadav, et al., "A New One-Pot, Three-Component Synthesis of 2,3,5-Substituted or Annulated-6-(Methylthio) pyridines," Dept. of Chemistry, vol. 17, pp. 2674-2680 (2008).
Yang, et al,. "Structural requirement of chalcones for the inhibitory activity of interleukin-5," Structural requirement of chalcones for the inhibitory activity of interleukin-5 Bioorg Med Chem, vol. 15(1), pp. 99, 104-111 (2007).
Yao, et al., "Design and Synthesis of a Series of (2R)-N4-Hydroxy-2-(3-hydroxybenzyl)-N1-[(1S,2R)-2-hydroxy-2,3-dihydro-1H-inden-1-yl]butanediamide Derivatives as Potent, Selective, and Orally Bioavailable Aggrecanase Inhibitors," Med Chem, vol. 44, pp. 3347 (2001).
Yao, et al., "Potent P10 Biphenylmethyl Substituted Aggrecanase Inhibitors," Bioorg Med Chem Lett, vol. 12 pp. 101 (2001).
Yue, et al., "Synthesis and evaluation of indenopyrazoles as cyclin-dependent kinase inhibitors. Part 4: Heterocycles at C3," Biorg Med Chem Lett, vol. 14 pp. 343 (2004).
Yue, et al., "Synthesis and Evaluation of Indenopyrazoles as Cyclin-Dependent Kinase Inhibitors. 3. Structure Activity Relationships at C31,2" Med Chem, vol. 45, pp. 5233 (2002).
Zefirov, et al., "Stereochemical Studies. XXXIV., Quantitative Description of Ring Puckering Via Torsional Angles, the Case of Six-Membered Rings," Journ. of Physical Organic Chemistry, vol. 3, pp. 147-158 (1990).
Zhang, et al., "Current prodrug strategies for improving oral absorption of nucleoside analogues Asian Journal of Pharmaceutical Sciences" Current prodrug strategies for improving oral absorption of nucleoside analogues Asian Journal of Pharmaceutical Sciences, vol. 9(2) pp. 65-74 (2014).
Zhu, et al., "Microwave-Assisted Synthesis of New Spiro[indoline-3,4'-quinoline] Derivatives via a One-Pot Multicomponent Reaction," Synthetic Communications, vol. 39, pp. 1355-1366 (2009).

* cited by examiner

20-HETE FORMATION INHIBITORS

CROSS-REFERENCE TO RELATED APPLICATIONS

This application is the U.S. National Stage of International Patent Application No. PCT/US2020/017170, filed Feb. 7, 2020, which claims priority from U.S. Provisional Patent Application No. 62/803,398, filed Feb. 8, 2019. The contents of these applications are incorporated herein by reference in their entirety.

FEDERAL FUNDING STATEMENT

This disclosure was made with government support under Grant Nos. NS107785, GM108340, RR023461, and TR001857 awarded by the NIH. The government has certain rights in the invention.

BACKGROUND

The current disclosure pertains to a new series of drug-like 20-HETE formation (CYP4) inhibitors.

Cytochrome P450 (CYP) enzymes produce mono-oxygenated metabolites of arachidonic acid (AA) that are highly vasoactive and are critical regulators of microvascular tone. Specifically, the terminal hydroxylation of AA to form 20-hydroxyeicosatetraenoic acid (20-HETE) is catalyzed by the CYP4 family of enzymes. In vivo and in vitro studies have demonstrated that 20-HETE is a potent vasoconstrictive eicosanoid and is involved in brain microvascular autoregulation (Edson et al., *Current Topics in Medicinal Chemistry* 2013, 13, 1429 and references therein; Elshenaway et al., *Pharmaceutics,* 2017, 9, 9 and references therein) Studies have shown that 20-HETE synthesis is increased after ischemic events and inhibitors of 20-HETE synthesis protect neurons and prevent cerebral blood flow impairment, brain edema, and blood-brain barrier (BBB) dysfunction after injury. For instance, inhibition of 20-HETE formation is neuroprotective in animal models of temporary focal ischemia (TFI), cardiac arrest (CA), stroke and subarachnoid hemorrhage (SAH) (see Edson et al. (2013); Elshenaway et al. (2017). Clinical studies have also demonstrated that 20-HETE is found in human cerebrospinal fluid (CSF) and that high 20-HETE CSF levels are associated with higher mortality and poor outcomes in aneurysmal subarachnoid hemorrhage (aSAH) patients (see Crago et al., *Stroke,* 2011, 42, 1872; Donelly et al., *J Cereb Blood Flow Metab.,* 2015, 35, 1515). 20-HETE formation is also implicated in proliferation of renal epithelial cells and has potential in treating polycystic kidney disease (PKD). 20-HETE formation is involved in the increased proliferation of renal epithelial cells in polycystic kidney disease (PKD) and inhibition of 20-HETE formation led to reduction of cyst formation and improvement in markers of kidney function in animal models of PKD (Elshenaway et al. (2017)). There is a need for small molecule 20-HETE formation (CYP4) inhibitors with good stability and appropriate blood brain barrier penetration ability and other physicochemical properties for treating post-injury hypoperfusion and secondary neuronal injury after CA or other ischemic events or for the treatment of PKD. An object of this disclosure is to provide such compounds, their compositions and methods of use.

SUMMARY

This disclosure provides novel compounds that are able to potently inhibit CYP4 and 20-HETE formation. Data on selected compounds from this series show that the series can provide compounds with excellent physicochemical properties, potency, solubility, high microsomal stability and/or high BBB penetration potential.

In one aspect, the present disclosure includes a compound of formula I:

(I)

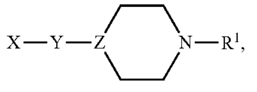

or a pharmaceutically acceptable salt or solvate thereof, wherein: X is optionally substituted aryl or optionally substituted heteroaryl; Y is a bond, O, S, S═O, $SO_2$, or an optionally substituted methylene; Z is N or CH; and $R^1$ is an optionally substituted pyrazolyl.

In another aspect, for the compound of formula I, or a pharmaceutically acceptable salt or solvate thereof, $R^1$ is optionally substituted pyrazol-5-yl, optionally substituted pyrazol-4-yl, or optionally substituted pyrazol-3-yl.

In another aspect, for the compound of formula I, or a pharmaceutically acceptable salt or solvate thereof, $R^1$ is optionally methyl substituted pyrazol-5-yl, optionally methyl substituted pyrazol-4-yl, or optionally methyl substituted pyrazol-3-yl.

In another aspect, for the compound of formula I, or a pharmaceutically acceptable salt or solvate thereof, Y is a bond.

In another aspect, for the compound of formula I, or a pharmaceutically acceptable salt or solvate thereof, X is optionally substituted phenyl, optionally substituted pyridinyl, or optionally substituted pyrimidinyl.

In another aspect, for the compound of formula I, or a pharmaceutically acceptable salt or solvate thereof, X is:

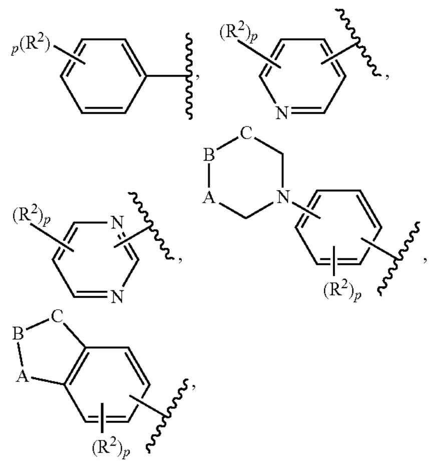

, or wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, —$SR^3$, —$S(O)R^3$, —$CH_2OR^3$, —$(CH_2)nS(O)R^3$, —$(CH_2)nS(O)_2R^3$, —$SO_2R^3$, —$CO_2R^3$, —$SO_2NHR^4$, —$(CH_2)n$-$OR^4$, —$OR^4$, —$CO_2R^4$, —$NR^5R^6$, —$NR^5C(O)R^6$, —$(CH_2)$n-$NR^5C(O)R^6$, —$CH(CH_3)$—$NR^5C(O)R^6$, —$CONR^5R^6$, —$N(R^5)S(O)_2R^6$, —$N(R^5)(CH_2)nS(O)R^6$, —$N(R^5)(CH_2)nS(O)_2R^6$, —$SO_2NR^5R^6$, and —$NR^4C(O)R^3$;

$R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent;

$R^4$ is H, optionally substituted $C_1$-$C_6$ alkyl, optionally substituted $C_3$-$C_6$ cycloalkyl, optionally substituted tetrahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

A, B and C are —$(C(R^{2'})_2)_{1-2}$— where in $R^{2'}$ is H or F and one of A, B and C is O or $SO_2$;

Y is a bond;

Z is CH; and n and p are each independently 1, 2, or 3.

In another aspect, for the compound of the prior paragraph, or a pharmaceutically acceptable salt or solvate thereof, $R^1$ is

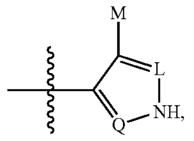

wherein

Q is N or CH;

L is N, CH or $CCH_3$, provided that L is not N when Q is N, and L is not CH or $CCH_3$ when Q is CH; and M is H or $CH_3$.

In another aspect, for the compound of formula I, or a pharmaceutically acceptable salt or solvate thereof, X is

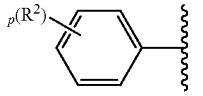

and $R^1$ is

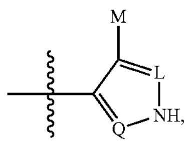

and wherein:

each $R^2$ is independently selected from a group consisting of H, F, Cl, optionally substituted $C_1$-$C_6$ alkyl, optionally substituted $C_3$-$C_6$ cycloalkyl, optionally substituted heterocyclyl, —$SR^3$, —$S(O)R^3$, —$SO_2R^3$, —$SO_2NHR^4$, —$OR^4$, —$(CH_2)n$-$OR^4$, —$CO_2R^4$, —$NR^5R^6$, —$NR^5C(O)R^6$, —$CONR^5R^6$, —$N(R^5)SO_2R^6$, and —$SO_2NR^5R^6$;

$R^3$ is optionally substituted $C_1$-$C_6$ alkyl or optionally substituted $C_3$-$C_6$ cycloalkyl;

$R^4$ is H, optionally substituted $C_1$-$C_6$ alkyl, optionally substituted $C_3$-$C_6$ cycloalkyl, optionally substituted tertahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is O;

Z is CH;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

In another aspect, for the compound of formula I, or a pharmaceutically acceptable salt or solvate thereof, X is

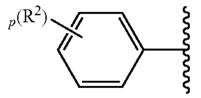

and $R^1$ is

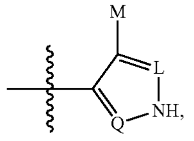

and wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, —$SR^3$, —$S(O)R^3$, —$CH_2OR^3$, —$(CH_2)nS(O)R^3$, —$(CH_2)nS(O)_2R^3$, —$SO_2R^3$, —$CO_2R^3$, —$SO_2NHR^4$, —$(CH_2)n$-$OR^4$, —$OR^4$, —$CO_2R^4$, —$NR^5R^6$, —$NR^5C(O)R^6$, —$(CH_2)n$-$NR^5C(O)R^6$, —$CH(CH_3)$—$NR^5C(O)R^6$, —$CONR^5R^6$, —$N(R^5)S(O)_2R^6$, —$N(R^5)(CH_2)nS(O)R^6$, —$N(R^5)(CH_2)nS(O)_2R^6$, —$SO_2NR^5R^6$, and —$NR^4C(O)R^3$;

$R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent;

$R^4$ is H, optionally substituted $C_1$-$C_6$ alkyl, optionally substituted $C_3$-$C_6$ cycloalkyl, optionally substituted tertahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is S, S═O, or $SO_2$;

Z is CH;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

In another aspect, for the compound of formula I, or a pharmaceutically acceptable salt or solvate thereof, X is

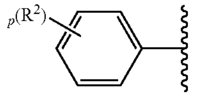

and $R^1$ is

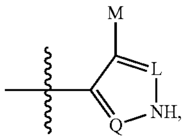

and wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, —$SR^3$, —$S(O)R^3$, —$CH_2OR^3$, —$(CH_2)nS(O)R^3$, —$(CH_2)nS(O)_2R^3$, —$SO_2R^3$, —$CO_2R^3$, —$SO_2NHR^4$, —$(CH_2)n$-$OR^4$, —$OR^4$, —$CO_2R^4$, —$NR^5R^6$, —$NR^5C(O)R^6$, —$(CH_2)n$-$NR^5C(O)R^6$, —$CH(CH_3)$—$NR^5C(O)R^6$, —$CONR^5R^6$, —$N(R^5)S(O)_2R^6$, —$N(R^5)(CH_2)nS(O)R^6$, —$N(R^5)(CH_2)nS(O)_2R^6$, —$SO_2NR^5R^6$, and —$NR^4C(O)R^3$;

$R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent;

$R^4$ is H, optionally substituted $C_1$-$C_6$ alkyl, optionally substituted $C_3$-$C_6$ cycloalkyl, optionally substituted tertahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is $CH_2$;

Z is CH;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

In another aspect, for the compound of formula I, or a pharmaceutically acceptable salt or solvate thereof, X is

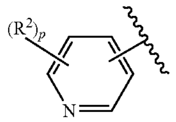

and $R^1$ is

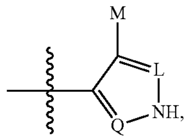

and wherein:

$R^2$ is selected from a group consisting of H, F, Cl, optionally substituted $C_1$-$C_6$ alkyl, optionally substituted $C_3$-$C_6$ cycloalkyl, optionally substituted heterocyclyl, —$OR^4$, —$(CH_2)n$-$OR^4$, —$CO_2R^4$, —$NR^5R^6$, —$NR^5C(O)R^6$, —$CONR^5R^6$, and —$N(R^5)SO_2R^6$;

$R^4$ is H, optionally substituted $C_1$-$C_6$ alkyl, optionally substituted $C_3$-$C_6$ cycloalkyl, optionally substituted tertahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is a bond or $CH_2$;

Z is CH;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

In another aspect, for the compound of formula I, or a pharmaceutically acceptable salt or solvate thereof, X is

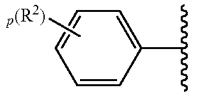

and $R^1$ is

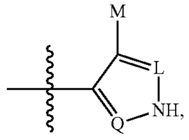

and wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, —$SR^3$, —$S(O)R^3$, —$CH_2OR^3$, —$(CH_2)nS(O)R^3$, —$(CH_2)$ $nS(O)_2R^3$, $—SO_2R^3$, $—CO_2R^3$, $—SO_2NHR^4$, $—(CH_2)n\text{-}OR^4$, $—OR^4$, $—CO_2R^4$, $—NR^5R^6$, $—NR^5C(O)R^6$, $—(CH_2)n\text{-}NR^5C(O)R^6$, $—CH(CH_3)—NR^5C(O)R^6$, $—CONR^5R^6$, $—N(R^5)S(O)_2R^6$, $—N(R^5)(CH_2)nS(O)R^6$, $—N(R^5)(CH_2)nS(O)_2R^6$, $—SO_2NR^5R^6$, and $—NR^4C(O)R^3$;

$R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent;

$R^4$ is H, optionally substituted $C_1$-$C_6$ alkyl, optionally substituted $C_3$-$C_6$ cycloalkyl, optionally substituted tertahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is a bond or $CH_2$;

Z is N;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

In another aspect, for the compound of formula I, or a pharmaceutically acceptable salt or solvate thereof, X is

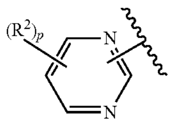

or

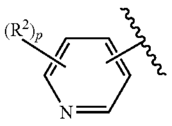

and $R^1$ is

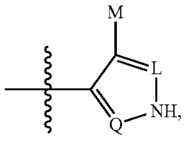

and wherein:

$R^2$ is selected from a group consisting of H, F, Cl, optionally substituted $C_1$-$C_6$ alkyl, optionally substituted $C_3$-$C_6$ cycloalkyl, optionally substituted heterocyclyl, $—OR^4$, $—(CH_2)n\text{-}OR^4$, $—CO_2R^4$, $—NR^5R^6$, $—NR^5C(O)R^6$, and $—CONR^5R^6$;

$R^4$ is H, optionally substituted $C_1$-$C_6$ alkyl, optionally substituted $C_3$-$C_6$ cycloalkyl, optionally substituted tertahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is a bond or $CH_2$;

Z is CH or N;

Q is N or CH;

L is N, CH or $CCH_3$, provided that L is not N when Q is N, and L is not CH or $CCH_3$ when Q is CH;

M is H or $CH_3$; and n and p are each independently is 1, 2, or 3.

In another aspect, for the compound of formula I, or a pharmaceutically acceptable salt or solvate thereof, X is

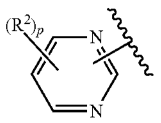

or

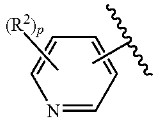

and $R^1$ is

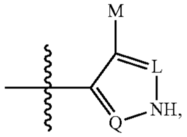

and wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, $—SR^3$, $—S(O)R^3$, $—CH_2OR^3$, $—(CH_2)nS(O)R^3$, $—(CH_2)nS(O)_2R^3$, $—SO_2R^3$, $—CO_2R^3$, $—SO_2NHR^4$, $—(CH_2)n\text{-}OR^4$, $—OR^4$, $—CO_2R^4$, $—NR^5R^6$, $—NR^5C(O)R^6$, $—(CH_2)n\text{-}NR^5C(O)R^6$, $—CH(CH_3)—NR^5C(O)R^6$, $—CONR^5R^6$, $—N(R^5)S(O)_2R^6$, $—N(R^5)(CH_2)nS(O)R^6$, $—N(R^5)(CH_2)nS(O)_2R^6$, $—SO_2NR^5R^6$, and $—NR^4C(O)R^3$;

$R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent;

$R^4$ is H, optionally substituted $C_1$-$C_6$ alkyl, optionally substituted $C_3$-$C_6$ cycloalkyl, optionally substituted tertahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is S;

Z is CH;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

In another aspect, for the compound of formula I, or a pharmaceutically acceptable salt or solvate thereof, Z is CH.

In another aspect of the disclosure, the compound is selected from the compounds listed in Table 1 below, or a pharmaceutically acceptable salt or solvate thereof:

TABLE 1
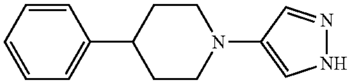 [SMILES: c1ccc(C2CCN(c3cn[nH]c3)CC2)cc1]
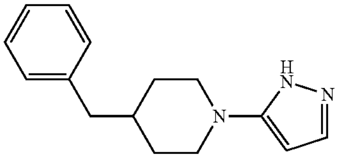
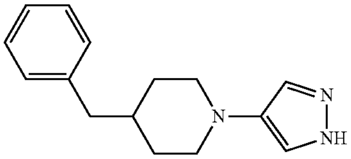 [SMILES: c1ccc(CC2CCN(c3cn[nH]c3)CC2)cc1]
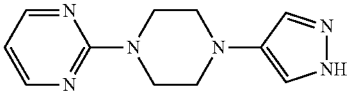 [SMILES: c1cnc(N2CCN(c3cn[nH]c3)CC2)nc1]
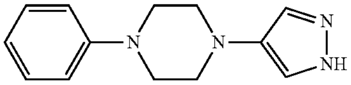
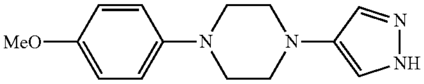 [SMILES: COc1ccc(N2CCN(c3cn[nH]c3)CC2)cc1]
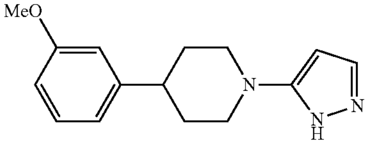 [SMILES: COc1cccc(C2CCN(c3ccn[nH]3)CC2)c1]
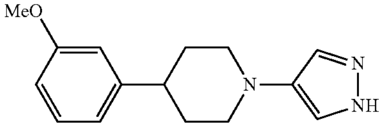 [SMILES: COc1cccc(C2CCN(c3cn[nH]c3)CC2)c1]
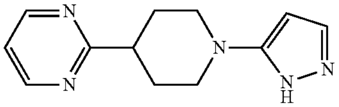 [SMILES: c1cnc(C2CCN(c3ccn[nH]3)CC2)nc1]
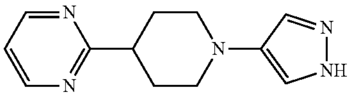
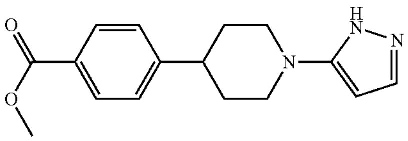 [SMILES: COC(=O)c1ccc(C2CCN(c3ccn[nH]3)CC2)cc1]
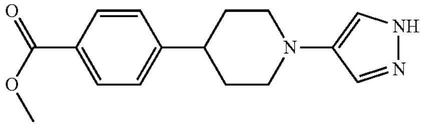 [SMILES: COC(=O)c1ccc(C2CCN(c3cn[nH]c3)CC2)cc1]
TABLE 1-continued
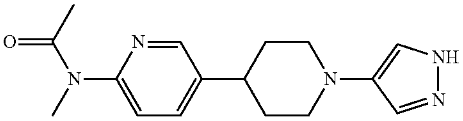 [SMILES: CC(=O)N(C)c1ccc(C2CCN(c3cn[nH]c3)CC2)cn1]
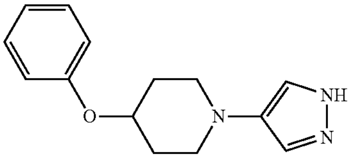
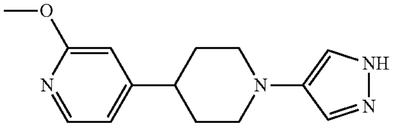
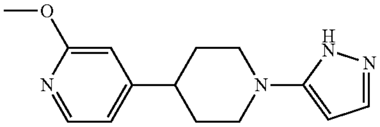 [SMILES: COc1cc(C2CCN(c3ccn[nH]3)CC2)ccn1]
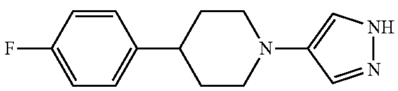 [SMILES: Fc1ccc(C2CCN(c3cn[nH]c3)CC2)cc1]
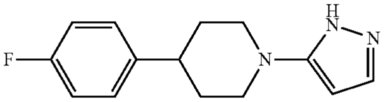 [SMILES: Fc1ccc(C2CCN(c3ccn[nH]3)CC2)cc1]
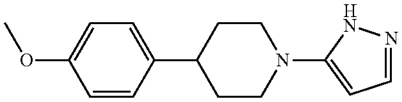
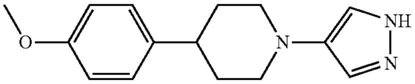 [SMILES: COc1ccc(C2CCN(c3cn[nH]c3)CC2)cc1]
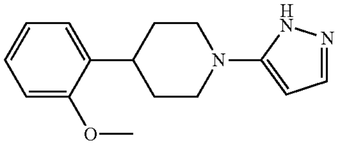
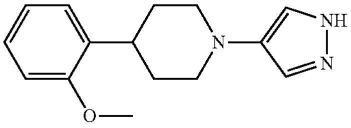 [SMILES: COc1ccccc1C1CCN(c2cn[nH]c2)CC1]
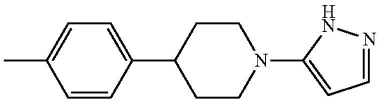 [SMILES: Cc1ccc(C2CCN(c3ccn[nH]3)CC2)cc1]
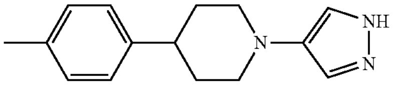 [SMILES: Cc1ccc(C2CCN(c3cn[nH]c3)CC2)cc1]
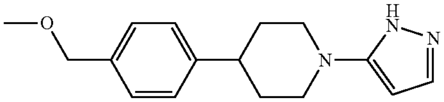 [SMILES: COCc1ccc(C2CCN(c3ccn[nH]3)CC2)cc1]

TABLE 1-continued
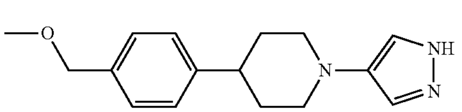
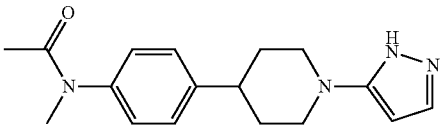 [SMILES: CC(=O)N(C)c1ccc(C2CCN(c3ccn[nH]3)CC2)cc1]
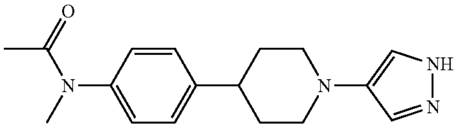 [SMILES: CC(=O)N(C)c1ccc(C2CCN(c3cn[nH]c3)CC2)cc1]
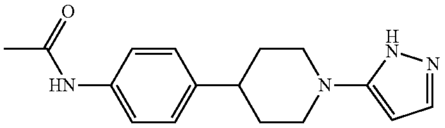 [SMILES: CC(=O)Nc1ccc(C2CCN(c3ccn[nH]3)CC2)cc1]
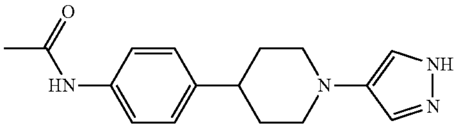 [SMILES: CC(=O)Nc1ccc(C2CCN(c3cn[nH]c3)CC2)cc1]
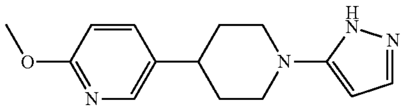
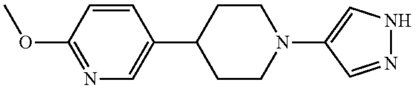 [SMILES: COc1ccc(C2CCN(c3cn[nH]c3)CC2)cn1]
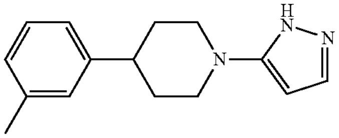 [SMILES: Cc1cccc(C2CCN(c3ccn[nH]3)CC2)c1]
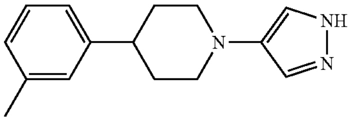 [SMILES: Cc1cccc(C2CCN(c3cn[nH]c3)CC2)c1]
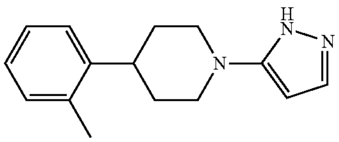
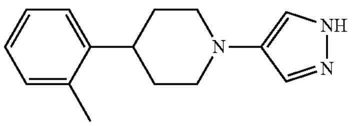 [SMILES: Cc1ccccc1C1CCN(c2cn[nH]c2)CC1]
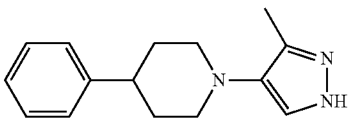 [SMILES: Cc1n[nH]cc1N1CCC(c2ccccc2)CC1]
TABLE 1-continued
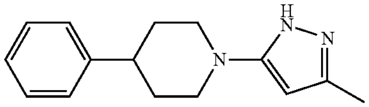
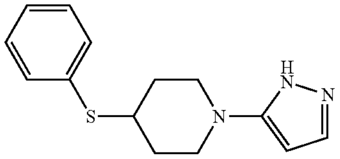
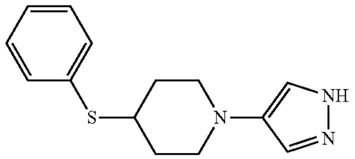 [SMILES: c1ccc(SC2CCN(c3cn[nH]c3)CC2)cc1]
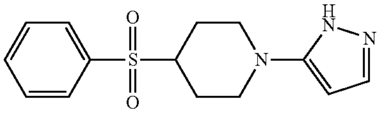 [SMILES: O=S(=O)(c1ccccc1)C1CCN(c2ccn[nH]2)CC1]
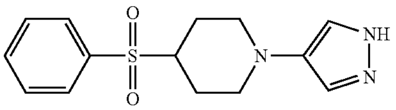
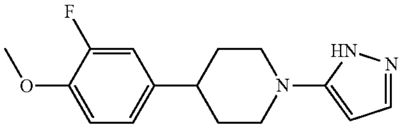
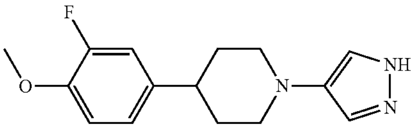 [SMILES: COc1ccc(C2CCN(c3cn[nH]c3)CC2)cc1F]
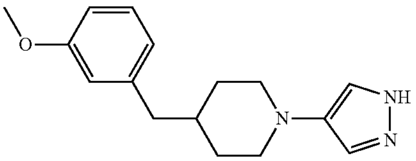 [SMILES: COc1cccc(CC2CCN(c3cn[nH]c3)CC2)c1]
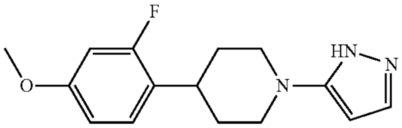
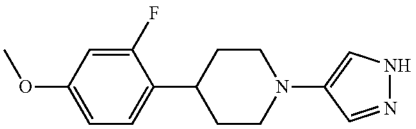
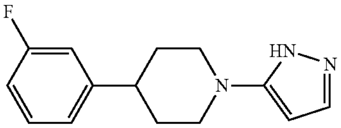 [SMILES: Fc1cccc(C2CCN(c3ccn[nH]3)CC2)c1]

TABLE 1-continued
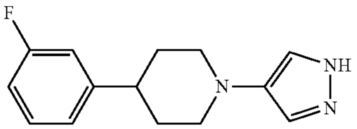 [SMILES: Fc1cccc(C2CCN(c3cn[nH]c3)CC2)c1]
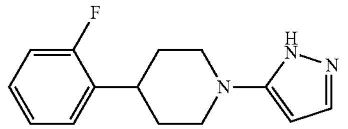 [SMILES: Fc1ccccc1C1CCN(c2ccn[nH]2)CC1]
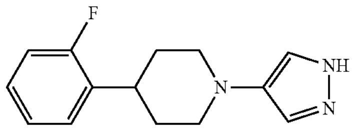 [SMILES: Fc1ccccc1C1CCN(c2cn[nH]c2)CC1]
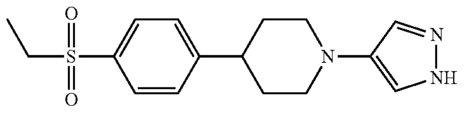 [SMILES: CCS(=O)(=O)c1ccc(C2CCN(c3cn[nH]c3)CC2)cc1]
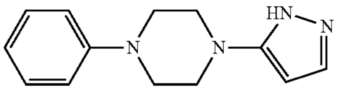
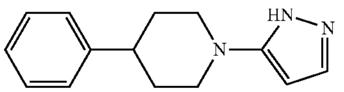 [SMILES: c1ccc(C2CCN(c3ccn[nH]3)CC2)cc1]
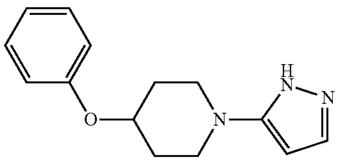
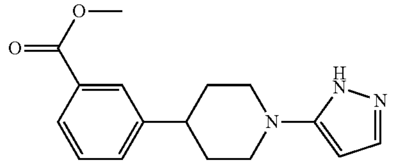 [SMILES: COC(=O)c1cccc(C2CCN(c3ccn[nH]3)CC2)c1]
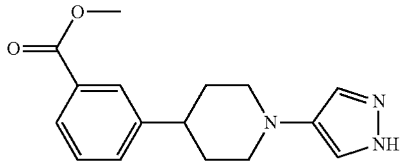 [SMILES: COC(=O)c1cccc(C2CCN(c3cn[nH]c3)CC2)c1]
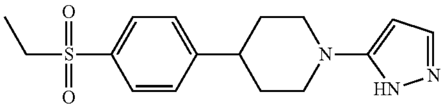 [SMILES: CCS(=O)(=O)c1ccc(C2CCN(c3ccn[nH]3)CC2)cc1]
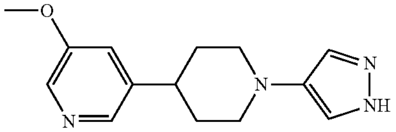
TABLE 1-continued
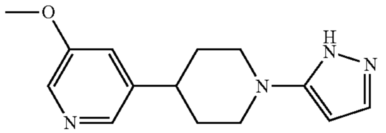 [SMILES: COc1cncc(C2CCN(c3ccn[nH]3)CC2)c1]
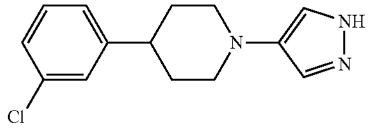 [SMILES: Clc1cccc(C2CCN(c3cn[nH]c3)CC2)c1]
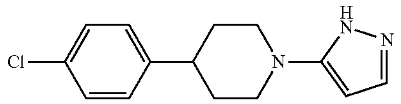 [SMILES: Clc1ccc(C2CCN(c3ccn[nH]3)CC2)cc1]
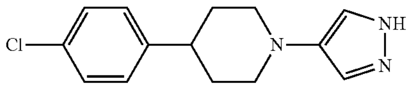
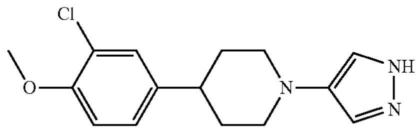
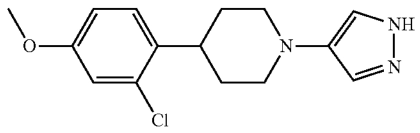 [SMILES: COc1ccc(C2CCN(c3cn[nH]c3)CC2)c(Cl)c1]
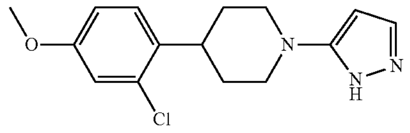 [SMILES: COc1ccc(C2CCN(c3ccn[nH]3)CC2)c(Cl)c1]
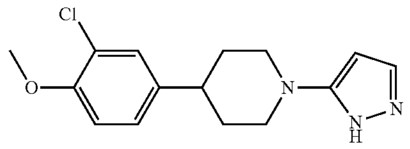 [SMILES: COc1ccc(C2CCN(c3ccn[nH]3)CC2)cc1Cl]
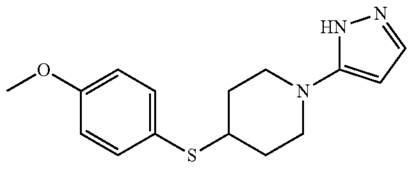 [SMILES: COc1ccc(SC2CCN(c3ccn[nH]3)CC2)cc1]
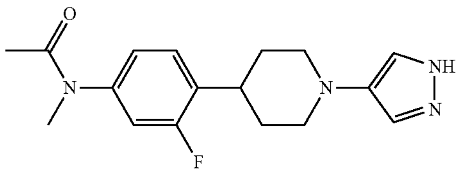 [SMILES: CC(=O)N(C)c1ccc(C2CCN(c3cn[nH]c3)CC2)c(F)c1]
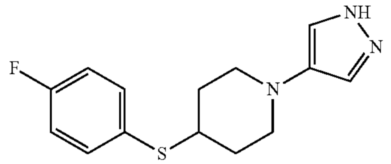 [SMILES: Fc1ccc(SC2CCN(c3cn[nH]c3)CC2)cc1]

TABLE 1-continued
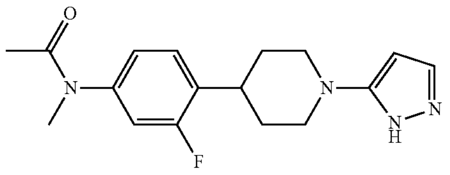
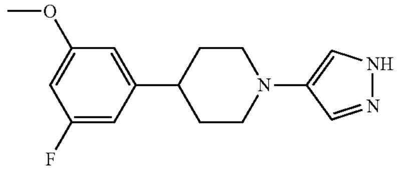 [SMILES: COc1cc(F)cc(C2CCN(c3cn[nH]c3)CC2)c1]
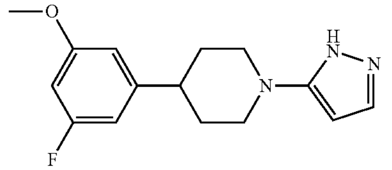 [SMILES: COc1cc(F)cc(C2CCN(c3ccn[nH]3)CC2)c1]
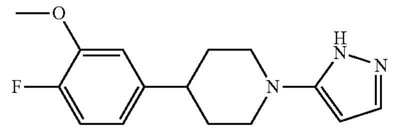 [SMILES: COc1cc(C2CCN(c3ccn[nH]3)CC2)ccc1F]
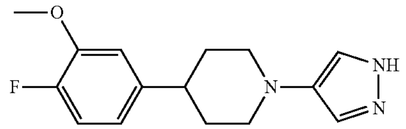
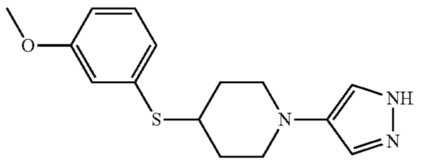
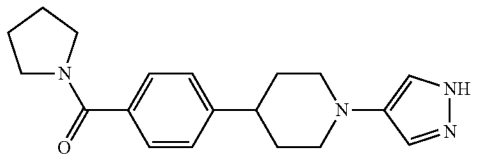
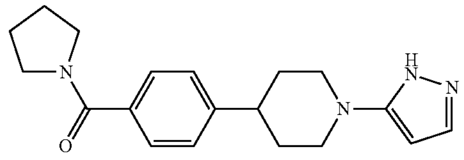 [SMILES: O=C(c1ccc(C2CCN(c3ccn[nH]3)CC2)cc1)N1CCCC1]
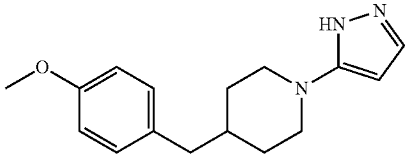 [SMILES: COc1ccc(CC2CCN(c3ccn[nH]3)CC2)cc1]
TABLE 1-continued
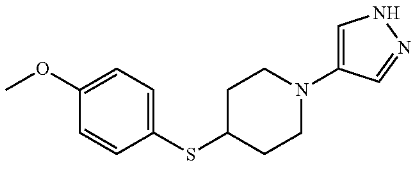 [SMILES: COc1ccc(SC2CCN(c3cn[nH]c3)CC2)cc1]
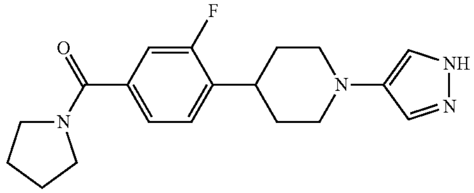 [SMILES: O=C(c1ccc(C2CCN(c3cn[nH]c3)CC2)c(F)c1)N1CCCC1]
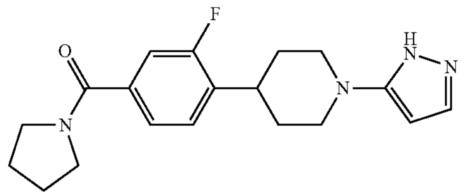 [SMILES: O=C(c1ccc(C2CCN(c3ccn[nH]3)CC2)c(F)c1)N1CCCC1]
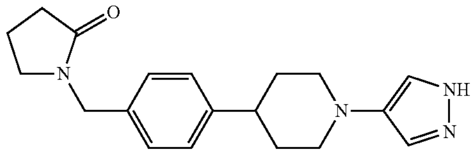 [SMILES: O=C1CCCN1Cc1ccc(C2CCN(c3cn[nH]c3)CC2)cc1]
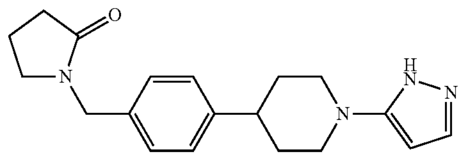 [SMILES: O=C1CCCN1Cc1ccc(C2CCN(c3ccn[nH]3)CC2)cc1]
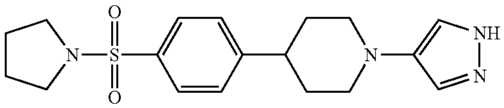 [SMILES: O=S(=O)(c1ccc(C2CCN(c3cn[nH]c3)CC2)cc1)N1CCCC1]
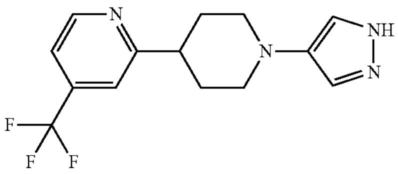 [SMILES: FC(F)(F)c1ccnc(C2CCN(c3cn[nH]c3)CC2)c1]
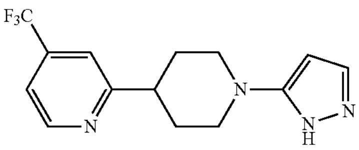 [SMILES: FC(F)(F)c1ccnc(C2CCN(c3ccn[nH]3)CC2)c1]
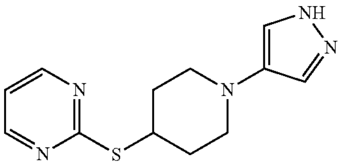 [SMILES: c1cnc(SC2CCN(c3cn[nH]c3)CC2)nc1]

TABLE 1-continued
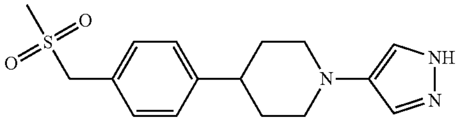 [SMILES: CS(=O)(=O)Cc1ccc(C2CCN(c3cn[nH]c3)CC2)cc1]
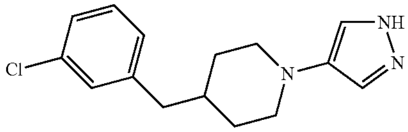 [SMILES: Clc1cccc(CC2CCN(c3cn[nH]c3)CC2)c1]
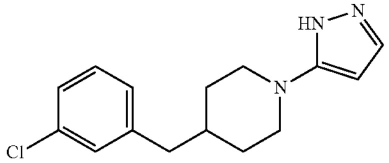 [SMILES: Clc1cccc(CC2CCN(c3ccn[nH]3)CC2)c1]
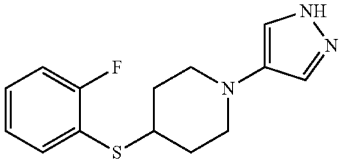 [SMILES: Fc1ccccc1SC1CCN(c2cn[nH]c2)CC1]
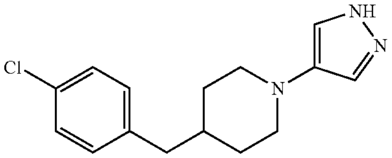 [SMILES: Clc1ccc(CC2CCN(c3cn[nH]c3)CC2)cc1]
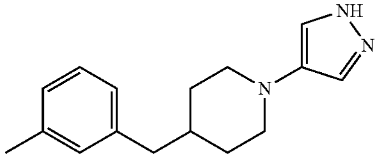 [SMILES: Cc1cccc(CC2CCN(c3cn[nH]c3)CC2)c1]
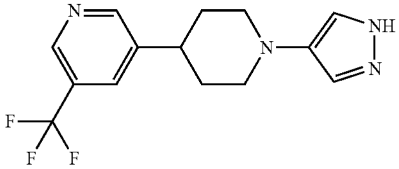 [SMILES: FC(F)(F)c1cncc(C2CCN(c3cn[nH]c3)CC2)c1]
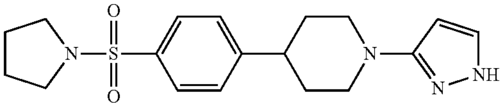 [SMILES: O=S(=O)(c1ccc(C2CCN(c3cc[nH]n3)CC2)cc1)N1CCCC1]
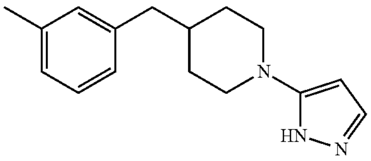 [SMILES: Cc1cccc(CC2CCN(c3ccn[nH]3)CC2)c1]
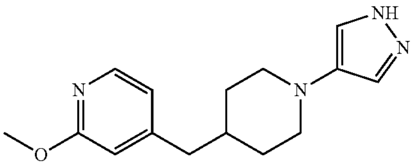 [SMILES: COc1cc(CC2CCN(c3cn[nH]c3)CC2)ccn1]
TABLE 1-continued
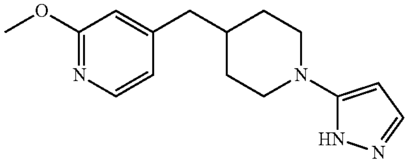 [SMILES: COc1cc(CC2CCN(c3ccn[nH]3)CC2)ccn1]
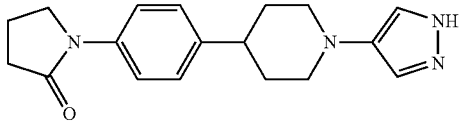 [SMILES: O=C1CCCN1c1ccc(C2CCN(c3cn[nH]c3)CC2)cc1]
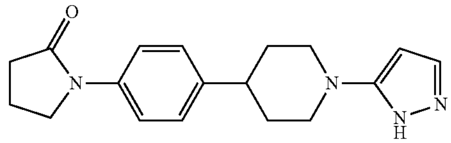 [SMILES: O=C1CCCN1c1ccc(C2CCN(c3ccn[nH]3)CC2)cc1]
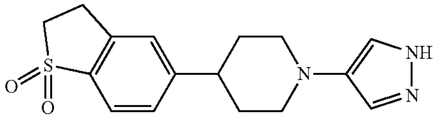 [SMILES: O=S1(=O)CCc2cc(C3CCN(c4cn[nH]c4)CC3)ccc21]
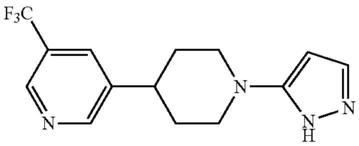
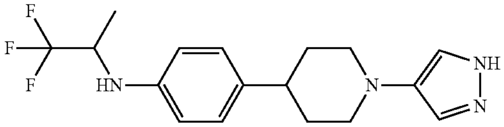 [SMILES: CC(Nc1ccc(C2CCN(c3cn[nH]c3)CC2)cc1)C(F)(F)F]
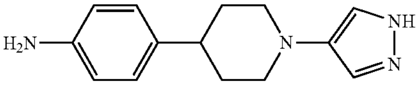 [SMILES: Nc1ccc(C2CCN(c3cn[nH]c3)CC2)cc1]
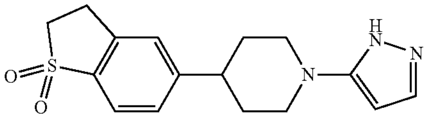 [SMILES: O=S1(=O)CCc2cc(C3CCN(c4ccn[nH]4)CC3)ccc21]
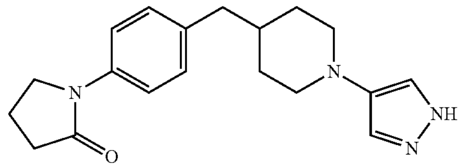 [SMILES: O=C1CCCN1c1ccc(CC2CCN(c3cn[nH]c3)CC2)cc1]
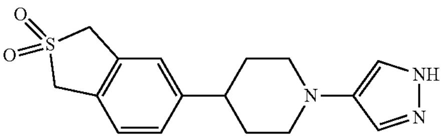 [SMILES: O=S1(=O)Cc2ccc(C3CCN(c4cn[nH]c4)CC3)cc2C1]
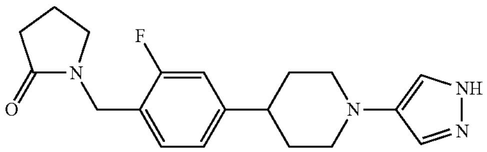 [SMILES: O=C1CCCN1Cc1ccc(C2CCN(c3cn[nH]c3)CC2)cc1F]

TABLE 1-continued
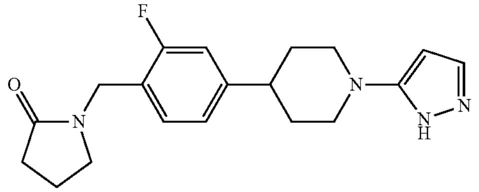 [SMILES: O=C1CCCN1Cc1ccc(C2CCN(c3ccn[nH]3)CC2)cc1F]
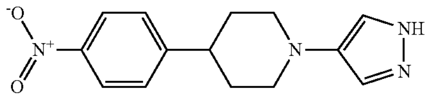
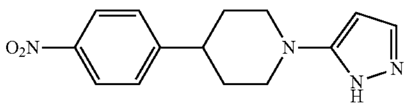 [SMILES: O=[N+]([O-])c1ccc(C2CCN(c3ccn[nH]3)CC2)cc1]
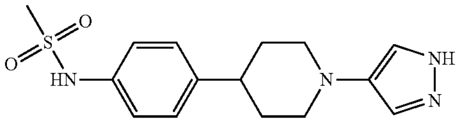
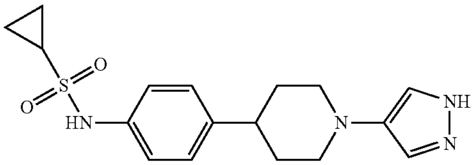 [SMILES: O=S(=O)(Nc1ccc(C2CCN(c3cn[nH]c3)CC2)cc1)C1CC1]
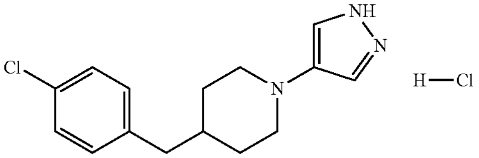
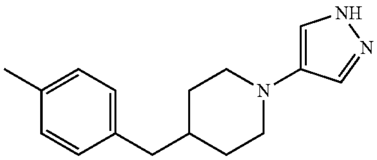 [SMILES: Cc1ccc(CC2CCN(c3cn[nH]c3)CC2)cc1]
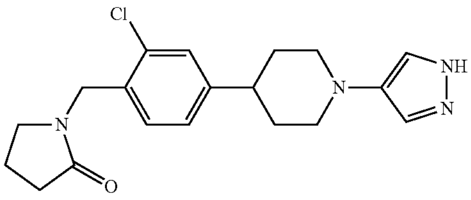 [SMILES: O=C1CCCN1Cc1ccc(C2CCN(c3cn[nH]c3)CC2)cc1Cl]
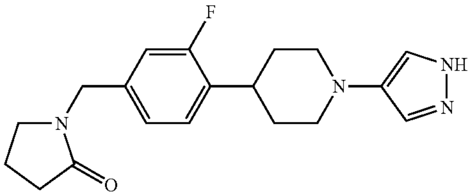 [SMILES: O=C1CCCN1Cc1ccc(C2CCN(c3cn[nH]c3)CC2)c(F)c1]
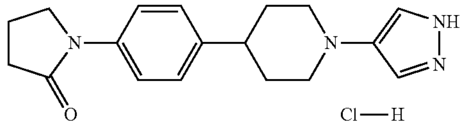
TABLE 1-continued
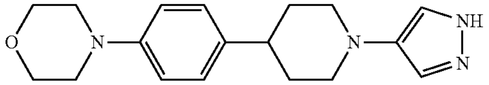 [SMILES: c1cc(N2CCOCC2)ccc1C1CCN(c2cn[nH]c2)CC1]
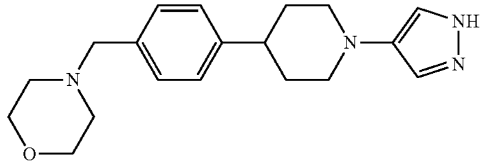 [SMILES: c1cc(C2CCN(c3cn[nH]c3)CC2)ccc1CN1CCOCC1]
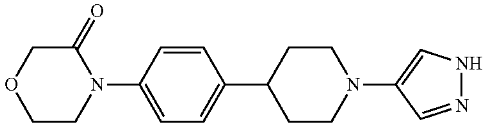 [SMILES: O=C1COCCN1c1ccc(C2CCN(c3cn[nH]c3)CC2)cc1]
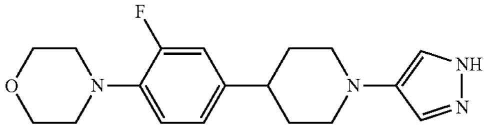
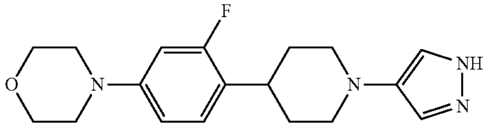 [SMILES: Fc1cc(N2CCOCC2)ccc1C1CCN(c2cn[nH]c2)CC1]
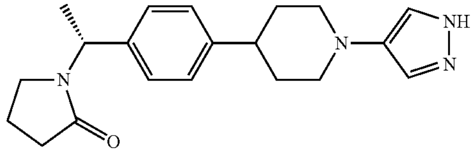 [SMILES: C[C@H](c1ccc(C2CCN(c3cn[nH]c3)CC2)cc1)N1CCCC1=O]
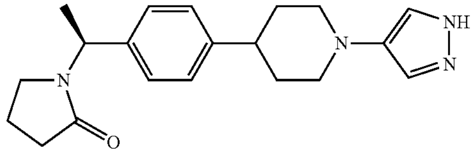 [SMILES: C[C@@H](c1ccc(C2CCN(c3cn[nH]c3)CC2)cc1)N1CCCC1=O]
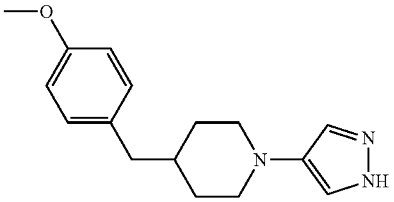 [SMILES: COc1ccc(CC2CCN(c3cn[nH]c3)CC2)cc1]
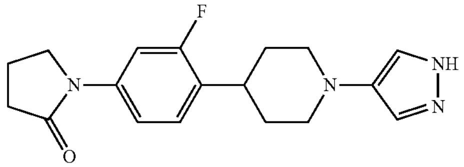 [SMILES: O=C1CCCN1c1ccc(C2CCN(c3cn[nH]c3)CC2)c(F)c1]
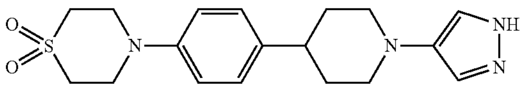 [SMILES: O=S1(=O)CCN(c2ccc(C3CCN(c4cn[nH]c4)CC3)cc2)CC1]
In another aspect, the present disclosure includes a method of inhibiting the biosynthesis of 20-hydroxyeicosatetraenoic acid (20-HETE) in a subject in need thereof, the method comprising administering to the subject a therapeutically effective amount of a compound of any embodiment herein, or a pharmaceutically acceptable salt or solvate thereof.

In another aspect, the present disclosure includes a method of inhibiting CYP4, the method comprising contacting CYP4 with a compound of any embodiment herein, or a pharmaceutically acceptable salt or solvate thereof. In another aspect, the contacting is in vitro. In yet another aspect, the contacting is in vivo in a subject in need.

In another aspect, the present disclosure provides a method of preventing cerebral blood flow impairment in a subject experiencing or having experienced an ischemic event, the method comprising administering to the subject a therapeutically effective amount of a compound of any embodiment herein, or a pharmaceutically acceptable salt or solvate thereof.

In another aspect, the present disclosure provides a method of producing neuroprotection and decreased brain damage by preventing cerebral microvascular blood flow impairment and anti-oxidant mechanisms in a subject experiencing or having experienced an ischemic event, comprising administering to the subject a therapeutically effective amount of o a compound of any embodiment herein, or a pharmaceutically acceptable salt or solvate thereof. Further, in yet another aspect, the ischemic event can comprise trauma, focal ischemia (TFI), subarachnoid hemorrhage (SAH), vasoconstriction, thrombosis, embolism, cardiac arrest, stroke, aneurysm, hypertension, sickle cell disease, application of g-forces, arteriovenous malformation, peripheral artery occlusive disease, central nervous system (CNS) depressant overdose, or a combination thereof.

In another aspect, the present disclosure provides a method of reducing the size or stop the growth of kidney cysts in polycystic kidney disease (PKD) by preventing 20-HETE formation and 20-HETE driven renal epithelial cell proliferation in a subject suffering from PKD comprising administering a therapeutically and/or pharmacologically effective amount of the compound of any of the embodiments herein, or pharmaceutically acceptable salt thereof. In another aspect, PKD is of the autosomal dominant or recessive type. In a further aspect, the subject is a human.

Both the foregoing summary and the following detailed description are exemplary and explanatory. They are intended to provide further details, but are not to be construed as limiting. Other objects, advantages, and novel features will be readily apparent to those skilled in the art from the following detailed description.

DETAILED DESCRIPTION

I. Compounds

In one aspect, the present disclosure includes a compound of formula I:

(I)

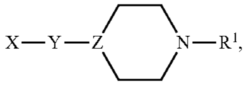

or a pharmaceutically acceptable salt or solvate thereof, wherein:

X is optionally substituted aryl or optionally substituted heteroaryl or optionally substituted heterocycle;

Y is a bond, O, S, S═O, $SO_2$, or an optionally substituted methylene;

Z is N or CH; and $R^1$ is an optionally substituted pyrazolyl.

In one embodiment, $R^1$ is optionally substituted pyrazol-5-yl, optionally substituted pyrazol-4-yl, or optionally substituted pyrazol-3-yl. In one embodiment, $R^1$ is optionally methyl substituted pyrazol-5-yl, optionally methyl substituted pyrazol-4-yl, or optionally methyl substituted pyrazol-3-yl.

In one embodiment, Y is a bond. In one embodiment, Y is a O. In one embodiment, Y is a S. In one embodiment, Y is a $SO_2$. In one embodiment Y is S═O. In one embodiment, Y is an optionally substituted methylene. In one embodiment, Y is a methylene. In one embodiment, Y is a methylene substituted with an alkyl, such as methyl. In one embodiment, Y is a methylene substituted with an alkyl, and the alkyl is (R) or (S).

In one embodiment, X is optionally substituted phenyl, optionally substituted pyridinyl, or optionally substituted pyrimidinyl. In one embodiment, X is optionally substituted phenyl. In one embodiment, X is optionally substituted pyridinyl. In one embodiment, X is optionally substituted pyrimidinyl. In one embodiment, X is phenyl, pyridinyl, or pyrimidinyl. In one embodiment, X is phenyl. In one embodiment, X is pyridinyl. In one embodiment, X is pyrimidinyl.

In one embodiment, Z is N. In one embodiment, Z is CH.

In one embodiment, X is:

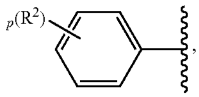
,
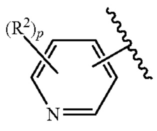
or
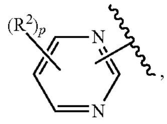
, wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, —$SR^3$, —$S(O)R^3$, —$CH_2OR^3$, —$(CH_2)nS(O)R^3$, —$(CH_2)nS(O)_2R^3$, —$SO_2R^3$, —$CO_2R^3$, —$SO_2NHR^4$, —$(CH_2)n$-$OR^4$, —$OR^4$, —$CO_2R^4$, —$NR^5R^6$, —$NR^5C(O)R^6$, —$(CH_2)$n-$NR^5C(O)R^6$, —$CH(CH_3)$—$NR^5C(O)R^6$, —$CONR^5R^6$, —$N(R^5)S(O)_2R^6$, —$N(R^5)(CH_2)nS(O)R^6$, —$N(R^5)(CH_2)nS(O)_2R^6$, —$SO_2NR^5R^6$, and —$NR^4C(O)R^3$;

$R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent;

$R^4$ is H, optionally substituted $C_1$-$C_6$ alkyl, optionally substituted $C_3$-$C_6$ cycloalkyl, optionally substituted tertahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is a bond;

Z is CH; and n and p are each independently 1, 2, or 3.

In some embodiments, X is:

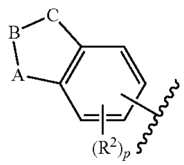

such as

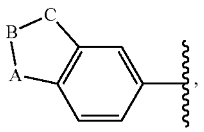
, or
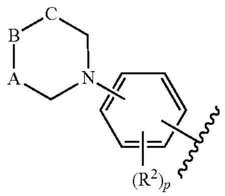

such as

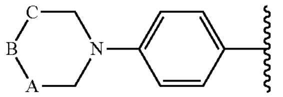

wherein A, B and C are —$(C(R^{2'})_2)_{1-2}$— where in $R^{2'}$ is H or F and one of A, B and C is O or $SO_2$. In some embodiments, B is O or $SO_2$. In some embodiments, B is O or $SO_2$ and A and C are each $CH_2$. In some embodiments, $R^2$ is selected from H, halo, and optionally substituted $C_1$-$C_6$ alkyl.

In some embodiments, X is:

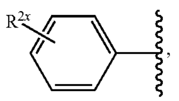
,
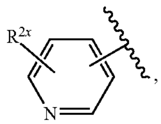
, or
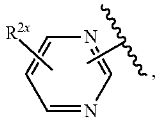
, wherein $R^{2x}$ is:

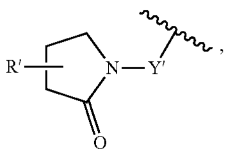
, where R' is H, F, or alkyl and Y' is a bond or an optionally substituted alkylene. In one embodiment, Y' is a methylene. In one embodiment, Y' is a methylene substituted with an alkyl, such as methyl. In one embodiment, Y' is a methylene substituted with an alkyl, and the alkyl is (R) or (S). In some embodiments, X is:

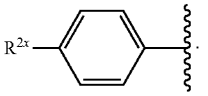
.

In one embodiment, $R^1$ is

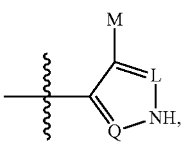
,
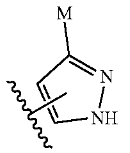
or
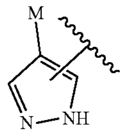
, wherein:

Q is N or CH;

L is N, CH or $CCH_3$, provided that L is not N when Q is N, and L is not CH or $CCH_3$ when Q is CH; and M is H or $CH_3$.

In one embodiment, X is

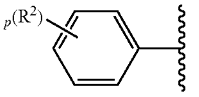

and $R^1$ is

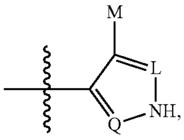

and wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, —$SR^3$, —$S(O)R^3$, —$CH_2OR^3$, —$(CH_2)nS(O)R^3$, —$(CH_2)nS(O)_2R^3$, —$SO_2R^3$, —$CO_2R^3$, —$SO_2NHR^4$, —$(CH_2)n$-$OR^4$, —$OR^4$, —$CO_2R^4$, —$NR^5R^6$, —$NR^5C(O)R^6$, —$(CH_2)n$-$NR^5C(O)R^6$, —$CH(CH_3)$—$NR^5C(O)R^6$, —$CONR^5R^6$, —$N(R^5)S(O)_2R^6$, —$N(R^5)(CH_2)nS(O)R^6$, —$N(R^5)(CH_2)nS(O)_2R^6$, —$SO_2NR^5R^6$, and —$NR^4C(O)R^3$;

$R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent;

$R^3$ is optionally substituted $C_1$-$C_6$ alkyl or optionally substituted $C_3$-$C_6$ cycloalkyl;

$R^4$ is H, optionally substituted $C_1$-$C_6$ alkyl, optionally substituted $C_3$-$C_6$ cycloalkyl, optionally substituted tertahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form a 4 to 6 membered ring;

Y is O;

Z is CH;

Q is N or CH;

L is N, CH or $CCH_3$, provided that L is not N when Q is N, and L is not CH or CCH3 when Q is CH;

M is H or $CH_3$; and n and p are each independently 1, 2, or 3.

In one embodiment, X is

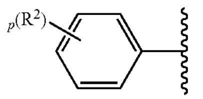

and $R^1$ is

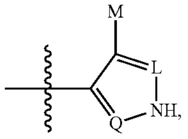

and wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, —$SR^3$, —$S(O)R^3$, —$CH_2OR^3$, —$(CH_2)nS(O)R^3$, —$(CH_2)nS(O)_2R^3$, —$SO_2R^3$, —$CO_2R^3$, —$SO_2NHR^4$, —$(CH_2)n$-$OR^4$, —$OR^4$, —$CO_2R^4$, —$NR^5R^6$, —$NR^5C(O)R^6$, —$(CH_2)$n-$NR^5C(O)R^6$, —$CH(CH_3)$—$NR^5C(O)R^6$, —$CONR^5R^6$, —$N(R^5)S(O)_2R^6$, —$N(R^5)(CH_2)nS(O)R^6$, —$N(R^5)(CH_2)nS(O)_2R^6$, —$SO_2NR^5R^6$, and —$NR^4C(O)R^3$;

$R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent;

$R^4$ is H, optionally substituted $C_1$-$C_6$ alkyl, optionally substituted $C_3$-$C_6$ cycloalkyl, optionally substituted tertahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is S, S═O, or $SO_2$;

Z is CH;

Q is N or CH;

L is N, CH or $CCH_3$, provided that L is not N when Q is N, and L is not CH or CCH3 when Q is CH;

M is H or $CH_3$; and n and p are each independently 1, 2, or 3.

In one embodiment, X is

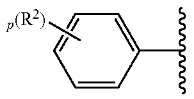

and $R^1$ is

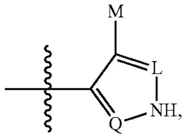

and wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, —$SR^3$, —$S(O)R^3$, —$CH_2OR^3$, —$(CH_2)nS(O)R^3$, —$(CH_2)nS(O)_2R^3$, —$SO_2R^3$, —$CO_2R^3$, —$SO_2NHR^4$, —$(CH_2)n$-$OR^4$, —$OR^4$, —$CO_2R^4$, —$NR^5R^6$, —$NR^5C(O)R^6$, —$(CH_2)$n-$NR^5C(O)R^6$, —$CH(CH_3)$—$NR^5C(O)R^6$, —$CONR^5R^6$, —$N(R^5)S(O)_2R^6$, —$N(R^5)(CH_2)nS(O)R^6$, —$N(R^5)(CH_2)nS(O)_2R^6$, —$SO_2NR^5R^6$, and —$NR^4C(O)R^3$;

$R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent;

$R^3$ is an optionally substituted $C_1$-$C_6$ alkyl or an optionally substituted $C_3$-$C_6$ cycloalkyl;

$R^4$ is H, optionally substituted $C_1$-$C_6$ alkyl, optionally substituted $C_3$-$C_6$ cycloalkyl, optionally substituted tertahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is $CH_2$;

Z is CH;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

In one embodiment, X is

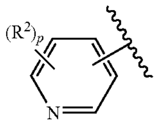

and $R^1$ is

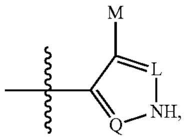

and wherein:

$R^2$ is selected from a group consisting of H, F, Cl, optionally substituted $C_1$-$C_6$ alkyl, optionally substituted $C_3$-$C_6$ cycloalkyl, optionally substituted heterocyclyl, —$OR^4$, —$(CH_2)n$-$OR^4$, —$CO_2R^4$, —$NR^5R^6$, —$NR^5C(O)R^6$, —$CONR^5R^6$, and —$N(R^5)SO_2R^6$;

$R^4$ is H, optionally substituted $C_1$-$C_6$ alkyl, optionally substituted $C_3$-$C_6$ cycloalkyl, optionally substituted tetrahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is a bond or $CH_2$;

Z is CH;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

In one embodiment, X is

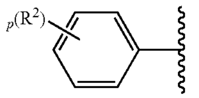

and $R^1$ is

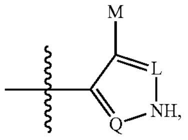

and wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, —$SR^3$, —$S(O)R^3$, —$CH_2OR^3$, —$(CH_2)nS(O)R^3$, —$(CH_2)nS(O)_2R^3$, —$SO_2R^3$, —$CO_2R^3$, —$SO_2NHR^4$, —$(CH_2)n$-$OR^4$, —$OR^4$, —$CO_2R^4$, —$NR^5R^6$, —$NR^5C(O)R^6$, —$(CH_2)n$-$NR^5C(O)R^6$, —$CH(CH_3)$—$NR^5C(O)R^6$, —$CONR^5R^6$, —$N(R^5)S(O)_2R^6$, —$N(R^5)(CH_2)nS(O)R^6$, —$N(R^5)(CH_2)nS(O)_2R^6$, —$SO_2NR^5R^6$, and —$NR^4C(O)R^3$;

$R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent;

$R^4$ is H, optionally substituted $C_1$-$C_6$ alkyl, optionally substituted $C_3$-$C_6$ cycloalkyl, optionally substituted tetrahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is a bond or $CH_2$;

Z is N;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

In one embodiment, X is

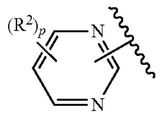

or

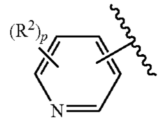

and $R^1$ is

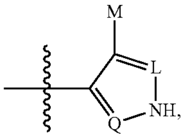

and wherein:

$R^2$ is selected from a group consisting of H, F, Cl, optionally substituted $C_1$-$C_6$ alkyl, optionally substituted $C_3$-$C_6$ cycloalkyl, optionally substituted heterocyclyl, —$OR^4$, —$(CH_2)n$-$OR^4$, —$CO_2R^4$, —$NR^5R^6$, —$NR^5C(O)R^6$, and —$CONR^5R^6$;

$R^4$ is H, optionally substituted $C_1$-$C_6$ alkyl, optionally substituted $C_3$-$C_6$ cycloalkyl, optionally substituted tetrahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form a 4 to 6 membered ring;

Y is a bond or $CH_2$;

Z is CH or N;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

In one embodiment X is

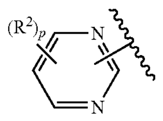

or

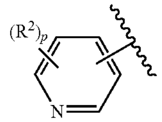

and $R^1$ is

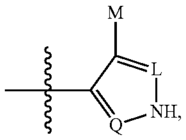

and wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, —$SR^3$, —$S(O)R^3$, —$CH_2OR^3$, —$(CH_2)nS(O)R^3$, —$(CH_2)nS(O)_2R^3$, —$SO_2R^3$, —$CO_2R^3$, —$SO_2NHR^4$, —$(CH_2)n$-$OR^4$, —$OR^4$, —$CO_2R^4$, —$NR^5R^6$, —$NR^5C(O)R^6$, —$(CH_2)$ n-$NR^5C(O)R^6$, —$CH(CH_3)$—$NR^5C(O)R^6$, —$CONR^5R^6$, —$N(R^5)S(O)_2R^6$, —$N(R^5)(CH_2)nS(O)$ $R^6$, —$N(R^5)(CH_2)nS(O)_2R^6$, —$SO_2NR^5R^6$, and —$NR^4C(O)R^3$;

$R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent;

$R^4$ is H, optionally substituted $C_1$-$C_6$ alkyl, optionally substituted $C_3$-$C_6$ cycloalkyl, optionally substituted tetrahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is S;

Z is CH;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

In some embodiments, $R^2$ is optionally substituted heterocyclyl, for example, optionally substituted heterocyclyl selected from morpholino, thiomorpholine oxide, and thiomopholine dioxide.

In one aspect, the present disclosure includes a compound, or a pharmaceutically acceptable salt or solvate thereof, wherein the compound is selected from a group consisting of:

TABLE 2

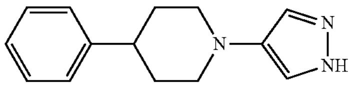 [SMILES: c1ccc(C2CCN(c3cn[nH]c3)CC2)cc1]

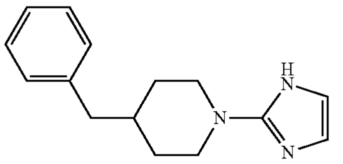 [SMILES: c1ccc(CC2CCN(c3ncc[nH]3)CC2)cc1]

TABLE 2-continued

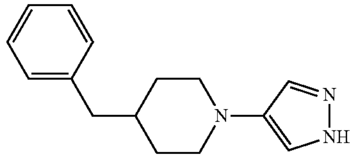 [SMILES: c1ccc(CC2CCN(c3cn[nH]c3)CC2)cc1]

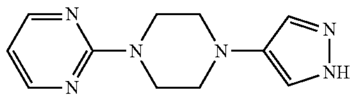 [SMILES: c1cnc(N2CCN(c3cn[nH]c3)CC2)nc1]

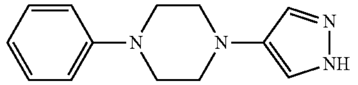 [SMILES: c1ccc(N2CCN(c3cn[nH]c3)CC2)cc1]

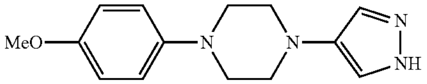 [SMILES: COc1ccc(N2CCN(c3cn[nH]c3)CC2)cc1]

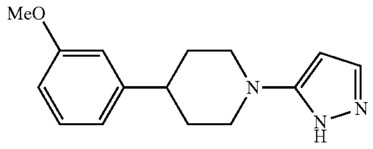 [SMILES: COc1cccc(C2CCN(c3ccn[nH]3)CC2)c1]

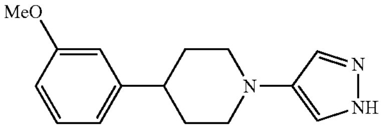 [SMILES: COc1cccc(C2CCN(c3cn[nH]c3)CC2)c1]

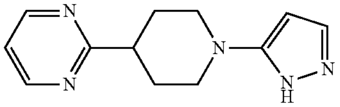

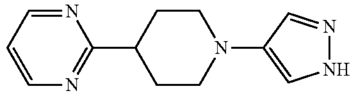

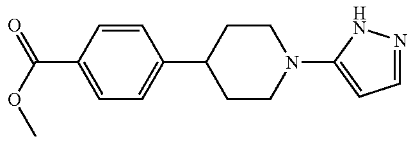 [SMILES: COC(=O)c1ccc(C2CCN(c3ccn[nH]3)CC2)cc1]

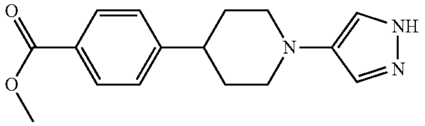 [SMILES: COC(=O)c1ccc(C2CCN(c3cn[nH]c3)CC2)cc1]

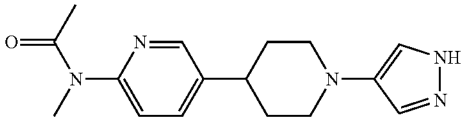 [SMILES: CC(=O)N(C)c1ccc(C2CCN(c3cn[nH]c3)CC2)cn1]

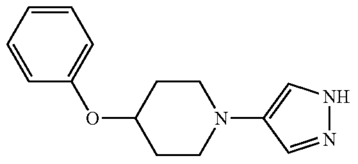

TABLE 2-continued
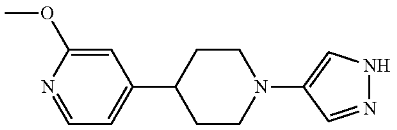 [SMILES: COc1cc(C2CCN(c3cn[nH]c3)CC2)ccn1]
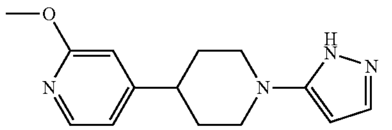 [SMILES: COc1cc(C2CCN(c3ccn[nH]3)CC2)ccn1]
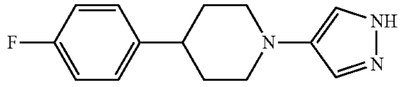 [SMILES: Fc1ccc(C2CCN(c3cn[nH]c3)CC2)cc1]
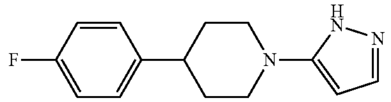 [SMILES: Fc1ccc(C2CCN(c3ccn[nH]3)CC2)cc1]
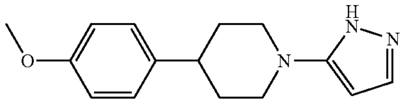
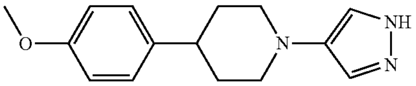 [SMILES: COc1ccc(C2CCN(c3cn[nH]c3)CC2)cc1]
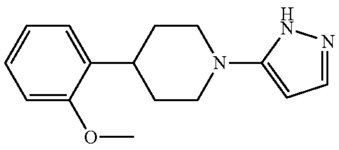 [SMILES: COc1ccccc1C1CCN(c2ccn[nH]2)CC1]
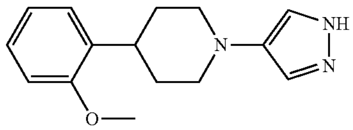 [SMILES: COc1ccccc1C1CCN(c2cn[nH]c2)CC1]
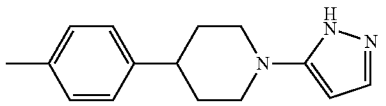
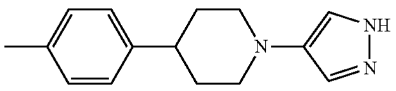 [SMILES: Cc1ccc(C2CCN(c3cn[nH]c3)CC2)cc1]
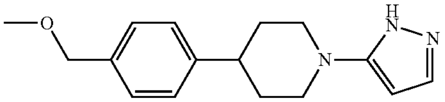 [SMILES: COCc1ccc(C2CCN(c3ccn[nH]3)CC2)cc1]
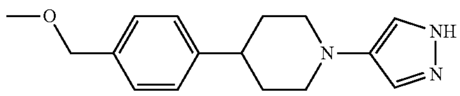
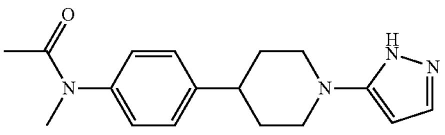 [SMILES: CC(=O)N(C)c1ccc(C2CCN(c3ccn[nH]3)CC2)cc1]
TABLE 2-continued
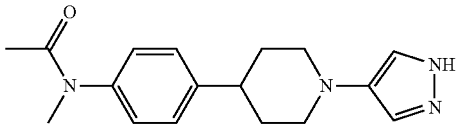
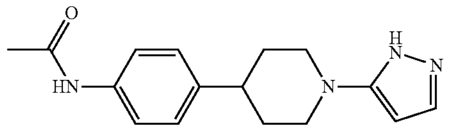
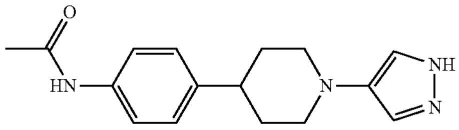 [SMILES: CC(=O)Nc1ccc(C2CCN(c3cn[nH]c3)CC2)cc1]
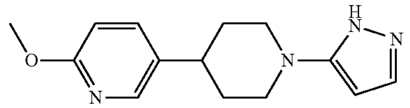 [SMILES: COc1ccc(C2CCN(c3ccn[nH]3)CC2)cn1]
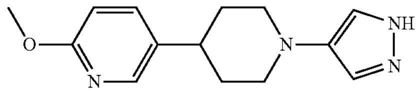 [SMILES: COc1ccc(C2CCN(c3cn[nH]c3)CC2)cn1]
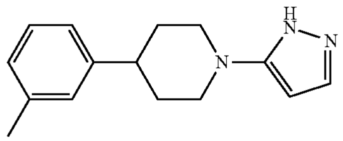 [SMILES: Cc1cccc(C2CCN(c3ccn[nH]3)CC2)c1]
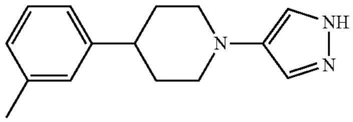 [SMILES: Cc1cccc(C2CCN(c3cn[nH]c3)CC2)c1]
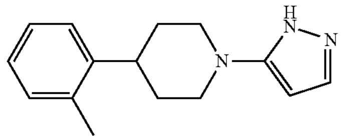 [SMILES: Cc1ccccc1C1CCN(c2ccn[nH]2)CC1]
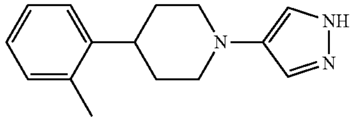 [SMILES: Cc1ccccc1C1CCN(c2cn[nH]c2)CC1]
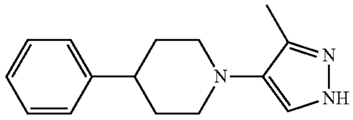 [SMILES: Cc1n[nH]cc1N1CCC(c2ccccc2)CC1]
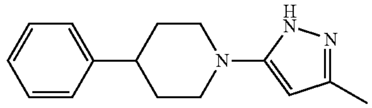
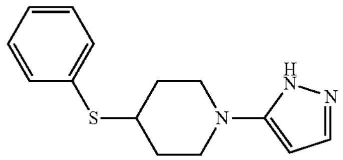

TABLE 2-continued
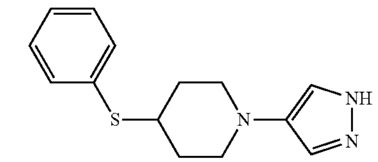
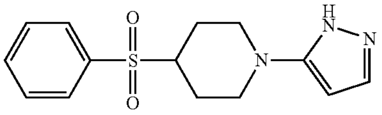 [SMILES: O=S(=O)(c1ccccc1)C1CCN(c2ccn[nH]2)CC1]
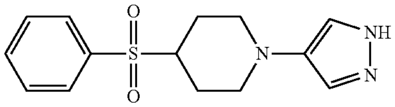 [SMILES: O=S(=O)(c1ccccc1)C1CCN(c2cn[nH]c2)CC1]
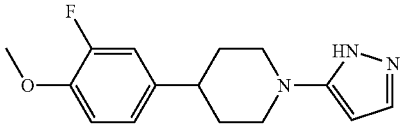 [SMILES: COc1ccc(C2CCN(c3ccn[nH]3)CC2)cc1F]
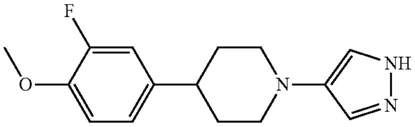 [SMILES: COc1ccc(C2CCN(c3cn[nH]c3)CC2)cc1F]
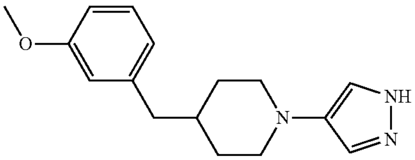
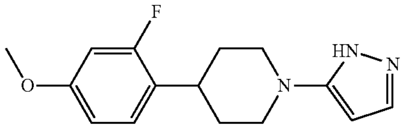 [SMILES: COc1ccc(C2CCN(c3ccn[nH]3)CC2)c(F)c1]
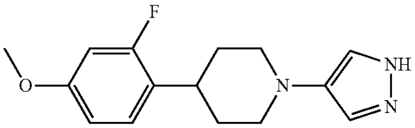
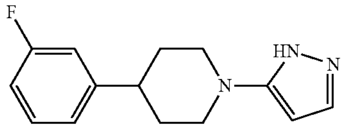
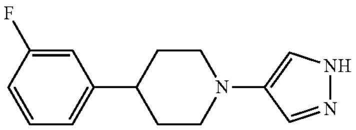 [SMILES: Fc1cccc(C2CCN(c3cn[nH]c3)CC2)c1]
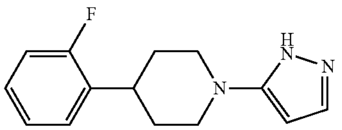 [SMILES: Fc1ccccc1C1CCN(c2ccn[nH]2)CC1]
TABLE 2-continued
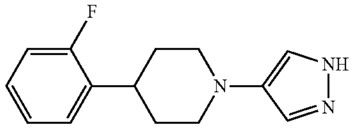 [SMILES: Fc1ccccc1C1CCN(c2cn[nH]c2)CC1]
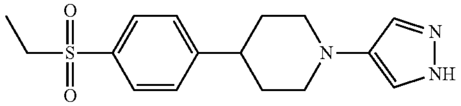 [SMILES: CCS(=O)(=O)c1ccc(C2CCN(c3cn[nH]c3)CC2)cc1]
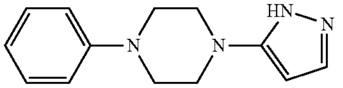 [SMILES: c1ccc(N2CCN(c3ccn[nH]3)CC2)cc1]
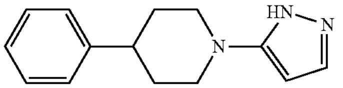 [SMILES: c1ccc(C2CCN(c3ccn[nH]3)CC2)cc1]
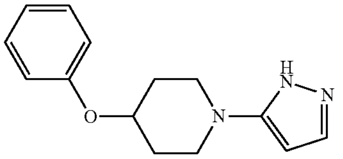
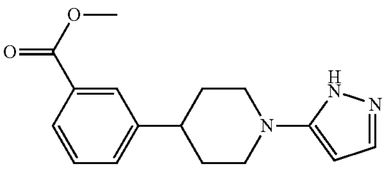 [SMILES: COC(=O)c1cccc(C2CCN(c3ccn[nH]3)CC2)c1]
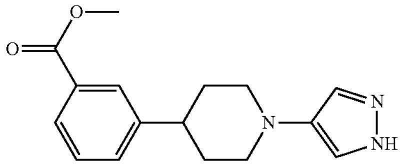 [SMILES: COC(=O)c1cccc(C2CCN(c3cn[nH]c3)CC2)c1]
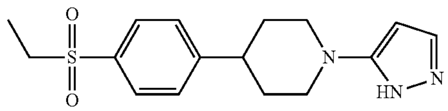 [SMILES: CCS(=O)(=O)c1ccc(C2CCN(c3ccn[nH]3)CC2)cc1]
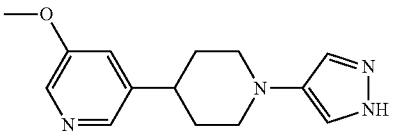 [SMILES: COc1cncc(C2CCN(c3cn[nH]c3)CC2)c1]
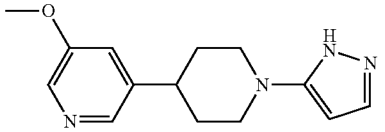 [SMILES: COc1cncc(C2CCN(c3ccn[nH]3)CC2)c1]
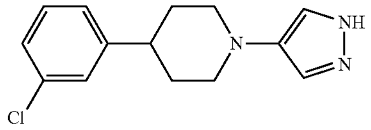 [SMILES: Clc1cccc(C2CCN(c3cn[nH]c3)CC2)c1]

TABLE 2-continued
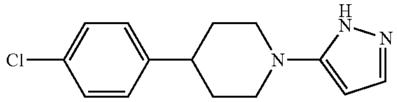 [SMILES: Clc1ccc(C2CCN(c3ccn[nH]3)CC2)cc1]
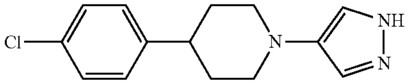
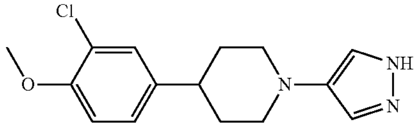
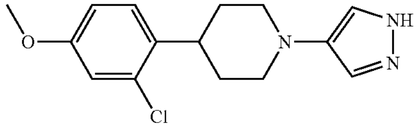 [SMILES: COc1ccc(C2CCN(c3cn[nH]c3)CC2)c(Cl)c1]
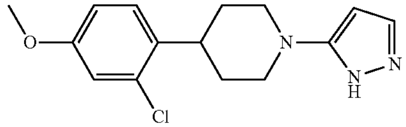 [SMILES: COc1ccc(C2CCN(c3ccn[nH]3)CC2)c(Cl)c1]
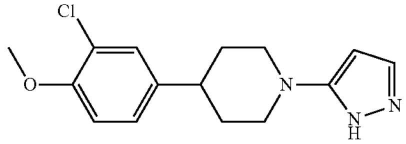 [SMILES: COc1ccc(C2CCN(c3ccn[nH]3)CC2)cc1Cl]
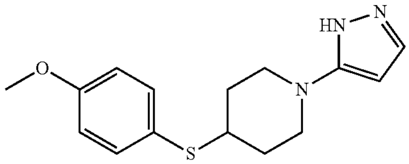 [SMILES: COc1ccc(SC2CCN(c3ccn[nH]3)CC2)cc1]
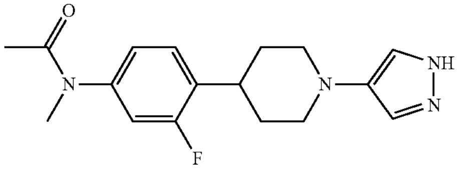 [SMILES: CC(=O)N(C)c1ccc(C2CCN(c3cn[nH]c3)CC2)c(F)c1]
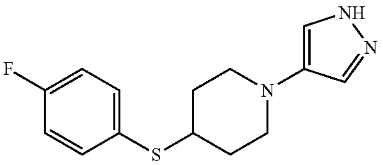 [SMILES: Fc1ccc(SC2CCN(c3cn[nH]c3)CC2)cc1]
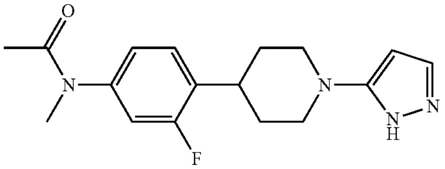 [SMILES: CC(=O)N(C)c1ccc(C2CCN(c3ccn[nH]3)CC2)c(F)c1]
TABLE 2-continued
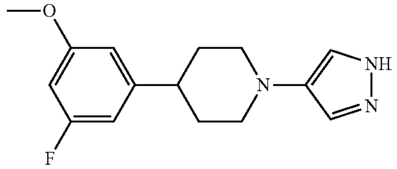 [SMILES: COc1cc(F)cc(C2CCN(c3cn[nH]c3)CC2)c1]
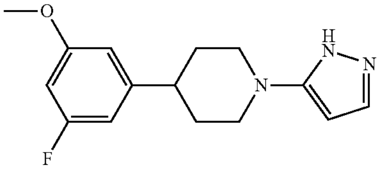 [SMILES: COc1cc(F)cc(C2CCN(c3ccn[nH]3)CC2)c1]
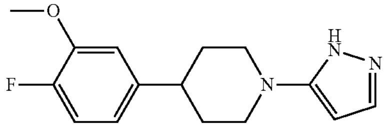 [SMILES: COc1cc(C2CCN(c3ccn[nH]3)CC2)ccc1F]
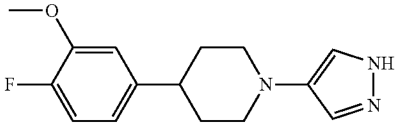 [SMILES: COc1cc(C2CCN(c3cn[nH]c3)CC2)ccc1F]
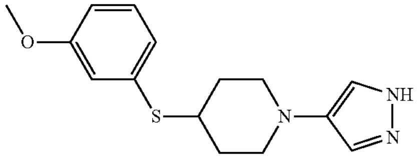
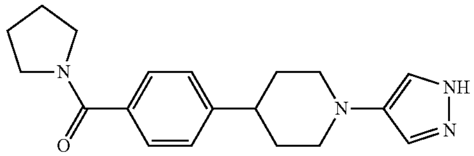 [SMILES: O=C(c1ccc(C2CCN(c3cn[nH]c3)CC2)cc1)N1CCCC1]
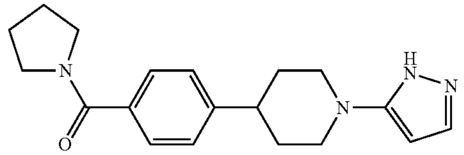 [SMILES: O=C(c1ccc(C2CCN(c3ccn[nH]3)CC2)cc1)N1CCCC1]
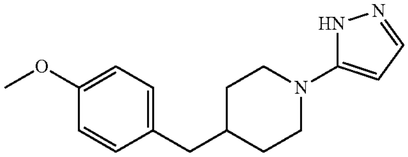 [SMILES: COc1ccc(CC2CCN(c3ccn[nH]3)CC2)cc1]
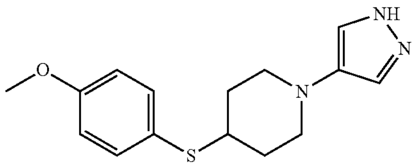 [SMILES: COc1ccc(SC2CCN(c3cn[nH]c3)CC2)cc1]

TABLE 2-continued
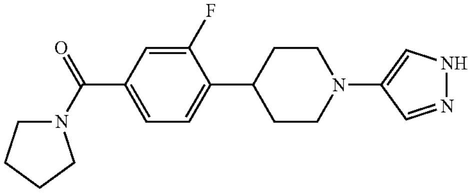 [SMILES: O=C(c1ccc(C2CCN(c3cn[nH]c3)CC2)c(F)c1)N1CCCC1]
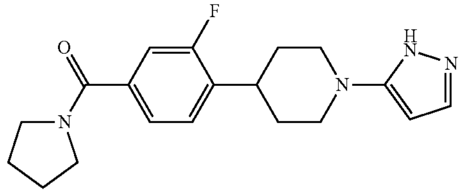 [SMILES: O=C(c1ccc(C2CCN(c3ccn[nH]3)CC2)c(F)c1)N1CCCC1]
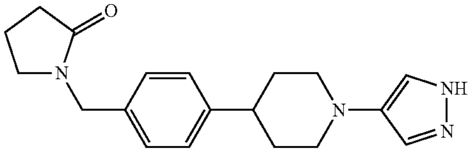 [SMILES: O=C1CCCN1Cc1ccc(C2CCN(c3cn[nH]c3)CC2)cc1]
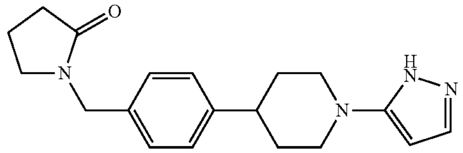 [SMILES: O=C1CCCN1Cc1ccc(C2CCN(c3ccn[nH]3)CC2)cc1]
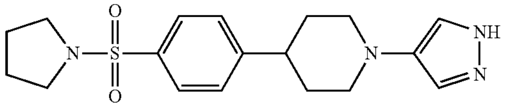 [SMILES: O=S(=O)(c1ccc(C2CCN(c3cn[nH]c3)CC2)cc1)N1CCCC1]
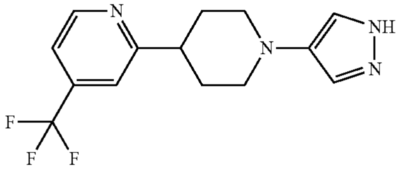
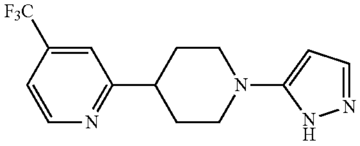 [SMILES: FC(F)(F)c1ccnc(C2CCN(c3ccn[nH]3)CC2)c1]
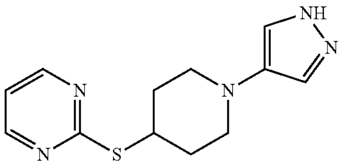 [SMILES: c1cnc(SC2CCN(c3cn[nH]c3)CC2)nc1]
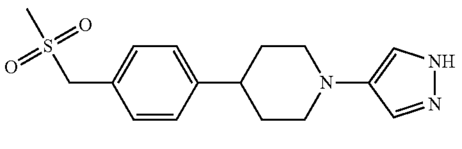 [SMILES: CS(=O)(=O)Cc1ccc(C2CCN(c3cn[nH]c3)CC2)cc1]
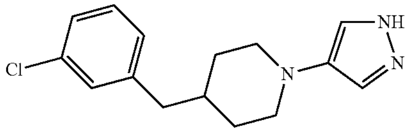 [SMILES: Clc1cccc(CC2CCN(c3cn[nH]c3)CC2)c1]
TABLE 2-continued
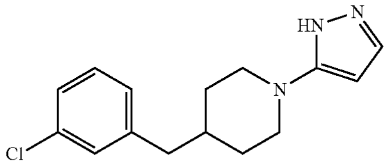 [SMILES: Clc1cccc(CC2CCN(c3ccn[nH]3)CC2)c1]
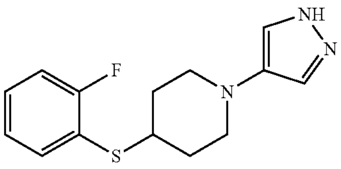 [SMILES: Fc1ccccc1SC1CCN(c2cn[nH]c2)CC1]
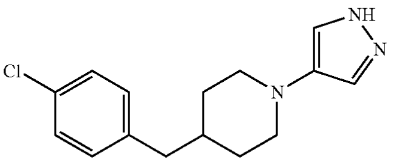 [SMILES: Clc1ccc(CC2CCN(c3cn[nH]c3)CC2)cc1]
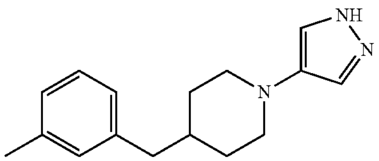 [SMILES: Cc1cccc(CC2CCN(c3cn[nH]c3)CC2)c1]
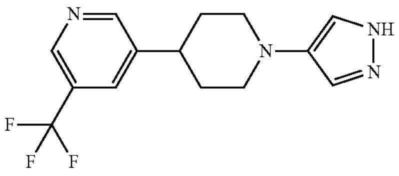 [SMILES: FC(F)(F)c1cncc(C2CCN(c3cn[nH]c3)CC2)c1]
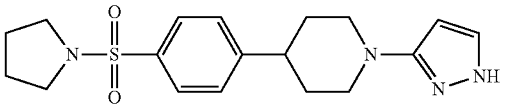 [SMILES: O=S(=O)(c1ccc(C2CCN(c3cc[nH]n3)CC2)cc1)N1CCCC1]
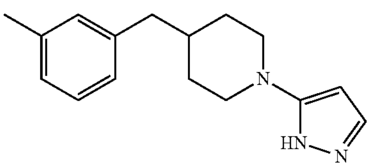 [SMILES: Cc1cccc(CC2CCN(c3ccn[nH]3)CC2)c1]
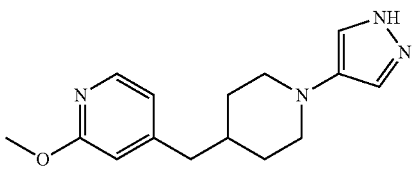 [SMILES: COc1cc(CC2CCN(c3cn[nH]c3)CC2)ccn1]
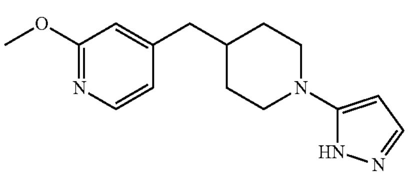 [SMILES: COc1cc(CC2CCN(c3ccn[nH]3)CC2)ccn1]

TABLE 2-continued
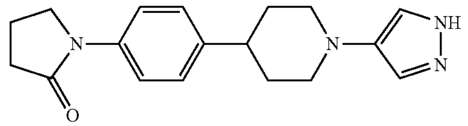 [SMILES: O=C1CCCN1c1ccc(C2CCN(c3cn[nH]c3)CC2)cc1]
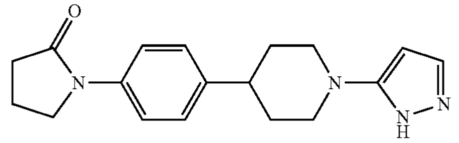 [SMILES: O=C1CCCN1c1ccc(C2CCN(c3ccn[nH]3)CC2)cc1]
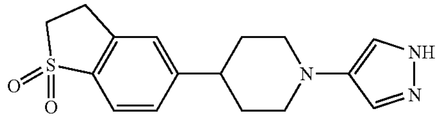 [SMILES: O=S1(=O)CCc2cc(C3CCN(c4cn[nH]c4)CC3)ccc21]
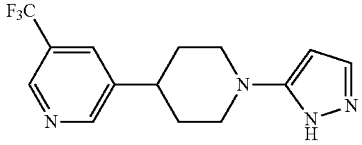 [SMILES: FC(F)(F)c1cncc(C2CCN(c3ccn[nH]3)CC2)c1]
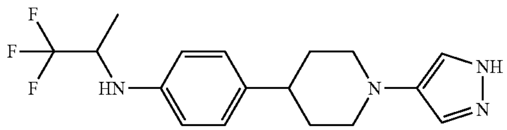 [SMILES: CC(Nc1ccc(C2CCN(c3cn[nH]c3)CC2)cc1)C(F)(F)F]
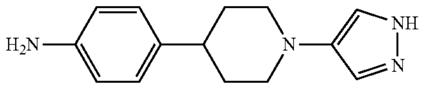 [SMILES: Nc1ccc(C2CCN(c3cn[nH]c3)CC2)cc1]
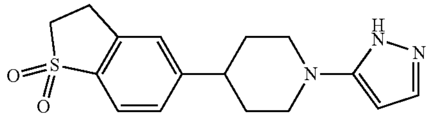 [SMILES: O=S1(=O)CCc2cc(C3CCN(c4ccn[nH]4)CC3)ccc21]
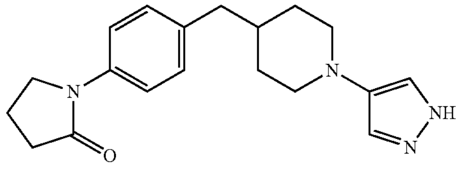 [SMILES: O=C1CCCN1c1ccc(CC2CCN(c3cn[nH]c3)CC2)cc1]
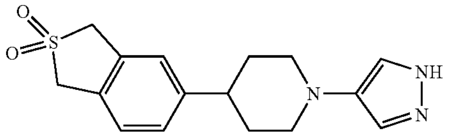 [SMILES: O=S1(=O)Cc2ccc(C3CCN(c4cn[nH]c4)CC3)cc2C1]
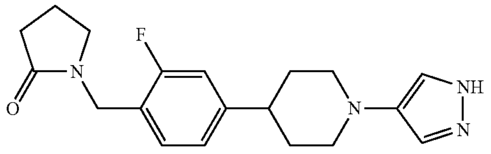 [SMILES: O=C1CCCN1Cc1ccc(C2CCN(c3cn[nH]c3)CC2)cc1F]
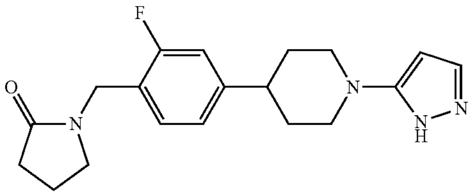 [SMILES: O=C1CCCN1Cc1ccc(C2CCN(c3ccn[nH]3)CC2)cc1F]
TABLE 2-continued
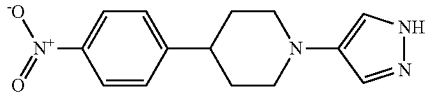
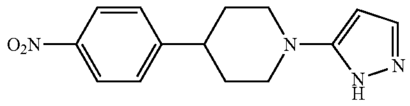
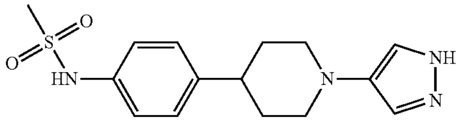 [SMILES: CS(=O)(=O)Nc1ccc(C2CCN(c3cn[nH]c3)CC2)cc1]
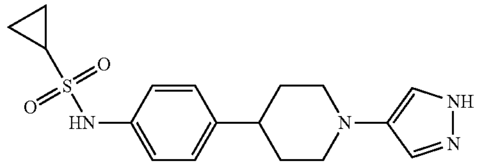 [SMILES: O=S(=O)(Nc1ccc(C2CCN(c3cn[nH]c3)CC2)cc1)C1CC1]
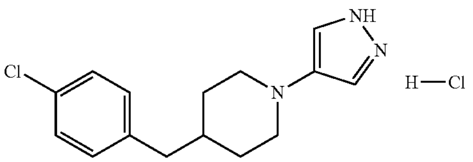
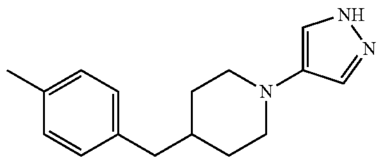 [SMILES: Cc1ccc(CC2CCN(c3cn[nH]c3)CC2)cc1]
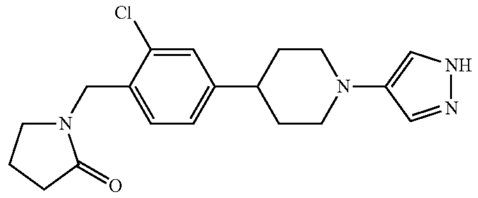 [SMILES: O=C1CCCN1Cc1ccc(C2CCN(c3cn[nH]c3)CC2)cc1Cl]
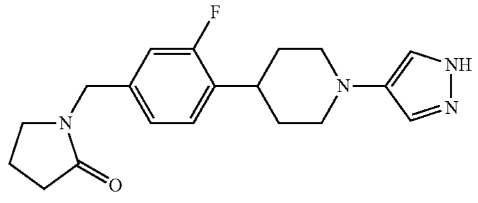 [SMILES: O=C1CCCN1Cc1ccc(C2CCN(c3cn[nH]c3)CC2)c(F)c1]
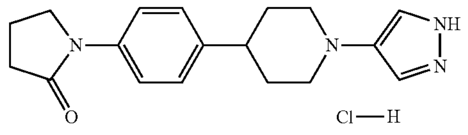
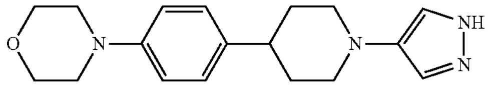 [SMILES: c1cc(N2CCOCC2)ccc1C1CCN(c2cn[nH]c2)CC1]

TABLE 2-continued

| |
|---|
| 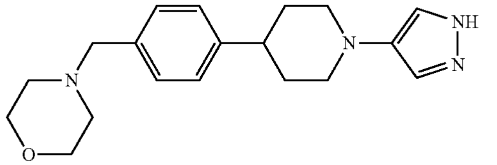 [SMILES: c1cc(C2CCN(c3cn[nH]c3)CC2)ccc1CN1CCOCC1] |
| 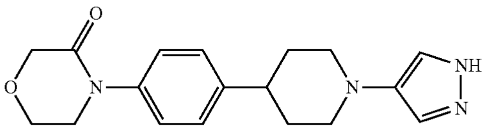 [SMILES: O=C1COCCN1c1ccc(C2CCN(c3cn[nH]c3)CC2)cc1] |
| 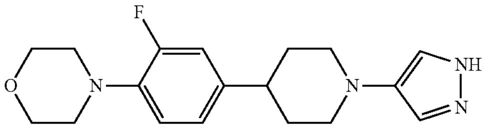 |
| 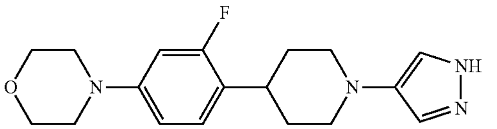 [SMILES: Fc1cc(C2CCN(c3cn[nH]c3)CC2)ccc1N1CCOCC1] |
| 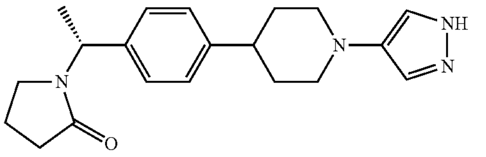 [SMILES: C[C@H](c1ccc(C2CCN(c3cn[nH]c3)CC2)cc1)N1CCCC1=O] |
| 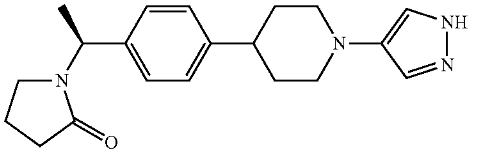 [SMILES: C[C@@H](c1ccc(C2CCN(c3cn[nH]c3)CC2)cc1)N1CCCC1=O] |
| 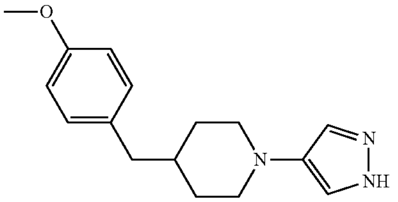 [SMILES: COc1ccc(CC2CCN(c3cn[nH]c3)CC2)cc1] |
| 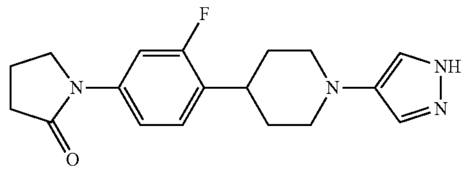 [SMILES: O=C1CCCN1c1ccc(C2CCN(c3cn[nH]c3)CC2)c(F)c1] |
| 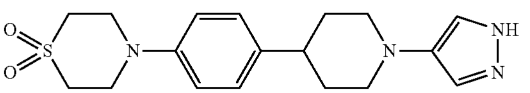 [SMILES: O=S1(=O)CCN(c2ccc(C3CCN(c4cn[nH]c4)CC3)cc2)CC1] |

In some embodiments, the compound is not

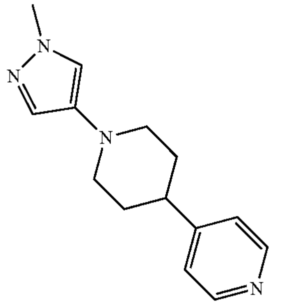

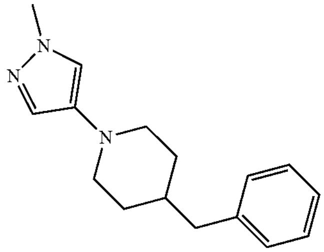

, or a pharmaceutically acceptable salt or solvate thereof.

II. Methods

In another aspect, the present disclosure includes a method of inhibiting the biosynthesis of 20-hydroxyeicosatetraenoic acid (20-HETE) in a subject in need thereof, the method comprising administering to the subject a therapeutically effective amount of a compound of any embodiment herein, or a pharmaceutically acceptable salt or solvate thereof.

In another aspect, the present disclosure includes a method of inhibiting CYP4, the method comprising contacting CYP4 with a compound of any embodiment herein, or a pharmaceutically acceptable salt or solvate thereof. In some embodiments, the contacting is in vitro. In some embodiments, the contacting is in vivo in a subject in need.

In another aspect, the present disclosure provides a method of preventing cerebral blood flow impairment in a subject experiencing or having experienced an ischemic event, the method comprising administering to the subject a therapeutically effective amount of a compound of any embodiment herein, or a pharmaceutically acceptable salt or solvate thereof.

In another aspect, the present disclosure provides a method of treating polycystic kidney disease (PKD) in a subject suffering from autosomal dominant polysistic kidney disease (ADPKD) or autosomal recessive polysistic disease (ARPKD), the method comprising of administering to the subject a therapeutically effective amount of a compound of any embodiment herein, or a pharmaceutically acceptable salt or solvate thereof.

In some embodiments, the ischemic event comprises, trauma, focal ischemia (TFI), subarachnoid hemorrhage (SAH), vasoconstriction, thrombosis, embolism, cardiac arrest, stroke, aneurysm, hypertension, sickle cell disease, application of g-forces, arteriovenous malformation, peripheral artery occlusive disease, central nervous system (CNS) depressant overdose, or a combination thereof.

One aspect provides for use of the compound or a pharmaceutically acceptable salt or solvate thereof of any embodiment herein, or the pharmaceutical composition herein, for use in the manufacture of a medicament for inhibiting the biosynthesis of 20-hydroxyeicosatetraenoic acid (20-HETE) in a subject in need thereof.

One aspect provides for use of the compound or a pharmaceutically acceptable salt or solvate thereof of any embodiment herein, or the pharmaceutical composition herein, for use in the manufacture of a medicament for inhibiting CYP4.

In some embodiments, the subject is a human. In some embodiments, the subject is a human, canine, feline, primate, aves, reptile, or murine.

III. Routes of Administration

Administration may be accomplished through various modes of delivery, and encompass any pharmaceutically acceptable method of administration. Preferred methods of delivery include systemic and localized delivery. Such routes of administration include but are not limited to, oral, intra-arterial, intrathecal, intraspinal, intramuscular, intraperitoneal, intranasal, and inhalation routes.

More particularly, compounds of the present disclosure may be administered for therapy by any suitable route, including without limitation, oral, rectal, nasal, topical (including transdermal, aerosol, buccal and sublingual), vaginal, parenteral (including subcutaneous, intravenous, intramuscular, and intradermal), intrathecal, and pulmonary. In some embodiments, the compound, or a pharmaceutically acceptable salt or solvate thereof, is administered orally. In some embodiments, the compound, or a pharmaceutically acceptable salt or solvate thereof, is administered through an injection. The preferred route will, of course, vary with the condition and age of the recipient, the particular syndrome being treated, and the specific combination of drugs employed.

IV. Dosage

"Therapeutically effective amount" can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated and the judgment of the health care professional.

Therapeutically effective amounts can be determined by those skilled in the art and will be adjusted to the requirements of each particular case. Generally, a therapeutically effective amount of the compound, or pharmaceutically acceptable salt or solvate thereof, will range from a total daily dosage of about 0.1 mg/day-about 4,000 mg/day, about 0.1 mg/day to about 720 mg/day, about 60-about 600 mg/day, or about 100-about 480 mg/day, or more preferably, in an amount between about 1-about 240 mg/day, about 30-about 240 mg/day, about 30-about 200 mg/day, about 30-about 120 mg/day, about 1-about 120 mg/day, about 50-about 150 mg/day, about 60-about 150 mg/day, about 60-about 120 mg/day, or about 60-about 100 mg/day, administered as either a single dosage or as multiple dosages. In some embodiments, the therapeutically effective amount of the compound, or pharmaceutically acceptable salt or solvate thereof, is from about 30-200 mg/day, administered as either a single dosage or as multiple dosages. In some embodiments, multiple dosages include two, three, or four doses per day. In some embodiments, multiple dosages include two or three doses per day.

In some embodiments, the dosage amounts of the compound, or pharmaceutically acceptable salt or solvate thereof, includes dosages greater than about 20 mg BID or TID. In some embodiments, the dosage amount of the compound, or pharmaceutically acceptable salt or solvate thereof, is greater than about 0.1 mg/day, about 1 mg/day, about 5 mg/day, about 10 mg/day, about 30 mg/day, about 60 mg/day, about 80 mg/day, about 90 mg/day, about 120 mg/day, about 150 mg/day, about 180 mg/day, about 210 mg/day, about 240 mg/day, about 270 mg/day, about 300 mg/day, about 360 mg/day, about 400 mg/day, about 440 mg/day, about 480 mg/day, about 520 mg/day, about 580 mg/day, about 600 mg/day, about 620 mg/day, about 640 mg/day, about 680 mg/day, and about 720 mg/day or more.

In some embodiments, the therapeutically effective amount of the compound, or pharmaceutically acceptable salt or solvate thereof, is at least about 30 mg/day, at least about 40 mg/day, at least about 50 mg/day, at least about 60 mg/day, at least about 70 mg/day, at least about 80 mg/day, at least about 90 mg/day, at least about 100 mg/day, at least about 110 mg/day, at least about 120 mg/day, at least about 130 mg/day, at least about 140 mg/day, at least about 150 mg/day, at least about 160 mg/day, at least about 170 mg/day, at least about 180 mg/day, at least about 190 mg/day, at least about 200 mg/day, at least about 225 mg/day, at least about 250 mg/day, at least about 275 mg/day, at least about 300 mg/day, at least about 325 mg/day, at least about 350 mg/day, at least about 375 mg/day, at least about 400 mg/day, at least about 425 mg/day, at least about 450 mg/day, at least about 475 mg/day, at least about 500 mg/day, at least about 525 mg/day, at least about 550 mg/day, at least about 575 mg/day, at least about 600 mg/day, at least about 625 mg/day, at least about 650 mg/day, at least about 675 mg/day, at least about 700 mg/day, or at least about 720 mg/day. In some embodiments, the therapeutically effective amount of the compound, or a pharmaceutically acceptable salt of solvate thereof is at least about 30 mg/day, at least about 60 mg/day, at least about 80 mg/day, or at least about 100 mg/day.

In some embodiments, the therapeutically effective amount of the compound, or a pharmaceutically acceptable salt of solvate thereof is about 30 mg/day, about 40 mg/day, about 50 mg/day, about 60 mg/day, about 70 mg/day, about 80 mg/day, about 90 mg/day, about 100 mg/day, about 110 mg/day, about 120 mg/day, about 130 mg/day, about 140 mg/day, about 150 mg/day, about 160 mg/day, about 170 mg/day, about 180 mg/day, about 190 mg/day, about 200 mg/day, about 225 mg/day, about 250 mg/day, about 275 mg/day, about 300 mg/day, about 325 mg/day, about 350 mg/day, about 375 mg/day, about 400 mg/day, about 425 mg/day, about 450 mg/day, about 475 mg/day, about 500 mg/day, about 525 mg/day, about 550 mg/day, about 575 mg/day, about 600 mg/day, about 625 mg/day, about 650 mg/day, about 675 mg/day, about 700 mg/day, or about 720 mg/day. In some embodiments, the therapeutically effective amount of the compound, or a pharmaceutically acceptable salt of solvate thereof is about 30 mg/day, about 60 mg/day, about 80 mg/day, or about 100 mg/day.

Depending upon the dosage amount and precise condition to be treated, administration can be one, two, three, or four times daily for a time course of one day to several days, weeks, months, and even years, and may even be for the life of the subject. Illustrative dosing regimens will last a period of at least about a week, from about 1-4 weeks, from about 1-8 weeks, from 1-12 weeks, from 1-16 weeks, from 1-20 weeks, from 1-24 weeks, from 1-36 weeks, from 1-48 weeks, from 1-52 weeks, from 1-60 weeks, from 1-72 weeks, from 1-84 weeks, from 1-96 weeks, from 1 week to 1 year, from 1 week to 2 years, from 1 week to 3 years, from 1 week to 4 years, from 1 week to 5 years, or longer. In some embodiments, a dosing regimen is for a period of at least about 12, 24, 36, 48, 60, 72, 84, or 96 weeks. In some embodiments, a dosing regimen is for a period of about 12, 24, 36, 48, 60, 72, 84, or 96 weeks. In some embodiments, a dosing regimen is for a period of at least about 1 year, 2 years, 3 years, 4 years, or 5 years. In some embodiments, a dosing regimen is for a period of about 1 year, 2 years, 3 years, 4 years, or 5 years, or longer.

Practically speaking, a unit dose of any given composition of the disclosure or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

V. Formulations

In another aspect, the present disclosure includes a pharmaceutical composition comprising a compound or a pharmaceutically acceptable salt of solvate thereof, according to any embodiment herein and a pharmaceutically acceptable excipient. In one embodiment the composition comprises a therapeutically effective amount of the compound or a pharmaceutically acceptable salt of solvate thereof. Pharmaceutical compositions of the disclosure may be formulated as described below.

The active agents described herein, such as the compound of formula I, or a pharmaceutically acceptable salt or solvate thereof, may be administered in a formulation which may optionally contain one or more additional components as described below.

In one aspect provided herein is a composition comprising, consisting essentially of, or consisting of a therapeutically effective amount of the compound of formula I, or a pharmaceutically acceptable salt or solvate thereof, and at least one pharmaceutically acceptable excipient and/or carrier. In some embodiments, the composition further comprises a neuroprotectant drug and/or a drug used to treat temporary focal ischemia (TFI), cardiac arrest (CA) and/or subarachnoid hemorrhage (SAH).

A. Excipients/Carriers

The compositions of the disclosure may further comprise one or more pharmaceutically acceptable excipients or carriers. Exemplary excipients include, without limitation, polyethylene glycol (PEG), PEG 400, (2-Hydroxypropyl)-β-cyclodextrin, hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition of the disclosure may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the disclosure are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

A composition of the disclosure may also contain one or more antioxidants. Antioxidants are used to prevent oxidation, thereby preventing the deterioration of the drug(s) or other components of the preparation. Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition of the disclosure may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15% to about 95% by weight of the excipient. In general, the amount of excipient present in the composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

These foregoing pharmaceutical excipients along with other excipients are described in "Remington: The Science & Practice of Pharmacy", 19th ed., Williams & Williams, (1995), the "Physician's Desk Reference", 52.sup.nd ed., Medical Economics, Montvale, N.J. (1998), and Kibbe, A.

H., Handbook of Pharmaceutical Excipients, 3.sup.rd Edition, American Pharmaceutical Association, Washington, D.C., 2000.

B. Other Actives

A formulation (or kit) in accordance with the disclosure may contain, in addition to the compound of the disclosure or a pharmaceutically acceptable salt or solvate thereof, optionally, one or more additional active agents. In some embodiments, the one or more active agents possesses a mechanism of action different from that of the compound of the disclosure or a pharmaceutically acceptable salt or solvate thereof. Such active ingredients can be found listed in the FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

C. Sustained Delivery Formulations

In some embodiments, the compositions of the disclosure are formulated in order to improve stability and extend the half-life of the compound of the disclosure or a pharmaceutically acceptable salt or solvate thereof. For example, the compound, or a pharmaceutically acceptable salt of solvate thereof may be delivered in a controlled or extended-release formulation. Controlled or extended-release formulations are prepared by incorporating the compound of the disclosure or a pharmaceutically acceptable salt or solvate thereof, into a carrier or vehicle such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, the compound, or a pharmaceutically acceptable salt of solvate thereof can be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; and McGee et al., J. Microencap. (1996).

Extended release polymers suitable for this purpose are known in the art and include hydrophobic polymers such as cellulose ethers. Non-limiting examples of suitable cellulose ethers include ethyl cellulose, cellulose acetate and the like; polyvinyl esters such as polyvinyl acetate, polyacrylic acid esters, methacrylic and acrylate polymers (pH-independent types); high molecular weight polyvinyl alcohols and waxes such as fatty acids and glycerides, methacrylic acid ester neutral polymers, polyvinyl alcohol-maleic anhydride copolymers and the like; ethylacrylate-methylmethacrylate copolymers; aminoalkyl methacrylate copolymers; and mixtures thereof.

D. Delivery Forms

The compositions described herein encompass all types of formulations, and in particular, those that are suited for systemic or intrathecal administration. Oral dosage forms include tablets, lozenges, capsules, syrups, oral suspensions, emulsions, granules, microbeads, and pellets. In some embodiments, the oral dosage form is a tablet, capsule, granule, or microbead dosage form. In some embodiments, the oral dosage form is a tablet. In some embodiments, the tablet is an extended release tablet. In some embodiments, the oral dosage form is a capsule. In some embodiments, the capsule is an extended release capsule. In some embodiments, the oral dosage form is in a liquid dosage form. In some embodiments, the oral dosage form is an extended release formulation.

Alternative formulations include aerosols, transdermal patches, gels, creams, ointments, suppositories, powders or lyophilates that can be reconstituted, as well as liquids. Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned. Preferably, the compound, or a pharmaceutically acceptable salt of solvate thereof, or the composition of the disclosure is one suited for oral administration.

For oral delivery formulations, tablets can be made by compression or molding, optionally with one or more accessory ingredients or additives. Compressed tablets are prepared, for example, by compressing in a suitable tableting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tableting machine, a mixture of powdered compounds moistened with an inert liquid diluent. The tablets may optionally be coated or scored and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

Formulations for topical administration in the mouth include lozenges comprising the active ingredients, generally in a flavored base such as sucrose and acacia or tragacanth and pastilles comprising the active ingredients in an inert base such as gelatin and glycerin or sucrose and acacia.

A pharmaceutical composition for topical administration may also be formulated as an ointment, cream, suspension, lotion, powder, solution, paste, gel, spray, aerosol or oil.

Alternatively, the formulation may be in the form of a patch (e.g., a transdermal patch) or a dressing such as a bandage or adhesive plaster impregnated with active ingredients and optionally one or more excipients or diluents. Topical formulations may additionally include a compound that enhances absorption or penetration of the ingredients through the skin or other affected areas, such as dimethylsulfoxidem bisabolol, oleic acid, isopropyl myristate, and D-limonene, to name a few.

For emulsions, the oily phase is constituted from known ingredients in a known manner. While this phase may comprise merely an emulsifier (otherwise known as an emulgent), it desirably comprises a mixture of at least one emulsifier with a fat and/or an oil. Preferably, a hydrophilic emulsifier is included together with a lipophilic emulsifier that acts as a stabilizer. Together, the emulsifier(s) with or without stabilizer(s) make up the so-called emulsifying wax, and the wax together with the oil and/or fat make up the so-called emulsifying ointment base which forms the oily dispersed phase of cream formulations. Illustrative emulgents and emulsion stabilizers include Tween 60, Span 80, cetostearyl alcohol, myristyl alcohol, glyceryl monostearate and sodium lauryl sulfate.

Formulations for rectal administration are typically in the form of a suppository with a suitable base comprising, for example, cocoa butter or a salicylate.

Formulations suitable for vaginal administration generally take the form of a suppository, tampon, cream, gel, paste, foam or spray.

Formulations suitable for nasal administration, wherein the carrier is a solid, include a coarse powder having a particle size, for example, in the range of about 20 to about 500 microns. Such a formulation is typically administered by rapid inhalation through the nasal passage, e.g., from a container of the powder held in proximity to the nose. Alternatively, a formulation for nasal delivery may be in the form of a liquid, e.g., a nasal spray or nasal drops.

Aerosolizable formulations for inhalation may be in dry powder form (e.g., suitable for administration by a dry powder inhaler), or, alternatively, may be in liquid form, e.g., for use in a nebulizer. Nebulizers for delivering an aerosolized solution include the AERx® (Aradigm), the Ultravent® (Mallinkrodt), and the Acorn II® (Marquest Medical Products). A composition of the disclosure may also be delivered using a pressurized, metered dose inhaler (MDI), e.g., the Ventolin® metered dose inhaler, containing a solution or suspension of a combination of drugs as described herein in a pharmaceutically inert liquid propellant, e.g., a chlorofluorocarbon or fluorocarbon.

Formulations suitable for parenteral administration include aqueous and non-aqueous isotonic sterile solutions suitable for injection, as well as aqueous and non-aqueous sterile suspensions.

Parenteral formulations of the disclosure are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the types previously described.

A formulation of the disclosure may also be an extended release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the disclosure may optionally include other agents conventional in the pharmaceutical arts and particular type of formulation being employed, for example, for oral administration forms, the composition for oral administration may also include additional agents as sweeteners, thickeners or flavoring agents.

E. Kits

Also provided herein is a kit containing at least one composition of the disclosure, compound (or pharmaceutically acceptable salt or solvate thereof) of the disclosure, accompanied by instructions for use.

For example, in instances in which each of the drugs themselves are administered as individual or separate dosage forms, the kit comprises the compound, or a pharmaceutically acceptable salt of solvate thereof along with instructions for use. The compound, or a pharmaceutically acceptable salt of solvate thereof may be packaged in any manner suitable for administration, so long as the packaging, when considered along with the instructions for administration, clearly indicates the manner in which drug component is to be administered.

For example, in an illustrative kit comprising the compound, or a pharmaceutically acceptable salt of solvate thereof the kit may be organized by any appropriate time period, such as by day. As an example, for Day 1, a representative kit may comprise unit dosages of each of the compound of the disclosure or a pharmaceutically acceptable salt or solvate thereof. If the drug is to be administered twice daily, then the kit may contain, corresponding to Day 1, two rows of unit dosage forms of the compound, or a pharmaceutically acceptable salt of solvate thereof along with instructions for the timing of administration. Various embodiments according to the above may be readily envisioned, and would of course depend upon the corresponding dosage form, recommended dosage, intended subject population, and the like. The packaging may be in any form commonly employed for the packaging of pharmaceuticals, and may utilize any of a number of features such as different colors, wrapping, tamper-resistant packaging, blister packs, dessicants, and the like.

It is to be understood that while the disclosure has been described in conjunction with preferred specific embodiments, the foregoing description as well as the examples that follow are intended to illustrate and not limit the scope of the disclosure. Other aspects, advantages and modifications within the scope of the disclosure will be apparent to those skilled in the art to which the disclosure pertains.

All references mentioned in this application, including any patents, published patent applications, books, handbooks, journal publications, or the FDA Orange Book are hereby incorporated by reference herein, in their entirety.

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the disclosure. Changes therein and other uses which are encompassed within the spirit of the disclosure as defined by the scope of the claims will occur to those skilled in the art.

VI. Definitions

The terms "pharmacologically effective amount" or "therapeutically effective amount" of a composition or agent, as provided herein, refer to a nontoxic but sufficient amount of the composition or agent to provide the desired response. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

As used in the specification and claims, the singular form "a," "an," and "the" include plural references unless the context clearly dictates otherwise. For example, the term "a cell" includes a plurality of cells, including mixtures thereof.

As used herein, the term "comprising" is intended to mean that the compounds, compositions and methods include the recited elements, but not exclude others. "Consisting essentially of" when used to define compounds, compositions and methods, shall mean excluding other elements of any essential significance to the combination. Thus, a composition consisting essentially of the elements as defined herein would not exclude trace contaminants, e.g., from the isolation and purification method and pharmaceutically acceptable carriers, preservatives, and the like. "Consisting of" shall mean excluding more than trace elements of other ingredients. Embodiments defined by each of these transition terms are within the scope of this technology.

All numerical designations, e.g., pH, temperature, time, concentration, and molecular weight, including ranges, are approximations which are varied (+) or (−) by increments of 1, 5, or 10%. It is to be understood, although not always explicitly stated that all numerical designations are preceded by the term "about." It also is to be understood, although not always explicitly stated, that the reagents described herein are merely exemplary and that equivalents of such are known in the art.

The term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

"Optional" or "optionally" means that the subsequently described circumstance may or may not occur, so that the description includes instances where the circumstance occurs and instances where it does not.

"Pharmaceutically acceptable excipient or carrier" refers to an excipient that may optionally be included in the compositions of the disclosure and that causes no significant adverse toxicological effects to the patient.

"Substantially" or "essentially" means nearly totally or completely, for instance, 95% or greater of some given quantity. In some embodiments, "substantially" or "essentially" means 95%, 96%, 97%, 98%, 99%, 99.5%, or 99.9%.

"20-HETE" or "20-Hydroxyeicosatetraenoic acid" is a compound represented by the formula:

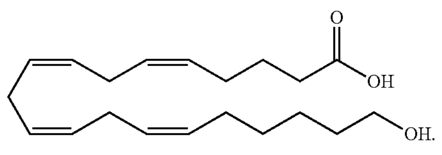 [SMILES: O=C(O)CCC/C=C\C/C=C\C/C=C\C/C=C\CCCCCO]

"Optionally substituted" refers to a group selected from that group and a substituted form of that group. A "substituted" group, refers to that group substituted with any substituent described or defined below. In one embodiment, substituents are selected from, for example, $CF_3$, $OCF_3$, halo, haloaryl, alkoxy, aryloxy, haloalkoxy, dihydroxy, aminohydroxy, carboxy, amido, sulfoxy, sulfonyl, haloaryloxy, aryl, benzyl, benzyloxy, heteroaryl, nitrile, $C_1$-$C_6$ alkyl, $C_1$-$C_6$ alkenyl, $C_1$-$C_6$ alkynyl, $C_3$-$C_6$ cycloalkyl, $C_1$-$C_6$ haloalkyl, $C_1$-$C_6$ haloalkenyl, $C_1$-$C_6$ haloalkynyl, $C_3$-$C_6$ halocycloalkyl, $C_6$-$C_{10}$ aryl, $C_3$-$C_8$ cycloalkyl, $C_2$-$C_{10}$ heterocyclyl, $C_1$-$C_{10}$ heteroaryl, $—N_3$, nitro, $—CO_2H$ or a $C_1$-$C_6$ alkyl ester thereof, any of the functional groups described or defined below, or combinations thereof.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3—$), ethyl ($CH_3CH_2—$), n-propyl ($CH_3CH_2CH_2—$), isopropyl ($(CH_3)_2CH—$), n-butyl ($CH_3CH_2CH_2CH_2—$), isobutyl ($(CH_3)_2CHCH_2—$), sec-butyl ($(CH_3)(CH_3CH_2)CH—$), t-butyl ($(CH_3)_3C—$), n-pentyl ($CH_3CH_2CH_2CH_2CH_2—$), and neopentyl ($(CH_3)_3CCH_2—$). A Cx-Cy alkyl will be understood to have from x to y carbons.

"Alkenyl" refers to monovalent straight or branched hydrocarbyl groups having from 2 to 6 carbon atoms and preferably 2 to 4 carbon atoms and having at least 1 and preferably from 1 to 2 sites of vinyl ($>C{=}C<$) unsaturation. Such groups are exemplified, for example, by vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic ($—C{\equiv}C—$) unsaturation. Examples of such alkynyl groups include acetylenyl ($—C{\equiv}CH$), and propargyl ($—CH_2C{\equiv}CH$).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxyl, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Alkylene" refers to divalent saturated aliphatic hydrocarbyl groups preferably having from 1 to 6 and more preferably 1 to 3 carbon atoms that are either straight-chained or branched. This term is exemplified by groups such as methylene ($—CH_2—$), ethylene ($—CH_2CH_2—$), n-propylene ($—CH_2CH_2CH_2—$), iso-propylene ($—CH_2CH(CH_3)—$ or $—CH(CH_3)CH_2—$), butylene ($—CH_2CH_2CH_2CH_2—$), isobutylene ($—CH_2CH(CH_3)CH_2—$), sec-butylene ($—CH_2CH_2(CH_3)CH—$), and the like. Similarly, "alkenylene" and "alkynylene" refer to an alkylene moiety containing respective 1 or 2 carbon-carbon double bonds or a carbon-carbon triple bond.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein. In some embodiments, the alkylene has 1 to 2 of the aforementioned groups, or having from 1-3 carbon atoms replaced with —O—, —S—, or $—NR^{Q}—$ moieties where $R^{Q}$ is H or $C_1$-$C_6$ alkyl. It is to be noted that when the alkylene is substituted by an oxo group, 2 hydrogens attached to the same carbon of the alkylene group are replaced by "═O". "Substituted alkenylene" and "substituted alkynylene" refer to alkenylene and substituted alkynylene moieties substituted with substituents as described for substituted alkylene.

A "protecting group" or "$P^{2}$" (wherein z is an integer) intends any protecting group suitable for alcohol(s) and amine(s) and which are well known in the art. Non-limiting examples include 2,2,2-trichloroethyl carbonate (Troc), 2-methoxyethoxymethyl ether (MEM), 2-naphthylmethyl ether (Nap), 4-methoxybenzyl ether (PMB), acetate (Ac), benzoate (Bz), benzyl ether (Bn), benzyloxymethyl acetal (BOM), benzyloxymethyl acetal (BOM), methoxymethyl acetal (MOM), methoxypropyl acetal (MOP), methyl ether, tetrahydropyranyl acetal (THP), triethylsilyl ether (TES), triisopropylsilyl ether (TIPS), trimethylsilyl ether (TMS), tert-Butyldimethylsilyl ether (TBS, TBDMS), or tert-butyldiphenylsilyl ether (TBDPS). In the case of a 1,2 diol or 1,2 aminoalcohols suitable protecting groups include acetonide, benzaldehyde acetal or carbonate and others. These protecting groups and others are well known to the skilled artisan, as evidenced by Green et al: Greene's Protective Groups in Organic Synthesis, Fourth Edition Author(s): Peter G. M. Wuts and Theodora W. Greene First published: 10 Apr. 2006, Copyright © 2007 John Wiley & Sons, Inc, the disclosure of which is incorporated by reference.

"Deprotection," "deprotecting," and the like, intend removal of the protecting group by any conventional means known to the skilled artisan or present in Green et al. It will be readily apparent that the conditions for deprotecting depend upon which protecting group is used.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)—$.

"Acylamino" refers to the groups $—NR^{46}C(O)R^{47}$ wherein $R^{46}$ and $R^{47}$ are each independently, hydrogen, alkyl, substituted alkyl, alkylene, substituted alkylene, cycloalkyl, substituted cycloalkyl, cycloalkenyl, substituted cycloalkenyl, alkenyl, substituted alkenyl, alkynyl, substituted alkynyl, aryl, substituted aryl, heteroaryl, substituted heteroaryl, heterocyclic, substituted heterocyclic, and wherein $R^{46}$ and $R^{47}$ are optionally joined, together to form a heterocyclic or substituted heterocyclic group, provided that $R^{46}$ and $R^{47}$ are both not hydrogen, and wherein alkyl, substituted alkyl, alkylene, substituted alkylene, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)

O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group $—NH_2$.

"Substituted amino" refers to the group $—NR^{48}R^{49}$ where $R^{48}$ and $R^{49}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, $—SO_2$-alkyl, $—SO_2$-substituted alkyl, $—SO_2—$ alkenyl, $—SO_2$-substituted alkenyl, $—SO_2$-cycloalkyl, $—SO_2$-substituted cycloalkyl, $—SO_2—$ cycloalkenyl, $—SO_2$-substituted cylcoalkenyl, $—SO_2$-aryl, $—SO_2$-substituted aryl, $—SO_2—$ heteroaryl, $—SO_2$-substituted heteroaryl, $—SO_2$-heterocyclic, and $—SO_2$-substituted heterocyclic and wherein $R^{48}$ and $R^{49}$ are optionally joined, together with the nitrogen bound thereto to form a heterocyclic or substituted heterocyclic group, provided that $R^{48}$ and $R^{49}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When $R^{48}$ is hydrogen and $R^{49}$ is alkyl, the substituted amino group is sometimes referred to herein as alkylamino. When $R^{48}$ and $R^{49}$ are alkyl, the substituted amino group is sometimes referred to herein as dialkylamino. When referring to a monosubstituted amino, it is meant that either $R^{48}$ or $R^{49}$ is hydrogen but not both. When referring to a disubstituted amino, it is meant that neither $R^{48}$ nor $R^{49}$ are hydrogen.

"Aminocarbonyl" refers to the group $—C(O)NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group $—C(S)NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group $—NR^{47}C(O)NR^{50}R^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group $—NR^{47}C(S)NR^{50}R^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group $—O—C(O)NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group $—SO_2NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group $—O—SO_2NR^{50}R^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —$NR^{47}SO_2NR^{50}R^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=$NR^{52}$)$NR^{50}R^{51}$ where $R^{50}$, $R^{51}$, and $R^{52}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Azide" refers to the group —N=$N^{\oplus}$=$N^{\ominus}$.

"Carbonyl" refers to the divalent group —C(O)— which is equivalent to —C(=O)—.

"Carboxyl" or "carboxy" refers to —COOH or salts thereof.

"Carboxyl ester" or "carboxy ester" refers to the groups —C(O)O-alkyl, —C(O)O— substituted alkyl, —C(O)O-alkenyl, —C(O)O-substituted alkenyl, —C(O)O-alkynyl, —C(O)O— substituted alkynyl, —C(O)O-aryl, —C(O)O-substituted aryl, —C(O)O-cycloalkyl, —C(O)O— substituted cycloalkyl, —C(O)O-cycloalkenyl, —C(O)O-substituted cycloalkenyl, —C(O)O— heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —$NR^{47}$C(O)O-alkyl, —$NR^{47}$C(O)O— substituted alkyl, —$NR^{47}$C(O)O-alkenyl, —$NR^{47}$C(O)O-substituted alkenyl, —$NR^{47}$C(O)O— alkynyl, —$NR^{47}$C(O)O-substituted alkynyl, —$NR^{47}$C(O)O-aryl, —$NR^{47}$C(O)O-substituted aryl, —$NR^{47}$C(O)O-cycloalkyl, —$NR^{47}$C(O)O-substituted cycloalkyl, —$NR^{47}$C(O)O-cycloalkenyl, —$NR^{47}$C(O)O-substituted cycloalkenyl, —$NR^{47}$C(O)O-heteroaryl, —$NR^{47}$C(O)O-substituted heteroaryl, —$NR^{47}$C(O)O-heterocyclic, and —$NR^{47}$C(O)O-substituted heterocyclic wherein $R^{47}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O— substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

An animal, subject or patient for diagnosis, treatment, or administration of the compounds if the disclosure thereto, refers to an animal such as a mammal, or a human, ovine, bovine, feline, canine, equine, simian, etc. Non-human animals subject to diagnosis, treatment, or administration thereto of compounds of the disclosure include, for example, simians, murine, such as, rat, mice, canine, leporid, livestock, sport animals, and pets.

A "composition" "pharmaceutical composition" as used herein, intends an active agent, such as a compound as disclosed herein and a carrier, inert or active. The carrier can be, without limitation, solid such as a bead or resin, or liquid, such as phosphate buffered saline.

Administration or treatment in "combination" refers to administering two agents such that their pharmacological effects are manifest at the same time. Combination does not require administration at the same time or substantially the same time, although combination can include such administrations.

"Cyano" refers to the group —CN.

"Cycloalkyl" refers to cyclic alkyl groups of from 3 to 10 carbon atoms having single or multiple cyclic rings including fused, bridged, and spiro ring systems. The fused ring can be an aryl ring provided that the non-aryl part is joined to the rest of the molecule. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C═C< ring unsaturation and preferably from 1 to 2 sites of >C═C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group $—NHC(═NH)NH_2$.

"Substituted guanidino" refers to $—NR^{53}C(═NR^{53})N(R^{53})_2$ where each $R^{53}$ is independently selected from the group consisting of hydrogen, alkyl, substituted alkyl, aryl, substituted aryl, heteroaryl, substituted heteroaryl, cycloalkyl, substituted cycloalkyl, heterocyclic, and substituted heterocyclic and two $R^{53}$ groups attached to a common guanidino nitrogen atom are optionally joined together with the nitrogen bound thereto to form a heterocyclic or substituted heterocyclic group, provided that at least one $R^{53}$ is not hydrogen, and wherein said substituents are as defined herein.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Certain non-limiting examples include pyridinyl, pyrrolyl, indolyl, thiophenyl, oxazolyl, thiazolyl, pyrazolyl, pyrazinyl, pyridazinyl, pyrimidinyl and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N-oxide, sulfinyl, or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, furan, thiophene, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group $—NO_2$.

"Oxo" refers to the atom (=O).

Phenylene refers to a divalent aryl ring, where the ring contains 6 carbon atoms.

Substituted phenylene refers to phenylenes which are substituted with 1 to 4, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Spirocycloalkyl" and "spiro ring systems" refers to divalent cyclic groups from 3 to 10 carbon atoms having a cycloalkyl or heterocycloalkyl ring with a spiro union (the union formed by a single atom which is the only common member of the rings) as exemplified by the following structure:

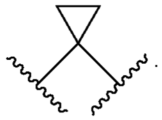 [SMILES: *C1(*)CC1]

"Sulfonyl" refers to the divalent group —S(O)2-.

"Substituted sulfonyl" refers to the group $—SO_2$-alkyl, $—SO_2$-substituted alkyl, $—SO_2—$ alkenyl, $—SO_2$-substituted alkenyl, $—SO_2$-cycloalkyl, $—SO_2$-substituted cycloalkyl, $—SO_2—$ cycloalkenyl, $—SO_2$-substituted cylcoalkenyl, $—SO_2$-aryl, $—SO_2$-substituted aryl, $—SO_2—$ heteroaryl, $—SO_2$-substituted heteroaryl, $—SO_2$-heterocyclic, $—SO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl-$SO_2—$, phenyl-$SO_2—$, and 4-methylphenyl-$SO_2—$.

"Substituted sulfonyloxy" refers to the group $—OSO_2$-alkyl, $—OSO_2$-substituted alkyl, $—OSO_2$-alkenyl, $—OSO_2$-substituted alkenyl, $—OSO_2$-cycloalkyl, $—OSO_2$-substituted cycloalkyl, $—OSO_2$-cycloalkenyl, $—OSO_2$-substituted cylcoalkenyl, $—OSO_2$-aryl, $—OSO_2$-substituted aryl, $—OSO_2$-heteroaryl, $—OSO_2$-substituted heteroaryl, $—OSO_2$-heterocyclic, $—OSO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thiocarbonyl" refers to the divalent group —C(S)— which is equivalent to —C(=S)—.

"Thioxo" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

"Pharmaceutically acceptable salt" refers to salts of a compound, which salts are suitable for pharmaceutical use and are derived from a variety of organic and inorganic counter ions well known in the art and include, when the compound contains an acidic functionality, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate (see Stahl and Wermuth, eds., "Handbook of Pharmaceutically Acceptable Salts," (2002), Verlag Helvetica Chimica Acta, Zürich, Switzerland), for a discussion of pharmaceutical salts, their selection, preparation, and use.

"Active molecule" or "active agent" as described herein includes any agent, drug, compound, composition of matter or mixture which provides some pharmacologic, often beneficial, effect that can be demonstrated in vivo or in vitro. This includes foods, food supplements, nutrients, nutraceuticals, drugs, vaccines, antibodies, vitamins, and other beneficial agents. As used herein, the terms further include any physiologically or pharmacologically active substance that produces a localized or systemic effect in a patient. In specific embodiments, the active molecule or active agent includes the compound of formula I, or a pharmaceutically acceptable salt or solvate thereof.

"Substantially" or "essentially" means nearly totally or completely, for instance, 95% or greater of some given quantity. In some embodiments, "substantially" or "essentially" means 95%, 96%, 97%, 98%, 99%, 99.5%, or 99.9%.

Generally, pharmaceutically acceptable salts are those salts that retain substantially one or more of the desired pharmacological activities of the parent compound and which are suitable for in vivo administration. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like.

Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion) or by an ammonium ion (e.g., an ammonium ion derived from an organic base, such as, ethanolamine, diethanolamine, triethanolamine, morpholine, piperidine, dimethylamine, diethylamine, triethylamine, and ammonia).

A solvate of a compound is a solid-form of a compound that crystallizes with less than one, one or more than one molecules of a solvent inside in the crystal lattice. A few examples of solvents that can be used to create solvates, such as pharmaceutically acceptable solvates, include, but are not limited to, water, C1-C6 alcohols (such as methanol, ethanol, isopropanol, butanol, and can be optionally substituted) in general, tetrahydrofuran, acetone, ethylene glycol, propylene glycol, acetic acid, formic acid, and solvent mixtures thereof. Other such biocompatible solvents which may aid in making a pharmaceutically acceptable solvate are well known in the art. Additionally, various organic and inorganic acids and bases can be added to create a desired solvate. Such acids and bases are known in the art. When the solvent is water, the solvate can be referred to as a hydrate. In some embodiments, one molecule of a compound can form a solvate with from 0.1 to 5 molecules of a solvent, such as 0.5 molecules of a solvent (hemisolvate, such as hemihydrate), one molecule of a solvent (monosolvate, such as monohydrate) and 2 molecules of a solvent (disolvate, such as dihydrate).

An "effective amount" or "therapeutically effective amount" is an amount sufficient to effect beneficial or desired results. An effective amount can be administered in one or more administrations, applications or dosages and is determined by the system in which the drug or compound is delivered, e.g., an effective amount for in vitro purposes is not the same as an effective amount for in vivo purposes. For in vivo purposes, the delivery and "effective amount" is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks.

As used herein, "treating" or "treatment" of a disease in a patient refers to (1) preventing the symptoms or disease from occurring in an animal that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of this technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable.

As used herein, the term "contacting" intends bringing the reagents into close proximity with each other so that a chemical or biochemical reaction can occur among the reagents. In one aspect, the term intends admixing the components, either in a reaction vessel or on a plate or dish. In another aspect, it intends in vivo administration to a subject.

The term "binding" or "binds" as used herein are meant to include interactions between molecules that may be covalent or non-covalent which, in one embodiment, can be detected using, for example, a hybridization assay. The terms are also meant to include "binding" interactions between molecules. Interactions may be, for example, protein-protein, antibody-protein, protein-nucleic acid, protein-small molecule or small molecule-nucleic acid in nature. This binding can result in the formation of a "complex" comprising the interacting molecules. A "complex" refers to the binding of two or more molecules held together by covalent or non-covalent bonds, interactions or forces.

VII. Examples

Example 1: Synthesis of Compounds

Abbreviations as used herein: (1) THF is tetrahydrofuran; (2) DMF is N,N-dimethylformamide; (3) DMA is N,N-dimethylacetamide; (4) NMP is N-methylpyrolidone DMSO is dimethylsulfoxide; (5) DCM is dichloromethane; (6) DME is dimethoxyethane, MeOH is methanol; (7) EtOH is ethanol; (8) TFA is 1,1,1-trifluoroacetatic acid; (9) HOBT is 1-hydroxybenzotriazole, (10) PyBroP is bromotripyrrolidinophosphonium hexafluorophosphate; (11) EDCI is 1-[3-(dimethylamino)propyl]-3-ethylcarbodiimide hydrochloride; (12) HATU is 1-[Bis(dimethylamino)methylene]-1H-1,2,3-triazolo[4,5-b]pyridinium 3-oxid hexafluorophosphate; (13) DCC is N,N'-dicyclohexylcarbodiimide; (14) Boc is tert-butyloxy carbonyl; (15) Cbz is carboxybenzyl; (16) DIPEA is diisopropylethylamine; (17) Boc is tert-butyloxycarbonyl; (18) NBS is N-bromosuccinimde; (19) NIS is N-iodosuccinimide; (20) NCS is N-chlorosuccinimide; (21) DMAP is N,N-dimethylamino-pyridine; (22) DEAD is diethyl azodicarboxylate; (23) Brine is saturated aqueous sodium chloride solution; (24) TLC is thin layer chromatography; (25) HR-MS is high resolution mass spectrometry; (26) NMR is nuclear magnetic resonance spectroscopy; (27) LC-MS is liquid chromatographic mass spectrometry, RT is room or ambient temperature; (28) ESI is electron spray ionization mass spectrometry; (29) HLM is Human Liver Microsomes; (30) 20-HETE is 20-hydroxyeicosatetraenoic acid; (31) AA is arachidonic acid; (32) 8,9-EET is 8, 9-epoxyeicosatrienoic acid; (33) 11,12-EET is 11,12-epoxyeicosatrienoic acid; (34) 14,15-EET is 14,15-epoxyeicosatrienoic acid; (35) 5,6-DiHET is 5,6-dihydroxyeicosatrienoic acid; (36) 8,9-DiHET is 8,9-dihydroxyeicosatrienoic acid; (37) 11,12-DiHET is 11,12-dihydroxyeicosatrienoic acid; (38) 14,15-DiHET is 14,15-dihydroxyeicosatrienoic acid; (39) THP is tetrahydropyranyl; (40)Trityl is triphenylmethyl DHP is 3,4 dihydro-2H-pyran; and (41) SEM is 2-(Trimethylsilyl) ethoxymethyl.

Compounds disclosed herein may be prepared by commercially available starting materials and via synthetic techniques and procedures known to those skilled in the art. Outlined below in scheme 1 is a general reaction scheme suitable for preparing the compounds of the general structure IV that are disclosed in the present disclosure. Further exemplification for the synthesis of disclosed compounds may be found in the specific examples listed below.

In general, the compounds of the general structure IV (see scheme 1), can be prepared via the coupling of a suitable N-protected iodopyrazole, or a suitable N-protected bromopyrazole, of the structure II (scheme 1) with a desired 4-substituted piperidine of the general structure Ia or Ib or a piperazine of the general structure Ic under appropriate Ullman or Buckwald/Hardwick coupling conditions to afford the intermediate coupling product III. This coupling, depending on the pyrazole halogen substituent and functionality present in Ia, Ib or Ic may be effected via appropriate transition metal catalyst/ligand systems in a suitable solvent and in the presence of a base under conditions available in the literature and known to the persons skilled in the art.

For example, the coupling could be effected under conditions seen in Kwong et al., *Org. Lett.*, 2002, 4, 581; Zhang et al., *J. Org. Chem.*, 2005, 70, 5164; Jiang et al., *J. Org. Chem.*, 2007, 72, 672; Yang et al., *J. Organometallic Chem.*, 1999, 576, 125; Alen et al., WO 2012/158413; Voss et al., WO 2015/022073; Bartels et al., WO 2017/97728; Albrecht et al., WO 2016/138114; Lohou et al., *Synthesis,* 2011, 16, 2651; Ioanidis et al., US 2016/0185785 A1; Basha et al., US2005/65178 A1 or other applicable conditions known to the persons skilled in the art. These disclosures are hereby incorporated by reference.

Desired compounds IV (scheme 1) can be obtained by deprotection of intermediates III, under a variety of conditions that depend on the protecting group used and the functionality present in the molecule, via methods known in the literature and to the people skilled in the art.

Scheme 1

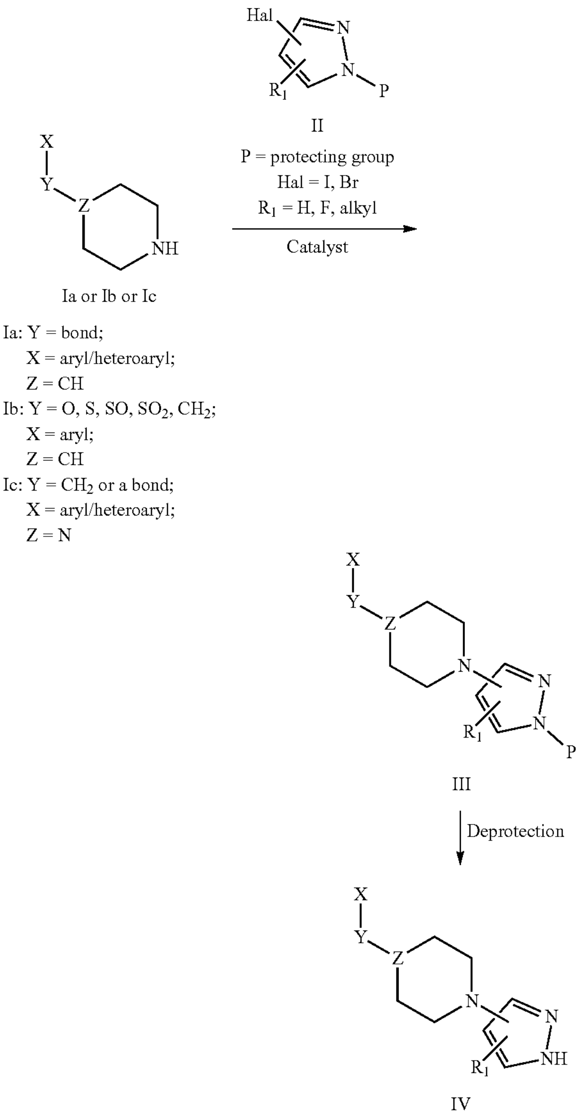

Desirable piperidines of the general structure Ia, where X is aryl or heteroaryl, Y is a bond, and Z is CH are commercially available or can easily be synthesized in a variety of methods known to persons skilled in the art. For example, piperidines of the type Ia, where X is aryl or heteroaryl, Y is a bond and Z is CH may be prepared as seen in Eastwood, P. R., *Tetrahedron Lett.* 2000, 41, 3705; Pasternak et al., *Bioorg. Med. Chem. Letters,* 2008, 18, 944; Sakhteman et al., *Bioorg. Med. Chem.*, 2009, 17, 6908; Kamei et al., *Bior. Med. Chem. Letters,* 2005, 15, 2990; Cox et al., *ACS Med. Chem. Letters,* 2017, 8, 49; Adams et al., WO 2016/001876; Yoshihara et al., WO 2012/124696; Allwood et al., *J. Org. Chem.*, 2014, 79, 328; Conway, R., Bioorg. *Med. Chem. Letters,* 2012, 2560; Oslob et al., WO 2014/008197 or other suitable methods or combination of conditions/methods available in the literature and known to persons skilled in the art. These disclosures are hereby incorporated by reference.

Piperidines of the general structure Ib, where X is aryl/heteroaryl; Y is O and Z is CH, are commercially available or they can easily be synthesized in a variety of methods available in the literature and known to persons skilled in the art. For example, piperidines of the general structure Ib, where X is aryl/heteroaryl; Y is O and Z is CH, can be prepared as seen in Lawrence et al., WO 2001/077101 A1; Aisaoui et al., WO 2003/048154 A1; Boettcher et al., WO 2008/119741; Eriksson, A., WO 2002/074767; Oberboersch et al., WO 2008/040492; Bodil van Niel et al., WO 2015/177325; Bischoff et al., WO 2009/117676; Liang et al., *Molecules,* 2014, 19, 6163; Liu, G., *ACS Med. Chem. Letters,* 2012, 3, 997; Carroll et al., WO 2013/179024 or another suitable method or combination of conditions/methods available in the literature and known to persons skilled in the art. These disclosures are hereby incorporated by reference.

Piperidines of the general structure Ib, where X is aryl/heteroaryl, Y is S and Z is CH are commercially available or they can easily be synthesized in a variety of methods described in the literature. For example, piperidines of the general structure Ib, where X is aryl or heteroaryl, Y is S, and Z is CH may be prepared as seen in Knutsen et al., *Bior. Med. Chem. Letters,* 1993, 12, 2661; Fletcher et al., *J. Med. Chem.,* 2002, 45, 492-503; Nagase et al., *J. Med Chem,* 2009, 52, 4111; Zak et al., *Bioorg. Med. Chem. Letters,* 2015, 25, 529; Nagase et al., WO 2009/038021; Shima et al., WO 2002/055541; Bacani, G., WO 2014/121055; Choi, J., WO 2000/9061131; Chassaing et al., WO 2016/005577; Bair et al., WO 2013/127267; Bromidge et al., WO 2016/001341 or another suitable method or combination of conditions/methods available in the literature and known to persons skilled in the art. These disclosures are hereby incorporated by reference.

Piperidines of the general structure Ib, where X is aryl or heteroaryl Y is SO or $SO_2$ and Z is CH are commercially available or they can be prepared by methods available in the literature and known to those skilled in the art. For example, such piperidines may be prepared from suitable N-protected thio-piperidines of the general structure Ib, where X is aryl/heteroaryl, Y is S and Z is CH, via oxidation of the sulfur atom and then N-deprotection via a variety of methods available in the literature and known to the persons skilled in the art. For example, piperidines of the general structure Ib, where X is aryl/heteroaryl, Y is SO or $SO_2$, and Z is CH may be prepared as seen in Imamura et al., *J. Med. Chem.,* 2006, 49, 2784; Fletcher et al., *J. Med. Chem.,* 2002, 45, 492; Bacani, G., WO 2014/121055; Bair et al., WO 2013/127267; Bromidge et al. WO 2016/001341; Nagase et al., *J. Med Chem.,* 2009, 52, 4111; Nagase et al., WO 2009/038021; Zak et al., *Bioorg. Med. Chem. Letters,* 2015, 25, 529; Muhlhausen et al., *Nucl. Med. Biology,* 2010, 37, 605; Thakur et al., *Tetrahedron Asymmetry,* 2003, 14, 407 or other suitable combination of conditions/methods available in the literature and known to the persons skilled in the art. These disclosures are hereby incorporated by reference.

Piperidines of the general structure Ib where X is aryl/heteroaryl, Y is $CH_2$ and Z is CH are commercially available or they can be prepared in a variety of methods available in the literature and known to persons skilled in the art. For instance, such piperidines may be prepared as seen in Imamura et al., *J. Med. Chem.,* 2006, 49, 2784; Imamura et al., WO 2001/025200; Ting et al., *Bior. Med. Chem. Letters,* 2005, 15, 1375; Chun et al., WO 2010/051245; Liu et al., *ACS Med. Chem. Letters,* 2012, 3, 997; Carroll et al., WO 2013/179024; Pandey et al., WO 2017/147328; Adjabebeng, G, WO 2009/076140; DiFranco et al., Synthesis, 45, 2949; Charvin et al., *J. Med. Chem.,* 2017, 60, 8515 or other suitable combination of conditions/methods available in the literature and known to the persons skilled in the art. These disclosures are hereby incorporated by reference.

Piperazines of the general structure Ic, where X is aryl/heteroaryl, Y is a bond and Z is N are commercially available or can be prepared in a number of methods described in the literature. For example, such piperazines may be prepared as seen in Jpn. Kokai Tokkyo Koho, 57042679; Yong, F. et al. Tetrahedron Lett. 2013, 54, 5332; Jaisinghani, H. et al. Syn. Comm. 1998, 28, 1175; Wodtke, R. et al. J. Med. Chem. J. Med. Chem 2018, 61, 4528; Yoshihara, K. et al. PCT Int. Appl. 2012124696; Duncton, M. et al. Tet. Lett. 2006, 47, 2549; Reilly, S. et al. Org. Lett. 2016, 18, 5272; Pennell, A. et al. PCT Int. Appl. 2003105853 or other suitable method or combination of conditions/methods available in the literature and known to persons skilled in the art. These disclosures are hereby incorporated by reference.

Piperazines of the general structure Ic, where X is aryl/heteroaryl, Y is $CH_2$ and Z is N are commercially available or can be prepared in a number of methods described in the literature. For example, such piperazines may be prepared as seen in Hoveyda, H. et al. Bioorg. Med. Chem. Letters, 2011, 21, 1991; Webster, S. et al. Bioorg. Med. Chem. Lett. 2007, 17, 2838; Bavetsias, V. et al. J. Med. Chem. 2012, 5, 8721 or other suitable method or combination of conditions/methods available in the literature and known to persons skilled in the art. These disclosures are hereby incorporated by reference.

Pyrazoles of the general structure II, where $R_1$ is H or alkyl or fluoro and P a suitable protecting group, can be prepared via the N protection of the corresponding unprotected pyrazoles. THP, trityl, SEM, Methoxybenzyl or other protecting group that will not interfere with the coupling conditions or its deprotection will not unwantedly affect existing functionality may be used. Methods for introducing and removing THP, trityl, SEM or other suitable groups can be seen in Green, T; Wuts, P. Protective Groups in Organic Synthesis, $2^{nd}$ edition, Willey Interscience, 1991, the disclosure of which is incorporated by reference, or other literature available to persons skilled in the art.

Unprotected pyrazoles of the general structure II (scheme1), where $R_1$ is H or F, or $R_1$ is methyl are commercially available. They also may be prepared via either direct synthesis and/or functionalization of an unprotected pyrazole or via the functionalization of a transiently protected pyrazole substrate followed by deprotection via methods and procedures available in the literature and known to persons skilled in the art. For example, such pyrazoles may be synthesized as seen in Reimlinger et al. Chemische Berichte, 1961, 94, 1036; Sakamoto, T. et al. Heterocycles 1992, 33, 813; Rodriguez-Franco, I. et al. Tet. Lett. 2001, 42, 863; Knorr, Chem. Berichte 1904, 37, 3051; Easton, N. U.S. Pat. No. 2,992,163; Moslin, R. et al. PCT Int. Appl. 201474661; Nicholaou. K. et al. ChemMedChem 2015, 10, 1974; Lahm, G. Bioorg. Med. Chem. Letters 2007, 17, 6274; Miethchen, R. et al. J. Prakt. Chem. 1989, 331, 799; Elguero, J. et al. Bulletin de la Societe Chimique de France, 1966, 2832; Alcalde et al. Anales de Quimica (1968-1979), 1974, 70, 959; Hanamoto, T. et al. Tetrahedron, 2007, 63, 5062; Levchenko, V. et al. J. Org. Chem. 2018, 83, 3265-3274 or other suitable method or combination of conditions/methods available in the literature and known to persons skilled in the art. These disclosures are incorporated by reference.

General Procedure 1: THP Protection of Iodopyrazoles

Desired iodopyrazole (1 eq) in $CH_2Cl_2$ was treated with dihydropyran (1.1 eq) and a p-toluolosulfonic acid monohydrate (0.1 eq) at room temperature. Reaction mixture was allowed to stir until consumption of starting material was seen on TLC and then it was partitioned between $CH_2Cl_2$ and aq. saturated $Na_2CO_3$ solution. Aqueous layer was extracted with $CH_2Cl_2$ (X3) and combined organic layer was dried over $Na_2SO_4$ and concentrated to a crude residue that was chromatographed with silica gel column to afford the desired THP-protected iodopyrazole.

Intermediate 1. THP-Protected 4-iodo-pyrazole

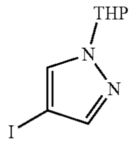

Prepared from commercially available 4-iodo-1H-pyrazole according to general procedure 1. The crude product was chromatographed using a 0-20% EtOAc in hexanes. The desired compound was isolated as a colorless viscous syrup (80% yield). $^1$H NMR (600 MHz, $CDCl_3$) δ 1.59-1.71 (m, 3H), 1.99-2.11 (m, 3H), 3.65-3.71 (m, 1H), 4.01-4.05 (m, 1H), 5.37 (dd, J=8.4, 3.6 Hz, 1H), 7.54 (s, 1H), 7.66 (s, 1H).

Intermediate 2. THP-Protected 3-iodo-pyrazole

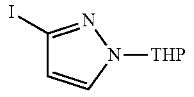

THP protection of commercially available 3-iodo-1H-pyrazole was carried out according to general method 1. The crude product was chromatographed using a 0-30% EtOAc in hexanes. The desired compound was isolated as a colorless viscous syrup (77% yield). Structure of the THP-protected product has been tentatively assigned as 3-iodo-1-(tetrahydro-2H-pyran-2-yl)-1H-pyrazole. $^1$H NMR (600 MHz, $CDCl_3$) δ 1.53-1.62 (m, 1H), 1.62-1.72 (m, 2H), 1.99-2.12 (m, 3H), 3.65-3.72 (m, 1H), 4.05-4.10 (m, 1H), 5.36 (dd, J=9.0, 3.0 Hz, 1H), 6.45 (d, J=2.4 Hz, 1H), 7.43 (d, J=2.4 Hz, 1H).

Intermediate 3. THP-Protected 4-iodo-3-methyl-1-pyrazole

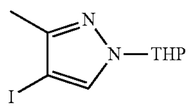

THP protection of commercially available 4-iodo-3-methyl-1H-pyrazole was carried out according to general method 1. Crude product was chromatographed using a 0-30% EtOAc in hexanes. Desired compound was isolated as a colorless viscous syrup (72% yield). Structure of the THP-protected product has been tentatively assigned as 4-iodo-3-methyl-1-(tetrahydro-2H-pyran-2-yl)-1H-pyrazole. $^1$H NMR (400 MHz, $CDCl_3$) δ 1.58-1.72 (m, 3H), 1.97-2.11 (m, 3H), 2.25 (s, 3H), 3.67 (apparent td, J=11.2, 2.8 Hz, 1H), 4.01-4.09 (m, 1H), 5.27 (dd, J=9.6, 2.8 Hz 1H), 7.57 (s, 1H).

Intermediate 4. THP-Protected 3-iodo-5-methyl-1H-pyrazole

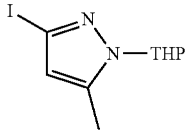

THP protection of commercially available 3-iodo-5-methyl-1H-pyrazole was carried out according to general method 1. Crude product was chromatographed using a 0-30% EtOAc in hexanes. Desired compound was isolated as a pale yellow syrup (99% yield). Structure of the THP-protected product has been tentatively assigned as 3-iodo-5-methyl-1terahydro-2H-pyranyl)-1H-pyrazole $^1$H NMR (400 MHz, $CDCl_3$) δ 1.53-1.75 (m, 3H), 1.89-1.98 (m, 1H), 2.06-2.13 (m, 1H), 2.32 (s, 3H), 2.38-2.48 (m, 1H), 3.62 (distorted td, J=11.2, 2.8 Hz, 1H), 3.98-4.04 (m, 1H), 5.21 (dd, J=10.0, 2.8 Hz, 1H), 6.19 (s, 1H).

Intermediate 5. N-(4-Bromo-3-fluorophenyl)-N-methylacetamide

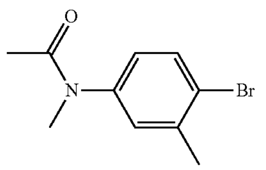

4-Bromo-3-fluoroaniline (2.00 g, 10.5 mmol) in $CH_2Cl_2$ (5 mL) was treated with $Et_3N$ (3.20 g, 4.32 mL, 31.5 mmol) and then acetic anhydride (1.30 g, 12.6 mmol). The reaction mixture was stirred at room temperature until TLC indicated that the limiting reagent was consumed. Followed partition between $CH_2Cl_2$ and aq. saturated $Na_2CO_3$. The organic layer was then dried over $Na_2SO_4$, filtered and concentrated to a solid residue that was dissolved in $CH_2Cl_2$. This solution was treated with excess of hexanes to precipitate the corresponding intermediate acetanilide as an off white solid. This solid, after drying, was dissolved in DMF under argon. Followed addition of NaH, as 60% dispersion in mineral oil, (590 mg. 14.8 mmol) in portions. Then followed slow (dropwise) addition of MeI (1.69 g, 11.9 mmol, and 0.74 mL). The reaction mixture was stirred for 4.5 hr and then partitioned between EtOAc and water. Aq. layer was extracted with $CH_2Cl_2$ and the combined organic layer was dried over $Na_2SO_4$, filtered and concentrated. The residue was chromatographed with silica gel column and 0-40% EtOAC in $CH_2Cl_2$ gradient to afford the product as a white solid (2.0 g, 77% yield). $^1$H NMR (600 MHz, $CDCl_3$) δ 1.91 (bs, 3H), 3.24 (bs, 3H), 6.91 (bd, J=8.4 Hz, 1H), 7.00 (bd, J=7.8 Hz, 1H), 7.60 (t, J=7.8 Hz, 1H)

Intermediate 6. (R)-1-(1-(4-Bromophenyl)ethyl) pyrrolidin-2-one (LMS-VI-86-II)

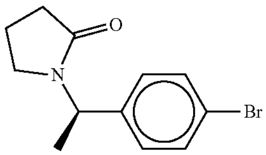

Commercially available (R)-(+)-1-(4-bromophenyl) ethylamine (1.2 g, 5.95 mmol) in THF (20 mL) was treated with $Et_3N$ (0.60 g, 5.95 mmol, and 0.81 mL). Followed slow addition of 4-chlorobutyryl chloride (0.84 g, 5.95 mmol) at 0° C. The reaction mixture was stirred for 30 min and then partitioned between $CH_2Cl_2$ and aq. saturated $NH_4Cl$. Aq. layer was extracted twice more with $CH_2Cl_2$ and the combined organic layer was dried over $Na_2SO_4$, filtered and concentrated to afford the corresponding (R)-chlorobutanamide intermediate. This intermediate without further purification was then dissolved in dry THF. Followed addition of NaH, as 60% dispersion in mineral oil, (290 mg 7.25 mmol) in portions under argon. The mixture stirred at room temperature under argon for 50 min and then the reaction vessel was sealed and the mixture was heated to 55° C. for 7 hrs. Reaction mixture was then cooled and partitioned between $CH_2Cl_2$ and aq. saturated $NH_4Cl$. The aqueous layer was extracted with $CH_2Cl_2$ (×3) and combined organic layer was dried over $Na_2SO_4$, filtered and concentrated. The residue was chromatographed on a silica gel column with 0-80% EtOAc in hexane to afford the product as colorless oil (1.48 g, 93% yield). $^1H$ NMR (600 MHz, $CDCl_3$) δ 1.50 (d, J=7.2 Hz, 3H), 1.70-1.94 (m, 1H), 1.94-2.03 (m, 1H), 2.35-2.46 (m, 2H), 2.96 (ddd, J=14.4, 9.0, 5.4 Hz, 1H), 5.45 (q, J=7.2 Hz, 1H), 3.31 (ddd, J=15.0, 8.4, 6.0 Hz, 1H), 7.17 (d, J=7.8 Hz, 2H), 7.45 (d, J=8.4 Hz, 2H).

Intermediate 7. (S)-1-(1-(4-Bromophenyl)ethyl) pyrrolidin-2-one (LMS-VI-87-II)

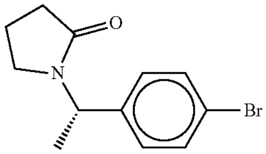

Commercially available (S)-1-(4-bromophenyl)ethan-1-amine (1.22 g, 6.09 mmol) in dry THF was treated with $Et_3N$ (620 mg, 0.84 mL, 6.09 mmol). Followed slow addition of 4-chlorobutyryl chloride (860 mg, 0.68 mL, 6.09 mmol) at 0° C. The reaction mixture was then stirred for 30 min at room temperature and partitioned between $CH_2Cl_2$ and aq. saturated $NH_4Cl$. Aq. layer was extracted with $CH_2Cl_2$ (×3) and the combined organic layer was dried over $Na_2SO_4$, filtered and concentrated to afford the corresponding (S)-chlorobutanamide intermediate. This intermediate, without further purification, was dissolved in dry THF. Followed addition of NaH, as 60% dispersion in mineral oil, (300 mg 7.46 mmol) in portions under argon. The mixture stirred at room temperature under argon for 2.5 hr and then partitioned between $CH_2Cl_2$ and aq. saturated $NH_4Cl$. The aqueous layer was extracted with $CH_2Cl_2$ (×3) and combined organic layer was dried over $Na_2SO_4$, filtered and concentrated. The residue was chromatographed on a silica gel column with 0-80% EtOAc in hexanes to afford the product as colorless oil (1.52 g, 93% yield). $^1H$ NMR (600 MHz, $CDCl_3$) δ 1.49 (d, J=7.2 Hz, 3H), 1.86-1.95 (m, 1H), 1.95-2.03 (m, 1H), 2.36-2.47 (m, 2H), 2.96 (ddd, J=14.4, 9.0, 5.4 Hz, 1H), 3.31 (ddd, J=15.0 Hz, 8.4 Hz, 6.0 Hz, 1H), 5.45 (q, J=7.2 Hz, 1H), 7.17 (d, J=8.4 Hz, 2H), 7.46 (d, J=8.4 Hz, 2H).

Intermediate 8. (4-Bromophenyl)(pyrrolidin-1-yl) methanone. (SHM-I-17-01)

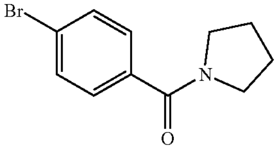 [SMILES: O=C(c1ccc(Br)cc1)N1CCCC1]

To a solution of 4-bromobenzoic acid (2.0 g, 9.95 mmol) in THF (12 mL) was added DMAP (121 mg, 0.99 mmol) and then EDCI·HCl (2.5 g, 12.93 mmol). The reaction mixture was stirred for 15 min. Then, pyrrolidine (708 mg, 0.830 mL, 9.95 mmol) was added and the reaction mixture and allowed to stir at room temperature for overnight. The reaction mixture was then diluted with water and extracted with EtOAc (3×50 mL). The combined organic layer was dried over $Na_2SO_4$, filtered and evaporated. The residue was chromatographed on a silica gel column with 0-80% EtOAc in hexanes gradient to afford the product as a white solid (2.1 g, 83% yield). $^1H$NMR (400 MHz, $CDCl_3$) δ 7.53 (d, J=8.4 Hz, 2H), 7.39 (d, J=8.4 Hz, 2H), 3.62-3.40 (m, 4H), 1.93-1.90 (m, 4H).

Intermediate 9. (4-Bromo-3-fluorophenyl)(pyrrolidin-1-yl)methanone (SHM-I-39-01)

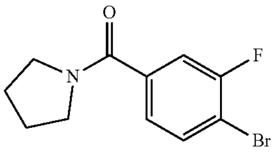 [SMILES: O=C(c1ccc(Br)c(F)c1)N1CCCC1]

To a solution of 4-bromo-3-fluorobenzoic acid (1.5 g, 6.84 mmol) in THF (15 mL), was added DMAP (83 mg, 0.68 mmol) and then EDCI·HCl (1.7 g, 8.90 mmol). The reaction mixture was stirred for 15 min. Then, pyrrolidine (535 mg, 0.627 mL, 7.53 mmol) was added and the reaction mixture was allowed to stir at room temperature for overnight. The reaction mixture was then diluted with water and extracted with EtOAc (3×50 mL). The combined organic layer was dried over $Na_2SO_4$ filtered and evaporated. The residue was chromatographed on a silica gel column with 0-80% EtOAc in hexanes to afford the product as white solid (1.4 g, 75% yield). $^1H$NMR (400 MHz, $CDCl_3$) δ 7.60 (t, J=6.5 Hz, 1H), 7.31 (dd, J=9.0, 2.0 Hz, 1H), 7.21 (dd, J=8.0, 1.5 Hz, 1H) 3.64 (s, 2H), 3.43 (s, 2H), 1.97-1.93 (m, 4H).

Intermediate 10. 1-((4-Bromophenyl)sulfonyl)pyrrolidine. (SHM-I-37-01)

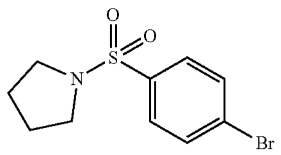 [SMILES: O=S(=O)(c1ccc(Br)cc1)N1CCCC1]

To a solution of pyrrolidine (278 mg, 0.326 mL, 3.92 mmol) and $Et_3N$ (396 mg, 0.545 mL, 3.92 mmol) in $CH_2Cl_2$, at 0° C. was added 4-bromobenzenesulfonyl chloride (1 g, 3.92 mmol) was added to the reaction mixture and the mixture was stirred and slowly allowed to warm up to rt by itself. After stirring overnight, this reaction mixture was diluted with water and extracted with EtOAc (3×50 mL). The combined organic layer was dried over $Na_2SO_4$, filtered and evaporated. The residue was chromatographed on a silica gel column with 0-80% EtOAc in hexanes gradient to afford the product as white solid (950 mg, 84% yield). $^1$HNMR (500 MHz, $CDCl_3$) δ 7.64-7.59 (m, 4H), 3.18-3.15 (m, 4H), 1.72-1.69 (m, 4H).

Intermediate 11. 5-Bromo-2,3-dihydrobenzo[b]thiophene 1,1-dioxide

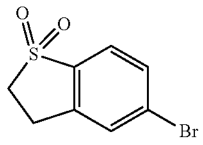 [SMILES: O=S1(=O)CCc2cc(Br)ccc21]

To a solution of 5-bromobenzo[b]thiophene (1.5 g, 7.04 mmol) in $CH_2Cl_2$, was added mCPBA (3.03 g, 17.60 mmol). The mixture was stirred at room temperature for overnight. Followed addition of 1N aq $Na_2SO_3$ solution and stirred at RT for 20 min. Then the reaction mixture was extracted with $CH_2Cl_2$ (3×50 mL). The combined organic layer was washed with 2N aqueous $NaHCO_3$ solution, dried over $Na_2SO_4$ filtered and concentrated. The crude product (1.1 g, 4.45 mmol) obtained from this operation was dissolved in EtOH and treated with $NaBH_4$ (259 mg, 6.73 mmol). The mixture was stirred at RT for overnight. The reaction mixture was quenched with 1M aq. HCl. Followed evaporation of the volatiles to a residue that was then treated with 2N aq. $NaHCO_3$ solution (pH 9). The mixture was extracted with EtOAc (3×50 mL) and combined organic layer was dried over $Na_2SO_4$ filtered and evaporated. The residue was chromatographed on a silica gel column with 0-80% EtOAc in hexanes gradient to afford the product as white solid (800 mg, 46% yield). $^1$HNMR (300 MHz, DMSO-$d_6$) δ 7.84 (d, J=2.1 Hz, 1H), 7.72-7.71 (m, 2H), 3.64-3.59 (m, 2H), 3.38-3.34 (m, 2H).

Intermediate 12. 4-Bromo-N-(1,1,1-trifluoropropan-2-yl)aniline

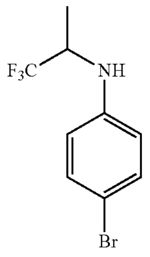

To a solution of 4-bromoaniline (2.0 g, 11.62 mmol) in toluene, was added commercially available 2-bromo-3,3,3-trifluoroprop-1-ene (2.44 g, 13.95 mmol). Then added $Pd_2(dba)_3$ (532 mg, 0.58 mmol), dppf (966 mg, 1.74 mmol), and subsequently $Cs_2CO_3$ (13.95 mmol) under Argon. The mixture was then sealed and stirred at 110° C. for overnight. The reaction mixture was cooled and partioned between EtOAc and water. Aqueous layer was extracted with EtOAc (3×50 mL) and then the combined organic layer was dried over $Na_2SO_4$, filtered and concentrated. The residue was chromatographed on silica gel using 0-10% EtOAc in Hexanes as gradient. The intermediate (Z)—N-(4-bromophenyl)-1,1,1-trifluoropropan-2-imine obtained from this operation (1 g, 3.75 mmol) was treated with 2M $LiAlH_4$ in THF (214 mg, 2.81 mL 5.6 mmol) in dry THF at 0° C. The mixture was slowly allowed to reach room temperature and stirred for 2 hours. The reaction mixture was then quenched with 1M aq. HCl and stirred for 20 min. The reaction mixture pH was then adjusted to 9 using $K_2CO_3$ aqueous solution. Followed extraction with EtOAc (3×50 mL). The combined organic layer was dried over $Na_2SO_4$, filtered and evaporated. The residue was chromatographed on a silica gel column with 0-80% EtOAc in hexanes gradient to afford the product as white solid (875 mg, 43% yield). $^1$HNMR (600 MHz, $CDCl_3$) δ 7.23-7.20 (m, 2H), 6.48 (d, J=9.0 Hz, 2H), 3.93-3.88 (m, 1H), 3.54-3.53 (m, 1H), 1.33 (d, J=6.6 Hz, 3H).

Intermediate 13. 1-(4-Bromobenzyl)pyrrolidin-2-one. (SHM-I-53-01)

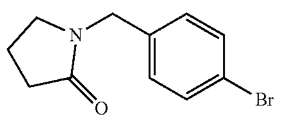 [SMILES: O=C1CCCN1Cc1ccc(Br)cc1]

To a solution of pyrrolidin-2-one (400 mg, 4.7 mmol) in DMF, followed addition of NaH, as 60% dispersion in mineral oil (283 mg, 7.05 mmol) in portions under argon and stirred for 30 min. Then, commercially available 1-bromo-4-(bromomethyl)benzene (1.3 g, 5.17 mmol) was added to the reaction mixture at 0° C. and allowed to stir at room temperature for overnight. The reaction mixture was diluted with water and extracted with EtOAc. Combined organic layer was then dried over $Na_2SO_4$ filtered and concentrated. The residue was chromatographed on a silica gel column with 0-80% EtOAc in hexane to afford the product as white solid (820 mg, 82% yield). $^1$HNMR (600 MHz, $CDCl_3$) δ

7.38 (d, J=8.4 Hz, 2H), 7.05 (d, J=8.4 Hz, 2H), 4.32 (s, 2H), 3.18 (t, J=6.6 Hz, 2H), 2.37 (t, J=7.8 Hz, 2H), 1.95-1.91 (m, 2H).

Intermediate 14.
1-(4-Bromo-2-fluorobenzyl)pyrrolidin-2-one

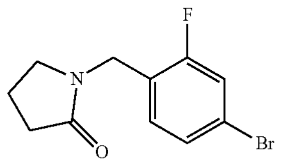 [SMILES: O=C1CCCN1Cc1ccc(Br)cc1F]

To a solution of pyrrolidin-2-one (1 g, 11.76 mmol) in DMF, followed addition of NaH, as 60% dispersion in mineral oil (566 mg, 14.11 mmol) in portions under argon and stirred for 30 min. Then, commercially available 4-bromo-1-(bromomethyl)-2-fluorobenzene (1.5 g, 11.76 mmol) was added to the reaction mixture at 0° C. The mixture was allowed warm up at room temperature and stir overnight. The reaction mixture was diluted with water and then extracted with EtOAc. Combined organic layer was dried over $Na_2SO_4$, filtered and evaporated and the residue was chromatographed on a silica gel column with 0-80% EtOAc in hexanes to afford the product as white solid (2.61 g, 82% yield). $^1$HNMR (600 MHz, $CDCl_3$) δ 7.23-7.19 (m, 2H), 7.14 (t, J=8.4 Hz, 1H), 4.42 (s, 2H), 3.27 (t, J=7.2 Hz, 2H), 2.37 (t, J=8.4 Hz, 2H), 1.99-1.94 (m, 2H).

Intermediate 15. 1-(4-Bromo-2-chlorobenzyl)pyrrolidin-2-one. (SHM-I-149-01)

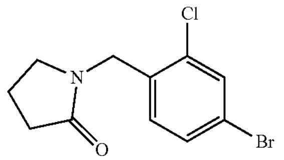 [SMILES: O=C1CCCN1Cc1ccc(Br)cc1Cl]

A solution of pyrrolidin-2-one (300 mg, 3.5 mmol) in DMF, was treated with NaH, as 60% dispersion in mineral oil (169 mg, 4.23 mmol), in portions under argon and stirred for 30 min. Then, commercially available 1-bromo-4-(bromomethyl)-2-chlorobenzene (1 g, 3.5 mmol) was added to the reaction mixture at 0° C. and the mixture was allowed warm up to rt and stir overnight. The mixture was then diluted with water and extracted with EtOAc. Combined organic layer was back extracted with cold water, dried over $Na_2SO_4$ filtered and concentrated. The residue was chromatographed on a silica gel column with 0-80% EtOAc in hexanes to afford the product as white solid (530 mg, 52% yield). $^1$HNMR (600 MHz, $CDCl_3$) δ 7.51 (d, J=1.8 Hz, 1H), 7.34 (d, J=7.8 Hz, 1H), 7.13 (d, J=8.4 Hz, 1H), 4.52 (s, 2H), 3.29 (t, J=7.2 Hz, 2H), 2.42 (t, J=7.8 Hz, 2H), 2.03-1.99 (m, 2H).

Intermediate 16.
1-(4-Bromo-3-fluorobenzyl)pyrrolidin-2-one

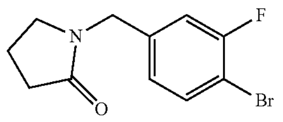 [SMILES: O=C1CCCN1Cc1ccc(Br)c(F)c1]

To the solution of pyrrolidin-2-one (1 g, 11.76 mmol) in DMF, followed addition of NaH, as 60% dispersion in mineral oil (566 mg, 14.11 mmol) in portions under argon and stirred for 30 min. Then, commercially available 1-bromo-4-(bromomethyl)-2-fluorobenzene (3.1 g, 11.76 mmol) was added to the reaction mixture at 0° C. The mixture was allowed to warm up to rt and stirred overnight. Followed dilution with water and then extraction with EtOAc. The combined organic layer was back extracted with cold water, dried over $Na_2SO_4$ filtered and concentrated. The residue was chromatographed with a silica gel column with 0-80% EtOAc in hexanes gradient to afford the product as white solid (1.9 g, 60% yield). $^1$HNMR (600 MHz, $CDCl_3$) δ 7.45 (d, J=1.8 Hz, 1H), 6.97 (d, J=7.8 Hz, 1H), 6.87 (d, J=8.4 Hz, 1H), 4.36 (s, 2H), 3.23 (t, J=7.2 Hz, 2H), 2.40 (t, J=7.8 Hz, 2H), 2.01-1.95 (m, 2H).

Intermediate 17. 1-(4-Bromo-3-fluorophenyl)pyrrolidin-2-one (SHM-JJ-64-02)

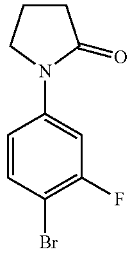 [SMILES: O=C1CCCN1c1ccc(Br)c(F)c1]

Commercially available 4-bromo-3-fluoroaniline (1.5 g, 7.894 mmol) in THF was treated with $Et_3N$ (798 mg, 1.1 mL, 7.89 mmol). Followed slow addition of 4-chlorobutyryl chloride (1.3 g, 1.68 mL, 7.89 mmol) at 0° C. The reaction mixture was then stirred for 30 min at room temperature and partitioned between $CH_2Cl_2$ and aq. saturated $NH_4Cl$. Aq. layer was extracted with $CH_2Cl_2$ (×3) and the combined organic layer was dried over $Na_2SO_4$, filtered and concentrated to afford the corresponding N-(4-bromo-3-fluorophenyl)-3-chloropropanamide (3.2 g, 10.86 mmol). This intermediate, without further purification, was dissolved in dry THF. Followed addition of NaH, as 60% dispersion in mineral oil, (651 mg, 16.29 mmol) in portions under argon. The mixture stirred at room temperature under argon for 2.5 hr and then partitioned between $CH_2Cl_2$ and aq. saturated $NH_4Cl$. The aqueous layer was extracted with $CH_2Cl_2$ (×3) and combined organic layer was dried over $Na_2SO_4$, filtered and concentrated. The residue was chromatographed on a silica gel column with 0-80% EtOAc in hexanes to afford the product as white solid (1.83 g, 90% yield). $^1$H NMR (400 MHz, $CDCl_3$) δ 7.63 (dd, J=11.2, 2.4 Hz, 1H), 7.49 (t, J=8.4 Hz, 1H), 7.25 (dd, J=8.0, 2.0 Hz, 1H), 3.82 (t, J=6.8 Hz, 2H), 2.61 (t, J=8.0 Hz, 2H), 2.21-2.13 (m, 2H).

General Procedure 2. Synthesis of N-Boc-protected 4-aryl/heteroaryl 3,6-dihydropyridines N-Boc protected 4-aryl-3,6-dihydropyridines were prepared in the general fashion described by Eastwood (Tetrahedron Letters, 2000, 41(19), 3705-3708), this is hereby incorporated by reference, from commercially available tert-butyl 4-(4,4,5,5-tetramethyl-1,3,2-dioxaborolan-2-yl)-3,6-dihydropyridine-1(2H)-carboxylate (1 eq) and a desired arylbromide (1 eq) using $PdCl_2$ dppf as catalyst (0.05 eq), $K_2CO_3$ (3 eq) as base and DMF or dioxane or dioxane/$H_2O$ as solvent.

Intermediate 18. tert-Butyl 4-(4-methoxyphenyl)-3,6-dihydropyridine-1(2H)-carboxylate

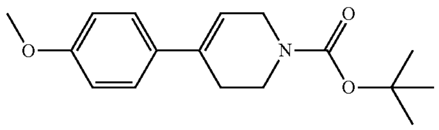 [SMILES: COc1ccc(C2=CCN(C(=O)OC(C)(C)C)CC2)cc1]

Prepared via the coupling of commercially available 4-bromoanisole and tert-butyl 4-(4,4,5,5-tetramethyl-1,3,2-dioxaborolan-2-yl)-3,6-dihydropyridine-1(2H)-carboxylate according to general procedure 2 and DMF as solvent. Crude coupling product was purified with silica gel column and 0-50% EtOAc in hexanes gradient to afford tert-butyl 4-(4-methoxyphenyl)-3,6-dihydropyridine-1(2H)-carboxylate as a white solid (50% yield). $^1$H NMR (400 MHz, $CDCl_3$) δ 1.49 (s, 9H), 2.50 (apparent bs, 2H), 3.62 (apparent t, J=6.0 Hz, 2H), 3.81 (s, 3H), 4.03-4.08 (m, 2H), 5.93 (s, 1H), 6.88 (d, J=6.8 Hz, 2H), 7.31 (d, J=6.8 Hz, 2H).

Intermediate 19. tert-Butyl 4-(3-methoxyphenyl)-3,6-dihydropyridine-1(2H)-carboxylate

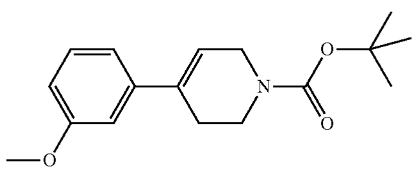 [SMILES: COc1cccc(C2=CCN(C(=O)OC(C)(C)C)CC2)c1]

Prepared via the coupling of commercially available 3-bromoanisidine and tert-butyl 4-(4,4,5,5-tetramethyl-1,3,2-dioxaborolan-2-yl)-3,6-dihydropyridine-1(2H)-carboxylate according to general procedure 2 using DMF as solvent. Crude coupling product was purified with silica gel column and 0-10% EtOAc in hexanes gradient to afford tert-butyl 4-(3-methoxyphenyl)-3,6-dihydropyridine-1(2H)-carboxylate (78% yield). $^1$H NMR (400 MHz, $CDCl_3$) δ 1.48 (s, 9H), 2.51 (apparent bs, 2H), 3.63 (apparent distorted t, J=5.6 Hz, 2H), 3.82 (s, 3H), 4.04-4.08 (m, 2H), 6.03 (bs, 1H), 6.80 (dd, J=8.0, 2.0 Hz, 1H), 6.90 (apparent t, J=2.0 Hz, 1H), 6.96 (apparent d, J=8.0 Hz, 1H), 7.25-7.28 (m, 1H).

Intermediate 20. tert-Butyl 4-(pyrimidin-2-yl)-3,6-dihydropyridine-1(2H)-carboxylate

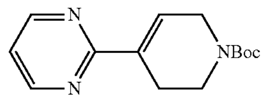

Prepared using commercially available 2-chloropyrimidine and tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (10/1 ratio) as solvent. Crude coupling product was chromatographed with silica gel column and 0-40% EtOAc in hexanes to afford the desired tert-butyl 4-(pyrimidin-2-yl)-3,6-dihydropyridine-1(2H)-carboxylate (88% yield). $^1$H NMR (400 MHz, $CDCl_3$) δ 1.52 (s, 9H), 2.75 (apparent bs, 2H), 3.67 (t, J=4.8 Hz, 2H), 4.20 (apparent broad-based d, J=2.4 Hz, 2H), 7.14 (t, J=4.8 Hz, 1H), 7.23 (bs, 1H), 8.72 (d, J=4.8 Hz, 2H).

Intermediate 21. tert-Butyl 4-(4-(methoxycarbonyl)phenyl)-3,6-dihydropyridine-1(2H)-carboxylate

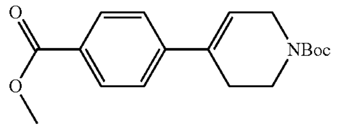

Prepared from commercially available methyl 4-bromobenzoate and tert-butyl 4-(4,4,5,5-tetramethyl-1,3,2-dioxaborolan-2-yl)-3,6-dihydropyridine-1(2H)-carboxylate according to general procedure 2 using DMF as solvent. Crude coupling product was purified with silica gel column and 0-15% EtOAc in Hexanes as elution system to afford desired tert-butyl 4-(4-(methoxycarbonyl)phenyl)-3,6-dihydropyridine-1(2H)-carboxylate (67% yield). $^1$H NMR (400 MHz, $CDCl_3$) δ 1.52 (s, 9H), 2.57 (apparent bs, 2H), 3.67 (t, J=5.2 Hz, 2H), 3.94 (s, 3H), 4.13 (apparent bs, 2H), 6.19 (bs, 1H), 7.45 (d, J=8.4 Hz, 2H), 8.01 (d, J=8.4 Hz, 2H).

Intermediate 22. tert-Butyl 6-nitro-3',6'-dihydro-[3,4'-bipyridine]-1'(2'H)-carboxylate

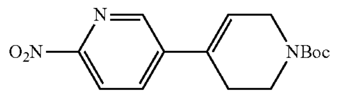

Prepared from commercially available 5-bromo-2-nitropyridine and tert-butyl 4-(4,4,5,5-tetramethyl-1,3,2-dioxaborolan-2-yl)-3,6-dihydropyridine-1(2H)-carboxylate according to general procedure 2 using dioxane as solvent. Crude coupling product was purified with silica gel column and 0-25% EtOAc in hexanes gradient to afford tert-butyl 6-nitro-3',6'-dihydro-[3,4'-bipyridine]-1'(2'H)-carboxylate as a white/off-white solid (73% yield). $^1$H NMR (400 MHz, $CDCl_3$) δ 1.50 (s, 9H), 2.57 (apparent bs, 2H), 3.69 (t, J=5.6 Hz, 2H), 4.16 (apparent broad based d, J=2.4 Hz, 2H), 6.33 (bs, 1H), 7.94 (dd, J=8.4, 2.4 Hz, 1H), 8.24 (d, J=8.4 Hz, 1H), 8.64 (d, J=2.0 Hz, 1H).

Intermediate 23. tert-Butyl 2'-methoxy-3,6-dihydro-[4,4'-bipyridine]-1(2H)-carboxylate

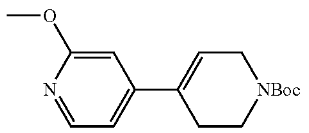 [SMILES: COc1cc(C2=CCN(C(=O)OC(C)(C)C)CC2)ccn1]

Compound was prepared from commercially available 4-bromo-2-methoxypyridine and tert-butyl 4-(4,4,5,5-tetramethyl-1,3,2-dioxaborolan-2-yl)-3,6-dihydropyridine-1(2H)-carboxylate according to general procedure 2 using dioxane as solvent. Crude coupling product was purified with silica gel column and 0-50% EtOAc in hexanes to afford, tert-butyl 2'-methoxy-3,6-dihydro-[4,4'-bipyridine]-1(2H)-carboxylate, as a light yellow viscous oil (71% yield). $^{1}H$ NMR (400 MHz, $CDCl_3$) δ 1.49 (s, 9H), 2.47 (apparent bs, 2H), 3.63 (t, J=5.6 Hz, 1H), 3.94 (s, 3H), 4.08-4.15 (m, 1H), 6.23 (bs, 1H), 6.68 (apparent s, 1H), 6.88 (dd, J=5.2, 1.6 Hz), 8.10 (dd, J=5.6, 0.8 Hz, 1H).

Intermediate 24. tert-Butyl 4-(2-methoxyphenyl)-3,6-dihydropyridine-1(2H)-carboxylate

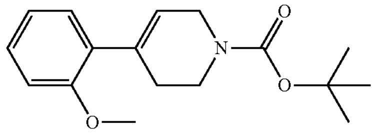 [SMILES: COc1ccccc1C1=CCN(C(=O)OC(C)(C)C)CC1]

Synthesized from commercially available 2-bromoanisole and tert-butyl 4-(4,4,5,5-tetramethyl-1,3,2-dioxaborolan-2-yl)-3,6-dihydropyridine-1(2H)-carboxylate according to general procedure 2. Crude coupling product was chromatographed with silica gel column and 0-100% EtOAc in hex gradient to afford tert-butyl 4-(2-methoxyphenyl)-3,6-dihydropyridine-1(2H)-carboxylate as colorless liquid (72% yield). $^{1}H$ NMR (400 MHz, $CDCl_3$) δ 1.49 (s, 9H), 2.5 (apparent bs, 2H), 3.59 (apparent t, 2H), 3.81 (s, 3H), 4.04 (s, 2H), 5.75 (s, 1H), 6.85-6.96 (m, 2H), 7.14 (dd, J=7.6, 1.6 Hz, 1H), 7.22-7.26 (m, 1H).

Intermediate 25. tert-Butyl 4-(p-tolyl)-3,6-dihydropyridine-1(2H)-carboxylate

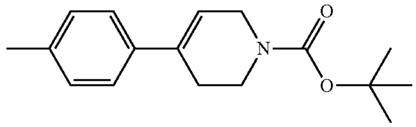 [SMILES: Cc1ccc(C2=CCN(C(=O)OC(C)(C)C)CC2)cc1]

Compound was prepared from commercially available 4-bromotoluene and tert-butyl 4-(4,4,5,5-tetramethyl-1,3,2-dioxaborolan-2-yl)-3,6-dihydropyridine-1(2H)-carboxylate according to general procedure 2 using DMF as solvent. The crude residue was chromatographed with silica gel column using 0-50% EtOAc in hexane gradient to afford the product, tert-butyl 4-(p-tolyl)-3,6-dihydropyridine-1(2H)-carboxylate, as a colorless oil (80% yield). $^{1}H$ NMR (400 MHz, $CDCl_3$) δ 1.49 (s, 9H), 2.34 (apparent s, 3H), 2.51 (apparent bs, 2H), 3.63 (apparent t, 2H), 4.06 (apparent s, 2H), 5.99 (s, 1H), 7.14 (d, J=7.6 Hz, 2H), 7.27 (d, J=7.6 Hz, 2H).

Intermediate 26. tert-Butyl 4-(4-(methoxymethyl)phenyl)-3,6-dihydropyridine-1(2H)-carboxylate

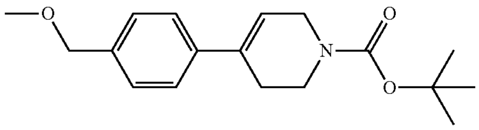 [SMILES: COCc1ccc(C2=CCN(C(=O)OC(C)(C)C)CC2)cc1]

Compound was prepared from 1-bromo-4-(methoxymethyl)benzene (prepared as in Rengan, K. et al. J. Chem. Soc. Perkin Trans. I, 1991, 987, incorporated herein by reference) and commercially available tert-butyl 4-(4,4,5,5-tetramethyl-1,3,2-dioxaborolan-2-yl)-3,6-dihydropyridine-1(2H)-carboxylate according to general procedure 2 using DMF as solvent. The crude residue was chromatographed with silica gel column using 0-40% EtOAc in hexane gradient to afford the product, tert-butyl 4-(4-(methoxymethyl)phenyl)-3,6-dihydropyridine-1(2H)-carboxylate, as a pale liquid (88% yield). $^{1}H$ NMR—(400 MHz, $CDCl_3$) δ 1.49 (s, 9H), 2.49-2.54 (broad m, 2H), 3.39 (s, 3H), 3.63 (apparent t, J=5.6 Hz, 2H), 4.07 (dd, J=5.6, 2.4 Hz, 2H), 4.45 (s, 2H), 6.04 (apparent bs, 1H), 7.30 (d, J=8.4 Hz, 2H), 7.36 (d, J=8.4 Hz, 2H).

Intermediate 27. tert-Butyl 4-(4-(N-methylacetamido)phenyl)-3,6-dihydropyridine-1(2H)-carboxylate

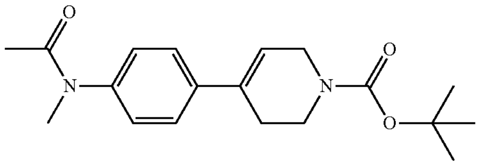 [SMILES: CC(=O)N(C)c1ccc(C2=CCN(C(=O)OC(C)(C)C)CC2)cc1]

Compound was prepared from N-(4-bromophenyl)-N-methylacetamide (prepared as in Shimma, N. et al. WO2008018426, the disclosure is hereby incorporated by reference) and commercially available tert-butyl 4-(4,4,5,5-tetramethyl-1,3,2-dioxaborolan-2-yl)-3,6-dihydropyridine-1(2H)-carboxylate following general procedure 2 using DMF as solvent. The crude residue was chromatographed with silica gel and 0-100% EtOAc in hexanes gradient to afford the product, tert-butyl 4-(4-(N-methylacetamido)phenyl)-3,6-dihydropyridine-1(2H)-carboxylate, as a pale yellow solid (82% yield). $^{1}H$ NMR (400 MHz, $CDCl_3$) δ 1.49 (s, 9H), 1.88 (s, 3H), 2.53 (bs, 2H), 3.26 (s, 3H), 3.66 (apparent distorted t, J=4.8 Hz, 2H), 4.09 (bs, 2H), 6.08 (bs, 1H), 7.15 (d, J=7.6 Hz, 2H), 7.41 (d, J=8.4 Hz, 2H).

Intermediate 28. tert-Butyl 4-(4-acetamidophenyl)-3,6-dihydropyridine-1(2H)-carboxylate

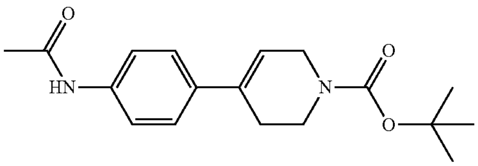 [SMILES: CC(=O)Nc1ccc(C2=CCN(C(=O)OC(C)(C)C)CC2)cc1]

Compound was synthesized from 4-bromoacetanilide (prepared as in Shimma, N. et al. WO2008018426, the disclosure is hereby incorporated by reference) and commercially available tert-butyl 4-(4,4,5,5-tetramethyl-1,3,2-dioxaborolan-2-yl)-3,6-dihydropyridine-1(2H)-carboxylate following general procedure 2 using DMF as solvent. The crude residue was chromatographed with a silica gel column and 0-100% EtOAc in hexanes gradient to afford the product, tert-butyl 4-(4-acetamidophenyl)-3,6-dihydropyridine-1(2H)-carboxylate, as a pale-yellow solid (77% yield). $^1$H NMR (400 MHz, $CDCl_3$) δ 1.49 (s, 9H), 2.18 (s, 3H), 2.49 (apparent bs, 2H), 3.62 (apparent t, J=5.6 Hz, 2H), 4.01-4.08 (m, 2H), 5.99 (bs, 1H), 7.23 (bs, 1H), 7.32 (d, J=8.8 Hz, 2H), 7.46 (d, J=8.8 Hz, 2H).

Intermediate 29. tert-Butyl 6-methoxy-3',6'-dihydro-[3,4'-bipyridine]-1'(2'H)-carboxylate

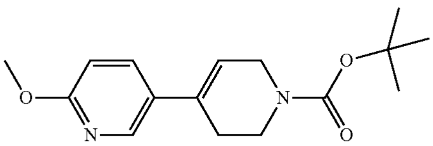 [SMILES: COc1ccc(C2=CCN(C(=O)OC(C)(C)C)CC2)cn1]

Synthesized from commercially available 5-bromo-2-methoxypyridine and tert-butyl 4-(4,4,5,5-tetramethyl-1,3,2-dioxaborolan-2-yl)-3,6-dihydropyridine-1(2H)-carboxylate according to general procedure 2 using DMF as solvent. Crude residue was purified with column chromatography and 0-20% EtOAc in $CH_2Cl_2$ gradient to afford the product as a pale liquid. $^1$H NMR (400 MHz, $CDCl_3$) δ 1.48 (s, 9H), 2.48 (apparent bs, 2H), 3.63 (apparent t, J=6.0 Hz, 2H), 3.94 (s, 3H), 4.05-4.08 (m, 2H), 5.95 (bs, 1H), 6.71 (dd, J=8.4, 0.4 Hz, 1H), 7.59 (dd, J=8.8, 2.8 Hz, 1H), 8.16 (d, J=2.0 Hz, 1H).

Intermediate 30. tert-Butyl 4-(m-tolyl)-3,6-dihydropyridine-1(2H)-carboxylate

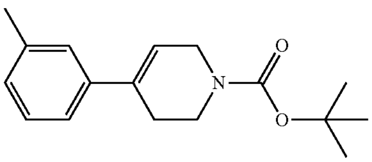 [SMILES: Cc1cccc(C2=CCN(C(=O)OC(C)(C)C)CC2)c1]

Compound was prepared from commercially available 3-bromotoluene and tert-butyl 4-(4,4,5,5-tetramethyl-1,3,2-dioxaborolan-2-yl)-3,6-dihydropyridine-1(2H)-carboxylate following general procedure 2 using DMF as solvent. The crude residue was chromatographed using silica gel column and 0-35% EtOAc in hexanes gradient to afford the product, tert-butyl 4-(m-tolyl)-3,6-dihydropyridine-1(2H)-carboxylate, as a colorless liquid (68% yield). $^1$H NMR (400 MHz, $CDCl_3$) δ 1.49 (s, 9H), 2.36 (s, 3H), 2.52 (apparent bs, 2H), 3.63 (apparent t, J=5.6 Hz, 2H), 4.07 (apparent s, 2H), 6.01 (bs, 1H), 7.07 (d, J=7.2 Hz, 1H), 7.15-7.25 (m, 3H).

Intermediate 31. tert-Butyl 4-(o-tolyl)-3,6-dihydropyridine-1(2H)-carboxylate

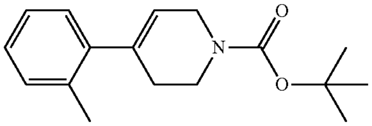 [SMILES: Cc1ccccc1C1=CCN(C(=O)OC(C)(C)C)CC1]

Compound was prepared from commercially available 2-bromotoluene and tert-butyl 4-(4,4,5,5-tetramethyl-1,3,2-dioxaborolan-2-yl)-3,6-dihydropyridine-1(2H)-carboxylate following general procedure 2 using DMF as solvent. The crude residue was chromatographed with silica gel column and 0-20% EtOAc in hexanes gradient to afford the product, tert-butyl 4-(o-tolyl)-3,6-dihydropyridine-1(2H)-carboxylate, as a clear liquid (70% yield). $^1$H NMR (400 MHz, $CDCl_3$) δ 1.50 (s, 9H), 2.79 (s, 3H), 2.31-2.38 (m, 2H), 3.62 (t, J=5.6 Hz, 2H), 4.03 (dd, J=6.0, 2.8 Hz, 2H), 5.55 (apparent bs, 1H), 7.04-7.09 (m, 1H), 7.13-7.19 (m, 3H).

Intermediate 32. tert-Butyl 4-(3-fluoro-4-methoxyphenyl)-3,6-dihydropyridine-1(2H)-carboxylate

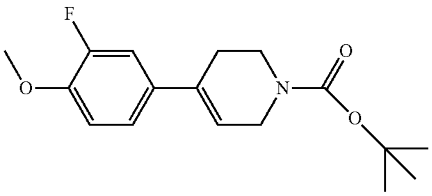 [SMILES: COc1ccc(C2=CCN(C(=O)OC(C)(C)C)CC2)cc1F]

Compound was prepared from commercially available 4-bromo-2-fluoro-1-methoxybenzene and tert-butyl 4-(4,4,5,5-tetramethyl-1,3,2-dioxaborolan-2-yl)-3,6-dihydropyridine-1(2H)-carboxylate following general procedure 2 using DMF as solvent. The crude residue was chromatographed using silica gel column and 0-15% EtOAc in hexanes gradient to afford the product as a colorless liquid (52% yield). $^1$H NMR (400 MHz, $CDCl_3$) δ 1.48 (s, 9H), 2.46 (s, 2H), 3.62 (t, J=5.6, 2H), 3.89 (s, 3H), 4.04-4.07 (m, 2H), 5.96 (bs, 2H), 6.91 (apparent t, J=8.8 Hz, 1H), 7.06-7.14 (m, 2H).

Intermediate 33. tert-Butyl 4-(2-fluoro-4-methoxyphenyl)-3,6-dihydropyridine-1(2H)-carboxylate

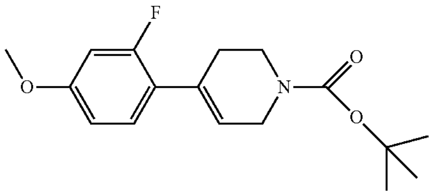 [SMILES: COc1ccc(C2=CCN(C(=O)OC(C)(C)C)CC2)c(F)c1]

Compound was prepared from commercially available 4-bromo-3-fluoro-1-methoxybenzene and tert-butyl 4-(4,4,5,5-tetramethyl-1,3,2-dioxaborolan-2-yl)-3,6-dihydropyridine-1(2H)-carboxylate following general procedure 2 using dioxane/$H_2O$ (10:1) as solvent. The crude residue was chromatographed using silica gel column and 0-10% EtOAc in hexanes gradient to afford the product as a colorless liquid (89% yield). $^1$H NMR (400 MHz, $CDCl_3$) δ 1.49 (s, 9H), 2.48 (apparent bs, 2H), 3.60 (t, J=5.6, 2H), 3.80 (s, 3H), 4.04-4.06 (m, 2H), 5.86 (bs, 1H), 6.60 (dd, J=12.8, 2.4 Hz, 1H), 6.66 (dd, J=8.0, 2.4 Hz, 1H), 7.15 (apparent t, J=8.4, 1H).

Intermediate 34. tert-Butyl 4-(2-fluorophenyl)-3,6-dihydropyridine-1(2H)-carboxylate

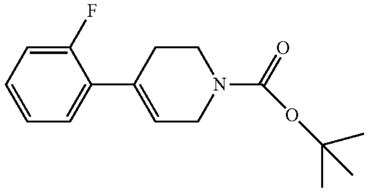 [SMILES: CC(C)(C)OC(=O)N1CC=C(c2ccccc2F)CC1]

Compound was prepared from commercially available 2-fluoro-bromobenzene and tert-butyl 4-(4,4,5,5-tetramethyl-1,3,2-dioxaborolan-2-yl)-3,6-dihydropyridine-1(2H)-carboxylate following general procedure 2 using dioxane/$H_2O$ (10:1) as solvent. The crude residue was chromatographed using silica gel column and 0-30% EtOAc in hexanes gradient to afford the product, tert-butyl 4-(2-fluorophenyl)-3,6-dihydropyridine-1(2H)-carboxylate, as a white solid (94% yield). $^1$H NMR (400 MHz, $CDCl_3$) δ 1.50 (s, 9H), 2.51 (apparent bs, 2H), 3.62 (t, J=5.6, 2H), 4.05-4.09 (m, 2H), 5.93 (bs, 1H), 7.00-7.07 (m, 1H), 7.07-7.13 (m, 1H), 7.19-7.26 (m, 2H).

Intermediate 35. tert-Butyl 4-(3-(methoxycarbonyl)phenyl)-3,6-dihydropyridine-1(2H)-carboxylate

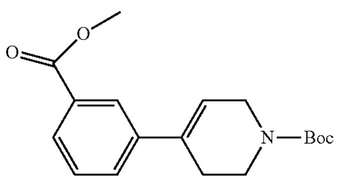 [SMILES: COC(=O)c1cccc(C2=CCN(C(=O)OC(C)(C)C)CC2)c1]

Prepared from commercially available methyl 3-bromobenzoate and tert-butyl 4-(4,4,5,5-tetramethyl-1,3,2-dioxaborolan-2-yl)-3,6-dihydropyridine-1(2H)-carboxylate according to general procedure 2 using DMF as solvent. Crude coupling product was purified with silica gel column and 0-100% EtOAc in hexanes gradient to afford tert-butyl 4-(3-(methoxycarbonyl)phenyl)-3,6-dihydropyridine-1(2H)-carboxylate as a viscous liquid (86% yield). $^1$H NMR (400 MHz, $CDCl_3$) δ 1.49 (s, 9H), 2.55 (apparent bs, 2H), 3.65 (t, J=6.0 Hz, 2H), 3.92 (s, 3H), 4.09 (apparent bs, 2H), 6.11 (bs 1H), 7.40 (distorted t, J=7.6 Hz, 1H), 7.56 (d, J=7.6 Hz, 1H), 7.92 (d, J=7.6 Hz, 1H), 8.05 (bs, 1H).

Intermediate 36. tert-Butyl 4-(4-(ethylsulfonyl)phenyl)-3,6-dihydropyridine-1(2H)-carboxylate

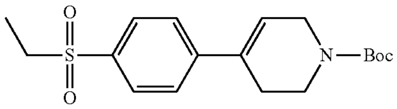 [SMILES: CCS(=O)(=O)c1ccc(C2=CCN(C(=O)OC(C)(C)C)CC2)cc1]

Compound was synthesized from commercially available tert-butyl 4-(4,4,5,5-tetramethyl-1,3,2-dioxaborolan-2-yl)-3,6-dihydropyridine-1(2H)-carboxylate and 1-bromo-4-(ethylsulfonyl)benzene (prepared according to Semple, G. et al. Bioorg. Med. Chem. Letters, 2012, 22(1), 71-75, incorporated herein by reference) according to the general procedure 2 using DMF as solvent. The crude residue was chromatographed using silica gel column and 0-100% Hex: EtOAC) to afford the product as a white solid (94%). $^1$H NMR (400 MHz, $CDCl_3$) δ 1.28 (t, J=7.6 Hz, 3H), 1.49 (s, 9H), 2.54 (apparent bs, 2H), 3.11 (q, J=7.6 Hz, 2H), 3.66 (t, J=5.6 Hz, 2H), 4.11-4.13 (m, 2H), 6.20 (bs, 1H), 7.54 (d, J=8.4 Hz, 2H), 7.85 (d, J=6.8 Hz, 2H).

Intermediate 37. tert-Butyl 5-methoxy-3',6'-dihydro-[3,4'-bipyridine]-1'(2'H)-carboxylate

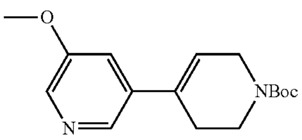 [SMILES: COc1cncc(C2=CCN(C(=O)OC(C)(C)C)CC2)c1]

Compound was prepared from commercially available tert-butyl 4-(4,4,5,5-tetramethyl-1,3,2-dioxaborolan-2-yl)-3,6-dihydropyridine-1(2H)-carboxylate and 3-bromo-5-methoxypyridine according to general procedure 2 using DMF as solvent. The crude residue was chromatographed using silica gel column and 0-100% EtOAc in hexanes gradient to afford the product as a pale yellow-brown viscous liquid (95% yield). $^1$H NMR (400 MHz, $CDCl_3$) δ 1.49 (s, 9H), 2.51 (apparent bs, 2H), 3.66 (t, J=5.2 Hz, 2H), 3.92 (s, 3H), 4.11 (apparent bs 2H), 6.17 (bs, 1H), 7.31 (bs, 1H), 8.20 (bs, 1H), 8.29 (bs, 1H).

Intermediate 38. tert-Butyl 4-(4-chlorophenyl)-3,6-dihydropyridine-1(2H)-carboxylate

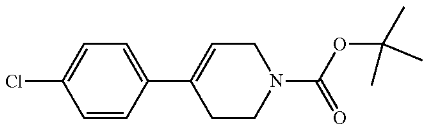 [SMILES: CC(C)(C)OC(=O)N1CC=C(c2ccc(Cl)cc2)CC1]

Compound was synthesized from commercially available 4-chloro-bromobenzene and tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (10:1) as solvent. The crude residue was purified by silica gel column chromatography and 0-20% EtOAc in hexanes gradient to afford the product as pale colorless syrup (86% yield). $^1$H NMR (400 MHz, $CDCl_3$) δ 1.49 (s, 9H), 2.48 (apparent bs, 2H), 3.63 (t, J=5.6 Hz, 2H), 4.04-4.08 (m, 2H), 6.02 (bs, 1H), 7.30 (s, 4H).

Intermediate 39. tert-Butyl 4-(3-chloro-4-methoxyphenyl)-3,6-dihydropyridine-1(2H)-carboxylate

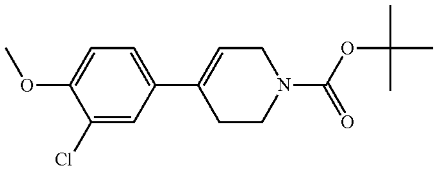 [SMILES: COc1ccc(C2=CCN(C(=O)OC(C)(C)C)CC2)cc1Cl]

Compound was synthesized from commercially available 4-bromo-2-chloro-1-methoxybenzene and tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (10:1) as solvent. The crude residue was purified by silica gel column chromatography and 0-10% EtOAc in hexanes gradient to afford the product as colorless syrup. (78% yield). $^1$H NMR (400 MHz, $CDCl_3$) δ 1.49 (s, 9H), 2.46 (apparent bs, 2H), 3.62 (t, J=5.6, 2H), 3.90 (s, 3H), 4.04-4.07 (m, 2H), 5.96 (bs, 1H), 6.89 (d, J=8.4 Hz, 1H), 7.23 (dd, J=8.4, 2.4, 1H), 7.39 (d, J=2.4 Hz, 1H).

Intermediate 40. tert-Butyl 4-(2-chloro-4-methoxyphenyl)-3,6-dihydropyridine-1(2H)-carboxylate

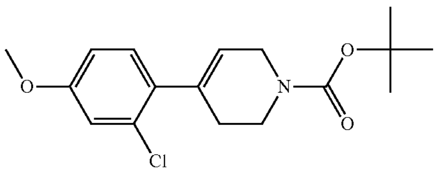 [SMILES: COc1ccc(C2=CCN(C(=O)OC(C)(C)C)CC2)c(Cl)c1]

Compound was synthesized from commercially available 4-bromo-3-chloro-1-methoxybenzene and tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (10:1). The residue was purified by silica gel column chromatography and 0-10% EtOAc in hexanes gradient to afford the product as yellowish syrup. (68% yield). $^1$H NMR (400 MHz, $CDCl_3$) δ 1.50 (s, 9H), 2.41 (bs, 2H), 3.60-3.62 (m, 2H), 3.79 (s, 3H), 4.03 (bs, 2H), 5.62 (bs, 1H), 6.77 (dd, J=8.8, 2.8 Hz, 1H), 6.91 (d, J=2.8 Hz, 1H), 7.08 (d, J=8.4 Hz, 1H).

Intermediate 41. tert-Butyl 4-(2-fluoro-4-(N-methylacetamido)phenyl)-3,6-dihydropyridine-1(2H)-carboxylate

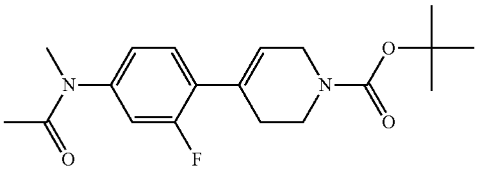 [SMILES: CC(=O)N(C)c1ccc(C2=CCN(C(=O)OC(C)(C)C)CC2)c(F)c1]

Compound was synthesized from commercially available tert-butyl 4-(4,4,5,5-tetramethyl-1,3,2-dioxaborolan-2-yl)-3,6-dihydropyridine-1(2H)-carboxylate and N-(4-bromo-3-fluorophenyl)-N-methylacetamide according to general procedure 2 using dioxane/H2O (10/1) as solvent. The crude residue was purified by silica gel column chromatography and 0-50% EtOAc in hexanes gradient to afford the product as yellowish solid (88% yield). $^1$H NMR (600 MHz, $CDCl_3$) δ 1.51 (s, 9H), 1.93 (s, 3H), 2.52 (bs, 2H), 3.27 (s, 3H), 3.64 (bs, 2H), 4.10 (bs, 2H), 5.99 (bs, 1H), 6.92 (d, J=11.4 Hz, 1H), 6.97 (d, J=7.8 Hz, 1H), 7.29-7.31 (m, 1H).

Intermediate 42. tert-Butyl 4-(3-fluoro-5-methoxyphenyl)-3,6-dihydropyridine-1(2H)-carboxylate

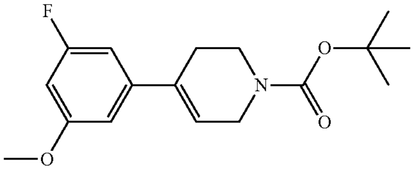 [SMILES: COc1cc(F)cc(C2=CCN(C(=O)OC(C)(C)C)CC2)c1]

Compound was synthesized from commercially available tert-butyl 4-(4,4,5,5-tetramethyl-1,3,2-dioxaborolan-2-yl)-3,6-dihydropyridine-1(2H)-carboxylate and 1-bromo-3-fluoro-5-methoxybenzene according to general procedure 2 using dioxane/$H_2O$ (10:1) as solvent. The crude residue was purified by silica gel column chromatography and 0-20% EtOAc in hexanes gradient to afford the product as yellowish liquid. (88% yield). $^1$H NMR (600 MHz, $CDCl_3$) δ 1.48 (s, 9H), 2.47 (bs, 2H), 3.62 (bs, 2H), 3.80 (s, 3H), 4.06 (bs, 2H), 6.02 (apparent s, 1H), 6.51 (apparent dt, J=4.2, 2.4 Hz, 1H), 6.66-8.68 (m, 2H).

Intermediate 43. tert-Butyl 4-(4-fluoro-3-methoxyphenyl)-3,6-dihydropyridine-1(2H)-carboxylate

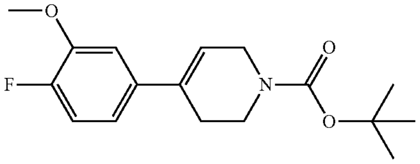 [SMILES: COc1cc(C2=CCN(C(=O)OC(C)(C)C)CC2)ccc1F]

Compound was synthesized from commercially available 4-bromo-1-fluoro-2-methoxybenzene and tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (10:1) as solvent. The crude residue was purified by silica gel column chromatography and 0-15% EtOAc in hexanes gradient to afford the product as white solid. (88% yield). $^1H$ NMR (600 MHz, $CDCl_3$) δ 1.49 (s, 1H), 2.49 (bs, 2H), 3.63 (t, J=5.4 Hz, 2H), 3.90 (s, 3H), 4.06 (bs, 2H), 5.96 (bs, 1H), 6.86-6.89 (m, 1H), 6.95 (dd, J=8.4, 2.4 Hz, 1H), 7.00-7.04 (m, 1H).

Intermediate 44. tert-Butyl 4-(4-(pyrrolidine-1-carbonyl)phenyl)-3,6-dihydropyridine-1(2H)-carboxylate

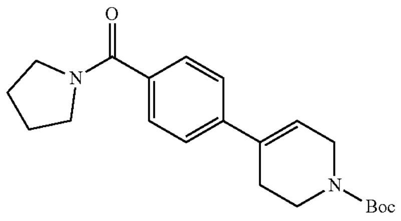 [SMILES: CC(C)(C)OC(=O)N1CC=C(c2ccc(C(=O)N3CCCC3)cc2)CC1]

Compound was synthesized from (4-bromophenyl)(pyrrolidin-1-yl)methanone and commercially available tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (5:1) as solvent. The crude residue was purified by silica gel column chromatography and 0-100% EtOAc in hexanes gradient to afford the product as white solid. (65% yield). $^1$HNMR (600 MHz, $CDCl_3$) δ 7.52 (d, J=6.0 Hz, 2H), 7.41 (d, J=6.0 Hz, 2H), 6.11 (bs, 1H), 4.16-4.13 (m, 2H), 3.66 (bs, 4H), 3.50-3.47 (m, 2H), 2.55 (bs, 2H), 1.98-1.91 (m, 4H), 1.51 (s, 9H).

Intermediate 45: tert-Butyl 4-(2-fluoro-4-(pyrrolidine-1-carbonyl)phenyl)-3,6-dihydropyridine-1(2H)-carboxylate

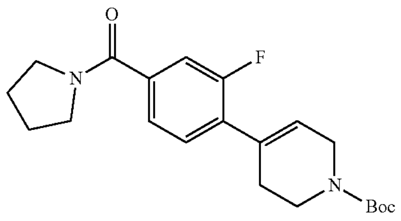 [SMILES: CC(C)(C)OC(=O)N1CC=C(c2ccc(C(=O)N3CCCC3)cc2F)CC1]

Compound was synthesized from (4-bromo-3-fluorophenyl)(pyrrolidin-1-yl)methanone and commercially available tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (4:1) as solvent. The crude residue was purified by silica gel column chromatography and 0-100% EtOAc in hexanes gradient to afford the product as white solid. (77% yield). $^1$HNMR (500 MHz, $CDCl_3$) δ 7.27-7.26 (m, 2H), 7.21 (d, $J_{C-F}$=11.5 Hz, 1H), 5.97 (bs, 1H), 4.07 (d, J=2.0 Hz, 2H), 3.63-3.61 (m, 4H), 3.45 (s, 2H), 2.50 (s, 2H), 1.96-1.89 (m, 4H), 1.49 (s, 9H).

Intermediate 46. tert-Butyl 4-(4-((2-oxopyrrolidin-1-yl)methyl)phenyl)-3,6-dihydropyridine-1(2H)-carboxylate

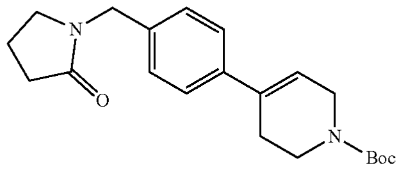 [SMILES: CC(C)(C)OC(=O)N1CC=C(c2ccc(CN3CCCC3=O)cc2)CC1]

Compound was synthesized from 1-(4-bromobenzyl)pyrrolidin-2-one and commercially available tert-butyl 4-(4,4,5,5-tetramethyl-1,3,2-dioxaborolan-2-yl)-3,6-dihydropyridine-1(2H)-carboxylate according to general procedure 2 using dioxane/water (6:1) as solvent. The crude residue was purified by silica gel column chromatography and 0-100% EtOAc in hexanes gradient to afford the product as transparent liquid (78% yield). $^1$HNMR (600 MHz, $CDCl_3$) δ 7.33 (d, J=8.4 Hz, 2H), 7.19 (d, J=8.4 Hz, 2H), 6.02 (bs, 1H), 4.43 (s, 2H), 4.06 (d, J=2.4 Hz, 2H), 3.62 (t, J=5.4 Hz, 2H), 3.25 (t, J=7.2 Hz, 2H), 2.50 (bs, 2H), 2.44 (t, J=8.4 Hz, 2H), 2.01-1.96 (m, 2H), 1.48 (s, 9H).

Intermediate 47. tert-Butyl 4-(4-(pyrrolidin-1-ylsulfonyl)phenyl)-3,6-dihydropyridine-1(2H)-carboxylate

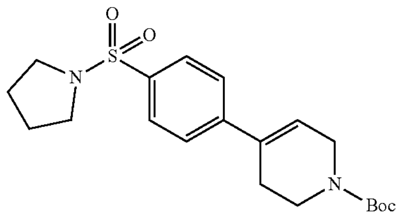 [SMILES: CC(C)(C)OC(=O)N1CC=C(c2ccc(S(=O)(=O)N3CCCC3)cc2)CC1]

Compound was synthesized from 1-((4-bromophenyl)sulfonyl)pyrrolidine and commercially available tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (4:1) as solvent. The crude residue was purified by silica gel column chromatography and 0-100% EtOAc in hexanes gradient to afford the product as white solid. (67% yield). $^1$HNMR (500 MHz, $CDCl_3$) δ 7.76 (d, J=8.5 Hz, 2H), 7.47 (d, J=8.5 Hz, 2H), 6.15 (bs, 1H), 4.08 (d, J=2.5 Hz, 2H), 3.63 (t, J=5.5 Hz, 2H), 3.23-3.21 (m, 4H), 2.51 (bs, 2H), 1.75-1.72 (m, 4H), 1.47 (s, 9H).

Intermediate 48. tert-Butyl 4-(trifluoromethyl)-3',6'-dihydro-[2,4'-bipyridine]-1'(2'H)-carboxylate

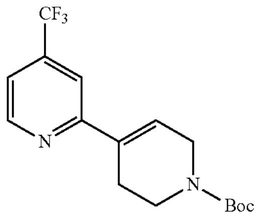 [SMILES: CC(C)(C)OC(=O)N1CC=C(c2cc(C(F)(F)F)ccn2)CC1]

Compound was synthesized from commercially available 2-chloro-4-(trifluoromethyl)pyridine and tert-butyl 4-(4,4,5,5-tetramethyl-1,3,2-dioxaborolan-2-yl)-3,6-dihydropyridine-1(2H)-carboxylate according to general procedure 2 using dioxane/water (4:1) as solvent. The crude residue was purified by silica gel column chromatography and 0-100% EtOAc in hexanes gradient to afford the product as white solid. (73% yield). $^1$HNMR (600 MHz, $CDCl_3$) δ 8.71 (d, J=4.8 Hz, 1H), 7.54 (s, 1H), 7.34 (d, J=4.8 Hz, 1H), 6.70 (bs, 1H), 4.14 (s, 2H), 3.64 (s, 2H), 2.64 (d, J=1.2 Hz, 2H), 1.47 (s, 9H).

Intermediate 49. tert-Butyl 4-(4-((methylsulfonyl)methyl)phenyl)-3,6-dihydropyridine-1(2H)-carboxylate

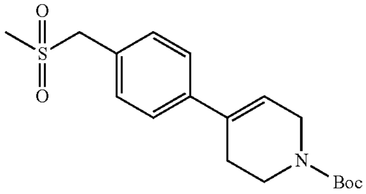 [SMILES: CC(C)(C)OC(=O)N1CC=C(c2ccc(CS(C)(=O)=O)cc2)CC1]

Compound was synthesized from commercially available 1-bromo-4-((methylsulfonyl)methyl)benzene and tert-butyl 4-(4,4,5,5-tetramethyl-1,3,2-dioxaborolan-2-yl)-3,6-dihydropyridine-1(2H)-carboxylate according to general procedure 2 using dioxane/water (3:1) as solvent. The crude residue was purified by silica gel column chromatography and 0-100% EtOAc in hexanes gradient to afford the product as transparent liquid. (78% yield). $^1$HNMR (600 MHz, $CDCl_3$) δ 7.37 (d, J=8.4 Hz, 2H), 7.33 (d, J=8.4 Hz, 2H), 6.04 (bs, 1H), 4.20 (s, 2H), 4.05 (s, 2H), 3.60 (t, J=5.4 Hz, 2H), 2.72 (s, 3H), 2.48 (bs, 2H), 1.45 (s, 9H).

Intermediate 50. tert-Butyl 5-(trifluoromethyl)-3',6'-dihydro-[3,4'-bipyridine]-1'(2'H)-carboxylate

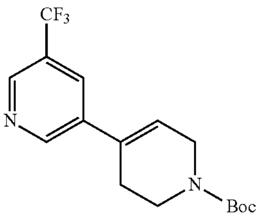 [SMILES: CC(C)(C)OC(=O)N1CC=C(c2cncc(C(F)(F)F)c2)CC1]

Compound was synthesized from commercially available 3-bromo-5-(trifluoromethyl)pyridine and tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (4:1) as solvent. The crude residue was purified by silica gel column chromatography and 0-100% EtOAc in hexanes gradient to afford the product as white solid. (69% yield). $^1$HNMR (600 MHz, $CDCl_3$) δ 8.83-8.77 (m, 2H), 7.86 (s, 1H), 6.21 (bs, 1H), 4.14 (s, 2H), 3.68 (t, J=5.4 Hz, 2H), 2.56 (s, 2H), 1.50 (s, 9H).

Intermediate 51. tert-Butyl 4-(1,1-dioxido-2,3-dihydrobenzo[b]thiophen-5-yl)-3,6-dihydropyridine-1(2H)-carboxylate

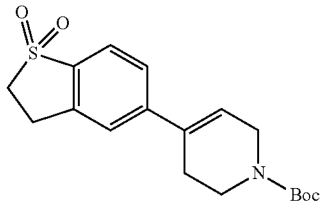 [SMILES: CC(C)(C)OC(=O)N1CC=C(c2ccc3c(c2)CCS3(=O)=O)CC1]

Compound was synthesized from 5-bromo-2,3-dihydrobenzo[b]thiophene 1,1-dioxide and commercially available tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (3:1) as solvent. The crude residue was purified by silica gel column chromatography and 0-100% EtOAc in hexanes gradient to afford the product as transparent liquid. (77% yield). $^1$HNMR (300 MHz, $CD_3OD$) δ 7.65 (d, J=8.1 Hz, 1H), 7.41 (d, J=8.4 Hz, 1H), 7.29 (s, 1H), 6.10 (bs, 1H), 4.06 (distorted q, J=2.7 Hz, 2H), 3.61 (t, J=5.7 Hz, 2H), 3.50-3.44 (m, 2H), 3.38-3.32 (m, 2H), 2.48 (bs, 2H), 1.46 (s, 9H).

Intermediate 52. tert-Butyl 4-(4-((1,1,1-trifluoropropan-2-yl)amino)phenyl)-3,6-dihydropyridine-1(2H)-carboxylate

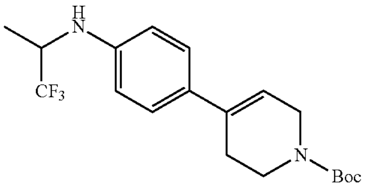 [SMILES: CC(Nc1ccc(C2=CCN(C(=O)OC(C)(C)C)CC2)cc1)C(F)(F)F]

Compound was synthesized from 4-bromo-N-(1,1,1-trifluoropropan-2-yl)aniline and commercially available tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (5:1) as solvent. The crude residue was purified by silica gel column chromatography and 0-100% EtOAc in hexanes gradient to afford the product as yellow liquid. (66% yield). $^1$HNMR (300 MHz, $CDCl_3$) δ 7.20 (d, J=9.0 Hz, 2H), 6.60 (d, J=8.7 Hz, 2H), 5.87 (bs, 1H), 4.04-3.97 (m, 3H), 3.58 (t, J=5.7 Hz, 2H), 2.44 (m, 2H), 1.45 (s, 9H), 1.37 (d, J=6.6 Hz, 3H).

Intermediate 53. tert-Butyl 4-(2,2-dioxido-1,3-dihydrobenzo[c]thiophen-5-yl)-3,6-dihydropyridine-1(2H)-carboxylate

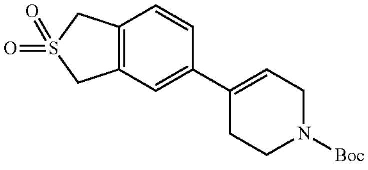 [SMILES: CC(C)(C)OC(=O)N1CC=C(c2ccc3c(c2)CS(=O)(=O)C3)CC1]

Compound was synthesized from commercially available 5-bromo-1,3-dihydrobenzo[c]thiophene 2,2-dioxide and tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (5:1) as solvent. The crude residue was purified by silica gel column chromatography and 0-100% EtOAc in hexanes gradient to afford the product as transparent liquid (62% yield). $^1$HNMR (600 MHz, $CDCl_3$) δ 7.33 (d, J=7.8 Hz, 1H), 7.24 (d, J=7.2 Hz, 2H), 6.01 (bs, 1H), 4.32 (d, J=3.6 Hz, 4H), 4.04 (s, 2H), 3.59 (t, J=5.4 Hz, 2H), 2.45 (bs, 2H), 1.45 (s, 9H).

Intermediate 54. tert-Butyl 4-(3-fluoro-4-((2-oxopyrrolidin-1-yl)methyl)phenyl)-3,6-dihydropyridine-1(2H)-carboxylate

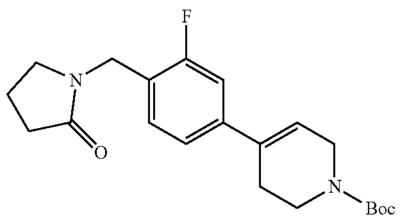 [SMILES: CC(C)(C)OC(=O)N1CC=C(c2ccc(CN3CCCC3=O)c(F)c2)CC1]

Compound was synthesized from 1-(4-bromo-2-fluorobenzyl)pyrrolidin-2-one and commercially available tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (5:1) as solvent. The crude residue was purified by silica gel column chromatography and 0-100% EtOAc in hexanes gradient to afford the product as gummy liquid (86% yield). $^1$HNMR (600 MHz, $CDCl_3$) δ 7.21-7.20 (m, 1H), 7.08 (d, J=7.8 Hz, 1H), 7.03-7.01 (m, 1H), 6.02 (bs, 1H), 4.47 (s, 2H), 4.04 (s, 2H), 3.59 (s, 2H), 3.28 (t, J=7.2 Hz, 2H), 2.44 (bs, 2H), 2.38 (t, J=4.8 Hz, 2H), 1.99-1.94 (m, 2H), 1.45 (s, 9H).

Intermediate 55. tert-Butyl 4-(3-chloro-4-((2-oxopyrrolidin-1-yl)methyl)phenyl)-3,6-dihydropyridine-1(2H)-carboxylate

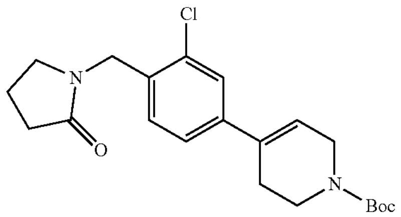

Compound was synthesized from 1-(4-bromo-2-chlorobenzyl)pyrrolidin-2-one and commercially available tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (5:1) as solvent. The crude residue was purified by silica gel column chromatography and 0-100% EtOAc in hexanes gradient to afford the product as transparent liquid (58% yield). $^1$HNMR (300 MHz, $CDCl_3$) δ 7.34 (s, 1H), 7.23-7.21 (m, 2H), 6.03 (bs, 1H), 4.56 (s, 2H), 4.04 (q, J=2.7 Hz, 2H), 3.60 (t, J=5.7 Hz, 2H), 3.29 (t, J=6.9 Hz, 2H), 2.45-2.39 (m, 4H), 2.04-1.94 (m, 2H), 1.46 (s, 9H).

Intermediate 56. tert-Butyl 4-(2-fluoro-4-((2-oxopyrrolidin-1-yl)methyl)phenyl)-3,6-dihydropyridine-1(2H)-carboxylate

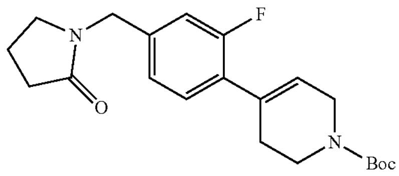 [SMILES: CC(C)(C)OC(=O)N1CC=C(c2ccc(CN3CCCC3=O)cc2F)CC1]

Compound was synthesized from 1-(4-bromo-3-fluorobenzyl)pyrrolidin-2-one (SHM-II-11-01) and commercially available tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (5:1) as solvent. The crude residue was purified by silica gel column chromatography and 0-100% EtOAc in hexanes gradient to afford the product as transparent liquid (90% yield). $^1$HNMR (300 MHz, $CDCl_3$) δ 7.15 (t, J=7.8 Hz, 1H), 6.95-6.86 (m, 2H), 5.88 (bs, 1H), 4.37 (s, 2H), 4.01 (q, J=2.7 Hz, 2H), 3.56 (t, J=5.7 Hz, 2H), 3.24 (t, J=7.2 Hz, 2H), 2.43-2.38 (m, 4H), 2.02-1.92 (m, 2H), 1.45 (s, 9H).

Intermediate 57. tert-Butyl 4-(4-morpholinophenyl)-3,6-dihydropyridine-1(2H)-carboxylate

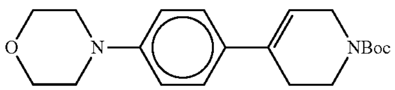

Compound was prepared from commercially available tert-butyl 4-(4,4,5,5-tetramethyl-1,3,2-dioxaborolan-2-yl)-3,6-dihydropyridine-1(2H)-carboxylate and 4-(4-bromophenyl)morpholine according to general procedure 2 using dioxane/water (5:1 ratio) as solvent. The crude residue was chromatographed with silica gel column and 0-30% EtOAc in hexanes gradient to afford the product (49% yield). $^1$H NMR (600 MHz, $CDCl_3$) δ 1.48 (s, 9H), 2.49 (apparent s, 2H), 3.16 (t, J=4.8 Hz, 4H), 3.62 (apparent s, 2H), 3.86 (t, J=4.8 Hz, 4H), 4.05 (apparent s, 2H), 5.94 (bs, 1H), 6.88 (d, J=8.4 Hz, 2H), 7.31 (d, J=9.0 Hz, 2H).

Intermediate 58. tert-Butyl 4-(4-(morpholinomethyl)phenyl)-3,6-dihydropyridine-1(2H)-carboxylate

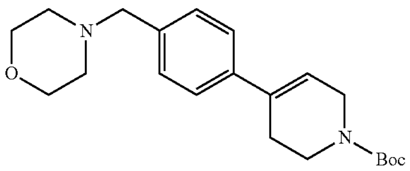 [SMILES: CC(C)(C)OC(=O)N1CC=C(c2ccc(CN3CCOCC3)cc2)CC1]

Compounds was synthesized from commercially available 4-(4-bromobenzyl)morpholine and tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (5:1) as solvent. The crude residue was purified by silica gel column chromatography and 0-100%

EtOAc in hexanes gradient to afford the product as transparent yellow liquid (61% yield). $^{1}H$ NMR (300 MHz, $CDCl_3$) δ 7.31-7.23 (m, 4H), 6.0 (s, 1H), 7.03 (q, J=2.7 Hz, 2H), 3.67 (d, J=4.8 Hz, 4H), 3.60 (t, J=5.7 Hz, 2H), 3.40 (s, 2H), 2.49 (bs, 2H), 2.41 (t, J=4.5 Hz, 4H), 1.46 (s, 9H).

Intermediate 59. tert-Butyl 4-(4-(3-oxomorpholino) phenyl)-3,6-dihydropyridine-1(2H)-carboxylate

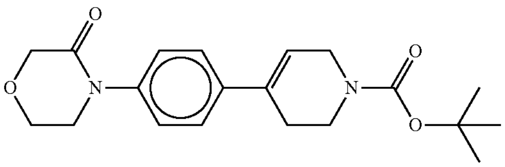

The compound was prepared from commercially available tert-butyl 4-(4,4,5,5-tetramethyl-1,3,2-dioxaborolan-2-yl)-3,6-dihydropyridine-1(2H)-carboxylate and 4-(4-bromophenyl)morpholin-3-one according to general procedure 2 using dioxane/$H_2O$ (5:1) as solvent. The crude residue was purified with silica gel column and 0-50% EtOAc in $CH_2Cl_2$ as eluent to afford the product as an off-white solid. $^{1}H$ NMR (600 MHz, $CDCl_3$) δ 1.49 (s, 9H), 2.51 (bs, 2H), 3.63 (apparent bs, 2H), 3.77 (apparent t, J=4.8 Hz, 2H), 4.03 (distorted t, J=4.8 Hz, 2H), 4.07 (s, 2H), 4.35 (s, 2H), 6.02 (bs, 1H), 7.30 (d, J=8.4 Hz, 2H), 7.41 (d, J=8.4 Hz, 2H).

Intermediate 60. tert-Butyl 4-(3-fluoro-4-morpholinophenyl)-3,6-dihydropyridine-1(2H)-carboxylate

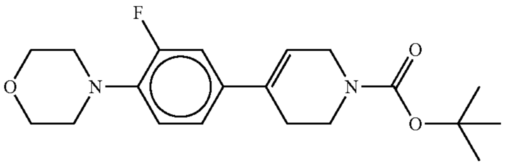

Compound was prepared according to general procedure 2 from commercially available tert-butyl 4-(4,4,5,5-tetramethyl-1,3,2-dioxaborolan-2-yl)-3,6-dihydropyridine-1(2H)-carboxylate and 4-(4-Bromo-2-fluorophenyl)morpholine using dioxane/$H_2O$ (5:1) as solvent. The crude reaction product was purified with a silica gel column and 0-30% EtOAc in hexanes as elution gradient to afford the product as a white/off-white solid (85% yield). $^{1}H$ NMR (600 MHz, $CDCl_3$) δ 1.49 (s, 9H), 2.46 (bs, 2H), 3.09 (apparent t, J=4.8 Hz, 4H), 3.62 (apparent bs, 2H), 3.87 (apparent t, J=4.2 Hz, 4H), 4.06 (bs, 2H), 5.98 (bs, 1H), 6.89 (t, J=8.4 Hz), 7.05-7.12 (m, 2H).

Intermediate 61. tert-Butyl 4-(2-fluoro-4-morpholinophenyl)-3,6-dihydropyridine-1(2H)-carboxylate

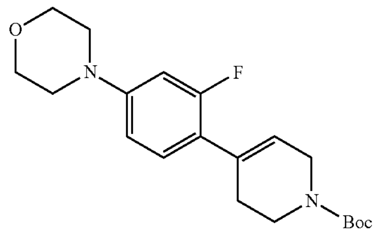 [SMILES: CC(C)(C)OC(=O)N1CC=C(c2ccc(N3CCOCC3)cc2F)CC1]

Compound was synthesized from commercially available 4-(4-bromo-3-fluorophenyl)morpholine and tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (5:1) as solvent. The crude residue was purified by silica gel column chromatography and 0-100% EtOAc in hexanes gradient to afford the product as transparent liquid. (86% yield). $^{1}H$ NMR (300 MHz, $CDCl_3$) δ 7.11 (t, J=8.7 Hz, 1H), 6.63-6.51 (m, 2H), 5.85 (s, 1H), 3.83 (t, J=4.5 Hz, 4H), 3.69 (t, J=6.3 Hz, 1H), 3.58 (t, J=5.7 Hz, 2H), 3.13 (t, J=5.1 Hz, 4H), 2.44-2.40 (m, 3H), 1.46 (s, 9H).

Intermediate 62. tert-Butyl (S)-4-(4-(1-(2-oxopyrrolidin-1-yl)ethyl)phenyl)-3,6-dihydropyridine-1(2H)-carboxylate

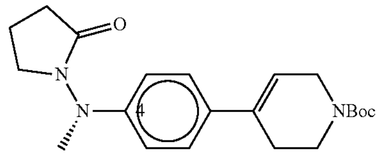

Compound was prepared from commercially available tert-butyl 4-(4,4,5,5-tetramethyl-1,3,2-dioxaborolan-2-yl)-3,6-dihydropyridine-1(2H)-carboxylate and (S)-1-(1-(4-bromophenyl)ethyl)pyrrolidin-2-one according to general procedure 2 using dioxane/$H_2O$ (5:1) as solvent. The crude residue was purified with 0-40% EtOAc in $CH_2Cl_2$ to afford the product as pale yellow very viscous syrup (72% yield). $^{1}H$ NMR (600 MHz, $CDCl_3$) δ 1.49 (s, 9H), 1.86-1.94 (m, 1H), 1.94-2.02 (m, 1H), 2.36-2.48 (m, 2H), 2.51 (bs, 2H), 2.98 (ddd, J=14.4, 9.0, 5.4 Hz, 1H), 3.32 (ddd, J=15.0, 9.0, 6.0 Hz, 1H), 3.63 (apparent bs, 2H), 4.07 (bs, 2H), 5.48 (q, J=7.2 Hz, 1H), 7.26 (d, J=8.4 Hz, 2H), 7.34 (d, J=7.8 Hz, 2H).

Intermediate 63. tert-Butyl (R)-4-(4-(1-(2-oxopyrrolidin-1-yl)ethyl)phenyl)-3,6-dihydropyridine-1(2H)-carboxylate

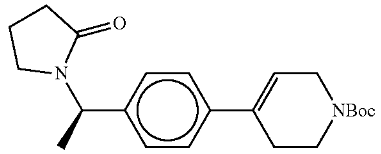

Compound was prepared from commercially available tert-butyl 4-(4,4,5,5-tetramethyl-1,3,2-dioxaborolan-2-yl)-3,6-dihydropyridine-1(2H)-carboxylate and (R)-1-(1-(4-bromophenyl)ethyl)pyrrolidin-2-one according to general procedure 2 using dioxane/$H_2O$ (5:1) as solvent. The crude residue was purified with 0-40% EtOAc in $CH_2Cl_2$ to afford the product as pale yellow very viscous sirup (34% yield). $^1$H NMR (600 MHz, $CDCl_3$) δ 1.49 (s, 9H), 1.51 (d, J=6.6 Hz, 2H), 1.86-1.94 (m, 1H), 1.94-2.02 (m, 1H), 2.35-2.47 (m, 2H), 2.51 (bs, 2H), 2.98 (ddd, J=13.8, 8.4, 4.8 Hz, 1H), 3.32 (ddd, J=15.6, 9.0, 6.6 Hz, 1H), 3.63 (apparent bs, 2H), 4.07 (bs, 2H), 5.49 (q, J=7.2 Hz, 1H), 6.03 (bs, 1H), 7.26 (d, J=8.4 Hz, 2H), 7.34 (d, J=7.8 Hz, 2H).

Intermediate 64. tert-Butyl 4-(2-fluoro-4-(2-oxopyrrolidin-1-yl)phenyl)-3,6-dihydropyridine-1(2H)-carboxylate

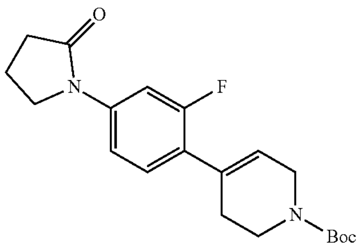 [SMILES: CC(C)(C)OC(=O)N1CC=C(c2ccc(N3CCCC3=O)cc2F)CC1]

Compound was synthesized from 1-(4-bromo-3-fluorophenyl)pyrrolidin-2-one and commercially available tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (6:1) as solvent. The crude residue was purified with silica gel column chromatography and 0-100% EtOAc in hexanes gradient to afford the product as transparent liquid. (71% yield). $^1$HNMR (300 MHz, $CDCl_3$) δ 7.50 (dd, J=13.5 Hz, 2.1 Hz, 1H), 7.35-7.31 (m, 1H), 7.23 (t, J=8.7 Hz, 1H), 5.94 (bs, 1H), 4.08 (q, J=3.0 Hz, 2H), 3.85 (t, J=7.2 Hz, 2H), 3.62 (t, J=5.7 Hz, 2H), 2.63 (t, J=7.8 Hz, 2H), 2.50 (bs, 2H), 2.23-2.13 (m, 2H), 1.50 (s, 9H).

Intermediate 65. tert-Butyl 4-(4-(1,1-dioxidothiomorpholino)phenyl)-3,6-dihydropyridine-1(2H)-carboxylate

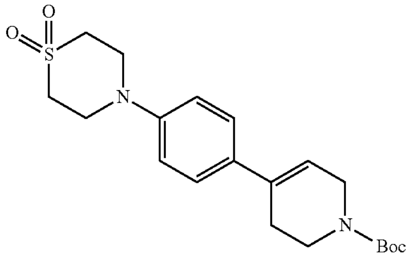 [SMILES: CC(C)(C)OC(=O)N1CC=C(c2ccc(N3CCS(=O)(=O)CC3)cc2)CC1]

Compound was synthesized from commercially available 4-(4-bromophenyl)thiomorpholine 1,1-dioxide and tert-butyl 4-(4,4,5,5-tetramethyl-1,3,2-dioxaborolan-2-yl)-3,6-dihydropyridine-1(2H)-carboxylate according to general procedure 2 using dioxane/$H_2O$ (6:1) as solvent. The crude residue was purified by silica gel column chromatography and 0-100% EtOAc in hexanes gradient to afford the product as transparent liquid. (46% yield). $^1$H NMR (300 MHz, $CDCl_3$) δ 7.31 (d, J=6.9 Hz, 2H), 6.86 (d, J=6.9 Hz, 2H), 5.95 (s, 1H), 4.04 (distorted q, J=2.7 Hz, 2H), 3.85 (t, J=5.1 Hz, 4H), 3.61 (t, J=5.7 Hz, 2H), 3.09 (t, J=5.1 Hz, 4H), 2.47 (bs, 2H), 1.47 (s, 9H).

Intermediate 66. tert-Butyl 4-(4-(2-oxopyrrolidin-1-yl)phenyl)-3,6-dihydropyridine-1(2H)-carboxylate

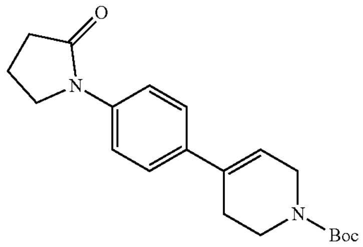 [SMILES: CC(C)(C)OC(=O)N1CC=C(c2ccc(N3CCCC3=O)cc2)CC1]

Compound was synthesized from commercially available 1-(4-bromophenyl)pyrrolidin-2-one and tert-butyl 4-(4,4,5,5-tetramethyl-1,3,2-dioxaborolan-2-yl)-3,6-dihydropyridine-1(2H)-carboxylate according to general procedure 2 using dioxane/H2O (5:1) as solvent. The crude residue was purified by silica gel column chromatography and 0-100% EtOAc in hexanes gradient to afford the product as transparent liquid (67% yield). 1HNMR (300 MHz, CDCl3) δ 7.56 (d, J=8.7 Hz, 2H), 7.35 (d, J=9.0 Hz, 2H), 6.00 (bs, 1H), 4.05 (distorted q, J=3.0 Hz, 2H), 3.85 (dt, J=6.9, 3.9 Hz, 2H), 3.61 (t, J=5.7 Hz, 2H), 2.60 (t, J=7.8 Hz, 2H), 2.49 (bs, 2H), 2.21-2.11 (m, 2H), 1.48 (s, 9H).

General Procedure 3. Synthesis of 4-aryl/heteroaryl piperidines from N-Boc-protected 4-aryl/heteroaryl 3,6-dihydropyridines A slurry of NBoc-4-aryl/heteroaryl-3.6-dihydropyridine of interest and Pd/C (0.1 eq) or $PtO_2$ (0.05 eq) in EtOH was hydrogenated at atmospheric pressure until consumption of starting material was judged to be complete by LCMS or TLC. The solids were then filtered and washed with EtOH and EtOAc or 10% MeOH in $CH_2Cl_2$. The combined organic layer was then concentrated to afford the corresponding N-Boc-protected 4-aryl/heteroaryl piperidine reduced intermediate which was purified, if needed, with silica gel column chromatography. This intermediate was then dissolved in 4 N HCl in dioxane at room temperature and stirred until TLC indicated that Boc deprotection was complete. Volatiles were evaporated and the resulting residue was partitioned between $CH_2Cl_2$ and aq. saturated $Na_2CO_3$. The aqueous layer was extracted with $CH_2Cl_2$ until no UV absorbance was detected in the organic layer and then the combined organic layer was dried over $Na_2SO_4$ and concentrated to afford the corresponding 4-aryl-piperidine of interest.

Intermediate 67. 4-(3-Methoxyphenyl)piperidine

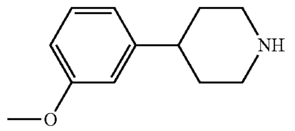

Prepared from tert-butyl 4-(3-methoxyphenyl)-3,6-dihydropyridine-1(2H)-carboxylate according to the general procedure 3 using 3% Pd/C as hydrogenation catalyst (66% yield). $^1$H NMR (400 MHz, $CDCl_3$) δ 1.71 (apparent qd, J=12.4, 2.8 Hz, 2H), 1.87 (apparent d, J=12.8 Hz, 2H), 2.50 (bs, 1H), 2.63 (tt, J=12.0, 3.6 Hz), 2.78 (apparent t, J=11.2, 2H), 3.24 (apparent d, J=11.2 Hz, 2H), 3.82 (s, 3H), 6.73-6.88 (m, 3H), 7.25 (t, J=8.0 Hz, 1H).

Intermediate 68. 2-(Piperidin-4-yl)pyrimidine

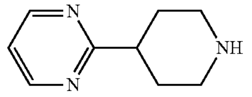 [SMILES: c1cnc(C2CCNCC2)nc1]

Prepared from tert-butyl 4-(pyrimidin-2-yl)-3,6-dihydropyridine-1(2H)-carboxylate according to the general procedure 3 using 3% Pd/C as hydrogenation catalyst. Intermediate hydrogenation product was purified with silica gel column and 0-100% EtOAc gradient prior to addition of 4N HCl. Desired product was isolated as an off-white light brown solid (73% yield) $^1$H NMR (400 MHz, $CDCl_3$) δ 1.81 (apparent qd, J=12.0, 4.0 Hz, 2H), 2.01 (apparent distorted d, J=12.8 Hz, 2H), 2.68 (bs, 1H), 2.79 (td, J=12.4, 2.0 Hz, 2 Hz), 3.02 (tt, J=11.6, 3.6 Hz, 1H), 3.22 (apparent distorted d, J=12.4 Hz, 2H), 7.12 (t, J=5.2 Hz, 1H), 8.68 (d, J=4.8 Hz, 2H).

Intermediate 69. Methyl 4-(piperidin-4-yl)benzoate

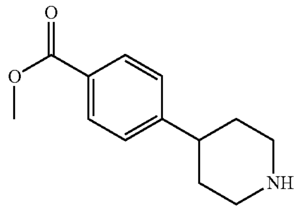 [SMILES: COC(=O)c1ccc(C2CCNCC2)cc1]

Prepared from tert-butyl 4-(4-(methoxycarbonyl)phenyl)-3,6-dihydropyridine-1(2H)-carboxylate according to the general procedure 3 using 3% Pd/C as hydrogenation catalyst. Isolated as a white solid (96% yield). $^1$H NMR (400 MHz, $CDCl_3$) δ 1.64 (apparent qd, J=12.8, 4.0 Hz, 2H), 1.83 (apparent d, J=12.4 Hz, 2H), 2.63-2.79 (m, 3H), 3.19 (apparent d, J=12.0 Hz, 2H), 3.89 (s, 3H), 7.28 (d, J=8.4 Hz, 2H), 7.97 (d, J=8.4 Hz, 2H).

Intermediate 70. N-Methyl-N-(5-(piperidin-4-yl)pyridin-2-yl)acetamide

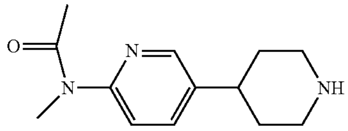 [SMILES: CC(=O)N(C)c1ccc(C2CCNCC2)cn1]

A mixture of tert-butyl 6-nitro-3',6'-dihydro-[3,4'-bipyridine]-1'(2'H)-carboxylate (550 mg, 1.80 mmol), 3% Pd/C (320 mg, 0.09 mmol) in 10 mL of EtOH and 3 mL of EtOAc was hydrogenated at 1 atm of pressure for 3 h. The reaction mixture was then filtered through a pad of celite and the solids washed with EtOH and EtOAc (1:1 mixture) until no UV was detected in the washings. The combined organic layer was evaporated to a light-brown solid. This solid was then dissolved in $CH_2Cl_2$ (13 mL) and then treated with $Et_3N$ (0.5 mL, 3.60 mmol) and then acetic anhydride (0.20 mL, 2.16 mmol). The reaction mixture was stirred until consumption of limiting reagent (as suggested by TLC) and partitioned between $CH_2Cl_2$ and water. The water layer was extracted with $CH_2Cl_2$ (×3) and the combined organic layer was dried over $Na_2SO_4$ filtered and concentrated. Silica gel column with 0-50% EtOAC in hexanes gradient yielded the corresponding intermediate tert-butyl 4-(6-acetamidopyridin-3-yl)piperidine-1-carboxylate, as an off-white solid (340 mg, 59% yield). $^1$H NMR (400 MHz, $CDCl_3$) δ 1.51 (s, 9H), 1.56-1.69 (m, 2H), 1.83 (apparent d, J=12.8 Hz, 2H), 2.22 (s, 3H), 2.67 (tt, J=12.0, 3.6 Hz, 1H), 2.82 (t, J=11.2 Hz, 2H), 4.28 (bs, 2H), 7.56 (dd, J=8.8, 2.4 Hz, 1H), 7.91 (s, 1H), 8.13-8.16 (m, 2H).

This intermediate (340 mg, 1.06 mmol) was then dissolved in in DMF (5 mL) and treated with NaH (60% dispersion, 64 mg, 1.59 mmol) and MeI (180 mg, 80 μL, 1.28 mmol). The reaction mixture stirred until consumption of the limited reagent (as indicated by TLC) and then partitioned between $CH_2Cl_2$ and water. The water layer was extracted with $CH_2Cl_2$ (×3) and the combined organic layer was dried over $Na_2SO_4$, filtered and evaporated. The residue was chromatographed with silica gel column and 0-100% gradient to afford the corresponding N-methylated derivative, tert-butyl 4-(6-(N-methylacetamido)pyridin-3-yl)piperidine-1-carboxylate, as a white solid (330 mg, 93% yield). $^1$H NMR (400 MHz, $CDCl_3$) δ 1.48 (s, 9H), 1.49-1.68 (m, 2H), 1.83 (apparent d, J=12.8 Hz, 2H), 2.07 (bs, 3H), 2.71 (tt, J=12.0, 3.2 Hz, 1H), 2.82 (apparent t, J=12.0 Hz), 3.36 (s, 3H), 4.27 (bs, 2H), 7.24 (bs, 1H), 7.56 (dd, J=8.4, 2.4 Hz, 1H), 8.33 (d, J=2 Hz, 1H).

This N-methylated intermediate was then deprotected using 4N HCl in dioxane as described in general procedure 3 to afford the desired compound, N-methyl-N-(5-(piperidin-4-yl)pyridin-2-yl)acetamide, as light brown solid (93% yield). $^1$H NMR (400 MHz, $CDCl_3$) δ 1.67 (qd, J=12.8, 4.4 Hz, 2H), 1.87 (apparent d, J=13.6 Hz, 2H), 2.09 (s, 3H), 2.70 (tt, J=12.4, 4.0 Hz, 1H), 2.79 (td, J=12.0, 2.4 Hz, 2H), 3.23 (apparent d, J=12.4 Hz, 2H), 3.38 (s, 3H), 7.23 (bs, 1H), 7.62 (dd, J=8.0, 2.4 Hz, 1H), 8.37 (d, J=2.0 Hz, 1H).

Intermediate 71.
2-Methoxy-4-(piperidin-4-yl)pyridine

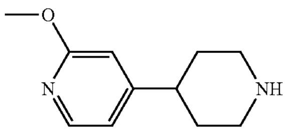

Synthesized from tert-butyl 2'-methoxy-3,6-dihydro-[4,4'-bipyridine]-1(2H)-carboxylate according to general procedure III using 10% Pd/C as hydrogenation catalyst. Isolated as a honey-like sirup (93% yield). $^1$H NMR (400 MHz, $CDCl_3$) δ 1.64 (qd, J=12.0, 4.0 Hz, 2H), 1.83 (apparent d, J=12.4 Hz, 2H), 2.39 (bs, 1H), 2.58 (tt, J=12.0, 4.0 Hz, 1H), 2.74 (apparent td, J=12.4, 2.4 Hz, 2H), 3.19-3.24 (m, 2H), 3.92 (s, 3H), 6.58 (apparent d, J=0.4 Hz, 1H), 6.74 (dd, J=5.6, 0.8 Hz, 1H), 8.07 (d, J=5.2 Hz, 1H).

Intermediate 72. 4-(4-Methoxyphenyl)piperidine

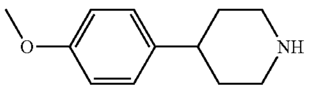

Prepared from tert-butyl 4-(4-methoxyphenyl)-3,6-dihydropyridine-1(2H)-carboxylate according to general procedure 3 using 3% Pd/C as hydrogenation catalyst. Isolated as a thick sirup (76% yield) $^1$H NMR (400 MHz, $CDCl_3$) δ 1.61 (qd, J=12.4 Hz, 4.0 Hz, 2H), 1.81 (apparent d, J=13.6 Hz, 2H), 2.56 (tt, J=12.4, 3.6 Hz, 1H), 2.73 (td, J=12.4, 2.4 Hz, 2H), 3.18 (apparent d, J=12.0 Hz, 2H), 3.79 (s, 3H), 6.85 (d, J=8.4 Hz, 2H), 7.14 (d, J=8.8 Hz, 2H).

Intermediate 73. 4-(2-Methoxyphenyl)piperidine

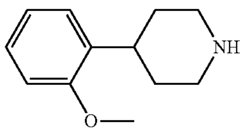

Synthesized from tert-butyl 4-(2-methoxyphenyl)-3,6-dihydropyridine-1(2H)-carboxylate following general procedure 3 using 10% Pd/C as hydrogenation catalyst (66% yield). $^1$H NMR (400 MHz, DMSO-d6) δ 1.47 (qd J=12.0, 3.6 Hz, 2H), 1.61 (apparent d, J=12.0 Hz, 2H), 2.60 (apparent td, J=12.0, 1.6 Hz, 2H), 2.90-3.03 (m, 3H), 3.77 (s, 3H), 6.86-6.96 (m, 2H), 7.12-7.20 (m, 2H).

Intermediate 74. 4-(p-Tolyl)piperidine

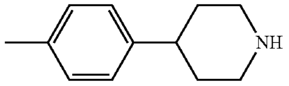

Synthesized from tert-butyl 4-(p-tolyl)-3,6-dihydropyridine-1(2H)-carboxylate following general procedure 3 using 10% Pd/C as hydrogenation catalyst. Isolated as a colorless/pale liquid (78% yield). $^1$H NMR (400 MHz, $CDCl_3$) δ 1.75 (qt, J=12.4, 4.4 Hz, 2H), 1.86 (apparent d, J=12.0 Hz, 2H), 2.32 (s, 3H), 2.61 (tt, J=12.0, 4.0 Hz, 1H), 2.79 (td, J=12.4, 2.8 Hz, 2H), 3.31 (apparent d, J=12.4 Hz, 2H), 4.77 (bs, 1H), 7.12 (s, 4H).

Intermediate 75.
4-(4-(Methoxymethyl)phenyl)piperidine

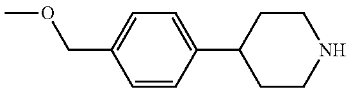

Synthesized from tert-butyl 4-(4-(methoxymethyl)phenyl)-3,6-dihydropyridine-1(2H)-carboxylate by following the general procedure 3 using 10% Pd/C as hydrogenation catalyst. Isolated as a pale solid (89% yield). $^1$H NMR (400 MHz, $CDCl_3$) δ 1.72 (apparent qd, J=12.4, 3.6 Hz, 2H), 1.86 (apparent d, J=12.4 Hz), 2.59-2.69 (m, 1H), 2.78 (apparent td, J=12.4, 2.0 Hz, 2H), 3.26 (apparent d, J=12.0 Hz, 2H), 3.39 (s, 3H), 4.24 (s, 2H), 7.20 (distorted d, J=8.0 Hz, 2H), 7.28 (distorted d, J=8.0 Hz, 2H).

Intermediate 76.
N-Methyl-N-(4-(piperidin-4-yl)phenyl)acetamide

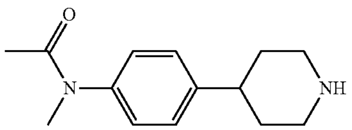 [SMILES: CC(=O)N(C)c1ccc(C2CCNCC2)cc1]

Synthesized from tert-butyl 4-(4-(N-methylacetamido)phenyl)-3,6-dihydropyridine-1(2H)-carboxylate by following the general procedure 3 using 10% Pd/C as hydrogenation catalyst. Isolated as a pale yellow oil (62% yield). $^1$H NMR (400 MHz, $CDCl_3$) δ 1.59-1.73 (m, 2H), 1.83-1.91 (s merged with apparent d, 5H), 2.67 (tt, J=12.0, 4 Hz, 1H), 2.78 (td, J=12.0, 2.4 Hz, 2H), 3.23 (apparent d, J=11.6 Hz, 2H), 3.27 (s, 3H), 7.10 (d, J=8.4 Hz, 2H), 7.25 (d, J=8.4 Hz, 2H).

Intermediate 77.
N-(4-(Piperidin-4-yl)phenyl)acetamide

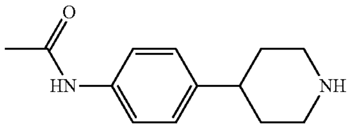 [SMILES: CC(=O)Nc1ccc(C2CCNCC2)cc1]

Synthesized from tert-butyl 4-(4-acetamidophenyl)-3,6-dihydropyridine-1(2H)-carboxylate following the general procedure 3 using 10% Pd/C as hydrogenation catalyst. Isolated as a pale yellow solid (73% yield). $^1$H NMR (400 MHz, $CDCl_3$) δ 1.54-1.66 (m, 2H), 1.80 (distorted apparent d, J=12.8 Hz, 2H), 2.16 (s, 3H), 2.54-2.63 (m, 1H), 2.73 (apparent td, J=13.6, 2.0 Hz J=2H), 3.18 (apparent d, 2H), 7.13 (s, 1H), 7.17 (d, J=8.0 Hz, 2H), 7.41 (d, J=8.4 Hz, 2H).

Intermediate 78. 2-Methoxy-5-(piperidin-4-yl)pyridine

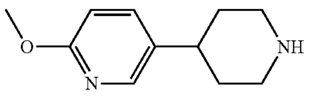

Synthesized from tert-butyl 6-methoxy-3',6'-dihydro-[3, 4'-bipyridine]-1'(2'H)-carboxylate following general procedure 3 using 3% Pd/C as hydrogenation catalyst. Isolated as pale-yellow solid (52% yield). $^1$H NMR (400 MHz, $CDCl_3$) δ 1.61 (qd, J=12.4, 4.0 Hz, 2H), 1.79 (apparent d, J=13.6 Hz, 2H), 2.57 (tt, J=12.0 Hz, 4.0 Hz, 1H), 2.74 (td, J=12.4 Hz, 2.4 Hz, 2H), 3.18-3.21 (apparent d, 2H), 3.91 (s, 3H), 6.69 (d, J=8.4 Hz, 1H), 7.43 (dd, J=8.4 Hz, 2.4 Hz, 1H), 8.05 (d, J=2.4 Hz, 1H).

Intermediate 79. 4-(m-Tolyl)piperidine

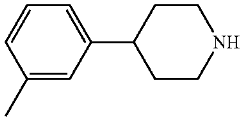

Synthesized from tert-butyl 4-(m-tolyl)-3,6-dihydropyridine-1(2H)-carboxylate following general procedure 3 using 10% Pd/C as hydrogenation catalyst. Isolated as a pale-yellow liquid (83% yield). $^1$H NMR (400 MHz, $CDCl_3$) δ 1.67 (qd, J=12.4, 3.6 Hz, 2H), 1.83 (apparent d, J=12.8 Hz, 2H), 2.33 (s, 3H), 2.60 (tt, J=12.0 Hz, 3.6 Hz, 1H), 2.78 (td, J=12.4 Hz, 2.4 Hz, 2H), 3.22 (apparent d, J=12.0 Hz, 2H), 6.99-7.05 (m, 3H), 7.19 (t, J=7.2 Hz, 1H).

Intermediate 80. 4-(o-Tolyl)piperidine

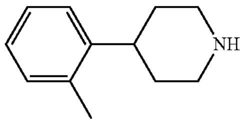

Synthesized from tert-butyl 4-(o-tolyl)-3,6-dihydropyridine-1(2H)-carboxylate, following the general procedure 3 using 10% Pd/C as hydrogenation catalyst. Isolated as a pale-yellow liquid (85% yield). $^1$H NMR (400 MHz, $CDCl_3$) δ 1.65 (apparent qd, J=12.8, 4.0 Hz, 2H), 1.76 (apparent d, J=13.2 Hz, 2H), 2.35 (s, 3H), 2.78 (td, J=12.0, 2.4 Hz, 3H), 3.21 (apparent d, J=12.0 Hz, 2H), 7.06-7.25 (m, 4H).

Intermediate 81. 4-(3-Fluoro-4-methoxyphenyl)piperidine

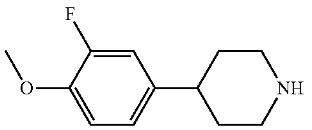

Synthesized from tert-butyl 4-(3-fluoro-4-methoxyphenyl)-3,6-dihydropyridine-1(2H)-carboxylate following general procedure 3 using 3% Pd/C as catalyst. The product was isolated as a colorless liquid (75% yield). $^1$H NMR (400 MHz, $CDCl_3$) δ 1.51-1.63 (m, 4H), 1.77-1.84 (m, 2H), 2.55 (apparent tt, J=12.0, 3.6 Hz, 1H), 2.72 (apparent td, J=12.0, 2.4 Hz, 2H), 3.15-3.20 (m, 2H), 3.87 (s, 3H), 6.85-6.97 (m, 3H).

Intermediate 82. 4-(2-fluoro-4-methoxyphenyl)piperidine

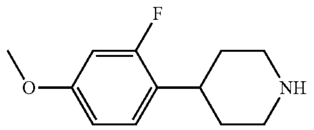

Prepared from tert-butyl 4-(2-fluoro-4-methoxyphenyl)-3,6-dihydropyridine-1(2H)-carboxylate according to general procedure 3 using 3% Pd/C as hydrogenation catalyst. The product was isolated as colorless liquid (59% yield). $^1$H NMR (400 MHz, $CDCl_3$) δ 1.62 (qd, J=12.4, 4.0 Hz, 2H), 1.74-1.81 (m, 2H), 2.75 (td, J=12.4, 2.8 Hz, 2H), 2.90 (tt, $J_1$=12.4, 3.6 Hz, 1H), 3.15-3.19 (m, 2H), 3.77 (s, 3H), 6.58 (dd, J=12.0, 2.4 Hz, 1H), 6.65 (apparent dd, J=8.8, 2.4 Hz, 1H), 7.13 (t, J=8.8 Hz, 1H).

Intermediate 83. 4-(2-Fluorophenyl)piperidine

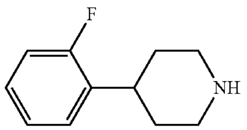 [SMILES: Fc1ccccc1C1CCNCC1]

Synthesized from tert-butyl 4-(2-fluorophenyl)-3,6-dihydropyridine-1(2H)-carboxylate according to general procedure 3 using 3% Pd/C as hydrogenation catalyst. The product was isolated as pale, light yellow syrup (78% yield). $^1$H NMR (400 MHz, $CDCl_3$) δ 1.66 (qd, J=12.4, 4.0 Hz, 2H), 1.78-1.85 (m, 2H), 2.78 (td, J=12.0, 2.4 Hz, 2H), 2.99 (tt, $J_1$=12.0, 3.6 MHz, 1H), 3.16-3.22 (m, 2H), 6.97-7.04 (m, 1H), 7.07-7.12 (m, 1H), 7.13-7.20 (m, 1H), 7.21-7.26 (m, 1H).

Intermediate 84. Methyl 3-(piperidin-4-yl)benzoate

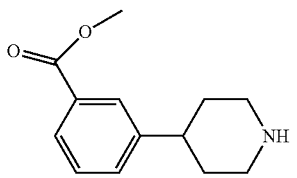 [SMILES: COC(=O)c1cccc(C2CCNCC2)c1]

Synthesized from tert-butyl 4-(3-(methoxycarbonyl)phenyl)-3,6-dihydropyridine-1(2H)-carboxylate by following general procedure 3 using 10% Pd/C as hydrogenation catalyst. Isolated as a light yellow viscous liquid (80% yield). $^1$H NMR (400 MHz, dmso-d6) δ 1.50 (apparent qd, J=12.4, 3.6 Hz, 2H), 1.69 (apparent d, J=12.0 Hz, 2H), 2.58 (td, J=12.0, 1.6 Hz, 2H), 2.63-2.71 (m, 1H), 3.02 (apparent d, J=12.0 Hz, 2H), 3.84 (s, 3H), 7.43-7.47 (distorted t, J=7.6 Hz, 1H), 7.52 (distorted d, J=7.6 Hz, 1H), 7.77-7.80 (m, 2H).

Intermediate 85. 4-(4-(Ethylsulfonyl)phenyl)piperidine

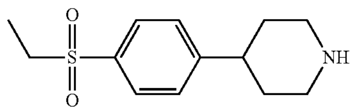 [SMILES: CCS(=O)(=O)c1ccc(C2CCNCC2)cc1]

Prepared from tert-butyl 4-(4-(ethylsulfonyl)phenyl)-3,6-dihydropyridine-1(2H)-carboxylate according to general procedure 3 using 10% Pd/C as hydrogenation catalyst. The product was isolated as an off white solid (75% yield). $^1$H NMR (400 MHz, $CDCl_3$) δ 1.28 (t, J=7.6 Hz, 3H), 1.78 (qd, J=12.4, 4.0 Hz, 2H), 1.89 (apparent d, J=12.0 Hz, 2H), 2.72-2.85 (m, 3H), 3.11 (q, J=7.6 Hz, 2H), 3.27-3.33 (m, 2H), 7.42 (d, J=8.4 Hz, 2H), 7.83 (d, J=8.4 Hz, 2H).

Intermediate 86. 3-Methoxy-5-(piperidin-4-yl)pyridine

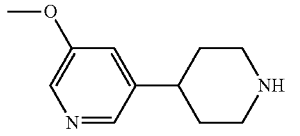

Prepared from tert-butyl 5-methoxy-3',6'-dihydro-[3,4'-bipyridine]-1'(2'H)-carboxylate according to general procedure 3 3 using 10% Pd/C as hydrogenation catalyst. The product was isolated as light brown-yellow viscus oil (42% yield). $^1$H NMR (400 MHz, DMSO-d6) δ 1.53 (apparent qd, J=11.6, 2.8 Hz, 2H), 1.68 (apparent d, J=11.2 Hz, 2H), 2.54-2.73 (m, 3H), 3.02 (apparent d, J=11.6 Hz, 2H), 3.81 (3, 3H), 7.20 (s, 1H), 8.06 (s, 1H), 8.11 (s, 1H).

Intermediate 87. 4-(4-Chloro-phenyl)-piperidine

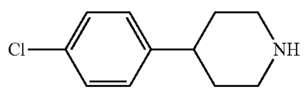 [SMILES: Clc1ccc(C2CCNCC2)cc1]

Synthesized from tert-butyl 4-(4-chlorophenyl)-3,6-dihydropyridine-1(2H)-carboxylate according to general procedure 3 using $PtO_2$ as hydrogenation catalyst. The reduced N-Boc-protected piperidine intermediate was purified by silica gel column chromatography and 0-20% $Et_2O$ in hexanes gradient before deprotection by treatment with 4N HCl. The product was obtained as colorless syrup (53% yield). $^1$H NMR (400 MHz, $CDCl_3$) δ 1.55-1.68 (m, 2H), 1.78-1.90 (bs overlapping with apparent d, J=9.2 Hz, 3H), 2.59 (tt, J=12.0, 3.6 Hz, 1H), 2.74 (apparent t, J=12.0 Hz, 2H), 3.20 (apparent broad based d, J=11.6 Hz, 2H), 7.13 (d, J=8.4 Hz, 2H), 7.27 (d, J=8.8 Hz, 2H).

Intermediate 88. 4-(3-Chloro-4-methoxyphenyl)piperidine

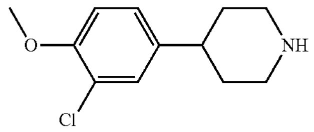

Synthesized from tert-butyl 4-(3-chloro-4-methoxyphenyl)-3,6-dihydropyridine-1(2H)-carboxylate according to general procedure 3 using $PtO_2$ as hydrogenation catalyst. The reduced N-Boc-protected piperidine intermediate was purified by silica gel column chromatography and 0-20% $Et_2O$ in hexanes gradient before deprotection with by treatment with 4N HCl. The product was obtained as colorless very viscous syrup/waxy solid (48% yield). $^1$H NMR (400 MHz, $CDCl_3$) δ 1.50-1.62 (m, 2H), 1.80 (apparent d, J=13.6 Hz, 2H), 2.54 (tt, J=12.0, 3.6 Hz, 1H), 2.72 (td, J=12.0, 2.4 Hz, 2H), 3.15-3.19 (m, 2H), 3.88 (s, 3H), 6.86 (d, J=8.4 Hz, 1H), 7.07 (ddd, J=8.4, 2.4, 0.4 Hz, 1H), 7.22 (d, J=2.4 Hz, 1H).

Intermediate 89. 4-(2-Chloro-4-methoxyphenyl)piperidine

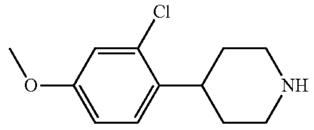

Synthesized from tert-butyl 4-(2-chloro-4-methoxyphenyl)-3,6-dihydropyridine-1(2H)-carboxylate according to general procedure 3 using $PtO_2$ as hydrogenation catalyst. The reduced N-Boc-protected piperidine intermediate was purified by silica gel column chromatography and 0-20% $Et_2O$ in hexanes gradient before deprotection by 4N HCl treatment. The product was obtained as yellowish very viscous syrup/waxy solid (40% yield). $^1$H NMR (600 MHz, $CDCl_3$) δ 1.52-1.61 (m, 4H), 1.83 (apparent d, J=11.4 Hz, 2H), 2.79 (td, J=12.0, 2.4 Hz, 2H), 3.20 (d, J=11.4 Hz, 1H), 3.79 (s, 3H), 6.82 (dd, J=8.4, 2.4 Hz, 1H), 6.92 (d, J=3.0 Hz, 1H), 7.20 (d, J=9.0 Hz, 1H).

Intermediate 90. N-(3-Fluoro-4-(piperidin-4-yl)phenyl)-N-methylacetamide

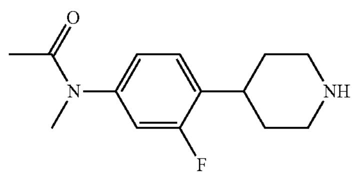 [SMILES: CC(=O)N(C)c1ccc(C2CCNCC2)c(F)c1]

Prepared from tert-butyl 4-(2-fluoro-4-(N-methylacetamido)phenyl)-3,6-dihydropyridine-1(2H)-carboxylate according to general procedure 3 using 10% Pd/C as hydrogenation catalyst. The product was isolated as yellowish waxy solid syrup (96% yield). $^1$H NMR (600 MHz, $CDCl_3$)

δ 1.69 (qd, J=12.0, 4.2 Hz, 2H), 1.84 (apparent d, J=10.8 Hz, 2H), 1.91 (s, 3H), 2.80 (td, J=12.0, 2.4 Hz, 2H), 2.97-3.03 (m, 1H), 3.21-3.24 (m, 2H), 3.25 (s, 3H)), 6.88 (d, J=10.2 Hz, 1H), 6.95 (d, J=7.8 Hz, 1H), 7.26-7.31 (m, 1H).

Intermediate 91. 4-(3-Fluoro-5-methoxyphenyl)piperidine

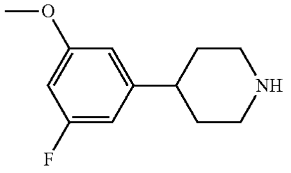

Prepared from tert-butyl 4-(3-fluoro-5-methoxyphenyl)-3,6-dihydropyridine-1(2H)-carboxylate according to general procedure 3 using 10% Pd/C as hydrogenation catalyst. The reduced N-Boc-protected piperidine intermediate was purified by silica gel column chromatography and 0-20% EtOAc in hexanes gradient before deprotection with 4N HCl treatment. The product was isolated as yellowish waxy solid (67% yield). $^{1}$H NMR (300 MHz, $CDCl_3$) δ 1.65 (qd, J=12.6 Hz, 3.6 Hz, 2H), 1.85 (apparent distorted d, J=12.0 Hz, 2H), 2.34 (bs, 1H), 2.60 (tt, J=18.0, 3.9 Hz, 1H), 2.76 (apparent t, J=11.7 Hz, 2H), 3.23 (apparent d, J=12.0 Hz, 2H), 3.80 (s, 3H), 6.45-6.58 (m, 3H).

Intermediate 92. 4-(4-Fluoro-3-methoxyphenyl)piperidine

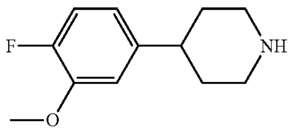

Prepared from tert-butyl 4-(4-fluoro-3-methoxyphenyl)-3,6-dihydropyridine-1(2H)-carboxylate according to general procedure 3 using 10% Pd/C as hydrogenation catalyst. The product was isolated as a yellowish very viscous sirup/waxy solid (58% yield). $^{1}$H NMR (300 MHz, $CDCl_3$) δ 1.59 (qd, J=11.7, 3.9 Hz, 2H), 1.78 (apparent broad d, J=12.3 Hz, 2H), 2.42 (bs, 1H), 2.52 (tt, J=12.0, 3.6 Hz, 1H), 2.69 (td, J=12.0, 2.1 Hz, 2H), 3.16 (apparent d, J=11.7 Hz, 2H), 3.81 (s, 3H), 6.63-6.69 (m, 1H), 6.76 (dd, J=8.1, 2.1 Hz, 1H), 6.92 (dd, J=11.4, 9.6 Hz, 1H).

Intermediate 93. (4-(Piperidin-4-yl)phenyl)(pyrrolidin-1-yl)methanone

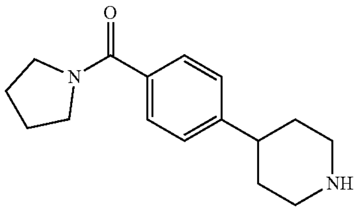 [SMILES: O=C(c1ccc(C2CCNCC2)cc1)N1CCCC1]

Prepared from tert-butyl 4-(4-(pyrrolidine-1-carbonyl)phenyl)-3,6-dihydropyridine-1(2H)-carboxylate according to general procedure 3 using 10% Pd/C as hydrogenation catalyst. The reduced N-Boc-protected piperidine intermediate was purified by silica gel column chromatography and 0-10% EtOAc in hexanes gradient. The product was isolated as a white solid (47% yield). $^{1}$HNMR (600 MHz, $CDCl_3$) δ 7.39 (d, J=8.4 Hz, 2H), 7.16 (d, J=8.4 Hz, 2H), 3.57 (t, J=6.6 Hz, 2H), 3.38 (t, J=6.6 Hz, 2H), 3.14-3.12 (m, 2H), 2.68 (dt, J=12.6, 2.4 Hz, 1H), 2.57 (tt, J=12.0, 3.6 Hz, 1H), 1.91-1.86 (m, 3H), 1.81-1.74 (m, 4H), 1.61-1.54 (m, 2H).

Intermediate 94. (3-Fluoro-4-(piperidin-4-yl)phenyl)(pyrrolidin-1-yl)methanone

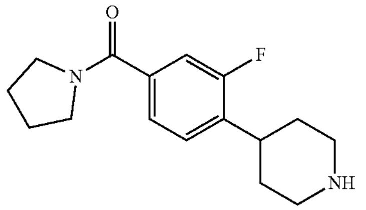 [SMILES: O=C(c1ccc(C2CCNCC2)c(F)c1)N1CCCC1]

Prepared from tert-butyl 4-(2-fluoro-4-(pyrrolidine-1-carbonyl)phenyl)-3,6-dihydropyridine-1(2H)-carboxylate according to general procedure 3 using 10% Pd/C as hydrogenation catalyst. The product was isolated as a white solid (73% yield). $^{1}$HNMR (600 MHz, $CDCl_3$) δ 7.51-7.21 (m, 2H), 7.18 (d, J=7.2 Hz, 1H), 3.66 (t, J=6.6 Hz, 2H), 3.47 (t, J=6.6 Hz, 2H), 3.25-3.23 (m, 2H), 3.03 (tt, J=12.6, 2.4 Hz, 1H), 2.81 (dt, J=12.0, 2.4 Hz, 1H), 2.10 (s, 1H), 2.0-1.96 (m, 2H), 1.93-1.88 (m, 2H), 1.85-1.83 (m, 2H), 1.76-1.69 (m, 2H).

Intermediate 95. 1-(4-(Piperidin-4-yl)benzyl)pyrrolidin-2-one

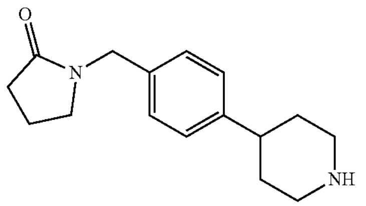 [SMILES: O=C1CCCN1Cc1ccc(C2CCNCC2)cc1]

Prepared from tert-butyl 4-(4-((2-oxopyrrolidin-1-yl)methyl)phenyl)-3,6-dihydropyridine-1(2H)-carboxylate according to general procedure 3 using 10% Pd/C as hydrogenation catalyst. The product was isolated as a white solid (72% yield). $^{1}$HNMR (600 MHz, $CDCl_3$) δ 7.15 (s, 4H), 4.39 (s, 2H), 3.24 (t, J=7.2 Hz, 2H), 3.19-3.17 (m, 2H), 2.72 (td, J=12.0, 2.4 Hz, 2H), 2.59 (tt, J=9.0, 3.6 Hz, 1H), 1.99-1.94 (m, 4H), 1.81-1.79 (m, 2H), 1.66-1.59 (m, 2H).

Intermediate 96. 4-(4-(Pyrrolidin-1-ylsulfonyl)phenyl)piperidine

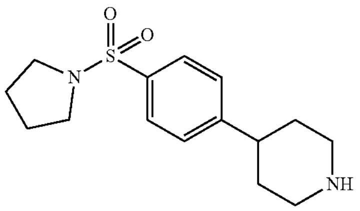 [SMILES: O=S(=O)(c1ccc(C2CCNCC2)cc1)N1CCCC1]

Prepared from tert-butyl 4-(4-(pyrrolidin-1-ylsulfonyl) phenyl)-3,6-dihydropyridine-1(2H)-carboxylate according to general procedure 3 using 10% Pd/C as hydrogenation catalyst. The product was isolated as a white solid (93% yield). $^1$HNMR (500 MHz, $CDCl_3$) δ 7.73 (d, J=8.5 Hz, 2H), 7.33 (d, J=8.5 Hz, 2H), 3.23-3.19 (m, 6H), 2.76-2.64 (m, 3H), 2.19 (s, 1H), 1.83-1.81 (m, 2H), 1.74-1.72 (m, 4H), 1.69-1.61 (m, 2H).

Intermediate 97. 2-(Piperidin-4-yl)-4-(trifluoromethyl)pyridine

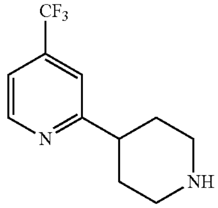 [SMILES: FC(F)(F)c1ccnc(C2CCNCC2)c1]

Prepared from tert-butyl 4-(trifluoromethyl)-3',6'-dihydro-[2,4'-bipyridine]-1'(2'H)-carboxylate according to general procedure 3 using 10% Pd/C as hydrogenation catalyst. The product was isolated as a white solid (60% yield). $^1$HNMR (600 MHz, $CDCl_3$) δ 8.69 (d, J=4.8 Hz, 1H), 7.37 (s, 1H), 7.32 (d, J=4.8 Hz, 1H), 3.22-3.20 (m, 2H), 2.91 (tt, J=12.0, 3.6 Hz, 1H), 2.76 (dt, J=12.0, 2.4 Hz, 2H), 1.94-1.92 (m, 2H), 1.74-1.67 (m, 2H), 1.62 (bs, 1H).

Intermediate 98. 4-(4-((Methylsulfonyl)methyl)phenyl)piperidine

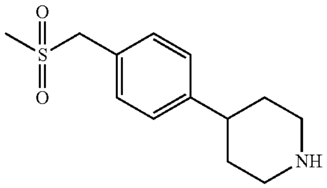 [SMILES: CS(=O)(=O)Cc1ccc(C2CCNCC2)cc1]

Prepared from tert-butyl 4-(4-((methylsulfonyl)methyl) phenyl)-3,6-dihydropyridine-1(2H)-carboxylate according to general procedure 3 using 10% Pd/C as hydrogenation catalyst. The product was isolated as a white solid (83% yield). $^1$HNMR (600 MHz, $CD_3OD$) δ 7.40 (d, J=7.8 Hz, 2H), 7.31 (d, J=7.8 Hz, 2H), 4.40 (s, 2H), 3.17-3.15 (m, 2H), 2.86 (s, 3H), 2.77-2.69 (m, 3H), 1.85-1.83 (m, 2H), 1.72-1.65 (m, 2H).

Intermediate 99. 3-(Piperidin-4-yl)-5-(trifluoromethyl)pyridine

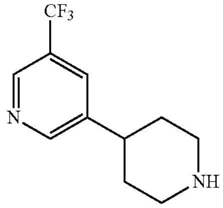 [SMILES: FC(F)(F)c1cncc(C2CCNCC2)c1]

Prepared from tert-butyl 5-(trifluoromethyl)-3',6'-dihydro-[3,4'-bipyridine]-1'(2'H)-carboxylate according to general procedure 3 using 10% Pd/C as hydrogenation catalyst. The product was isolated as a white solid (72% yield). $^1$HNMR (600 MHz, $CDCl_3$) δ 8.76 (d, J=1.2 Hz, 1H), 8.71 (d, J=1.8 Hz, 1H), 7.79 (s, 1H), 3.29-3.27 (m, 2H), 2.83-2.76 (m, 3H), 2.24 (bs, 1-NH), 1.91-1.89 (m, 2H), 1.76-1.69 (m, 2H).

Intermediate 100. 1-(4-(Piperidin-4-yl)phenyl)pyrrolidin-2-one

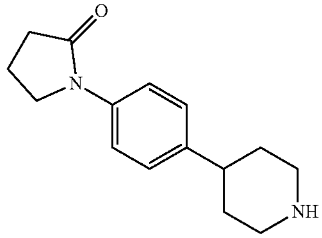 [SMILES: O=C1CCCN1c1ccc(C2CCNCC2)cc1]

Prepared from tert-butyl 4-(4-(2-oxopyrrolidin-1-yl)phenyl)-3,6-dihydropyridine-1(2H)-carboxylate according to general procedure 3 using 10% Pd/C as hydrogenation catalyst. The product was isolated as a white solid (76% yield). $^1$HNMR (600 MHz, $CDCl_3$) δ 7.48 (d, J=8.4 Hz, 2H), 7.18 (d, J=8.4 Hz, 2H), 3.85-3.79 (m, 2H), 3.14 (d, J=12.0 Hz, 2H), 2.70 (dt, J=12.6, 2.4 Hz, 1H), 2.59-2.54 (m, 3H), 2.14-2.09 (m, 2H), 1.78-1.76 (m, 2H), 1.61-1.53 (m, 3H).

Intermediate 101. 5-(Piperidin-4-yl)-2,3-dihydrobenzo[b]thiophene 1,1-dioxide

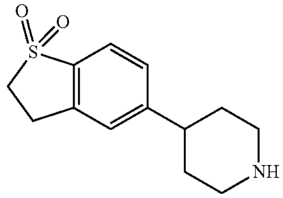 [SMILES: O=S1(=O)CCc2cc(C3CCNCC3)ccc21]

Prepared from tert-butyl 4-(1,1-dioxido-2,3-dihydrobenzo[b]thiophen-5-yl)-3,6-dihydropyridine-1(2H)-carboxylate according to general procedure 3 using 10% Pd/C as hydrogenation catalyst. The product was isolated as a white solid (79% yield). $^1$HNMR (300 MHz, $CD_3OD$) δ

7.69 (d, J=8.1 Hz, 1H), 7.48-7.45 (s, 2H), 3.58-3.51 (m, 4H), 3.43-3.39 (m, 2H), 3.18-3.01 (m, 3H), 2.15-2.11 (m, 2H), 2.01-1.87 (m, 2H).

Intermediate 102. 4-(piperidin-4-yl)-N-(1,1,1-trifluoropropan-2-yl)aniline

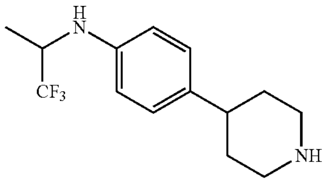 [SMILES: CC(Nc1ccc(C2CCNCC2)cc1)C(F)(F)F]

Prepared from tert-butyl 4-(4-((1,1,1-trifluoropropan-2-yl)amino)phenyl)-3,6-dihydropyridine-1(2H)-carboxylate according to general procedure 3. The product was isolated as a white solid (72% yield). $^1$HNMR (300 MHz, $CDCl_3$) δ 7.03 (d, J=8.7 Hz, 2H), 6.59 (d, J=8.4 Hz, 2H), 3.99-3.92 (m, 1H), 3.46 (d, J=9.0 Hz, 1H), 3.18-3.14 (m, 2H), 2.70 (td, J=12.0, 2.4 Hz, 2H), 2.49 (dt, J=12.0, 3.6 Hz, 1H), 1.80-1.75 (m, 2H), 1.64-1.51 (m, 2H), 1.35 (d, J=6.9 Hz, 3H).

Intermediate 103. 5-(Piperidin-4-yl)-1,3-dihydrobenzo[c]thiophene 2,2-dioxide

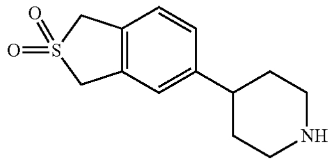 [SMILES: O=S1(=O)Cc2ccc(C3CCNCC3)cc2C1]

Prepared from tert-butyl 4-(2,2-dioxido-1,3-dihydrobenzo[c]thiophen-5-yl)-3,6-dihydropyridine-1(2H)-carboxylate according to general procedure 3 using 10% Pd/C as hydrogenation catalyst. The product was isolated as a white solid (96% yield). $^1$HNMR (300 MHz, $CDCl_3$) δ 7.25-7.15 (m, 3H), 4.33 (d, J=3.3 Hz, 4H), 3.23-3.18 (m, 2H), 2.78-2.56 (m, 3H), 1.82-1.79 (m, 3H), 1.69-1.56 (m, 2H).

Intermediate 104. 1-(2-Fluoro-4-(piperidin-4-yl)benzyl)pyrrolidin-2-one

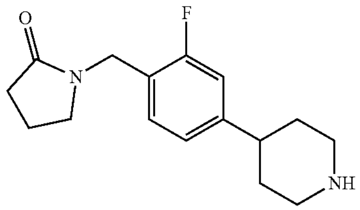 [SMILES: O=C1CCCN1Cc1ccc(C2CCNCC2)cc1F]

Prepared from tert-butyl 4-(3-fluoro-4-((2-oxopyrrolidin-1-yl)methyl)phenyl)-3,6-dihydropyridine-1(2H)-carboxylate) according to general procedure 3 using 10% Pd/C as hydrogenation catalyst. The product was isolated as a white solid (79% yield). $^1$HNMR (600 MHz, $CDCl_3$) δ 7.18 (t, J=7.8 Hz, 1H), 6.94 (d, J=7.8 Hz, 1H), 6.89-6.87 (m, 1H), 4.45 (s, 2H), 3.67 (s, 1H), 3.17-3.15 (m, 2H), 2.70 (dt, J=12.6, 2.4 Hz, 2H), 2.57 (td, J=12.6, 3.6 Hz, 1H), 2.39 (t, J=8.4 Hz, 2H), 1.99-1.94 (m, 2H), 1.80-1.78 (m, 3H), 1.60-1.56 (m, 2H).

Intermediate 105. 1-(2-Chloro-4-(piperidin-4-yl)benzyl)pyrrolidin-2-one

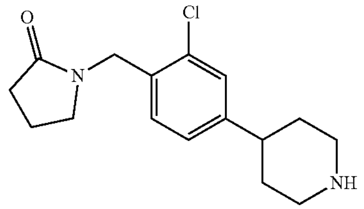 [SMILES: O=C1CCCN1Cc1ccc(C2CCNCC2)cc1Cl]

Prepared from tert-butyl 4-(3-chloro-4-((2-oxopyrrolidin-1-yl)methyl)phenyl)-3,6-dihydropyridine-1(2H)-carboxylate according to general procedure 3 using 10% Pd/C as hydrogenation catalyst. The product was isolated as white solid (63% yield). $^1$HNMR (600 MHz, $CDCl_3$) δ 7.19-7.16 (m, 2H), 7.06-7.05 (m, 1H), 4.53 (s, 2H), 3.28 (t, J=7.2 Hz, 2H), 3.16-3.14 (m, 2H), 2.2.69 (dt, J=12.0 Hz, 1.8 Hz, 2H), 2.58 (tt, J=12.0, 3.0 Hz, 1H), 2.41 (t, J=8.4 Hz, 2H), 2.01-1.97 (m, 2H), 1.78-1.66 (m, 3H), 1.59-1.55 (m, 2H).

Intermediate 106. 1-(3-Fluoro-4-(piperidin-4-yl)benzyl)pyrrolidin-2-one

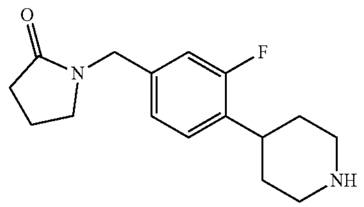 [SMILES: O=C1CCCN1Cc1ccc(C2CCNCC2)c(F)c1]

Prepared from tert-butyl 4-(2-fluoro-4-((2-oxopyrrolidin-1-yl)methyl)phenyl)-3,6-dihydropyridine-1(2H)-carboxylate according to general procedure 3 using 10% Pd/C as hydrogenation catalyst. The product was isolated as white solid (65% yield). $^1$HNMR (300 MHz, $CDCl_3$) δ 7.20-7.17 (m, 1H), 6.99-6.88 (m, 2H), 4.39 (s, 2H), 3.58-3.54 (m, 2H), 3.25 (t, J=6.9 Hz, 2H), 3.07-2.97 (m, 3H), 2.43 (t, J=7.8 Hz, 2H), 2.18-1.88 (m, 6H).

Intermediate 107. 4-(4-(Piperidin-4-yl)phenyl)morpholine

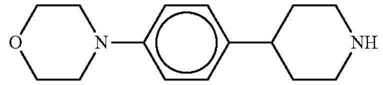

Prepared from tert-butyl 4-(4-morpholinophenyl)-3,6-dihydropyridine-1(2H)-carboxylate according to general procedure 3 using 10% Pd/C as hydrogenation catalyst. The product was isolated as white solid (70% yield). $^1$HNMR (600 MHz, $CDCl_3$) δ 1.61 (apparent qd, J=12.6, 3.6 Hz, 2H), 1.81 (bd, J=13.2 Hz, 2H), 2.55 (tt, J=12.0, 3.6 Hz, 1H), 2.73 (td, J=12.0, 1.8 Hz, 2H), 3.13 (apparent t, J=4.8 Hz, 4H), 3.18 (d, J=12.0 Hz, 2H), 3.85 (apparent t, J=4.8 Hz, 4H), 6.87 (d, J=9.0 Hz, 2H), 7.14 (d, J=8.4 Hz, 2H).

Intermediate 108. 4-(4-(Piperidin-4-yl)benzyl)morpholine

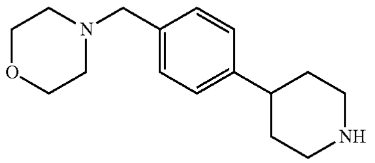 [SMILES: c1cc(C2CCNCC2)ccc1CN1CCOCC1]

Prepared from tert-butyl 4-(4-(morpholinomethyl)phenyl)-3,6-dihydropyridine-1(2H)-carboxylate according to general procedure 3 using 10% Pd/C as hydrogenation catalyst. The product was isolated as viscous liquid (24% yield). $^1$H NMR (300 MHz, $CDCl_3$) δ 7.21 (d, J=6.0 Hz, 2H), 7.13 (d, J=8.1 Hz, 2H), 3.67 (t, J=4.5 Hz, 4H), 3.43 (s, 2H), 3.17-3.13 (m, 2H), 2.70 (td, J=12.0 Hz, 2.1 Hz, 2H), 2.56 (tt, J=8.7 Hz, 3.6 Hz, 1H), 2.4 (t, J=4.5 Hz, 4H), 1.81-1.77 (m, 2H), 1.65-1.54 (m, 3H).

Intermediate 109. 4-(4-(Piperidin-4-yl)phenyl)morpholin-3-one

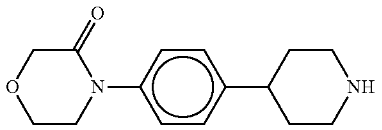

Prepared from tert-butyl 4-(4-(3-oxomorpholino)phenyl)-3,6-dihydropyridine-1(2H)-carboxylate according to general procedure 3 using 10% Pd/C as hydrogenation catalyst. The product was isolated as an off-white solid (79% yield). $^1$HNMR (600 MHz, $CDCl_3$) δ 1.57-1.66 (m, 2H), 1.82 (apparent d, J=13.2 Hz), 2.62 (tt, J=12.0, 3.6 Hz, 1H), 2.73 (td, J=12.6, 2.4 Hz, 2H), 3.18 (apparent d, J=12.0 Hz, 2H), 3.75 (apparent t, J=5.4 Hz, 2H), 4.02 (apparent t, J=5.4 Hz, 2H), 4.34 (s, 2H), 7.23-7.28 (m, 4H).

Intermediate 110. 4-(2-fluoro-4-(piperidin-4-yl)phenyl)morpholine

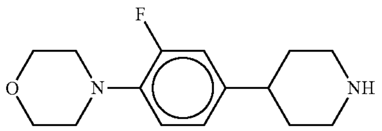

Prepared from tert-butyl 4-(3-fluoro-4-morpholinophenyl)-3,6-dihydropyridine-1(2H)-carboxylate according to general procedure 3 using 10% Pd/C as hydrogenation catalyst. The product was isolated as a white solid (68% yield). $^1$HNMR (600 MHz, $CDCl_3$) δ 1.58 (apparent qd, J=12.6, 3.6 Hz, 2H), 1.80 (apparent d, J=13.2 Hz, 2H), 2.55 (tt, J=12.0, 3.6 Hz, 1H), 2.73 (td, J=12.0, 1.8 Hz, 2H). 3.06 (apparent t, J=4.8 Hz, 4H), 3.18 (apparent d, J=12.0 Hz, 2H), 3.86 (apparent t, J=4.8 Hz, 4H), 6.85-6.94 (m, 3H).

Intermediate 111. 4-(3-Fluoro-4-(piperidin-4-yl)phenyl)morpholine

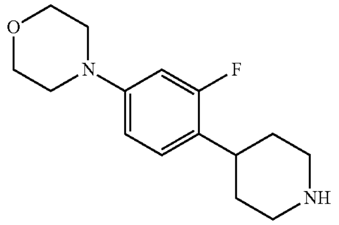 [SMILES: Fc1cc(N2CCOCC2)ccc1C1CCNCC1]

Prepared from tert-butyl 4-(2-fluoro-4-morpholinophenyl)-3,6-dihydropyridine-1(2H)-carboxylate according to general procedure 3 using 10% Pd/C as hydrogenation catalyst. The product was isolated as white solid (37% yield). $^1$H NMR (300 MHz, $CDCl_3$) δ 7.13-7.06 (m, 1H), 6.61 (dd, J=8.1 Hz, 2.8 Hz 1H), 6.55-6.50 (m, 1H), 4.26 (s, 1H), 3.81 (t, J=4.8 Hz, 4H), 3.28-3.24 (m, 1H), 3.09 (t, J=5.1 Hz, 4H), 2.96-2.75 (m, 3H), 1.83-1.68 (m, 4H).

Intermediate 112. (S)-1-(1-(4-(Piperidin-4-yl)phenyl)ethyl)pyrrolidin-2-one

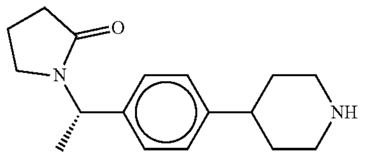

Prepared from tert-butyl (S)-4-(4-(1-(2-oxopyrrolidin-1-yl)ethyl)phenyl)-3,6-dihydropyridine-1(2H)-carboxylate according to general procedure 3 using 10% Pd/C as hydrogenation catalyst. The product was isolated as an off-white solid (81% yield). $^1$H NMR (600 MHz, $CDCl_3$) δ 1.49 (d, J=7.2 Hz, 1.65 (apparent qt, J=12.6, 3.0 Hz, 2H), 1.82 (apparent d, J=12.6 Hz, 2H), 1.86-1.93 (m, 1H), 1.93-2.01 (m, 1H), 2.25 (bs, 1H), 2.35-2.47 (m, 2H), 2.75 (td, J=12.0, 1.8 Hz, 2H), 3.00 (ddd, J=14.4, 8.4, 5.4 Hz, 1H), 3.21 (apparent d, J=12.0 Hz, 2H), 3.31 (ddd, J=15.0, 9.0, 6.0 Hz, 1H), 5.47 (q, J=7.2 Hz, 1H), 7.18 (distorted d, J=8.4 Hz, 2H), 7.23 (distorted d, J=8.4 Hz, 2H).

Intermediate 113. (R)-1-(1-(4-(Piperidin-4-yl)phenyl)ethyl)pyrrolidin-2-one

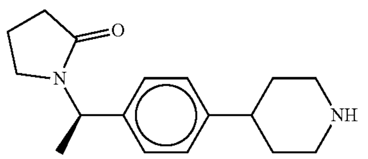

Prepared from tert-butyl (R)-4-(4-(1-(2-oxopyrrolidin-1-yl)ethyl)phenyl)-3,6-dihydropyridine-1(2H)-carboxylate according to general procedure 3 using 10% Pd/C as hydrogenation catalyst. The product was isolated as an off-white solid (75% yield). $^1$H NMR (600 MHz, $CDCl_3$) δ 1.52 (d, J=7.2 Hz, 3H), 1.68 (apparent qt, J=12.6, 3.0 Hz, 2H), 1.84 (apparent d, J=12.6 Hz, 2H), 1.90-1.94 (m, 1H), 1.94-2.03 (m, 1H), 2.21 (bs, 1H), 2.37-2.48 (m, 2H), 2.63 (tt, J=12.0, 3.6 Hz, 1H), 2.77 (td, J=12.6, 2.4 Hz, 2H), 3.02 (ddd, J=14.4, 9.0, 5.4 Hz, 1H), 3.23 (apparent bd, J=12.0 Hz, 2H), 3.34 (ddd, J=15.0, 9.0, 6.0 Hz), 5.48 (q, J=7.2 Hz, 1H), 7.20 (distorted d, J=8.4 Hz, 2H), 7.25 (distorted d, J=8.4 Hz, 2H).

Intermediate 114. 1-(3-Fluoro-4-(piperidin-4-yl)phenyl)pyrrolidin-2-one

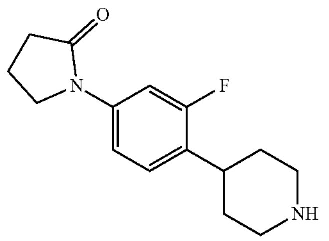 [SMILES: O=C1CCCN1c1ccc(C2CCNCC2)c(F)c1]

Prepared from tert-butyl 4-(2-fluoro-4-(2-oxopyrrolidin-1-yl)phenyl)-3,6-dihydropyridine-1(2H)-carboxylate according to general procedure 3 using 10% Pd/C as hydrogenation catalyst. The product was isolated as white solid (70% yield). $^1$HNMR (400 MHz, $CDCl_3$) δ 7.43 (dd, J=12.4, 2.0 Hz, 1H), 7.26-7.17 (m, 2H), 3.80 (t, J=6.8 Hz, 2H), 3.16-3.13 (m, 2H), 2.92 (tt, J=12.4, 8.4 Hz, 1H), 2.74 (dt, J=12.4, 2.4 Hz, 2H), 2.58 (t, J=8.0 Hz, 2H), 2.17-2.09 (m, 2H), 1.78-1.74 (m, 2H), 1.65-1.56 (m, 3H).

Intermediate 115. 4-(4-(piperidin-4-yl)phenyl)thiomorpholine 1,1-dioxide

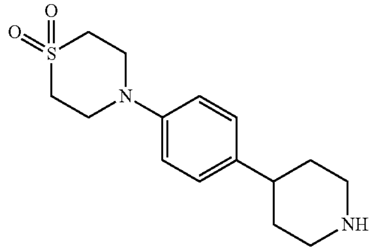 [SMILES: O=S1(=O)CCN(c2ccc(C3CCNCC3)cc2)CC1]

Prepared from tert-butyl 4-(4-(1,1-dioxidothiomorpholino)phenyl)-3,6-dihydropyridine-1(2H)-carboxylate according to general procedure 3 using 10% Pd/C as hydrogenation catalyst. The product was isolated as white solid (72% yield). $^1$H NMR (300 MHz, $CDCl_3$) δ 7.12 (d, J=8.4 Hz, 2H), 6.84 (d, J=8.4 Hz, 2H), 3.78 (t, J=7.2 Hz, 4H), 3.18-3.14 (m, 2H), 3.09 (t, J=8.0 Hz, 4H), 2.70 (dt, J=12.3, 2.7 Hz, 2H), 2.53 (tt, J=12.3, 3.6 Hz, 1H), 1.80-1.75 (m, 2H), 1.64-1.52 (m, 2H).

General Procedure 4. Synthesis of 4-(thioaryl/thio-heteroaryl)piperidines

A mixture of a desired aryl/heteroaryl thiol (1.1 eq.) and $K_2CO_3$ (1.1 eq) in DMF was treated at room temperature with tert-butyl 4-((methylsulfonyl)oxy)piperidine-1-carboxylate (1 eq), prepared according to De Crescezo, G. et al. WO 2000046221 A1 and Iyobe, A. et al. Chem. Pharm. Bull. 2001, 49(7) 822, disclosures incorporated here in by reference. The reaction vessel was then sealed, warmed up to 70° C. and stirred until TLC indicated consumption of the limiting reagent. The mixture was then cooled and partitioned between $CH_2Cl_2$ and water. The aq. layer was extracted with $CH_2Cl_2$ and combined organic layer was dried over $Na_2SO_4$, filtered and evaporated. The residue was chromatographed with silica gel column to afford the corresponding intermediate N-Boc protected 4-thioaryl/4-thio heteroaryl piperidine. This intermediate was then treated with 4 N HCl in dioxane at room temperature and stirred until TLC indicated consumption of the starting material. Followed evaporation of the volatiles and partition of the residue between aq. saturated $Na_2CO_3$ and $CH_2Cl_2$. The aq. layer was extracted with $CH_2Cl_2$ and the combined organic layer was dried over $Na_2SO_4$, filtered and concentrated to afford the corresponding 4-thioaryl/4-thioheteroaryl piperidine of interest.

Intermediate 116. 4-((4-Methoxyphenyl)thio)piperidine

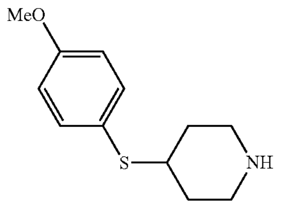 [SMILES: COc1ccc(SC2CCNCC2)cc1]

Prepared from commercially available 4-methoxybenzenethiol according to general procedure 4. The crude intermediate N-Boc-4-((4-methoxy-phenyl)thio)piperidine was purified with silica gel column and 0-50% EtOAc in hexanes gradient prior to treatment/deprotection with 4N HCl in dioxane. The desired compound, 4-((4-methoxyphenyl)thio)piperidine, was isolated as a white solid (49% yield). $^1$H NMR (600 MHz, $CDCl_3$) δ 1.43-1.51 (m, 2H), 1.85-1.95 (m, 3H), 2.58-2.63 (m, 2H), 2.98 (tt, J=10.8, 3.6 Hz, 1H), 3.09 (dt, J=13.2, 3.6 Hz, 2H), 3.79 (s, 3H), 6.84 (apparent d, J=9.0 Hz, 2H), 7.39 (apparent d, J=8.4 Hz, 2H).

Intermediate 117. 4-((4-Fluorophenyl)thio)piperdine

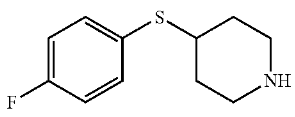 [SMILES: Fc1ccc(SC2CCNCC2)cc1]

Prepared according to general procedure 4 from commercially available 4-fluorobenzenethiol. The crude intermediate N-Boc-4-((4-fluorophenyl)thio)piperidine was purified with silica gel column and 0-25% EtOAc in hexanes prior to treatment/deprotection with 4N HCl in dioxane. The desired compound, 4-((4-fluorophenyl)thio)piperdine, was isolated as colorless viscous oil (58% yield). $^1$H NMR (600 MHz, $CDCl_3$) δ 1.47-1.55 (m, 2H), 1.93 (apparent dd, J=13.2, 3.0 Hz, 2H), 2.19 (bs, 1H), 2.61-2.67 (m, 2H), 3.07 (tt, J=6.6, 4.2 Hz, 1H), 3.12 (dt, J=13.2, 3.6 Hz, 2H), 7.00 (apparent t, J=9.0 Hz, 2H), 7.40-7.43 (m, 2H).

Intermediate 118. 4-((3-methoxyphenyl)thio)piperidine

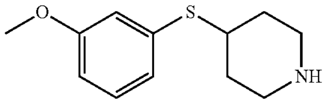

Prepared from commercially available 3-methoxybenzenethiol according to general procedure 4. The crude intermediate N-Boc-4-((3-methoxyphenyl)thio)piperidine was purified with silica gel column and 0-30% EtOAc in hexanes gradient prior to treatment/deprotection with 4N HCl in dioxane. The desired compound, 4-((3-methoxyphenyl)thio)piperidine, was isolated as light yellow oil (50% yield). $^1$H NMR (600 MHz, $CDCl_3$) δ 1.49-1.56 (m, 2H), 1.97 (apparent dd, J=13.8, 3.6 Hz, 2H), 2.65 (ddd, J=13.2, 10.8, 2.4 Hz, 2H), 3.11 (dt, J=13.2, 3.6 Hz, 2H), 3.20 (tt, J=10.8, 3.6 Hz, 1H), 6.78 (ddd, J=7.8, 2.4, 0.6 Hz), 6.95-6.96 (m, 1H), 6.99 (ddd, J=7.8, 1.8, 1.2 Hz, 1H), 7.21 (apparent t, J=7.8 Hz, 1H).

Intermediate 119. 2-(Piperidin-4-ylthio)pyrimidine

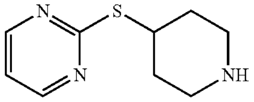 [SMILES: c1cnc(SC2CCNCC2)nc1]

Prepared from commercially available pyrimidine-2-thiol according to general procedure 4. The crude intermediate N-Boc-2-(piperidin-4-ylthio)pyrimidine was purified with silica gel column and 0-100% EtOAc in hexanes gradient prior to treatment/deprotection with 4N HCl in dioxane. The desired compound, 2-(piperidin-4-ylthio)pyrimidine, was isolated as pale yellow viscous sirup (40% yield). $^1$H NMR (600 MHz, $CDCl_3$) δ 1.62-1.70 (m, 2H), 2.10-2.15 (m, 2H), 2.79 (ddd, J=13.2, 10.8, 3.0 Hz, 2H), 3.12 (dt, J=13.2, 3.6 Hz, 2H), 3.86-3.92 (m, 2H), 6.93 (t, J=4.8 Hz, 1H), 8.50 (d, J=4.8 Hz, 2H).

Intermediate 120. 4-((2-Fluorophenyl)thio)piperidine

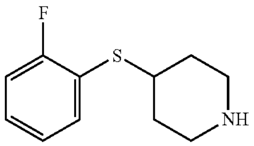 [SMILES: Fc1ccccc1SC1CCNCC1]

Prepared from commercially available 2-fluorobenzenethiol according to general procedure 4. The crude intermediate N-Boc-4-((2-fluorophenyl)thio)piperidine, was purified with silica gel column and 0-25% EtOAc in hexanes gradient prior to treatment/deprotection with 4N HCl in dioxane. The desired compound, 4-((2-fluorophenyl)thio)piperidine, was obtained as clear, pale yellow, sirup (35% yield). $^1$H NMR (300 MHz, $CD_3OD$) δ 1.46-1.60 (m, 2H), 1.89-1.97 (m, 2H), 2.64 (ddd, J=13.8, 11.1, 2.7 Hz, 2H), 3.07 (dt, J=13.2, 3.9 Hz, 2H), 3.25-3.30 (m, 1H), 7.10-7.19 (m, 2H), 7.31-7.39 (m, 1H), 7.51 (apparent td, J=7.2, 1.8 Hz).

General Procedure 5. Synthesis of 4-(benzyl/heterobenzyl)piperidines

To commercially available tert-butyl 4-methylenepiperidine-1-carboxylate (1 mmol) was added 9-BBN (1.1 mmol, 0.5 M in THF). The mixture was refluxed for 2.5 hours under inert atmosphere then cooled and transfer slowly (under inert atmosphere) to a mixture of a desired arylbromide (1.1 mmol), $K_2CO_3$ (3 mmol) and $PdCl_2$(dppf) (0.04 mmol) in dioxane:water (2:1). The resulting mixture was stirred for 48 h at 90° C., then cooled to room temperature, quenched with 1N NaOH and extracted with EtOAc (3×30 mL). The combined organic layer was dried over $Na_2SO_4$ filtered and concentrated to a residue that was chromatographed on a silica gel column using 0-50% EtOAc in hexanes to afford the corresponding N-Boc-4-(benzyl/heterobenzyl)piperidine. This intermediate was then treated with 4 N HCl in dioxane at room temperature until TLC indicated consumption of the starting material. Followed evaporation of the volatiles and partition of the residue between aq. saturated $K_2CO_3$ and $CH_2Cl_2$. The aq. layer was extracted with either EtOAc or $CH_2Cl_2$ or 10% MeOH in $CH_2Cl_2$ and the combined organic layer was dried over $Na_2SO_4$, filtered and concentrated to afford the corresponding 4-(benzyl/heterobenzyl)piperidine of interest.

Intermediate 121. 4-(3-chlorobenzyl)piperidine

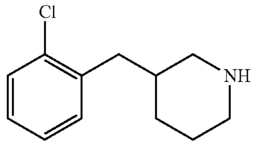 [SMILES: Clc1ccccc1CC1CCCNC1]

Prepared from commercially available 1-bromo-3-chlorobenzene and tert-butyl 4-methylenepiperidine-1-carboxylate according to general procedure 5. The product was isolated as a transparent liquid (23% yield). $^1$HNMR (600 MHz, $CD_3OD$) δ 7.30 (t, J=7.8 Hz, 1H), 7.26-7.20 (m, 2H), 7.15 (d, J=7.8 Hz, 1H), 3.39-3.36 (m, 2H), 2.98-2.94 (m, 2H), 2.64 (d, J=7.2 Hz, 2H), 1.96-1.85 (m, 3H), 1.47-1.40 (m, 2H).

Intermediate 122 4-(4-chlorobenzyl)piperidine hydrochloride

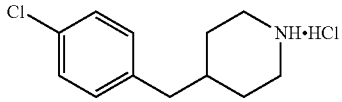

Prepared from commercially available 1-bromo-4-chlorobenzene and tert-butyl 4-methylenepiperidine-1-carboxylate according to general procedure 5. The piperidine product was characterized as the HCl salt (39% yield). $^1$HNMR (600 MHz, $CD_3OD$) δ 7.31 (d, J=8.4 Hz, 2H), 7.20 (d, J=7.8

Hz, 2H), 3.39-3.37 (m, 2H), 2.98-2.93 (m, 2H), 2.62 (d, J=6.6 Hz, 2H), 1.95-1.86 (m, 3H), 1.47-1.40 (m, 2H).

Intermediate 123. 4-(3-Methylbenzyl)piperidine

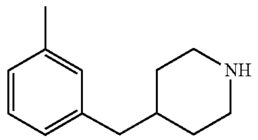

Prepared from commercially available 1-bromo-3-methylbenzene and tert-butyl 4-methylenepiperidine-1-carboxylate according to the general procedure 5. The product was isolated as a transparent liquid (57% yield). $^1$HNMR (600 MHz, $CDCl_3$) δ 7.16-7.13 (m, 1H), 7.00-6.97 (m, 1H), 6.94-6.92 (m, 2H), 3.08-3.06 (m, 2H), 2.55 (td, J=12.0, 1.8 Hz, 2H), 2.47 (d, J=6.6 Hz, 2H), 2.32 (s, 3H), 1.65-1.57 (m, 3H), 1.27-1.16 (m, 2H).

Intermediate 124. 2-Methoxy-4-(piperidin-4-ylmethyl)pyridine

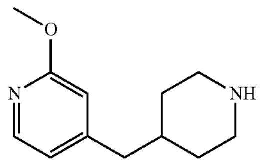

Prepared from commercially available 4-bromo-2-methoxypyridine and tert-butyl 4-methylenepiperidine-1-carboxylate according to general procedure 5. The product was isolated as a white solid (55% yield). $^1$HNMR (300 MHz, DMSO-$d_6$) δ 8.02 (d, J=5.4 Hz, 1H), 6.82 (dd, J=5.4, 1.5 Hz, 1H), 6.64 (d, J=0.6 Hz, 1H), 3.89 (s, 3H), 3.22-3.06 (m, 2H), 2.62 (td, J=12.6, 2.7 Hz, 2H), 2.56 (d, J=7.2 Hz, 2H), 1.87-1.73 (m, 1H) 1.68 (apparent d, J=13.5, 2H), 1.26 (qd, J=12.3, 3.9 Hz, 2H).

Intermediate 125. 1-(4-(Piperidin-4-ylmethyl)phenyl)pyrrolidin-2-one

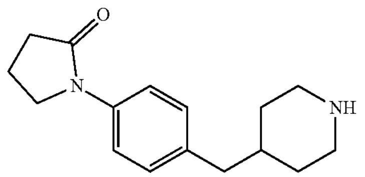 [SMILES: O=C1CCCN1c1ccc(CC2CCNCC2)cc1]

Prepared from commercially available tert-butyl 4-methylenepiperidine-1-carboxylate and commercially available 1-(4-bromophenyl)pyrrolidin-2-one according to the general procedure 5. The product was isolated as a viscous liquid (41% yield). $^1$HNMR (300 MHz, $CDCl_3$) δ 7.47 (d, J=8.4 Hz, 2H), 7.11 (d, J=8.4 Hz, 2H), 3.82 (t, J=7.0 Hz, 2H), 3.02-2.98 (m, 2H), 2.61-2.52 (m, 2H), 2.51-2.46 (m, 3H), 2.12 (m, 2H), 1.62-1.51 (m, 4H), 1.18-1.04 (m, 2H).

Intermediate 126. 4-(4-methylbenzyl)piperidine

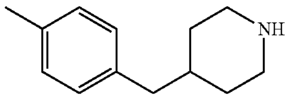

Prepared from commercially available tert-butyl 4-methylenepiperidine-1-carboxylate and 1-bromo-4-methylbenzene according to the general procedure 5. The product was isolated as transparent liquid (49% yield). $^1$HNMR (600 MHz, $CDCl_3$) δ 7.06 (d, J=7.8 Hz, 2H), 7.01 (d, J=8.4 Hz, 2H), 3.02-3.00 (m, 2H), 2.53-2.46 (m, 4H), 2.30 (s, 3H), 1.62-1.53 (m, 4H), 1.15-1.08 (m, 2H).

General Procedure 6. Synthesis of piperidine/piperazine pyrazoles IV

A mixture of the desired substituted piperidine or substituted piperazine (2 eq), desired THP-protected iodopyrazole (1 eq) and $K_2CO_3$ (3-5 eq) in DMSO was treated with CuI (0.2 eq) and proline (0.4 eq) and then heated at 95-100° C. until TLC indicated consumption of the limiting reagent. The reaction mixture was then cooled and partitioned between EtOAc and aq saturated $NH_4Cl$ or dilute aqueous ammonia. The aq. layer was extracted with $CH_2Cl_2$ until no UV absorption in the organic extract. The combined organic layer was dried over $Na_2SO_4$ and evaporated to the crude THP-protected coupling product that was chromatographed with silica gel column. The THP-protected coupling intermediate obtained after column purification was then dissolved in 4N HCl in dioxane at room temperature and stirred until TLC indicated consumption of the starting material. Evaporation of volatiles and partitioning of the resulting residue between $CH_2Cl_2$ or EtOAC and aq. saturated $Na_2CO_3$ or direct addition of EtOAc to the dioxane mixture and then addition of aq saturated $Na_2CO_3$ to pH 10-11 in aq layer followed. The aqueous layer was extracted with EtOAc or $CH_2Cl_2$ until no UV absorption in the organic extract. The combined organic layer was then dried over $Na_2SO_4$, evaporated to afford the crude THP deprotection product that was purified via silica gel column.

Compound 1. 4-Phenyl-1-(1H-pyrazol-4-yl)piperidine

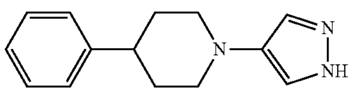 [SMILES: c1ccc(C2CCN(c3cn[nH]c3)CC2)cc1]

Synthesized from the coupling of THP-protected 4-iodopyrazole with commercially available 4-phenylpiperidine according to the general procedure 6. The crude THP-protected coupling intermediate was chromatographed with silica gel column and 0-60% EtOAc in hexanes gradient. The crude THP deprotection product was chromatographed with silica gel column and 0-100% EtOAc in $CHCl_3$ gradient to afford the product as a white solid (32% yield). $^1$H NMR (400 MHz, $CDCl_3$) δ 2.0-2.02 (m, 4H), 2.55-2.72 (m, 3H), 3.49-3.53 (m, 2H), 7.18-7.35 (m, 7H), 9.68 (bs, 1H).

Compound 2. 4-Benzyl-1-(1H-pyrazol-5-yl)piperidine

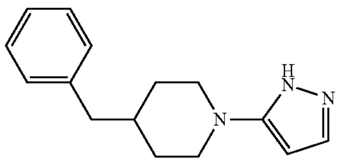 [SMILES: c1ccc(CC2CCN(c3ccn[nH]3)CC2)cc1]

Synthesized from THP-protected 3-iodo-pyrazole and commercially available 4-benzylpiperidine according to the general procedure 6. The crude THP-protected coupling intermediate was chromatographed with silica gel column and 0-70% EtOAc in hexanes gradient. The product, 4-benzyl-1-(1H-pyrazol-5-yl)piperidine, was isolated as a semi-solid after purification of the crude THP deprotection product with silica gel column and 0-100% EtOAc in $CH_2Cl_2$ (33% yield). $^1H$ NMR (400 MHz, $CDCl_3$) δ 1.37-1.46 (m, 2H), 1.61-1.76 (m, 3H), 2.57 (d, J=6.8 Hz, 2H), 2.67 (td, J=12.4, 2.8 Hz, 2H), 3.65-3.72 (m, 2H), 5.74 (d, J=2.0 Hz, 1H), 7.10-7.23 (m, 3H), 7.27-7.32 (m, 2H), 7.38 (d, J=2.4 Hz).

Compound 3. 4-Benzyl-1-(1H-pyrazol-4-yl)piperidine

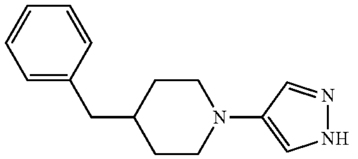 [SMILES: c1ccc(CC2CCN(c3cn[nH]c3)CC2)cc1]

Synthesized from THP-protected 4-iodo-pyrazole and commercially available 4-benzylpiperidine according to the general procedure 6. The crude THP protected coupling intermediate was chromatographed with silica gel column and 0-70% EtOAc in hexanes gradient. The desired product, 4-benzyl-1-(1H-pyrazol-4-yl)piperidine, was isolated as an off white solid after purification of the crude THP deprotection product with silica gel column and 0-100% EtOAc in $CH_2Cl_2$ and a precipitation of the chromatographed product out of $CH_2Cl_2$ with excess of hexanes $^1H$ NMR (400 MHz, $CDCl_3$) δ 1.45 (apparent qd, J=11.6, 4.0 Hz, 2H), 1.58-1.67 (m, 1H), 1.73 (apparent d, J=13.2 Hz, 2H), 2.50 (td, J=11.6, 2.4 Hz, 2H), 2.59 (d, J=7.2 Hz, 2H), 3.31-3.36 (m, 2H), 7.13-7.24 (m, 5H), 7.27-7.32 (m, 2H).

Compound 4. 2-(4-(1H-Pyrazol-4-yl)piperazin-1-yl) pyrimidine

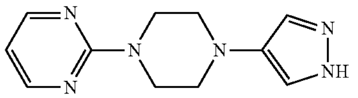

Synthesized from THP-protected 4-iodo-pyrazole and commercially available 2-(1-piperazinyl)pyrimidine as described in the general procedure 6. The crude THP-protected coupling intermediate was chromatographed with silica gel column and 0-100% EtOAc in hexanes gradient. The desired product 2-(4-(1H-pyrazol-4-yl)piperazin-1-yl) pyrimidine, was isolated as white solid after purification of the crude THP deprotection product with silica gel column and 0-5% MeOH in EtOAc and a precipitation of the chromatographed product out of $CH_2Cl_2$ with excess of hexanes (10% yield). $^1H$ NMR (400 MHz, DMSO-d6) δ 2.89 (t, J=5.2 Hz, 4H), 3.83 (t, J=5.2 Hz, 4H), 6.63 (t, J=4.8 Hz, 1H), 7.29 (s, 2H), 8.36 (d, J=4.8 Hz), 12.30 (bs, 1H).

Compound 5. 1-Phenyl-4-(1H-pyrazol-4-yl)piperazine

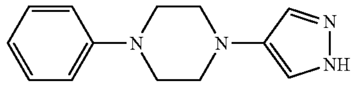 [SMILES: c1ccc(N2CCN(c3cn[nH]c3)CC2)cc1]

Synthesized from THP-protected 4-iodo-pyrazole and commercially available 1-phenylpiperazine according to general procedure 6. The crude THP-protected intermediate was chromatographed with silica gel column and 0-60% EtOAc in hexanes gradient. The desired product 1-phenyl-4-(1H-pyrazol-4-yl)piperazine, was isolated as an off-white solid after purification of the crude THP deprotection product with silica gel column with 0-2.5% MeOH in EtOAc and a precipitation of the chromatographed product out of $CH_2Cl_2$ with excess of hexanes (18% yield). 1H NMR (400 MHz, $CDCl_3$) δ 3.11-3.16 (m, 4H), 3.31-3.36 (m, 4H), 6.89 (apparent t, J=7.6 Hz, 1H), 6.98 (d, J=8.0 Hz, 2H), 7.26-7.32 (m, 5H).

Compound 6. 1-(4-Methoxyphenyl)-4-(1H-pyrazol-4-yl)piperazine

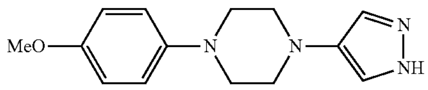 [SMILES: COc1ccc(N2CCN(c3cn[nH]c3)CC2)cc1]

Synthesized from THP-protected 4-iodo-pyrazole and commercially available 1-(4-methoxyphenyl)piperazine according to general procedure 6. The crude THP-protected coupling intermediate was chromatographed with column and 0-80% EtOAc in hexanes. The desired product 1-(4-methoxyphenyl)-4-(1H-pyrazol-4-yl)piperazine was isolated as a white solid after purification of the crude THP deprotection product with silica gel column and 0-5% MeOH in EtOAc in hexanes gradient and a precipitation of the chromatographed product out of $CH_2Cl_2$ with excess of hexanes (8% yield). $^1H$ NMR (400 MHz, $CDCl_3$) δ 3.10-3.15 (m, 4H), 3.20-3.26 (m, 4H), 3.78 (s, 3H), 6.85 (d, J=9.2 Hz), 6.95 (d, J=8.8 Hz, 2H), 7.29 (bs, 2H).

Compound 7. 4-(3-Methoxyphenyl)-1-(1H-pyrazol-5-yl)piperidine

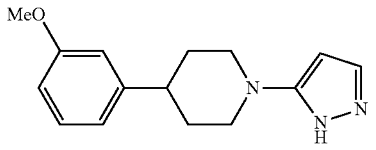 [SMILES: COc1cccc(C2CCN(c3ccn[nH]3)CC2)c1]

Synthesized from THP-protected 3-iodo-pyrazole and 4-(3-methoxyphenyl)piperidine according to general procedure 6. The crude THP-protected coupling intermediate was chromatographed with column and 0-30% EtOAc in hexanes. The desired product, 4-(3-methoxyphenyl)-1-(1H-pyrazol-5-yl)piperidine, was isolated as an off-white solid after purification of the THP deprotection product with 0-100% EtOAc in hexanes gradient and a precipitation of the chromatographed product out of $CH_2Cl_2$ with excess of hexanes. $^1$H NMR (400 MHz, $CDCl_3$) δ 1.82-1.97 (m, 4H), 2.59-2.68 (m, 1H), 2.85 (apparent td, J=11.6, 3.2 Hz, 2H), 3.81 (s, 3H), 3.85 (apparent d, J=12.4 Hz, 2H), 5.80 (d, 1H), 6.66-6.77 (m, 1H), 6.79-6.82 (m, 1H), 6.83-6.87 (m, 1H), 7.24 (apparent t, J=8.0 Hz, 1H), 7.42 (d, J=2.4 Hz, 1H).

Compound 8. 4-(3-Methoxyphenyl)-1-(1H-pyrazol-4-yl)piperidine

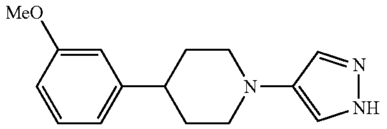 [SMILES: COc1cccc(C2CCN(c3cn[nH]c3)CC2)c1]

Synthesized from THP-protected 4-iodo-pyrazole and 4-(3-methoxyphenyl)piperidine according to general procedure 6. The crude THP-protected coupling intermediate was chromatographed with column and 0-40% EtOAc in hexanes. The desired product, 4-(3-methoxyphenyl)-1-(1H-pyrazol-4-yl)piperidine, was isolated as an off-white solid after purification of the THP deprotection product with 0-100% EtOAc in hexanes gradient and a precipitation of the chromatographed product out of $CH_2Cl_2$ with excess of hexanes. $^1$H NMR (400 MHz, $CDCl_3$) δ 1.93-2.07 (m, 4H), 2.56-2.66 (m, 1H), 2.73 (apparent td, J=12.0, 3.6 Hz, 2H), 3.52 (apparent d, J=11.6 Hz, 2H), 3.81 (s, 3H), 6.75-6.79 (m, 1H), 6.80-6.82 (m, 1H), 6.85 (apparent d, J=7.6 Hz, 1H), 7.25 (apparent t, J=8 Hz, 1H), 7.35 (bs, 2H).

Compound 9. 2-(1-(1H-Pyrazol-5-yl)piperidin-4-yl) pyrimidine

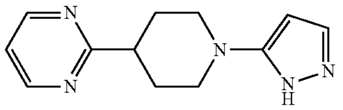 [SMILES: c1cnc(C2CCN(c3ccn[nH]3)CC2)nc1]

Synthesized from THP-protected 3-iodo-pyrazole and 2-(piperidin-4-yl)pyrimidine according to general procedure 6. The crude THP-protected coupling intermediate was chromatographed with silica gel column and 0-100% EtOAc in hexanes gradient. The desired product, 2-(1-(1H-pyrazol-5-yl)piperidin-4-yl)pyrimidine, was isolated as an off-white solid after purification of the THP deprotection product with silica gel column and 0-10% MeOH in EtOAc and a precipitation of the chromatographed product out of $CH_2Cl_2$ with excess of hexanes (39% yield). $^1$H NMR (400 MHz, $CDCl_3$) δ 2.00-2.17 (m, 4H), 2.92 (td, J=12.0, 2.8 Hz, 2H), 3.03 (apparent tt, J=11.6, 4.0 Hz, 1H), 3.83-3.89 (m, 2H), 5.80 (d, J=2.0 Hz, 1H), 7.14 (t, J=4.8 Hz, 1H), 7.41 (d, J=2.4 Hz, 1H), 8.70 (d, J=5.2 Hz, 2H).

Compound 10. 2-(1-(1H-Pyrazol-4-yl)piperidin-4-yl)pyrimidine

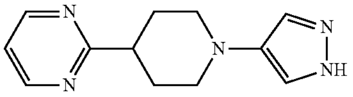 [SMILES: c1cnc(C2CCN(c3cn[nH]c3)CC2)nc1]

Synthesized from THP-protected 4-iodo-pyrazole and 2-(piperidin-4-yl)pyrimidine according to general procedure 6. The crude THP-protected coupling intermediate was chromatographed with column and 0-100% EtOAc in hexanes gradient. The desired product, 2-(1-(1H-pyrazol-4-yl)piperidin-4-yl)pyrimidine, was isolated as an off-white solid after purification of the THP deprotection product with silica gel column and 0-10% MeOH in EtOAc and a precipitation of the chromatographed product out of $CH_2Cl_2$ with excess of hexanes (28% yield). $^1$H NMR (400 MHz, $CDCl_3$) δ 2.06-2.17 (m, 4H), 2.76 (apparent td, J=11.6, 3.6 Hz, 2H), 2.95-3.10 (m, 1H), 3.45-3.53 (m, 2H), 7.15 (t, J=4.8 Hz, 1H), 7.29 (s, 2H), 8.70 (d, J=4.8 Hz, 2H).

Compound 11. Methyl 4-(1-(1H-pyrazol-5-yl)piperidin-4-yl)benzoate

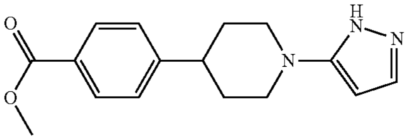 [SMILES: COC(=O)c1ccc(C2CCN(c3ccn[nH]3)CC2)cc1]

Synthesized from THP-protected 3-iodo-pyrazole and methyl 4-(piperidin-4-yl)benzoate according to general procedure 6. The crude THP-protected coupling intermediate was chromatographed with column and 0-70% EtOAc in hexanes gradient. The desired product, methyl 4-(1-(1H-pyrazol-5-yl)piperidin-4-yl)benzoate, was isolated as a white solid after purification of the THP deprotection product with silica gel column and 0-100% EtOAc in hexanes gradient and a precipitation of the chromatographed product out of $CH_2Cl_2$ with excess of hexanes (20% yield). $^1$H NMR (400 MHz, $CDCl_3$) δ 1.83-1.97 (m, 4H), 2.67-2.77 (m, 1H), 2.86 (apparent td, 2H), 3.85-3.93 (s and m overlapping, 5H), 5.81 (d, J=1.2 Hz, 1H), 7.31 (d, J=8.4 Hz, 2H), 7.42 (d, J=2.4 Hz, 1H), 7.98 (d, J=8.0 Hz, 2H), 9.11 (bs, 1H).

Compound 12. Methyl 4-(1-(1H-pyrazol-4-yl)piperidin-4-yl)benzoate

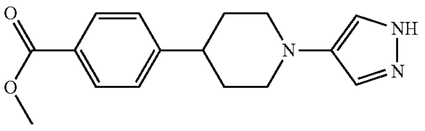

Synthesized from THP-protected 4-iodo-pyrazole and methyl 4-(piperidin-4-yl)benzoate according to general procedure 6. The crude THP-protected intermediate was chromatographed with column and 0-90% EtOAc in hexanes gradient. The desired product, methyl 4-(1-(1H-pyrazol-4-yl)piperidin-4-yl)benzoate, was isolated as a white solid after purification of the THP deprotection product with silica gel column and 0-5% MeOH in EtOAc gradient and a precipitation of the chromatographed product out of $CH_2Cl_2$ with excess of hexanes. $^1H$ NMR (400 MHz, DMSO-$d_6$) δ 1.78-1.89 (m, 4H), 2.50-2.68 (m, 2H), 2.68-2.75 (m, 1H), 3.45 (apparent d, J=10.0 Hz, 2H), 3.85 (s, 3H), 7.28 (s, 2H), 7.45 (d, J=8.0 Hz, 2H), 7.91 (d, J=8.0 Hz, 2H), 12.26 (bs, 1H).

Compound 13. N-(5-(1-(1H-Pyrazol-4-yl)piperidin-4-yl)pyridin-2-yl)-N-methylacetamide

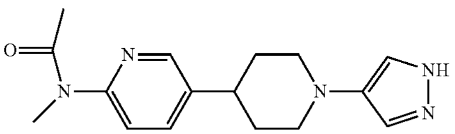 [SMILES: CC(=O)N(C)c1ccc(C2CCN(c3cn[nH]c3)CC2)cn1]

Synthesized from THP-protected 4-iodo-pyrazole and N-methyl-N-(5-(piperidin-4-yl)pyridin-2-yl)acetamide according to general procedure IV. The crude THP-protected intermediate was chromatographed with column and 0-10% MeOH in EtOAc gradient and then 0-30% EtOH in hexanes gradient. The desired product, N-(5-(1-(1H-pyrazol-4-yl) piperidin-4-yl)pyridin-2-yl)-N-methylacetamide, was isolated as a white solid after purification of the THP deprotection product with silica gel column and 0-5% MeOH in EtOAc gradient and a precipitation of the chromatographed product out of $CH_2Cl_2$ with excess of hexanes (27% yield). $^1H$ NMR (400 MHz, DMSO-$d_6$) δ 1.80-1.87 (m, 4H), 2.00 (s, 3H), 2.50-2.58 (m, 2H), 2.65-2.75 (m, 1H), 3.25 (s, 3H), 3.42-3.48 (m, 2H), 7.27 (s, 1H), 7.30 (s, 1H), 7.43 (d, J=8.4 Hz, 1H), 7.81 (dd, J=8.4, 2.4 Hz, 1H), 8.41 (d, J=2.4 Hz, 2H), 12.29 (s, 1H).

Compound 14. 4-Phenoxy-1-(1H-pyrazol-4-yl)piperidine

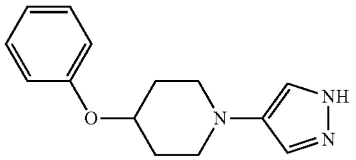

Synthesized according to general procedure 6 from THP-protected 4-iodo-1-pyrazole and 4-phenoxypiperidine (prepared as described in Hudskins, R. L. et al. Biorg. Med. Chem. Lett 2014, 24 (5), 1303-1306, incorporated herein by reference). The crude THP-protected coupling intermediate was chromatographed with column and 0-100% EtOAc in hexanes gradient. The desired product, 4-phenoxy-1-(1H-pyrazol-4-yl)piperidine, was isolated as an off-white solid after purification of the THP deprotection product with silica gel column and 0-5% MeOH in EtOAc gradient and a precipitation of the chromatographed product out of $CH_2Cl_2$ with excess of hexanes (11% yield). $^1H$ NMR (400 MHz, DMSO-d6) δ 1.67-1.78 (m, 2H), 1.96-2.06 (m, 2H), 2.71-2.78 (distorted t, 2H), 3.15-3.22 (m, 2H), 4.45-4.51 (m, 1H), 6.91 (t, J=7.2 Hz, 1H), 6.96 (d, J=8.0 Hz, 2H), 7.23-7.31 (m, 4H), 12.26 (bs, 1H).

Compound 15. 4-(1-(1H-Pyrazol-4-yl)piperidin-4-yl)-2-methoxypyridine

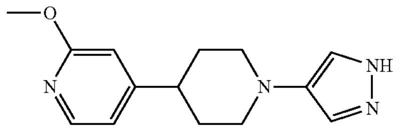 [SMILES: COc1cc(C2CCN(c3cn[nH]c3)CC2)ccn1]

Synthesized from THP-protected 4-iodo-pyrazole and 2-methoxy-4-(piperidin-4-yl)pyridine according to general procedure 6. The crude THP-protected intermediate was chromatographed with column and 0-100% EtOAc in hexanes gradient. The desired product, 4-(1-(1H-pyrazol-4-yl)piperidin-4-yl)-2-methoxypyridine, was isolated as an off-white solid after purification of the THP deprotection product with silica gel column and 0-5% MeOH in EtOAc gradient and a precipitation of the chromatographed product out of $CH_2Cl_2$ with excess of hexanes (45% yield). $^1H$ NMR (400 MHz, $CDCl_3$) δ 1.83-1.95 (m, 4H), 2.52-2.61 (m, 1H), 2.64-2.71 (m, 2H), 3.45-3.51 (m, 2H), 3.93 (s, 3H), 6.61-6.62 (m, 1H), 6.77 (dd, J=5.2, 1.2 Hz, 1H), 7.27 (s, 2H), 8.09 (d, J=5.2 Hz, 1H), 9.73 (bs, 1H).

Compound 16. 4-(1-(1H-Pyrazol-5-yl)piperidin-4-yl)-2-methoxypyridine

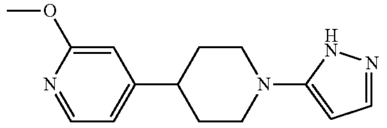 [SMILES: COc1cc(C2CCN(c3ccn[nH]3)CC2)ccn1]

Synthesized from THP-protected 3-iodo-pyrazole and 2-methoxy-4-(piperidin-4-yl)pyridine according to general procedure 6. The crude THP-protected coupling intermediate was chromatographed with column and 0-70% EtOAc in hexanes gradient. The desired product, 4-(1-(1H-pyrazol-5-yl)piperidin-4-yl)-2-methoxypyridine, was isolated as an off-white solid after purification of the THP deprotection product with silica gel column and 0-100% EtOAc in hexanes gradient and a precipitation of the chromatographed product out of $CH_2Cl_2$ with excess of hexanes (13% yield). $^1H$ NMR (400 MHz, $CDCl_3$) δ 1.78-1.95 (m, 4H), 2.62 (tt, J=12.0, 4.0 Hz, 1H), 2.89 (td, J=12.0, 2.8 Hz, 2H), 3.87 (apparent d, J=12.8 Hz, 2H), 3.93 (s, 3H), 5.78 (s, 1H), 6.61 (s, 1H), 6.76 (d, J=5.2 Hz, 1H), 7.44 (s, 1H), 8.08 (d, J=5.6, 1H).

Compound 17. 4-(4-Fluorophenyl)-1-(1H-pyrazol-4-yl)piperidine

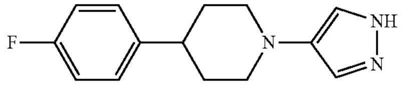 [SMILES: Fc1ccc(C2CCN(c3cn[nH]c3)CC2)cc1]

Synthesized from THP-protected 4-iodo-pyrazole and commercially available 4-(4-fluorophenyl)piperidine according to the general procedure 6. The crude THP-protected intermediate was chromatographed with column and 0-70% EtOAc in hexanes gradient. The desired product, 4-(4-fluorophenyl)-1-(1H-pyrazol-4-yl)piperidine, was isolated as a white solid after purification of the THP deprotection product with silica gel column and 0-100% EtOAc in $CH_2Cl_2$ gradient and a precipitation of the chromatographed product out of $CH_2Cl_2$ with excess of hexanes (18% yield). $^1$H NMR (400 MHz, $CDCl_3$) δ 1.84-1.93 (m, 4H), 2.54-2.64 (m, 1H), 2.64-2.72 (m, 2H), 3.46-3.51 (m, 2), 6.97-7.04 (m, 2H), 7.17-7.23 (m, 2H), 7.29 (s, 2H), 9.76 (bs, 1H).

Compound 18. 4-(4-Fluorophenyl)-1-(1H-pyrazol-5-yl)piperidine

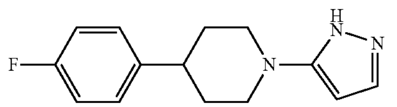 [SMILES: Fc1ccc(C2CCN(c3ccn[nH]3)CC2)cc1]

Synthesized from THP-protected 3-iodo-pyrazole and commercially available 4-(4-fluorophenyl)piperidine according to general procedure 6. The crude THP-protected coupling intermediate was chromatographed with column and 0-45% EtOAc in hexanes gradient. The desired product, 4-(4-fluorophenyl)-1-(1H-pyrazol-5-yl)piperidine, was isolated as a white solid after purification of the THP deprotection product with silica gel column and 0-100% EtOAc in $CH_2Cl_2$ gradient and a precipitation of the chromatographed product out of $CH_2Cl_2$ with excess of hexanes (10% yield). $^1$H NMR (400 MHz, $CDCl_3$) δ 1.78-1.93 (m, 4H), 2.64 (tt, J=12.0, 4.0 Hz, 1H), 2.84 (td, J=12.0, 3.2 Hz, 2H), 3.86 (apparent d, J=12.0 Hz, 2H), 5.80 (d, J=2.4 Hz, 1H), 6.96-7.03 (m, 2H), 7.17-7.30 (m, 2H), 7.42 (d, J=2.4 Hz, 1H), 9.20 (bs, 1H).

Compound 19. 4-(4-Methoxyphenyl)-1-(1H-pyrazol-5-yl)piperidine

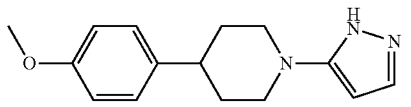 [SMILES: COc1ccc(C2CCN(c3ccn[nH]3)CC2)cc1]

Synthesized from THP-protected 3-iodo-pyrazole and 4-(4-methoxyphenyl)piperidine according to general procedure 6. The crude THP-protected coupling intermediate was chromatographed with column and 0-50% EtOAc in hexanes gradient. The desired product, 4-(4-methoxyphenyl)-1-(1H-pyrazol-5-yl)piperidine, was isolated as white solid after purification of the THP deprotection product with silica gel column and 0-100% EtOAc in hexanes gradient (21% yield). $^1$H NMR (400 MHz, $CDCl_3$) δ 1.78-1.95 (m, 4H), 2.56-2.66 (m, 1H), 2.85 (apparent t, J=12.0 Hz, 2H), 3.80 (s, 3H), 3.85 (apparent d, J=11.6 Hz, 2H), 5.80 (s, 1H), 6.86 (d, J=7.6 Hz, 2H), 7.17 (d, J=7.2 Hz, 2H), 7.42 (s, 1H).

Compound 20. 4-(4-Methoxyphenyl)-1-(1H-pyrazol-4-yl)piperidine

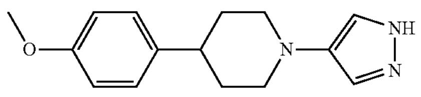 [SMILES: COc1ccc(C2CCN(c3cn[nH]c3)CC2)cc1]

Synthesized from THP-protected 4-iodo-pyrazole and 4-(4-methoxyphenyl)piperidine according to general procedure 6. The crude THP-protected coupling intermediate was chromatographed with column and 0-100% EtOAc in hexanes gradient. The desired product, 4-(4-methoxyphenyl)-1-(1H-pyrazol-4-yl)piperidine, was isolated as off-white solid after purification of the THP deprotection product with silica gel column and 0-100% EtOAc in $CH_2Cl_2$ gradient (15% yield). $^1$H NMR (400 MHz, $CDCl_3$) δ 1.86-1.96 (m, 4H), 2.50-2.62 (m, 1H), 2.63-2.73 (m, 2H), 3.48 (apparent d, J=11.6 Hz, 2H), 3.80 (s, 3H), 6.87 (d, J=8.8 Hz, 2H), 7.17 (d, J=8.4 Hz, 2H), 7.29 (s, 2H).

Compound 21. 4-(2-Methoxyphenyl)-1-(1H-pyrazol-5-yl)piperidine

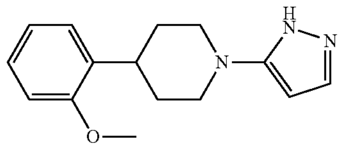 [SMILES: COc1ccccc1C1CCN(c2ccn[nH]2)CC1]

Synthesized from THP-protected 3-iodo-pyrazole and 4-(2-methoxyphenyl)piperidine according to general procedure 6. The crude THP-protected coupling intermediate was chromatographed with column and 0-100% EtOAc in hexanes gradient. The desired product 4-(2-methoxyphenyl)-1-(1H-pyrazol-5-yl)piperidine, was isolated as off-white solid after purification of the THP deprotection product with silica gel column and 0-100% EtOAc in hexanes gradient (20% Yield). $^1$H NMR (400 MHz, DMSO-d6) δ 1.67-1.82 (m, 4H), 2.60-2.71 (apparent t, J=9.6 Hz, 2H), 2.90-3.05 (m, 1H), 3.70-3.85 (m, 5H), 5.70 (s, 1H), 6.85-6.99 (m, 2H), 7.15-7.20 (m, 2H), 7.44 (s, 1H), 11.76 (s, 1H).

Compound 22. 4-(2-Methoxyphenyl)-1-(1H-pyrazol-4-yl)piperidine

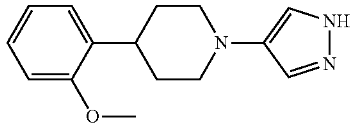 [SMILES: COc1ccccc1C1CCN(c2cn[nH]c2)CC1]

Synthesized from THP-protected 4-iodo-pyrazole and 4-(2-methoxyphenyl)piperidine according to general procedure 6. The crude THP-protected coupling intermediate was chromatographed with column and 0-100% EtOAc in hexanes gradient. The desired product, 4-(2-methoxyphenyl)-1-(1H-pyrazol-4-yl)piperidine, was isolated as off-white solid after purification of the THP deprotection product with silica gel column and 0-100% EtOAc in hexanes gradient (11% yield). $^1$H NMR (400 MHz, $CDCl_3$) δ 1.85-1.95 (m, 4H), 2.65-2.77 (m, 2H), 2.99-3.11 (m, 1H), 3.44-3.51 (m, 2H), 3.84 (s, 3H), 6.88 (d, J=8.4 Hz, 1H), 6.95 (apparent t, J=7.6 Hz, 1H), 7.16-7.25 (m, 2H), 7.28 (s, 2H).

Compound 23. 1-(1H-Pyrazol-5-yl)-4-(p-tolyl)piperidine

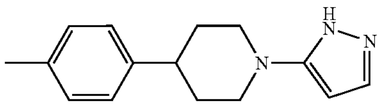 [SMILES: Cc1ccc(C2CCN(c3ccn[nH]3)CC2)cc1]

Synthesized from THP-protected 3-iodo-pyrazole and 4-(p-tolyl)piperidine according to general procedure 6. The crude THP-protected coupling intermediate was chromatographed with column and 0-50% EtOAc in hexanes gradient. The desired product, 1-(1H-pyrazol-5-yl)-4-(p-tolyl) piperidine, was isolated as off-white solid after purification of the THP deprotection product with silica gel column and 0-100% EtOAc in hexanes gradient (7% yield). $^{1}$H NMR (400 MHz, DMSO-d6) δ 1.62-1.81 (m, 4H), 2.26 (s, 3H), 2.57 (tt, J=12.0, 3.6 Hz, 1H), 2.62-2.72 (apparent td, 2H), 3.74 (apparent bd, J=11.6 Hz, 2H), 5.71 (s, 1H), 7.09 (d, J=8.0 Hz, 2H), 7.13 (d, J=8.0 Hz, 2H), 7.44 (s, 1H), 11.76 (bs, 1H).

Compound 24. 1-(1H-Pyrazol-4-yl)-4-(p-tolyl)piperidine

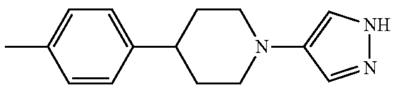 [SMILES: Cc1ccc(C2CCN(c3cn[nH]c3)CC2)cc1]

Synthesized from THP-protected 4-iodo-pyrazole and 4-(p-tolyl)piperidine according to general procedure 6. The crude THP-protected coupling intermediate was chromatographed with column and 0-50% EtOAc in hexanes gradient. The desired product, 1-(1H-pyrazol-4-yl)-4-(p-tolyl) piperidine, was isolated as an off-white solid after purification of the THP deprotection product with silica gel column and 0-100% EtOAc in hexanes gradient (10% yield). $^{1}$H NMR (400 MHz, $CDCl_3$) δ 1.88-1.97 (m, 2H), 2.33 (s, 3H), 2.51-2.63 (m, 1H), 2.63-2.73 (m, 2H), 3.45-3.52 (m, 2H), 7.10-7.19 (apparent s, 4H), 7.28 (s, 2H).

Compound 25. 4-(4-(Methoxymethyl)phenyl)-1-(1H-pyrazol-5-yl)piperidine

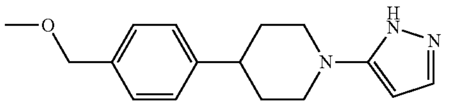 [SMILES: COCc1ccc(C2CCN(c3ccn[nH]3)CC2)cc1]

Synthesized from THP-protected 3-iodo-pyrazole and 4-(4-(methoxymethyl)phenyl)piperidine according to general procedure 6. The crude THP-protected coupling intermediate was chromatographed with column and 0-100% EtOAc in hexanes gradient. The desired product, 4-(4-(methoxymethyl)phenyl)-1-(1H-pyrazol-5-yl)piperidine, was isolated as an off-white fluffy solid after purification of the THP deprotection product with silica gel column and 0-100% EtOAc in hexanes gradient (13% yield). $^{1}$H NMR (400 MHz, DMSO-d6) δ 1.65-1.84 (m, 4H), 2.58-2.73 (m, 3H), 3.27 (s, 3H), 3.75 (apparent d, J=11.2 Hz, 2H), 4.36 (s, 2H), 5.71 (s, 1H), 7.24 (s, 4H), 7.44 (s, 1H), 11.78 (bs, 1H).

Compound 26. 4-(4-(Methoxymethyl)phenyl)-1-(1H-pyrazol-4-yl)piperidine

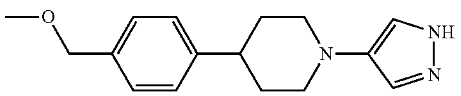

Synthesized from THP-protected 4-iodo-pyrazole and 4-(4-(methoxymethyl)phenyl)piperidine according to general procedure 6. The crude THP-protected coupling intermediate was chromatographed with column and 0-100% EtOAc in hexanes gradient. The desired product, 4-(4-(methoxymethyl)phenyl)-1-(1H-pyrazol-4-yl)piperidine, was obtained as an off-white solid after purification of the THP deprotection product with silica gel column and 0-100% EtOAc in hexanes gradient (6% yield). $^{1}$H NMR (400 MHz, DMSO-d6) δ 1.71-1.81 (m, 4H), 2.50-2.63 (m, 3H), 3.27 (s, 3H), 3.42 (apparent d, J=11.6 Hz, 2H), 4.36 (s, 2H), 7.24-7.27 (s overlapping, 6H), 12.23 (bs, 1H).

Compound 27. N-(4-(1-(1H-Pyrazol-5-yl)piperidin-4-yl)phenyl)-N-methylacetamide

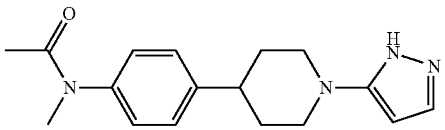 [SMILES: CC(=O)N(C)c1ccc(C2CCN(c3ccn[nH]3)CC2)cc1]

Synthesized from THP-protected 3-iodo-pyrazole and N-methyl-N-(4-(piperidin-4-yl)phenyl)acetamide according to general procedure 6. The crude THP-protected coupling intermediate was chromatographed with column and 0-10% MeOH in $CH_2Cl_2$ gradient. The desired product, N-(4-(1-(1H-pyrazol-5-yl)piperidin-4-yl)phenyl)-N-methylacetamide, was obtained as a white solid after purification of the THP deprotection product with silica gel column and 0-10% EtOH in DCM gradient (8% yield). $^{1}$H NMR (400 MHz, $CDCl_3$) δ 1.80-1.98 (m, 7H), 2.64-2.74 (m, 1H), 2.86 (apparent td, J=12.0, 2.4 Hz, 2H), 3.25 (s, 3H), 3.87 (apparent d, J=12.8 Hz, 2H), 5.81 (s, 1H), 7.12 (d, J=8.0 Hz, 2H), 7.28 (d, J=8.4 Hz, 2H), 7.43 (s, 1H).

Compound 28. N-(4-(1-(1H-Pyrazol-4-yl)piperidin-4-yl)phenyl)-N-methylacetamide

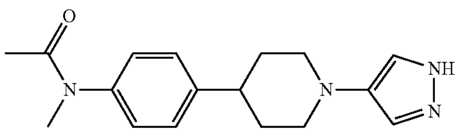 [SMILES: CC(=O)N(C)c1ccc(C2CCN(c3cn[nH]c3)CC2)cc1]

Synthesized from THP-protected 4-iodo-pyrazole and N-methyl-N-(4-(piperidin-4-yl)phenyl)acetamide according to general procedure 6. The crude THP-protected coupling intermediate was chromatographed with column and 0-10% EtOH in $CH_2Cl_2$ gradient. The desired product, N-(4-(1-

(1H-pyrazol-4-yl)piperidin-4-yl)phenyl)-N-methylacetamide, was obtained as an off-white solid after purification of the THP deprotection product with silica gel column and 0-20% EtOH in $CH_2Cl_2$ (10% yield). $^1$H NMR (400 MHz, $CDCl_3$) δ 1.90 (s, 3H), 1.95-2.11 (m, 4H), 2.63-2.83 (m, 3H), 3.28 (s, 3H), 3.56 (apparent d, J=11.6 Hz, 2H), 7.14 (d, J=8.0 Hz, 2H), 7.32 (d, J=8.0 Hz, 2H), 7.40 (s, 2H). $^1$HNMR (400 MHz, DMSO-d6) δ 1.70-1.90 (s and m overlapping, 7H), 2.53-2.67 (m, 3H), 3.12 (s, 3H), 3.43 (apparent d, J=11.8 Hz, 2H); 7.22-7.27 (s overlapping with d, 4H), 7.33-7.35 (d, J=7.2 Hz, 2H), 12.21 (bs, 1H).

Compound 29. N-(4-(1-(1H-Pyrazol-5-yl)piperidin-4-yl)phenyl)acetamide

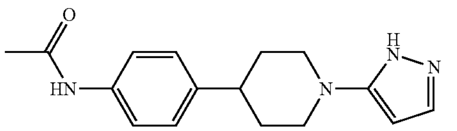 [SMILES: CC(=O)Nc1ccc(C2CCN(c3ccn[nH]3)CC2)cc1]

Synthesized from THP-protected 3-iodo-pyrazole and N-(4-(piperidin-4-yl)phenyl)acetamide according to general procedure 6. The crude THP-protected coupling intermediate was chromatographed with column and 0-10% EtOH in $CH_2Cl_2$ gradient. The desired product, N-(4-(1-(1H-pyrazol-5-yl)piperidin-4-yl)phenyl)acetamide, was obtained as an off-white solid after purification of the THP deprotection product with silica gel column and 0-10% EtOH in $CH_2Cl_2$ gradient (8% yield). $^1$H NMR (400 MHz, $CD_3OD$) δ 1.78-1.91 (m, 4H), 2.10 (s, 3H), 2.59-2.68 (m, 1H), 2.82 (td, J=12.0 Hz, 3.6 Hz, 2H), 3.79 (apparent d, J=12.4 Hz, 2H), 5.81 (d, J=2.4 Hz, 1H), 7.20 (d, J=8.4 Hz, 2H), 7.43-7.49 (m, 3H).

Compound 30. N-(4-(1-(1H-Pyrazol-4-yl)piperidin-4-yl)phenyl)acetamide

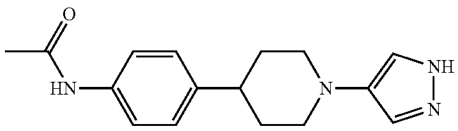

Synthesized from THP-protected 4-iodo-pyrazole and N-(4-(piperidin-4-yl)phenyl)acetamide according to general procedure 6. The crude THP-protected coupling intermediate was chromatographed with column and 0-10% MeOH in $CH_2Cl_2$ gradient. The desired product, N-(4-(1-(1H-pyrazol-4-yl)piperidin-4-yl)phenyl)acetamide, was obtained as an off-white solid after purification of the THP deprotection product with silica gel column and 0-10% MeOH in $CH_2Cl_2$ gradient (18% yield). $^1$H NMR (400 MHz, $CDCl_3$) δ 1.86-1.96 (m, 4H), 2.18 (s, 3H), 2.52-2.64 (m, 1H), 2.64-2.73 (m, 2H), 3.48 (apparent d, J=10.8 Hz, 2H), 7.09 (s, 1H), 7.20 (d, J=8.0 Hz, 2H), 7.27 (s, 2H), 7.43 (d, J=8.0 Hz, 2H).

Compound 31. 5-(1-(1H-Pyrazol-5-yl)piperidin-4-yl)-2-methoxypyridine

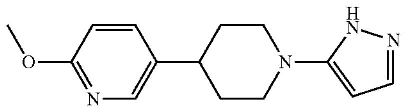 [SMILES: COc1ccc(C2CCN(c3ccn[nH]3)CC2)cn1]

Synthesized from THP-protected 3-iodo-pyrazole and 2-methoxy-5-(piperidin-4-yl)pyridine according to general procedure 6. The crude THP-protected coupling intermediate was chromatographed with column and 0-100% EtOAc in hexanes gradient. The desired product, 5-(1-(1H-pyrazol-5-yl)piperidin-4-yl)-2-methoxypyridine, was obtained as an off-white solid after purification of the THP deprotection product with silica gel column and 0-100% EtOAc in hexanes gradient (9% yield). $^1$H NMR (400 MHz, $CDCl_3$) δ 1.76-1.93 (m, 4H), 2.56-2.66 (m, 1H), 2.81-2.88 (m, 2H), 3.86 (apparent d, J=12.0 Hz, 2H), 3.92 (s, 3H), 5.80 (s, 1H), 6.70 (d, J=8.4 Hz, 1H), 7.42 (s, 1H), 7.46 (dd, J=8.8, 2.4 Hz, 2H), 8.04 (d, 1H).

Compound 32. 5-(1-(1H-Pyrazol-4-yl)piperidin-4-yl)-2-methoxypyridine

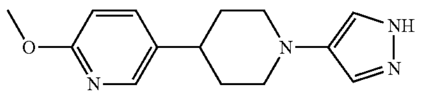 [SMILES: COc1ccc(C2CCN(c3cn[nH]c3)CC2)cn1]

Synthesized from THP-protected 4-iodo-pyrazole and 2-methoxy-5-(piperidin-4-yl)pyridine according to general procedure 6. The crude THP-protected coupling intermediate was chromatographed with column and 0-100% EtOAc in $CH_2Cl_2$ gradient. The desired product, 5-(1-(1H-pyrazol-4-yl)piperidin-4-yl)-2-methoxypyridine, was obtained as an off-white solid after purification of the THP deprotection product with silica gel column and 0-15% MeOH in $CH_2Cl_2$ gradient (12% yield). $^1$H NMR (400 MHz, $CDCl_3$) δ 1.70-1.93 (m, 4H), 2.52-2.62 (m, 1H), 2.63-2.73 (m, 2H), 3.46-3.52 (m, 2H), 3.92 (s, 3H), 6.71 (d, J=8.8 Hz, 1H), 7.28 (bs, 2H), 7.47 (dd, J=8.4 Hz, 2.4 Hz, 8.05 (d, J=2.0 Hz, 1H).

Compound 33. 1-(1H-Pyrazol-5-yl)-4-(m-tolyl)piperidine

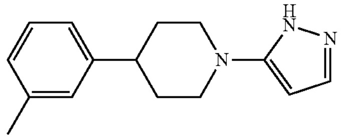 [SMILES: Cc1cccc(C2CCN(c3ccn[nH]3)CC2)c1]

Synthesized from THP-protected 3-iodo-pyrazole and 4-(m-tolyl)piperidine according to general procedure 6. The crude THP-protected coupling intermediate was chromatographed with silica gel column and 0-50% EtOAc in hexanes gradient. The desired product, 1-(1H-pyrazol-5-yl)-4-(m-tolyl)piperidine, was obtained as an oil after purification of the crude THP deprotection product with silica gel column and 0-70% EtOAc in hexanes gradient (20% yield).

$^1$H NMR (400 MHz, $CDCl_3$) δ 1.83-1.93 (m, 4H), 2.34 (s, 3H), 2.57-2.67 (m, 1H), 2.87 (apparent t, J=11.6 Hz, 2H), 3.86 (apparent d, J=12.4 Hz, 2H), 5.79 (s, 1H), 7.00-7.09 (m, 3H), 7.17-7.25 (m, 1H), 7.42 (s, 1H).

Compound 34. 1-(1H-Pyrazol-4-yl)-4-(m-tolyl)piperidine

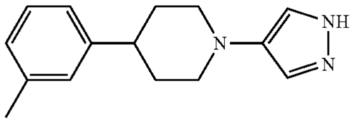

Synthesized from THP-protected 4-iodo-pyrazole and 4-(m-tolyl)piperidine according to general procedure 6. The crude THP-protected coupling intermediate was chromatographed with silica gel column and 0-70% EtOAc in hexanes gradient. The desired product, 1-(1H-pyrazol-4-yl)-4-(m-tolyl)piperidine, was obtained as an off-white solid after purification of the crude THP deprotection product with silica gel column and 0-10% MeOH in $CH_2Cl_2$ gradient (7% yield). $^1$H NMR (400 MHz, $CDCl_3$) δ 1.88-2.00 (m, 4H), 2.35 (s, 3H), 2.51-2.63 (m, 1H), 2.64-2.73 (m, 2H), 3.45-3.52 (m, 2H), 7.01-7.08 (m, 3H), 7.22 (t, J=7.2 Hz, 1H), 7.28 (s, 2H).

Compound 35. 1-(1H-Pyrazol-5-yl)-4-(o-tolyl)piperidine

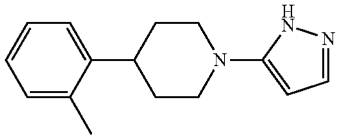 [SMILES: Cc1ccccc1C1CCN(c2ccn[nH]2)CC1]

Synthesized from THP-protected 3-iodo-pyrazole and 4-(o-tolyl)piperidine according to general procedure 6. The crude THP-protected intermediate was chromatographed with silica gel column and 0-60% EtOAc in hexanes gradient. The desired product 1-(1H-pyrazol-5-yl)-4-(o-tolyl)piperidine was isolated as an oil after purification of the crude THP deprotection product with silica gel column and 0-50% EtOAc in $CH_2Cl_2$ (8% yield). $^1$H NMR (400 MHz, $CDCl_3$) δ 1.82-1.93 (m, 4H), 2.38 (s, 3H), 2.82-2.92 (m, 3H), 3.88 (apparent d, J=12.4 Hz, 2H), 5.82 (s, 1H), 7.07-7.28 (m, 4H), 7.43 (s, 1H).

Compound 36. 1-(1H-Pyrazol-4-yl)-4-(o-tolyl)piperidine

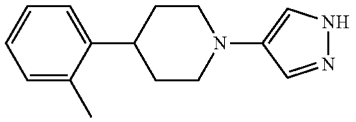 [SMILES: Cc1ccccc1C1CCN(c2cn[nH]c2)CC1]

Synthesized from THP-protected 4-iodo-pyrazole and 4-(o-tolyl)piperidine according to general procedure 6. The crude THP-protected coupling intermediate was chromatographed with silica gel column and 0-100% EtOAc in hexanes gradient. The desired product, 1-(1H-pyrazol-4-yl)-4-(o-tolyl)piperidine, was isolated as an off-white solid after purification of the crude THP deprotection product with silica gel column and 0-100% EtOAc in hexanes gradient (8% yield). $^1$H NMR (400 MHz, $CDCl_3$) δ 1.82-2.01 (m, 4H), 2.36 (s, 3H), 2.71 (td, J=11.6, 2.4 Hz), 2.76-2.87 (m, 1H), 3.51 (apparent d, J=11.2 Hz, 2H), 7.08-7.24 (m, 4H), 7.28 (s, 2H).

Compound 37. 1-(3-Methyl-1H-pyrazol-4-yl)-4-phenylpiperidine

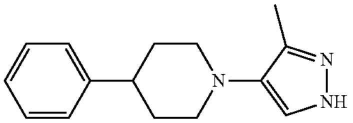 [SMILES: Cc1n[nH]cc1N1CCC(c2ccccc2)CC1]

Synthesized from THP-protected 4-iodo-3-methyl-pyrazole and commercially available 4-phenylpiperidine according to the general procedure 6. The crude THP-protected coupling intermediate was chromatographed with silica gel column and 0-100% EtOAc in hexanes gradient. The desired product, 1-(3-methyl-1H-pyrazol-4-yl)-4-phenylpiperidine, was isolated as an off-white solid after purification of the crude THP deprotection product with silica gel column and 0-100% EtOAc in hexanes gradient (15% yield). $^1$H NMR (400 MHz, DMSO-d6) δ 1.76-1.83 (m, 4H), 2.12 (s, 3H), 2.53-2.62 (m, 3H), 3.17 (apparent d, J=11.2 Hz, 2H), 7.15-7.22 (m, 1H), 7.27-7.35 (m, 5H), 12.03 (bs, 1H).

Compound 38. 1-(5-Methyl-1H-pyrazol-5-yl)-4-phenylpiperidine

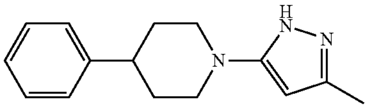 [SMILES: Cc1cc(N2CCC(c3ccccc3)CC2)[nH]n1]

Synthesized from THP-protected 3-iodo-5-methyl-pyrazole and commercially available 4-phenylpiperidine according to the general procedure 6. The crude THP-protected coupling intermediate was chromatographed with silica gel column and 0-50% EtOAc in hexanes gradient. The desired product, 1-(5-methyl-1H-pyrazol-5-yl)-4-phenylpiperidine, was isolated as an off-white solid after silica gel column chromatography with 0-100% EtOAc in hexanes and a precipitation out of $CH_2Cl_2$ with excess of hexanes (27% yield). $^1$H NMR (400 MHz, DMSO-d6) δ 1.64-1.82 (m, 4H), 2.12 (s, 3H), 2.55-2.68 (m, 3H), 3.7 (apparent d, J=11.2 Hz, 2H), 5.47 (s, 1H), 7.17-7.20 (m, 1H), 7.24-7.31 (m, 4H), 11.43 (bs, 1H).

Compound 39. 4-(Phenylthio)-1-(1H-pyrazol-5-yl)piperidine

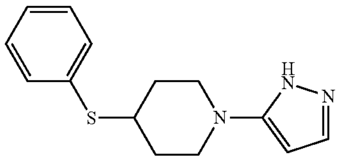

Synthesized according to the general procedure 6 from THP-protected 3-iodo-pyrazole and 4-(phenylthio)piperidine (prepared according to general procedure 4 using benzenethiol as the arylthiol of choice). The crude THP-protected coupling intermediate was chromatographed with silica gel column and 0-50% EtOAc in hexanes gradient. The desired product, 4-(phenylthio)-1-(1H-pyrazol-5-yl)piperidine, was isolated as an oil after purification of the crude THP deprotection product with silica gel column and 0-100% EtOAc in hexanes gradient (15% yield). $^1$H NMR (400 MHz, DMSO-d6) δ 1.50-1.59 (m, 2H), 1.93 (apparent d, J=11.2 Hz, 2H), 2.76 (apparent t, 2H), 3.34-3.42 (m, 1H), 3.56 (apparent d, J=12.0 Hz, 2H), 5.68 (s, 1H), 7.25 (apparent distorted t, J=7.2 Hz, 1H), 7.35 (apparent t, J=7.2 Hz, 2H), 7.39-7.46 (m, 3H), 11.76 (bs, 1H).

Compound 40. 4-(Phenylthio)-1-(1H-pyrazol-4-yl)piperidine

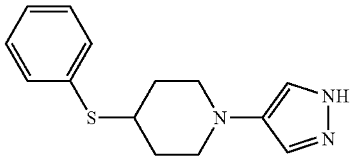 [SMILES: c1ccc(SC2CCN(c3cn[nH]c3)CC2)cc1]

Synthesized according to the general procedure 6 from THP-protected 4-iodo-pyrazole and 4-(phenylthio)piperidine (prepared according to general procedure 4 using benzenethiol as the arylthiol of choice). The crude THP-protected coupling intermediate was chromatographed with silica gel column and 0-50% EtOAc in hexanes gradient. The desired product, 4-(phenylthio)-1-(1H-pyrazol-4-yl)piperidine, was isolated as off-white solid after purification of the crude THP deprotection product with silica gel column and 0-100% EtOAc in hexanes gradient (23% yield). $^1$H NMR (400 MHz, DMSO-d6) 1.54-1.65 (m, 2H), 1.92-1.98 (m, 2H), 2.59 (apparent t, J=9.6 Hz, 2H), 3.23-3.38 (m, 3H), 7.22-7.28 (s overlapping with m, 3H), 7.30-7.37 (m, 2H), 7.40-7.42 (m, 2H), 12.29 (bs, 1H).

Compound 41. 4-(Phenylsulfonyl)-1-(1H-pyrazol-5-yl)piperidine

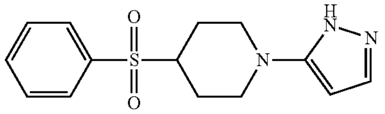

Synthesized according to the general procedure 6 from THP-protected 3-iodo-pyrazole and 4 (phenylsulfonyl)piperidine (prepared from tert-butyl 4-(phenylthio)piperidine-1-carboxylate, Buchanan, J. L. et al. WO2010022055, the disclosure hereby incorporated by reference, via an mCPBA oxidation and then Boc deprotection with 4N HCl). The crude THP-protected coupling intermediate was chromatographed with silica gel column and 0-100% EtOAc in hexanes gradient. The desired product, 4-(phenylsulfonyl)-1-(1H-pyrazol-5-yl)piperidine, was isolated as off-white solid after purification of the crude THP deprotection product with silica gel column and 0-100% EtOAc in hexanes (22% yield). $^1$H NMR (400 MHz, $CDCl_3$) δ 1.83 (qd, 12.4, 4.4 Hz, 2H), 2.09 (apparent d, J=13.2 Hz, 2H), 2.72 (td, J=12.4 Hz, 2.4 Hz, 2H), 3.05 (tt, J=12.4 Hz, 3.2 Hz, 1H), 3.86 (apparent d, J=12.4 Hz, 2H), 5.72 (d, J=2.4 Hz, 1H), 7.39 (d, J=2.8 Hz, 1H), 7.58 (distorted t, J=7.2 Hz, 2H), 7.64-7.68 (m, 1H), 7.90 (apparent d, J=7.2 Hz, 2H).

Compound 42. 4-(Phenylsulfonyl)-1-(1H-pyrazol-4-yl)piperidine

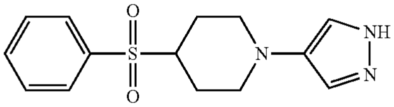

Synthesized according to the general procedure 6 from THP-protected 4-iodo-pyrazole and 4-(phenylsulfonyl)piperidine (prepared from tert-butyl 4-(phenylthio)piperidine-1-carboxylate, Buchanan, J. L. et al. WO2010022055, the disclosure hereby incorporated by reference, via an mCPBA oxidation and then Boc deprotection with 4N HCl). The crude THP-protected coupling intermediate was chromatographed with silica gel column and 0-100% EtOAc in hexanes. The desired product, 4-(phenylsulfonyl)-1-(1H-pyrazol-4-yl)piperidine, was isolated as off-white solid after purification of the crude THP deprotection product with silica gel column and 0-100% EtOAc in hexanes and a precipitation out of $CH_2Cl_2$ with excess of hexanes (5% yield). $^1$H NMR (400 MHz, $CDCl_3$) δ 1.80-1.93 (m, 2H), 2.09 (apparent d, J=18.8 Hz, 2H), 2.49-2.58 (m, 2H), 2.99 (apparent tt, J=12.4 Hz, 2.8 Hz, 1H), 3.43 (apparent d, J=11.6 Hz, 2H), 7.20 (s, 2H), 7.55-7.62 (distorted t, J=7.6 Hz, 2H), 7.68 (distorted t, J=7.6 Hz, 1H), 7.89 (d, J=8.0 Hz, 2H).

Compound 43. 4-(3-Fluoro-4-methoxyphenyl)-1-(1H-pyrazol-5-yl)piperidine

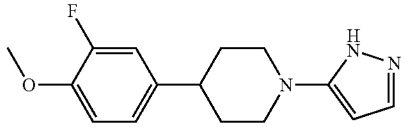

Synthesized from THP-protected 3-iodo-pyrazole and 4-(3-fluoro-4-methoxyphenyl)piperidine according to the general procedure 6. The crude THP-protected coupling intermediate was chromatographed with silica gel column and 0-30% EtOAc in hexanes gradient. The desired product, 4-(3-fluoro-4-methoxyphenyl)-1-(1H-pyrazol-5-yl)piperidine, was isolated as an off-white solid after purification of the crude THP deprotection product with silica gel column and 0-100% EtOAc in hexanes (19% yield). $^1$H NMR (400 MHz, $CDCl_3$) δ 1.81 (qd, J=12.0, 4.0 Hz, 2H), 1.91 (distorted apparent d, J=12.8, 2H), 2.58 (tt, J=11.6, 4.0 Hz, 1H), 2.83 (td, J=12.4, 2.8 Hz, 2H), 3.82-3.88 (s overlap with d, 5H), 5.79 (d, J=2.4, 1H), 6.85-7.01 (m, 3H), 7.41 (d, J=2.4, 1H).

Compound 44. 4-(3-Fluoro-4-methoxyphenyl)-1-(1H-pyrazol-4-yl)piperidine

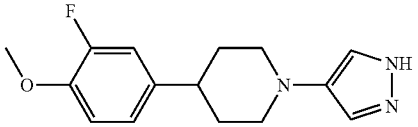 [SMILES: COc1ccc(C2CCN(c3cn[nH]c3)CC2)cc1F]

Synthesized from THP-protected 4'-iodo-pyrazole and 4-(3-fluoro-4-methoxyphenyl)piperidine according to the general procedure 6. The crude THP protected coupling intermediate was chromatographed with silica gel column and 0-60% EtOAc in hexanes. The desired product, 4-(3-fluoro-4-methoxyphenyl)-1-(1H-pyrazol-4-yl)piperidine, was isolated as off-white solid after purification of the crude THP deprotection product with silica gel column and 0-10% MeOH in $CH_2Cl_2$ (14% yield). $^1$H NMR (400 MHz, $CDCl_3$) δ 1.83-1.94 (m, 4H), 2.50-2.59 (m, 1H), 2.66 (apparent td, J=11.6, 4.0 Hz, 2H), 3.45-3.50 (m, 2H), 3.88 (s, 3H), 6.87-7.00 (m, 3H), 7.27 (s, 2H), 9.71 (bs, 1H). $^1$H NMR (400 MHz, DMSO-d6) δ 1.66-1.82 (m, 4H), 2.49-2.59 (m, 3H), 3.40 (apparent d, J=11.6, 2H), 3.80 (s, 3H), 7.01-7.15 (m, 3H), 7.25 (s, 2H), 12.24 (s, 1H).

Compound 45. 4-(3-Methoxybenzyl)-1-(1H-pyrazol-4-yl)piperidine

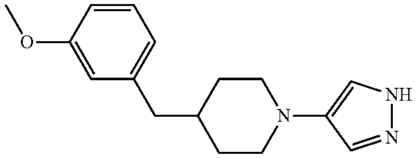

Synthesized from THP-protected 4-iodo-pyrazole and commercially available 4-(3-methoxybenzyl)piperidine according to the general procedure 6. The crude THP-protected coupling intermediate was chromatographed with silica gel column and 0-100% EtOAc in hexanes gradient. The desired product, 4-(3-methoxybenzyl)-1-(1H-pyrazol-4-yl)piperidine, was isolated as off-white solid after purification of the crude THP deprotection product with silica gel column and 0-10% MeOH in EtOAc (15% yield). $^1$H NMR (400 MHz, $CDCl_3$) δ 1.45 (qd, J=12.0, 4.0 Hz, 2H), 1.60-1.67 (m, 1H), 1.73 (apparent d, J=12.8 Hz, 2H), 2.50 (td, J=11.6, 2.4 Hz, 2H), 2.55 (d, J=7.2 Hz, 2H), 3.31-3.36 (m, 2H), 3.81 (s, 3H), 6.71-6.79 (m, 3H), 7.18-7.23 (m, 3H), 9.65 (bs, 1H).

Compound 46. 4-(2-Fluoro-4-methoxyphenyl)-1-(1H-pyrazol-5-yl)piperidine

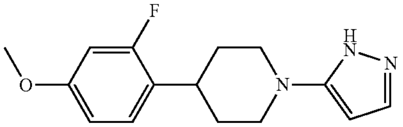 [SMILES: COc1ccc(C2CCN(c3ccn[nH]3)CC2)c(F)c1]

Synthesized from THP-protected 3-iodo-pyrazole and 4-(2-fluoro-4-methoxyphenyl)piperidine according to the general procedure 6. The crude THP-protected coupling intermediate was chromatographed with silica gel column and 0-100% EtOAc in hexanes gradient. The desired product, 4-(2-fluoro-4-methoxyphenyl)-1-(1H-pyrazol-5-yl)piperidine, was isolated as an off-white solid after purification of the crude THP deprotection product with silica gel column and 0-100% EtOAc in hexanes gradient (9% yield). $^1$H NMR (400 MHz, DMSO-d6) δ 1.71-1.81 (m, 4H), 2.45-2.73 (m, 2H), 2.79-2.86 (m, 1H), 3.73-3.80 (s overlapping with d, 5H), 5.71 (d, J=2.4 Hz, 1H), 6.72-6.80 (m, 2H), 7.23 (t, J=8.8 Hz, 1H), 7.46 (d, J=2.0 Hz, 1H), 11.86 (bs, 1H).

Compound 47. 4-(2-Fluoro-4-methoxyphenyl)-1-(1H-pyrazol-4-yl)piperidine

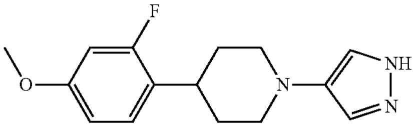 [SMILES: COc1ccc(C2CCN(c3cn[nH]c3)CC2)c(F)c1]

Synthesized from THP-protected 4-iodo-pyrazole and 4-(2-fluoro-4-methoxyphenyl)piperidine according to the general procedure 6. The crude THP-protected coupling intermediate was chromatographed with silica gel column and 0-100% EtOAc in hexanes gradient. The desired product, 4-(2-fluoro-4-methoxyphenyl)-1-(1H-pyrazol-4-yl)piperidine, was isolated as off-white solid after purification of the crude THP deprotection product with silica gel column and 0-100% EtOAc in hexanes gradient (17% yield). $^1$H NMR (400 MHz, $CDCl_3$) δ 1.86-1.98 (m, 4H), 2.64-2.74 (m, 2H), 2.84-2.93 (m, 1H), 3.48 (apparent d, J=11.6 Hz, 2H), 3.78 (s, 3H), 6.61 (dd, J=12.4, 2.4 Hz, 1H), 6.67 (dd, J=8.8, 2.4 Hz, 1H), 7.15 (t, J=8.4 Hz, 1H), 7.27 (s, 2H) 9.74 (bs, 1H).

Compound 48. 4-(3-Fluorophenyl)-1-(1H-pyrazol-5-yl)piperidine

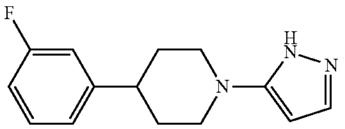 [SMILES: Fc1cccc(C2CCN(c3ccn[nH]3)CC2)c1]

Synthesized from THP-protected 3-iodo-pyrazole and commercially available 4-(3-fluorophenyl)piperidine according to the general procedure 6. The crude THP-protected coupling intermediate was chromatographed with silica gel column and 0-100% EtOAc in hexanes gradient. The product, 4-(3-fluorophenyl)-1-(1H-pyrazol-5-yl)piperidine, was isolated as off-white solid after purification of the crude THP deprotection product with silica gel column and 0-100% EtOAc in hexanes gradient (27% yield). $^1$H NMR (400 MHz, $CDCl_3$) δ 1.80-1.97 (m, 4H), 2.66 (tt, J=12.0, 4.0 Hz, 1H), 2.86 (td, J=12.0, 2.8 Hz, 2H), 3.87 (apparent d, J=12.4 Hz, 2H), 5.79 (d, J=2.4 Hz, 1H), 6.86-6.97 (m, 2H), 7.02 (d, J=7.6 Hz, 1H), 7.23-7.30 (m, 1H), 7.42 (d, J=2.4, 1H).

Compound 49. 4-(3-Fluorophenyl)-1-(1H-pyrazol-4-yl)piperidine

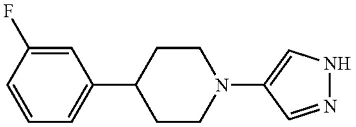 [SMILES: Fc1cccc(C2CCN(c3cn[nH]c3)CC2)c1]

Synthesized from THP-protected 4-iodo-pyrazole and commercially available 4-(3-fluorophenyl)piperidine according to the general procedure 6. The crude THP-protected coupling intermediate was chromatographed with silica gel column and 0-100% EtOAc in hexanes gradient. The product, 4-(3-fluorophenyl)-1-(1H-pyrazol-4-yl)piperidine, was isolated as off-white solid after purification of the crude THP deprotection product with silica gel column and 0-100% EtOAc in hexanes gradient (22% yield). $^1$H NMR (400 MHz, $CDCl_3$) δ 1.92-2.03 (m, 4H), 2.58-2.67 (m, 1H), 2.67-2.76 (m, 2H), 3.51 (apparent d, J=12.0 Hz, 2H), 6.80-6.98 (m, 2H), 7.03 (d, J=7.6 Hz, 1H), 7.25-7.31 (m, 1H), 7.32 (s, 2H).

Compound 50. 4-(2-Fluorophenyl)-1-(1H-pyrazol-5-yl)piperidine

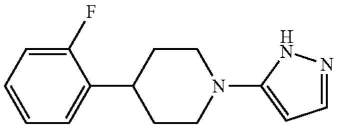 [SMILES: Fc1ccccc1C1CCN(c2ccn[nH]2)CC1]

Synthesized from THP-protected 3-iodo-pyrazole and 4-(2-fluorophenyl)piperidine according to the general procedure 6. The crude THP-protected coupling intermediate was chromatographed with silica gel column and 0-100% EtOAc in hexanes gradient. The desired product, 4-(2-fluorophenyl)-1-(1H-pyrazol-5-yl)piperidine, was isolated as white solid after purification of the crude THP deprotection product with 0-100% EtOAc in hexanes gradient (13% yield). $^1$H NMR (400 MHz, DMSO-d6) δ 1.75-1.82 (m, 4H), 2.66-2.72 (m, 2H), 2.87-2.97 (m, 1H), 3.77 (d, J=12.0 Hz, 2H), 5.72 (s, 1H), 7.11-7.19 (m, 2H), 7.23-7.30 (m, 1H), 7.31-7.38 (m, 1H), 7.45 (s, 1H), 11.78 (s, 1H).

Compound 51. 4-(2-Fluorophenyl)-1-(1H-pyrazol-4-yl)piperidine

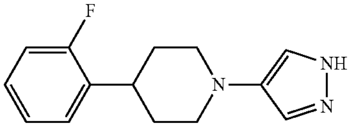 [SMILES: Fc1ccccc1C1CCN(c2cn[nH]c2)CC1]

Synthesized from THP-protected 4-iodo-pyrazole and 4-(2-fluorophenyl)piperidine according to the general procedure 6. The crude THP-protected coupling intermediate was chromatographed with column and 0-100% EtOAc in hexanes. The desired product, 4-(2-fluorophenyl)-1-(1H-pyrazol-4-yl)piperidine, was isolated as off-white solid after purification of the crude THP deprotection product with silica gel column and 0-100% EtOAc gradient (13% yield). $^1$H NMR (400 MHz, $CDCl_3$) δ 1.90-2.05 (m, 4H), 2.74 (td, J=11.6, 2.8 Hz, 2H), 2.99 (apparent tt J=12.0, 4.0 Hz, 1H), 3.51 (d, J=11.6 Hz, 2H), 7.00-7.06 (m, 1H), 7.09-7.14 (m, 1H), 7.16-7.23 (m, 1H), 7.27-7.32 (m and s overlapping, 3H).

Compound 52. 4-(4-(Ethylsulfonyl)phenyl)-1-(1H-pyrazol-4-yl)piperidine

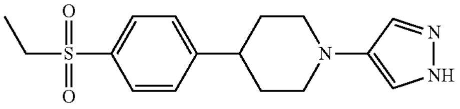 [SMILES: CCS(=O)(=O)c1ccc(C2CCN(c3cn[nH]c3)CC2)cc1]

Synthesized from THP-protected 4-iodo-pyrazole and 4-(4-(ethylsulfonyl)phenyl)piperidine according to the general procedure 6. The crude THP-protected coupling intermediate was chromatographed with silica gel column and 0-100% EtOAc in DCM gradient. The desired product, 4-(4-(ethylsulfonyl)phenyl)-1-(1H-pyrazol-4-yl)piperidine, was isolated as off-white/beige solid after purification of the crude THP deprotection product with silica gel column and 0-5% MeOH in $CH_2Cl_2$ gradient and a precipitation out of $CH_2Cl_2$ with excess of hexanes (14% yield). $^1$H NMR (400 MHz, $CD_3CN$) δ 1.17 (t, J=7.2 Hz, 3H), 1.85-1.91 (m, 4H), 2.59-2.65 (m, 2H), 2.72-2.80 (m, 1H), 3.13 (q, J=7.2 Hz, 2H), 3.45-3.52 (m, 2H), 7.22 (s, 2H), 7.53 (apparent d, J=8.0 Hz, 2H), 7.80 (apparent d, J=8.4 Hz, 2H), 10.57 (bs, 1H).

Compound 53. 1-Phenyl-4-(1H-pyrazol-5-yl)piperazine

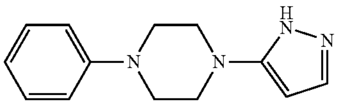 [SMILES: c1ccc(N2CCN(c3ccn[nH]3)CC2)cc1]

Synthesized from THP-protected 3-iodo-pyrazole and commercially available 1-phenylpiperazine according to the general procedure 6. The crude THP-protected coupling intermediate was chromatographed with silica gel column and 0-100% EtOAc in hexanes gradient. The desired product, 1-phenyl-4-(1H-pyrazol-5-yl)piperazine, was isolated as off-white solid after purification of the crude THP deprotection product with silica gel column and 0-100% EtOAc in $CH_2Cl_2$ (37% yield). $^1H$ NMR (600 MHz $CDCl_3$) δ 3.31-3.33 (m, 4H), 3.39-3.41 (m, 4H), 5.83 (s, 1H), 6.89 (t, J=7.2 Hz, 1H), 6.99 (d, J=8.4 Hz, 2H), 7.29 (t, J=7.2 Hz, 2H), 7.43 (s, 1H).

Compound 54. 4-Phenyl-1-(1H-pyrazol-5-yl)piperidine

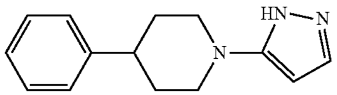 [SMILES: c1ccc(C2CCN(c3ccn[nH]3)CC2)cc1]

Synthesized from THP-protected 3-iodo-pyrazole and commercially available 4-phenylpiperidine according to the general procedure 6. The crude THP-protected coupling intermediate was chromatographed with silica gel column and 0-50% EtOAc in hexanes gradient. The desired product, 4-phenyl-1-(1H-pyrazol-5-yl)piperidine, was isolated as white solid after purification of the crude THP deprotection product with silica gel column and 0-100% EtOAc in $CH_2Cl_2$ (13% yield). $^1H$ NMR (600 MHz $CDCl_3$) δ 1.86-1.95 (m, 4H), 2.65 (apparent tt, J=12.0, 4.2 Hz, $^1H$), 2.86 (td, J=12.0, 3.0 Hz, 2H), 3.86 (apparent d, J=12.0 Hz, 2H), 5.81 (s, 1H), 7.20-7.23 (m, 2H), 7.29-7.33 (m, 2H), 7.42 (s, 1H).

Compound 55. 4-Phenoxy-1-(1H-pyrazol-5-yl)piperidine

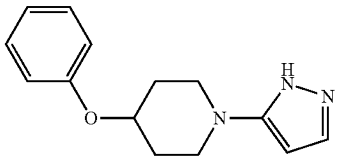

Synthesized according to general method 6 from THP-protected 3-iodo-pyrazole and 4-phenoxypiperidine (prepared as in Hudskins, R. L. et al. Biorg. Med. Chem. Lett 2014, 24 (5), 1303-1306, incorporated herein by reference). The crude THP-protected coupling intermediate was chromatographed with silica gel column and 0-100% EtOAc in hexanes gradient. The desired product, 4-phenoxy-1-(1H-pyrazol-5-yl)piperidine, was isolated after purification of the crude THP deprotection product with silica gel column and 0-100% EtOAc in hexanes gradient. $^1H$ NMR (600 MHz, $CDCl_3$) δ 1.91-1.93 (m, 2H), 2.05-2.11 (m, 2H), 3.09-3.12 (m, 2H), 3.56-3.59 (m, 2H), 4.40-4.50 (m, 1H), 5.78 (s, 1H), 6.90-6.96 (m, 3H), 7.23-7.30 (m, 2H), 7.40 (s, 1H).

Compound 56. Methyl 3-(1-(1H-pyrazol-5-yl)piperidin-4-yl)benzoate

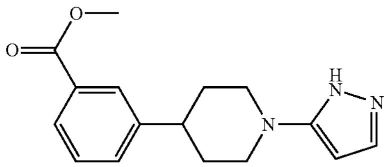 [SMILES: COC(=O)c1cccc(C2CCN(c3ccn[nH]3)CC2)c1]

Synthesized from THP-protected 3-iodo-pyrazole and methyl 3-(piperidin-4-yl)benzoate according to general method 6. The crude THP-protected coupling intermediate was chromatographed with column and 0-100% EtOAc in hexanes gradient. The desired product, methyl 3-(1-(1H-pyrazol-5-yl)piperidin-4-yl)benzoate, was isolated as off-white solid after silica gel column chromatography with 0-100% Hex in EtOAC gradient (23% yield). $^1H$ NMR (400 MHz, DMSO-d6) δ 1.66-1.78 (m, 2H), 1.83 (apparent d, J=11.2 Hz, 2H), 2.67-2.79 (m, 3H), 3.77 (apparent d, J=11.2 Hz, 2H), 3.85 (s, 3H), 5.72 (s, 1H), 7.44-7.49 (m, 2H), 7.57 (d, J=7.6 Hz, 1H), 7.78-7.84 (m, 2H), 11.80 (bs, 1H).

Compound 57. Methyl 3-(1-(1H-pyrazol-4-yl)piperidin-4-yl)benzoate

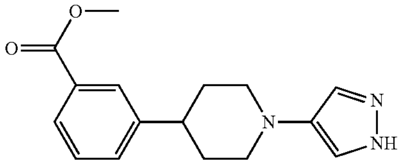 [SMILES: COC(=O)c1cccc(C2CCN(c3cn[nH]c3)CC2)c1]

Synthesized from THP-protected 4-iodo-pyrazole and methyl 3-(piperidin-4-yl)benzoate according to the general procedure 6. The crude THP-protected coupling intermediate was chromatographed with column and 0-100% EtOAc in hexanes gradient. The desired product, methyl 3-(1-(1H-pyrazol-4-yl)piperidin-4-yl)benzoate, was isolated as an off-white solid after purification of the THP deprotection product with 0-100% EtOAc in $CH_2Cl_2$ and a precipitation out of $CH_2Cl_2$ with excess of hexanes (23% yield). $^1H$ NMR (400 MHz, DMSO-d6) δ 1.73-1.85 (m, 4H), 2.54-2.60 (m, 2H), 2.67-2.72 (m, 1H), 3.44 (apparent d, J=10.0 Hz, 2H), 3.85 (s, 3H), 7.24-7.29 (m, 2H), 7.47 (apparent t, J=7.6 Hz, 1H), 7.57-7.60 (m, 1H), 7.79-7.86 (m, 2H), 12.28 (bs, 1H).

Compound 58. 4-(4-(Ethylsulfonyl)phenyl)-1-(1H-pyrazol-5-yl)piperidine

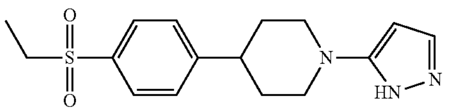 [SMILES: CCS(=O)(=O)c1ccc(C2CCN(c3ccn[nH]3)CC2)cc1]

Synthesized from THP-protected 3-iodo-pyrazole and 4-(4-(ethylsulfonyl)phenyl)piperidine according to the general procedure 6. The crude THP-protected coupling intermediate was chromatographed with column and 0-100% EtOAc in hexanes gradient. The desired product, 4-(4-(ethylsulfonyl)phenyl)-1-(1H-pyrazol-5-yl)piperidine, was isolated as an off-white solid after purification of the THP deprotection product with 0-5% MeOH in $CH_2Cl_2$ and a precipitation out of $CH_2Cl_2$ with excess of hexanes (25% yield). $^1H$ NMR (400 MHz, $CD_3CN$) δ 1.16 (t, J=7.2, 3H), 1.73-1.88 (m, 4H), 2.73-2.85 (m, 3H), 3.13 (q, 7.6 Hz, 2H), 3.81-3.84 (m, 2H), 5.74 (d, J=2.4 Hz, 1H), 7.40 (d, J=2.4 Hz, 1H), 7.52 (d, J=8.0 Hz, 2H), 7.81 (d, J=8.0 Hz, 2H).

Compound 59. 3-(1-(1H-Pyrazol-4-yl)piperidin-4-yl)-5-methoxypyridine

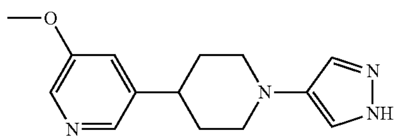

Synthesized from THP-protected 4-iodo-pyrazole and 3-methoxy-5-(piperidin-4-yl)pyridine according to the general procedure 6. The crude THP-protected coupling intermediate was chromatographed with silica gel column and 0-10% MeOH in EtOAc. The desired product, 3-(1-(1H-pyrazol-4-yl)piperidin-4-yl)-5-methoxypyridine, was isolated as off-white/beige solid after purification of the THP deprotection product with silica gel column and 0-10% MeOH in $CH_2Cl_2$ and a precipitation out of $CH_2Cl_2$ with excess of hexanes (18% yield). $^1H$ NMR (400 MHz, $CD_3OD$) δ 1.91-1.98 (m, 4H), 2.69-2.73 (m, 3H), 3.52 (apparent d, J=11.2 Hz, 2H), 3.89 (s, 3H), 7.33 (bs, 1H), 7.37 (bs, 2H), 8.07-8.09 (m, 2H).

Compound 60. 3-(1-(1H-Pyrazol-5-yl)piperidin-4-yl)-5-methoxypyridine

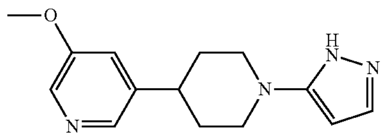 [SMILES: COc1cncc(C2CCN(c3ccn[nH]3)CC2)c1]

Synthesized from THP-protected 3-iodo-pyrazole and 3-methoxy-5-(piperidin-4-yl)pyridine according to the general procedure 6. The crude THP-protected coupling intermediate was chromatographed with silica gel column and 0-5% MeOH in EtOAc gradient. The desired product, 3-(1-(1H-pyrazol-5-yl)piperidin-4-yl)-5-methoxypyridine, was isolated as off-white/beige solid after purification of the THP deprotection product with silica gel column and 0-10% MeOH in $CH_2Cl_2$ and a precipitation out of $CH_2Cl_2$ with excess of hexanes (25% yield). $^1H$ NMR (600 MHz, DMSO-d6) δ 1.70-1.90 (m 4H), 2.66-2.68 (m, 3H), 3.70-3.90 (m, 5H), 5.72 (s, 1H), 7.25-7.30 (m, 1H), 7.45 (s, 1H), 8.12-8.14 (m, 2H), 11.78 (bs, 1H).

Compound 61. 4-(3-Chlorophenyl)-1-(1H-pyrazol-4-yl)piperidine

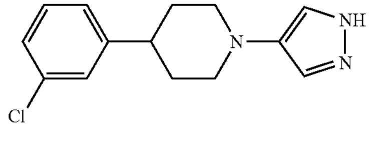 [SMILES: Clc1cccc(C2CCN(c3cn[nH]c3)CC2)c1]

Compound was prepared from THP-protected 4-iodo-pyrazole and commercially available 4-(3-chlorophenyl)piperidine according to the general procedure 6. The crude THP-protected coupling intermediate was chromatographed with silica gel column and 0-5% MeOH in EtOAc gradient. The desired product, 4-(3-chlorophenyl)-1-(1H-pyrazol-4-yl)piperidine, was isolated as off-white/beige solid after purification of the THP deprotection product with silica gel column and 0-10% MeOH in $CH_2Cl_2$ and a precipitation out of $CH_2Cl_2$ with excess of hexanes (8% yield). $^1$HNMR (500 MHz, $CD_3OD$) δ 7.38 (s, 2H), 7.32-7.29 (m, 2H), 7.23-7.21 (m, 2H), 3.54-3.51 (m, 2H), 2.72-2.65 (m, 3H), 1.95-1.88 (m, 4H).

Compound 62. 4-(4-chlorophenyl)-1-(1H-pyrazol-5-yl)piperidine

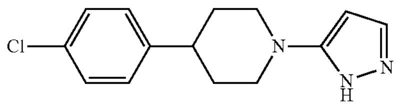 [SMILES: Clc1ccc(C2CCN(c3ccn[nH]3)CC2)cc1]

Compound was synthesized from THP-protected 3-iodo-pyrazole and 4-(4-chloro-phenyl)-piperidine according to the general procedure 6. The crude THP-protected coupling intermediate was chromatographed with silica gel column and 0-40% EtOAc in hexanes gradient. The desired product, 4-(4-chlorophenyl)-1-(1H-pyrazol-3-yl)piperidine, was isolated as an off-white solid after purification of the THP deprotection product with silica gel column chromatography and 0-100% EtOAc in hexanes gradient (18% yield). $^1H$ NMR (400 MHz, $CDCl_3$) δ 1.77-1.93 (m, 4H), 2.63 (apparent tt, J=11.6 Hz, 4.0 Hz, 1H), 2.83 (td, J=12.4 Hz, 3.6 Hz, 2H), 3.83-3.89 (m, 2H), 5.80 (d, J=2.4 Hz, 1H), 7.18 (apparent d, J=8.4 Hz, 2H), 7.28 (apparent d, J=8.4 Hz, 2H), 7.42 (d, J=2.4 Hz, 1H).

Compound 63. 4-(4-chlorophenyl)-1-(1H-pyrazol-4-yl)piperidine

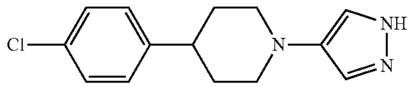 [SMILES: Clc1ccc(C2CCN(c3cn[nH]c3)CC2)cc1]

Compound was synthesized from THP-protected 4-iodo-pyrazole and 4-(4-chloro-phenyl)-piperidine according to the general procedure 6. The crude THP-protected coupling intermediate was chromatographed with silica gel column and 0-60% EtOAc in hexanes gradient. The product, 4-(4-chlorophenyl)-1-(1H-pyrazol-4-yl)piperidine, was isolated as an off-white solid after purification of the crude THP deprotection product with silica gel column and 0-100% EtOAc in hexanes gradient (23% yield). $^1H$ NMR (400 MHz, $CDCl_3$) δ 1.86-1.93 (m, 4H), 2.53-2.63 (m, 1H), 2.63-2.72 (m, 2H), 3.45-3.51 (m, 2H), 7.18 (apparent d, J=8.0 Hz, 2H), 7.28 (apparent d, J=8.4 Hz, 2H); $^1H$ NMR (400 MHz, DMSO-d6) δ 1.68-1.82 (m, 4H), 2.50-2.57 (m, 2H), 2.57-2.64 (m, 1H), 3.42 (apparent d, J=11.6 Hz, 2H), 7.26 (s, 2H), 7.29-7.37 (m, 4H), 12.24 (s, 1H).

Compound 64. 4-(3-Chloro-4-methoxyphenyl)-1-(1H-pyrazol-4-yl)piperidine

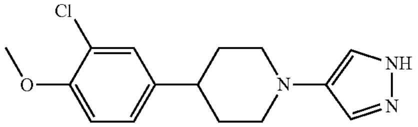 [SMILES: COc1ccc(C2CCN(c3cn[nH]c3)CC2)cc1Cl]

Compound was synthesized from THP-protected 4-iodo-1H-pyrazole and 4-(3-chloro-4-methoxyphenyl)piperidine according to the general procedure 6. The crude THP-protected coupling intermediate was chromatographed with silica gel column and 0-35% EtOAc in hexanes gradient. The product, 4-(3-chloro-4-methoxyphenyl)-1-(1H-pyrazol-4-yl)piperidine, was isolated as a as white solid after purification of the crude THP deprotection product with silica gel column chromatography and 0-100% EtOAc in hexanes gradient (16% yield). $^1$H NMR (600 MHz, $CD_3OD$) δ 1.80-1.91 (m, 4H), 2.58 (apparent tt, J=12.0, 3.6 Hz, 1H), 2.66 (td, J=12.0, 2.4 Hz, 2H), 3.49 (apparent d, J=11.4 Hz, 2H), 3.85 (s, 3H), 7.00 (d, J=8.4 Hz, 1H), 7.16 (dd, J=12.0, 1.8 Hz, 1H), 7.26 (d, J=2.4 Hz, 1H), 7.37 (s, 2H); H NMR (600 MHz, $CDCl_3$) δ 1.86-1.92 (m, 4H), 2.51-2.57 (m, 1H), 2.67 (td, J=10.8, 4.2 Hz, 2H), 3.48 (d, J=11.4 Hz, 1H), 3.89 (s, 3H), 6.89 (d, J=8.4 Hz, 1H), 7.10 (dd, J=8.4, 2.4 Hz, 2H).

Compound 65. 4-(2-Chloro-4-methoxyphenyl)-1-(1H-pyrazol-4-yl)piperidine

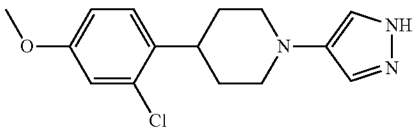 [SMILES: COc1ccc(C2CCN(c3cn[nH]c3)CC2)c(Cl)c1]

Compound was synthesized from THP-protected 4-iodo-pyrazole and 4-(2-chloro-4-methoxyphenyl)piperidine according to the general procedure 6. The crude THP-protected coupling intermediate was chromatographed with silica gel column and 0-35% EtOAc in hexanes. The product, 4-(2-chloro-4-methoxyphenyl)-1-(1H-pyrazol-4-yl)piperidine was isolated as a white solid after purification of the crude THP deprotection product with silica gel column chromatography and 0-100% EtOAc in hexanes gradient (13% yield). $^1$H NMR (300 MHz, DMSO-$d_6$) δ 1.73-1.79 (m, 4H), 2.54-2.59 (m, 2H), 2.87-2.97 (m, 1H), 3.45 (apparent d, J=11.7 Hz, 2H), 3.76 (s, 3H), 6.92 (dd, J=8.7, 2.7 Hz, 1H), 7.02 (d, J=2.7, 1H), 7.28 (s, 2H), 7.32 (d, J=8.7 Hz, 1H), 12.14 (bs, 1H).

Compound 66. 4-(2-Chloro-4-methoxyphenyl)-1-(1H-pyrazol-5-yl)piperidine

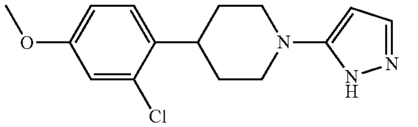 [SMILES: COc1ccc(C2CCN(c3ccn[nH]3)CC2)c(Cl)c1]

Compound was synthesized from THP-protected 3-iodo-pyrazole and 4-(2-chloro-4-methoxyphenyl)piperidine according to the general procedure 6. The crude THP-protected coupling intermediate was chromatographed with silica gel column and 0-30% EtOAc in hexanes. The product, 4-(2-chloro-4-methoxyphenyl)-1-(1H-pyrazol-3-yl)piperidine was isolated as a white solid after purification of the crude THP deprotection product with silica gel column chromatography and 0-100% EtOAc in hexanes gradient (16% yield). $^1$H NMR (600 MHz, $CDCl_3$) δ 1.81 (apparent qd, J=12.0 Hz, 3.6 Hz, 2H), 1.92-1.94 (m, 2H), 3.11 (tt, J=12.0 Hz, 3.6, 1H), 2.90 (td, J=12.0 Hz, 2.4, 2H), 3.80 (s, 3H), 3.86-3.90 (m, 2H), 5.82 (s, 1H), 6.82 (dd, J=9.0 Hz, 3.0 Hz, 1H), 6.94 (d, J=2.4 Hz, 1H), 7.20 (d, J=8.4 Hz, 1H), 7.43 (d, J=2.4 Hz, 1H), 9.25 (bs, 1H).

Compound 67. 4-(3-Chloro-4-methoxyphenyl)-1-(1H-pyrazol-5-yl)piperidine

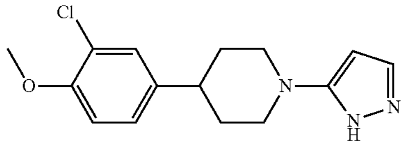 [SMILES: COc1ccc(C2CCN(c3ccn[nH]3)CC2)cc1Cl]

Compound was prepared from THP-protected 3-iodo-pyrazole and 4-(3-chloro-4-methoxyphenyl)piperidine according to the general procedure 6. The crude THP-protected coupling intermediate was chromatographed with silica gel column and 0-40% EtOAc in hexanes gradient. The product, 4-(3-chloro-4-methoxyphenyl)-1-(1H-pyrazol-5-yl)piperidine, was isolated as a white solid after purification of the crude THP deprotection product with silica gel column chromatography and 0-100% EtOAc in hexanes gradient (18% yield). $^1$H NMR (600 MHz, $CDCl_3$) δ 1.82 (apparent qd, J=11.4, 4.2 Hz, 2H), 1.90 (apparent distorted d, J=13.2 Hz, 2H), 2.59 (tt, J=12.6, 3.6 Hz, 1H), 2.83 (td, J=12.0, 3.0 Hz, 2H), 3.83-3.86 (m, 2H), 3.89 (s, 3H), 5.80 (d, J=1.8 Hz, 1H), 6.88 (d, J=9.0 Hz, 1H), 7.10 (dd, J=8.4, 2.4 Hz, 1H), 7.25 (d, J=2.4 Hz, 1H), 7.42 (d, J=2.4 Hz, 1H).

Compound 68. 4-((4-Methoxyphenyl)thio)-1-(1H-pyrazol-5-yl)piperidine

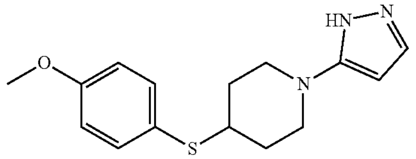 [SMILES: COc1ccc(SC2CCN(c3ccn[nH]3)CC2)cc1]

Compound was prepared from THP-protected 3-iodo-pyrazole and 4-((4-methoxy-phenyl)thio)piperidine according to general procedure 6. The crude THP-protected coupling intermediate was chromatographed with silica gel column and 0-100% EtOAc in hexanes gradient. The crude THP deprotection product was chromatographed with 0-100% EtOAc in hexanes to afford the desired product, 4-((4-methoxyphenyl)thio)-1-(1H-pyrazol-3-yl)piperidine, as a white/off-white solid (22% yield). $^1$H NMR (600 MHz, $CDCl_3$) δ 1.67-1.74 (m, 2H), 1.80-2.05 (m, 2H), 2.81 (ddd, J=13.8, 9.6, 3.0 Hz, 2H), 3.02 (tt, J=10.8, 3.6, 1H), 3.68

(apparent dt, J=13.2, 3.6 Hz, 2H), 3.81 (s, 3H), 5.73 (broad d, J=1.8 Hz, 1H), 6.85 (apparent d, J=8.4, 2H), 7.38 (broad d, J=2.4 Hz, 1H), 7.42 (apparent d, J=8.4, 2H).

Compound 69. N-(4-(1-(1H-Pyrazol-4-yl)piperidin-4-yl)-3-fluorophenyl)-N-methylacetamide

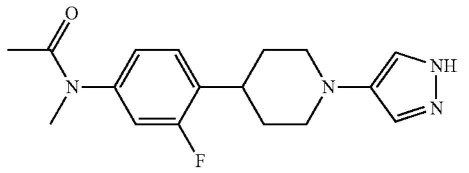 [SMILES: CC(=O)N(C)c1ccc(C2CCN(c3cn[nH]c3)CC2)c(F)c1]

Compound was prepared from THP-protected 4-iodo-pyrazole and N-(3-fluoro-4-(piperidin-4-yl)phenyl)-N-methylacetamide according to the general procedure 6. The THP-protected intermediate was purified with silica gel column chromatography and 0-100% EtOAc in hexanes gradient. The desired product, N-(4-(1-(1H-pyrazol-4-yl)piperidin-4-yl)-3-fluorophenyl)-N-methylacetamide, was obtained as a white solid after purification of the crude THP deprotection product with silica gel column chromatography and 0-5% MeOH in $CH_2Cl_2$ gradient (9% yield). $^1H$ NMR (600 MHz, $CD_3OD$) δ 1.88-2.01 (m overlap with s, 7H), 2.72-2.76 (m, 2H), 3.00-3.04 (m, 1H), 3.23 (s, 3H), 3.54 (d, J=11.4 Hz, 2H), 7.12 (apparent d, J=9.0 Hz, 2H), 7.40-7.45 (m overlap with s, 3H).

Compound 70. 4-((4-Fluorophenyl)thio)-1-(1H-pyrazol-4-yl)piperidine

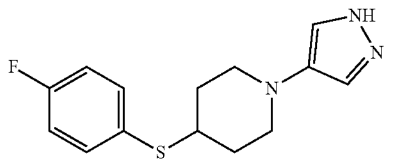 [SMILES: Fc1ccc(SC2CCN(c3cn[nH]c3)CC2)cc1]

Compound was prepared from THP-protected 4-iodo-pyrazole and 4-((4-fluorophenyl)thio)piperdine according to general procedure 6. The THP-protected intermediate was purified with silica gel column chromatography and 0-65% EtOAc in hexanes gradient. The desired product, 4-((4-fluorophenyl)thio)-1-(1H-pyrazol-4-yl)piperidine, was isolated as an off-white solid after purification of the crude THP deprotection product with silica gel column chromatography and 0-100% EtOAc in hexanes gradient (11% yield). $^1H$ NMR (500 MHz, DMSO-d6) 1.53-1.62 (m, 2H), 1.89-1.93 (m, 2H), 3.21-3.28 (m, 3H), 7.17-7.20 (m, 4H), 7.48 (apparent dd, J=8.5, 5.5 Hz, 2H), 12.25 (bs, 1H).

Compound 71. N-(4-(1-(1H-Pyrazol-5-yl)piperidin-4-yl)-3-fluorophenyl)-N-methylacetamide

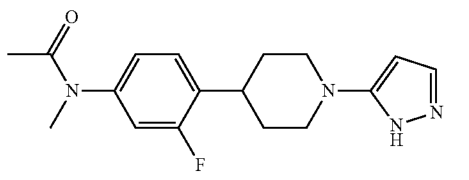 [SMILES: CC(=O)N(C)c1ccc(C2CCN(c3ccn[nH]3)CC2)c(F)c1]

Compound was prepared from THP-protected 3-iodo-pyrazole and N-(3-fluoro-4-(piperidin-4-yl)phenyl)-N-methylacetamide according to the general procedure 6. The THP-protected intermediate was purified with silica gel column chromatography and 0-100% EtOAc in hexanes gradient. The desired product, N-(4-(1-(1H-pyrazol-3-yl)piperidin-4-yl)-3-fluorophenyl)-N-methylacetamide, was obtained as a white solid after purification of the crude THP deprotection product with 0-100% EtOAc in hexanes gradient (22% yield). $^1H$ NMR (300 MHz, DMSO-$d_6$) δ 1.78-1.83 (m, 7H), 2.66-2.77 (m, 2H), 2.88-2.99 (m, 1H), 3.16 (s, 3H), 3.78 (apparent d, J=12.3 Hz, 2H), 5.73 (d, J=2.1 Hz, 1H), 7.16 (apparent d, J=7.8 Hz, 1H), 7.26 (apparent d, J=11.7 Hz, 1H), 7.41 (apparent t, J=8.4 Hz, 1H), 7.47 (d, J=1.8 Hz, 1H), 11.81 (bs, 1H).

Compound 72. 4-(3-Fluoro-5-methoxyphenyl)-1-(1H-pyrazol-4-yl)piperidine

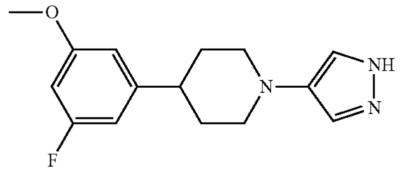 [SMILES: COc1cc(F)cc(C2CCN(c3cn[nH]c3)CC2)c1]

Compound was prepared from THP-protected 4-iodo-pyrazole and 4-(3-fluoro-5-methoxyphenyl)piperidine according to general procedure 6. The THP-protected intermediate was purified with silica gel column chromatography and 0-45%. EtOAc in hexanes gradient. The desired product, 4-(3-fluoro-5-methoxyphenyl)-1-(1H-pyrazol-4-yl)piperidine was isolated as an off-white solid after purification of the crude THP-deprotection product with silica gel column chromatography and 0-100% EtOAc in hexanes gradient (23% yield). $^1H$ NMR (300 MHz, $CDCl_3$) δ 1.91-2.03 (m, 4H), 2.53-2.64 (m, 1H), 2.67-2.76 (m, 2H), 3.47-3.54 (m, 2H), 3.80 (s, 3H), 6.48 (dt, J=10.5, 2.4 Hz, 1H), 6.54-6.61 (m, 2H), 7.33 (s, 2H).

Compound 73. 4-(3-Fluoro-5-methoxyphenyl)-1-(1H-pyrazol-5-yl)piperidine

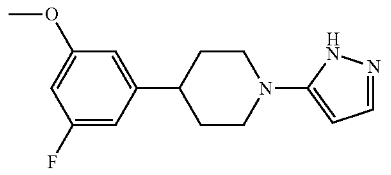 [SMILES: COc1cc(F)cc(C2CCN(c3ccn[nH]3)CC2)c1]

Compound was prepared from THP-protected 3-iodo-pyrazole and 4-(3-fluoro-5-methoxyphenyl)piperidine according to general procedure 6. The THP-protected coupling intermediate was purified with silica gel column chromatography and 0-35% EtOAc in hexanes gradient. The desired product, 4-(3-Fluoro-5-methoxyphenyl)-1-(1H-pyrazol-5-yl)piperidine, was isolated as an off white/tan solid after purification of the crude THP-deprotection product with silica gel column chromatography and 0-100% EtOAc in hexanes gradient (38% yield). $^1H$ NMR (300 MHz, $CDCl_3$) δ 1.76-1.95 (m, 4H), 2.62 (apparent tt, J=11.7, 3.9 Hz, 1H), 2.87 (td, J=12.4, 3.0 Hz, 2H), 3.78 (s, 3H), 3.83-3.89 (m, 2H), 5.78 (d, J=2.4 Hz, 1H), 6.47 (apparent dt, J=10.5, 2.4 Hz, 1H), 6.53-6.59 (m, 2H), 6.84 (bs, 1H), 7.43 (d, J=2.4 Hz, 1H).

Compound 74. 4-(4-Fluoro-3-methoxyphenyl)-1-(1H-pyrazol-5-yl)piperidine

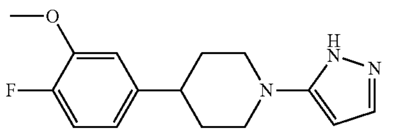 [SMILES: COc1cc(C2CCN(c3ccn[nH]3)CC2)ccc1F]

Compound was prepared from THP-protected 3-iodo-pyrazole and 4-(4-fluoro-3-methoxyphenyl)piperidine according to general procedure 6. The THP-protected intermediate was purified with silica gel column chromatography and 0-50% EtOAc in hexanes gradient. The desired product, (4-fluoro-3-methoxyphenyl)-1-(1H-pyrazol-5-yl)piperidine, was isolated as a white solid after purification of the crude THP deprotection product with 0-100% EtOAc in hexanes gradient (24% yield). $^1$H NMR (300 MHz, DMSO-$d_6$) δ 1.66-1.83 (m, 4H), 2.57-2.72 (m, 3H), 3.76 (apparent d, J=12.0 Hz, 2H), 3.84 (s, 3H), 5.72 (d, J=2.4 Hz, 1H), 6.78-6.84 (m, 1H), 7.04-7.14 (m, 2H), 7.45 (d, J=2.1 Hz, 1H), 11.79 (bs, 1H).

Compound 75. 4-(4-Fluoro-3-methoxyphenyl)-1-(1H-pyrazol-4-yl)piperidine

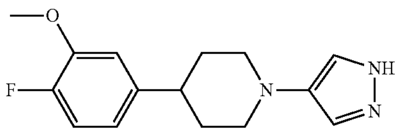 [SMILES: COc1cc(C2CCN(c3cn[nH]c3)CC2)ccc1F]

Compound was prepared from THP-protected 4-iodo-pyrazole and 4-(4-fluoro-3-methoxyphenyl)piperidine according to general procedure 6. The THP-protected intermediate was purified with silica gel column chromatography and 0-50% EtOAc in hexanes gradient. The desired product, 4-(4-fluoro-3-methoxyphenyl)-1-(1H-pyrazol-4-yl)piperidine, was isolated as a white solid after purification of the crude THP deprotection product with 0-10% MeOH in $CH_2Cl_2$ (29% yield). $^1$H NMR (300 MHz, $CDCl_3$) δ 1.90-2.02 (m, 4H), 2.53-2.63 (m, 1H), 2.66-2.75 (m, 2H), 3.47-3.52 (m, 2H), 3.89 (s, 3H), 6.73-6.79 (m, 1H), 6.84 (dd, J=8.4 Hz, 2.1 Hz, 1H), 7.01 (dd, J=11.1, 8.1 Hz, 1H), 7.31 (s, 2H).

Compound 76. 4-((3-Methoxyphenyl)thio)-1-(1H-pyrazol-4-yl)piperidine

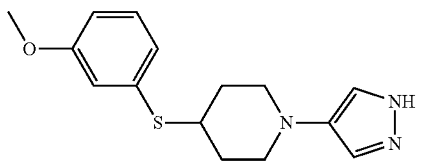

Compound was prepared from THP-protected 4-iodo-pyrazole and 4-((3-methoxyphenyl)thio)piperidine according to general procedure 6. The THP-protected intermediate was purified with silica gel column chromatography and 0-100% EtOAc in hexanes gradient. The desired product, 4-((3-methoxyphenyl)thio)-1-(1H-pyrazol-4-yl)piperidine, was isolated as a white solid after purification of the crude THP deprotection product with 0-100% EtOAc in $CH_2Cl_2$ gradient (32% yield). $^1$H NMR (600 MHz, $CDCl_3$) δ 1.76-1.85 (m, 2H), 2.05-2.10 (m, 2H), 2.69 (ddd, J=13.2, 11.4, 3.0 Hz, 2H), 3.20 (tt, J=10.2, 3.6 Hz, 1H), 3.33 (dt, J=12.2, 4.0 Hz, 2H), 3.81 (s, 3H), 6.79 (ddd, J=8.4, 3.0, 1.2 Hz, 1H), 6.97 (apparent dd, J=2.4, 1.8 Hz 1H), 7.00-7.03 (m, 1H), 7.20-7.24 (m, 3H).

Compound 77. (4-(1-(1H-Pyrazol-4-yl)piperidin-4-yl)phenyl)(pyrrolidin-1-yl)methanone

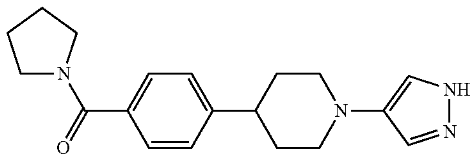 [SMILES: O=C(c1ccc(C2CCN(c3cn[nH]c3)CC2)cc1)N1CCCC1]

Compound was prepared from THP protected 4-iodo-pyrazole and (4-(piperidin-4-yl)phenyl)(pyrrolidin-1-yl)methanone according to general procedure 6. The THP-protected intermediate was purified with silica gel column chromatography and 0-100% EtOAc in hexanes gradient. The desired product, (4-(1-(1H-pyrazol-4-yl)piperidin-4-yl)phenyl)(pyrrolidin-1-yl)methanone, was isolated as a white/off-white solid after purification of the crude THP deprotection product with silica gel column and 0-12% $CH_2Cl_2$ in $CH_3OH$ gradient (8% yield). $^1$HNMR (400 MHz, $CD_3OD$) δ 7.44 (distorted d, J=8.4 Hz, 2H), 7.33 (distorted t, J=3.2 Hz, 4H), 3.55 (t, J=6.8 Hz, 2H), 3.49-3.42 (m, 4H), 2.69-2.62 (m, 3H), 1.97-1.84 (m, 8H).

Compound 78. (4-(1-(1H-Pyrazol-5-yl)piperidin-4-yl)phenyl)(pyrrolidin-1-yl)methanone

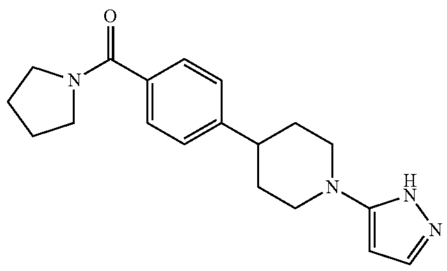 [SMILES: O=C(c1ccc(C2CCN(c3ccn[nH]3)CC2)cc1)N1CCCC1]

Compound was prepared from THP-protected 3-iodo-pyrazole and (4-(piperidin-4-yl)phenyl)(pyrrolidin-1-yl)methanone according to general procedure 6. The THP-protected intermediate was purified with silica gel column chromatography and 0-100% EtOAc in hexanes gradient. The desired product, (4-(1-(1H-pyrazol-5-yl)piperidin-4-yl)phenyl)(pyrrolidin-1-yl)methanone, was isolated as a white solid after purification of the crude THP deprotection product with silica gel column and 0-12% $CH_2Cl_2$ in $CH_3OH$ gradient (23% yield). $^1$HNMR (400 MHz, $CD_3OD$) δ 7.50-7.47 (m, 3H), 7.37 (d, J=8.0 Hz, 2H), 5.84 (bs, 1H), 3.83 (d, J=9.0 Hz, 2H), 3.60 (t, J=7.0 Hz, 2H), 3.49 (t, J=6.5 Hz, 2H), 2.84 (dt, J=11.5, 2.0 Hz, 2H), 2.75 (tt, J=11.5, 4.5 Hz, 1H), 2.02-1.98 (m, 2H), 1.94-1.86 (m, 6H).

Compound 79. 4-(4-Methoxybenzyl)-1-(1H-pyrazol-5-yl)piperidine

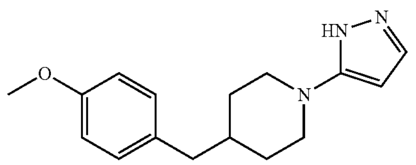 [SMILES: COc1ccc(CC2CCN(c3ccn[nH]3)CC2)cc1]

Compound was prepared from THP-protected 3-iodopyrazole and commercially available 4-(4-methoxybenzyl)piperidine according to general procedure 6. The THP-protected intermediate was purified with silica gel column chromatography and 0-100% EtOAc in hexanes gradient. The desired product, 4-(4-methoxybenzyl)-1-(1H-pyrazol-5-yl)piperidine, was isolated as a gummy colorless solid after silica gel column purification of the crude THP deprotection product with 0-100% EtOAc in $CH_2Cl_2$ gradient (10% yield). $^1$HNMR (400 MHz, $CD_3OD$) δ 7.42 (s, 1H), 7.09 (d, J=8.4 Hz, 2H), 6.84 (d, J=8.4 Hz, 2H), 5.75 (bs, 1H), 3.78 (s, 3H), 3.64 (d, J=12.0 Hz, 2H), 2.63 (t, J=11.2.0 Hz, 2H), 2.52 (d, J=6.8 Hz, 2H), 1.72-1.61 (m, 3H), 1.40-1.31 (m, 2H).

Compound 80. 4-((4-Methoxyphenyl)thio)-1-(1H-pyrazol-4-yl)piperidine

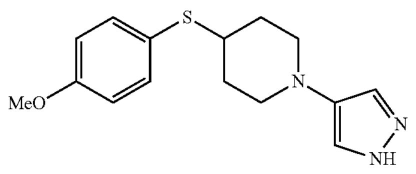 [SMILES: COc1ccc(SC2CCN(c3cn[nH]c3)CC2)cc1]

Compound was prepared from THP-protected 4-iodopyrazole and 4-((4-methoxyphenyl)thio)piperidine according to general procedure 6. The THP-protected intermediate was purified with silica gel column chromatography and 0-100% EtOAc in hexanes gradient. The desired product, 4-((4-methoxyphenyl)thio)-1-(1H-pyrazol-4-yl)piperidine, was isolated as a white/off-white solid after silica gel column purification of the crude THP deprotection product with 0-100% EtOAc in $CH_2Cl_2$ gradient (15% yield). $^1$HNMR (600 MHz, DMSO-$d_6$) δ 12.25 (s, 1-NH), 7.41-7.39 (m, 2H), 7.23-7.19 (m, 2H), 6.94 (d, J=9.0 Hz, 2H), 3.76 (s, 3H), 3.27-3.23 (m, 2H), 3.08 (tt, J=10.8, 4.2 Hz, 1H), 2.54-2.53 (m, 2H), 1.89-1.86 (m, 2H), 1.58-1.52 (m, 2H).

Compound 81. (4-(1-(1H-Pyrazol-4-yl)piperidin-4-yl)-3-fluorophenyl)(pyrrolidin-1-yl)methanone

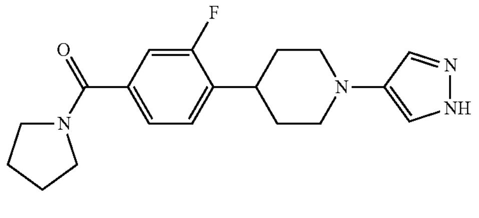 [SMILES: O=C(c1ccc(C2CCN(c3cn[nH]c3)CC2)c(F)c1)N1CCCC1]

Compound was prepared from THP-protected 4-iodopyrazole and (3-fluoro-4-(piperidin-4-yl)phenyl)(pyrrolidin-1-yl)methanone according to general procedure 6. The THP-protected intermediate was purified with silica gel column chromatography and 0-100% EtOAc in hexanes gradient. The desired product, (4-(1-(1H-pyrazol-4-yl)piperidin-4-yl)-3-fluorophenyl)(pyrrolidin-1-yl)methanone, was isolated as a white/off-white solid after purification of the crude THP deprotection product with silica gel column and 0-15% $CH_2Cl_2$ in MeOH gradient (10% yield). $^1$HNMR (500 MHz, DMSO-$d_6$) δ 12.28 (s, 1H), 7.43 (t, J=7.5 Hz, 1H), 7.34-7.25 (m, 4H), 3.47-3.39 (m, 6H), 2.90 (tt, J=11.5, 3.5 Hz, 1H), 2.55 (td, J=12.0, 2.5 Hz, 2H), 1.87-1.78 (m, 8H).

Compound 82. ((4-(1-(1H-pyrazol-5-yl)piperidin-4-yl)-3-fluorophenyl)(pyrrolidin-1-yl)methanone

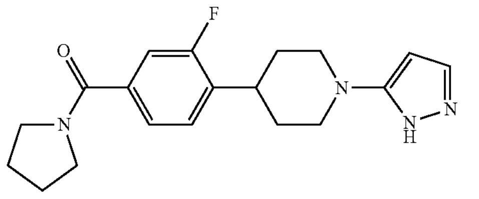 [SMILES: O=C(c1ccc(C2CCN(c3ccn[nH]3)CC2)c(F)c1)N1CCCC1]

Compound was prepared from THP-protected 3-iodopyrazole and (3-fluoro-4-(piperidin-4-yl)phenyl)(pyrrolidin-1-yl)methanone according to general procedure 6. The THP-protected intermediate was purified with silica gel column chromatography and 0-100% EtOAc in hexanes gradient. The desired product, (4-(1-(1H-pyrazol-3-yl)piperidin-4-yl)-3-fluorophenyl)(pyrrolidin-1-yl)methanone, was isolated as a white/off-white solid after silica gel column purification of the crude THP deprotection product with 0-15% $CH_2Cl_2$ in MeOH gradient (7% yield). $^1$HNMR (600 MHz, $CD_3OD$) δ 7.48-7.42 (m, 2H), 7.34 (dd, J=7.8 Hz, 1.2 Hz, 1H), 7.27 (d, J=10.8 Hz, 2.4 Hz, 1H), 5.86 (bs, 1H), 3.85 (bs, 2H), 3.60 (t, J=7.2 Hz, 2H), 3.50 (t, J=6.6 Hz, 2H), 3.10-3.05 (m, 1H), 2.86 (t, J=9.6 Hz, 2H), 2.03-1.99 (m, 2H), 1.96-1.91 (m, 6H).

Compound 83. 1-(4-(1-(1H-Pyrazol-4-yl)piperidin-4-yl)benzyl)pyrrolidin-2-one

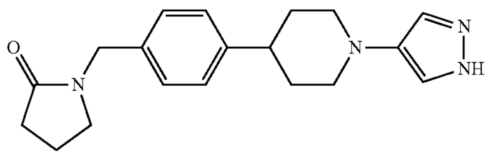 [SMILES: O=C1CCCN1Cc1ccc(C2CCN(c3cn[nH]c3)CC2)cc1]

Compound was prepared from THP-protected 4-iodopyrazole and 1-(4-(piperidin-4-yl)benzyl)pyrrolidin-2-one according to general procedure 6. The THP-protected intermediate was purified with silica gel column chromatography and 0-100% EtOAc in hexanes gradient. The desired product, 1-(4-(1-(1H-pyrazol-4-yl)piperidin-4-yl)benzyl)pyrrolidin-2-one, was isolated as a white/off-white solid after silica gel column purification of the crude THP deprotection product using 0-15% $CH_2Cl_2$ in MeOH gradient (25% yield): $^1$HNMR (600 MHz, $CD_3OD$) δ 7.39 (s, 2H), 7.28 (d, J=8.4 Hz, 2H), 7.22 (d, J=8.4 Hz, 2H), 4.44 (s, 2H), 3.54-3.52 (m, 2H), 3.37-3.34 (m, 2H), 2.72-2.65 (m, 3H), 2.46 (t, J=7.8 Hz, 2H), 2.06-2.01 (m, 2H), 1.93-1.88 (m, 4H).

Compound 84. 1-(4-(1-(1H-Pyrazol-5-yl)piperidin-4-yl)benzyl)pyrrolidin-2-one

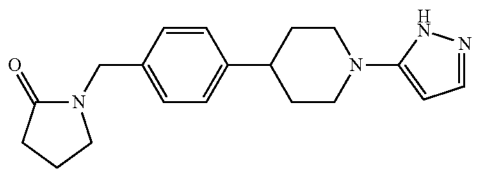 [SMILES: O=C1CCCN1Cc1ccc(C2CCN(c3ccn[nH]3)CC2)cc1]

Compound was prepared from THP-protected 3-iodopyrazole and 1-(4-(piperidin-4-yl)benzyl)pyrrolidin-2-one according to general procedure 6. The THP-protected intermediate was purified with silica gel column chromatography and 0-100% EtOAc in hexanes gradient. The desired product, 1-(4-(1-(1H-pyrazol-5-yl)piperidin-4-yl)benzyl)pyrrolidin-2-one, was isolated as a white/off-white solid after silica gel column purification of the crude THP deprotection product using 0-15% $CH_2Cl_2$ in MeOH gradient (26% yield): $^1$HNMR (500 MHz, $CD_3OD$) δ 7.46 (s, 1H), 7.26 (d, J=8.0 Hz, 2H), 7.21 (d, J=8.5 Hz, 2H), 5.82 (bs, 1H), 4.44 (s, 2H), 3.81 (d, J=11.0 Hz, 2H), 3.36-3.35 (m, 2H), 2.83 (td, J=12.0 Hz, 3.0 Hz, 2H), 2.71-2.65 (m, 1H), 2.45 (t, J=8.0 Hz, 2H), 2.06-2.00 (m, 2H), 1.90-1.81 (m, 4H).

Compound 85. 1-(1H-Pyrazol-4-yl)-4-(4-(pyrrolidin-1-ylsulfonyl)phenyl)piperidine

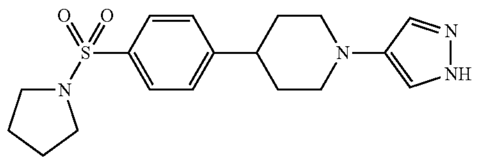 [SMILES: O=S(=O)(c1ccc(C2CCN(c3cn[nH]c3)CC2)cc1)N1CCCC1]

Compound was prepared from THP-protected 4-iodopyrazole and 4-(4-(pyrrolidin-1-ylsulfonyl)phenyl)piperidine according to general procedure 6. The THP-protected intermediate was purified with silica gel column chromatography and 0-100% EtOAc in hexanes gradient. The desired product, 1-(1H-pyrazol-4-yl)-4-(4-(pyrrolidin-1-ylsulfonyl)phenyl)piperidine, was isolated as a white/off-white solid after silica gel column purification of the crude THP deprotection product using 0-15% $CH_2Cl_2$ in MeOH gradient (8% yield): $^1$HNMR (600 MHz, $CD_3OD$) δ 7.81-7.79 (m, 2H), 7.54 (d, J=8.4 Hz, 2H), 7.39 (s, 2H), 3.56-3.54 (m, 2H), 3.26-3.23 (m, 4H), 2.82-2.78 (m, 1H), 2.73 (td, J=11.5, 3.6 Hz, 2H), 1.98-1.92 (m, 4H), 1.78-1.75 (m, 4H).

Compound 86. 2-(1-(1H-pyrazol-4-yl)piperidin-4-yl)-4-(trifluoromethyl)pyridine

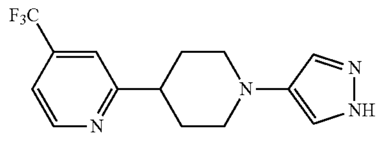

Compound was prepared from THP-protected 4-iodopyrazole and 2-(piperidin-4-yl)-4-(trifluoromethyl)pyridine according to general procedure 6. The THP-protected intermediate was purified with silica gel column chromatography and 0-100% EtOAc in hexanes gradient. The desired product, 2-(1-(1H-pyrazol-4-yl)piperidin-4-yl)-4-(trifluoromethyl)pyridine, was isolated after purification of the crude THP deprotection product with 0-15% $CH_2Cl_2$ in MeOH gradient as a white/off-white solid (16% yield): $^1$HNMR (600 MHz, DMSO-$d_6$) δ 12.28 (s, 1-NH), 8.81 (d, J=5.4 Hz, 1H), 7.70 (s, 1H), 7.61 (d, J=5.4 Hz, 1H), 7.30-7.26 (m, 2H), 3.46-3.42 (m, 2H), 2.95-2.90 (m, 1H), 2.59-2.54 (m, 2H), 1.94-1.90 (m, 4H).

Compound 87. 2-(1-(1H-Pyrazol-5-yl)piperidin-4-yl)-4-(trifluoromethyl)pyridine

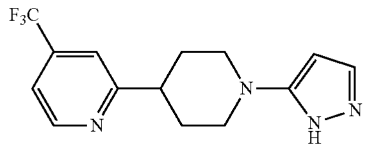 [SMILES: FC(F)(F)c1ccnc(C2CCN(c3ccn[nH]3)CC2)c1]

Compound was prepared from THP-protected 3-iodopyrazole and 2-(piperidin-4-yl)-4-(trifluoromethyl)pyridine according to general procedure 6. The THP-protected intermediate was purified with silica gel column chromatography and 0-100% EtOAc in hexanes gradient. The desired product, 2-(1-(1H-pyrazol-5-yl)piperidin-4-yl)-4-(trifluoromethyl)pyridine, was isolated after purification of the crude THP deprotection product with 0-15% $CH_2Cl_2$ in MeOH gradient as a white/off-white solid (22% yield): $^1$HNMR (600 MHz, DMSO-$d_6$) δ 11.77 (s, 1H), 8.80 (d, J=4.8 Hz, 1H), 7.69 (s, 1H), 7.60 (dd, J=4.8, 1.2 Hz, 1H), 7.49 (s, 1H), 5.75 (bs, 1H), 3.78 (s, 2H), 2.97 (tt, J=11.4, 4.2 Hz, 1H), 2.72 (t, J=10.8 Hz, 2H), 1.91-1.83 (m, 4H).

Compound 88. 2-((1-(1H-Pyrazol-4-yl)piperidin-4-yl)thio)pyrimidine

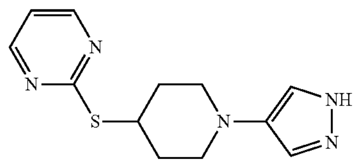 [SMILES: c1cnc(SC2CCN(c3cn[nH]c3)CC2)nc1]

Compound was prepared from THP-protected 4-iodopyrazole and 2-(piperidin-4-ylthio)pyrimidine according to general procedure 6. The THP-protected intermediate was purified with silica gel column chromatography and 0-100% EtOAc in hexanes. The desired product, 2-((1-(1H-pyrazol-4-yl)piperidin-4-yl)thio)pyrimidine, was isolated as off-white solid after silica gel column purification of the THP deprotection product with 0-10% MeOH in $CH_2Cl_2$ (28% yield). $^1$H NMR (500 MHz, DMSO-d6) δ 1.71-1.80 (m, 2H), 2.10-2.14 (m, 2H), 2.67 (m, 2H), 3.25 (dt, J=12.0, 4.0 Hz, 2H), 3.77-3.84 (m, 1H), 7.21 (t, J=5.0 Hz, 1H), 7.25 (bs, 2H), 8.64 (d, J=5.0 Hz, 2H), 12.28 (bs, 1H).

Compound 89. 4-(4-((methylsulfonyl)methyl)phenyl)-1-(1H-pyrazol-4-yl)piperidine

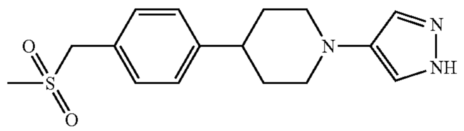 [SMILES: CS(=O)(=O)Cc1ccc(C2CCN(c3cn[nH]c3)CC2)cc1]

Compound was prepared from THP-protected 4-iodopyrazole and 4-(4-((methylsulfonyl)methyl)phenyl)piperidine according to general procedure 6. The THP-protected intermediate was purified with silica gel column chromatography and 0-100% EtOAc in hexanes gradient. The desired product, 4-(4-((methylsulfonyl)methyl)phenyl)-1-(1H-pyrazol-4-yl)piperidine, was isolated after purification of the crude THP deprotection product with 0-100% EtOAc in $CH_2Cl_2$ gradient as a white/off-white solid (12% yield): $^1$HNMR (400 MHz, DMSO-$d_6$) δ 12.27 (s, 1H), 7.35-7.27 (m, 6H), 4.44 (s, 2H), 3.45-3.42 (m, 2H), 2.90 (s, 3H), 2.64-2.55 (m, 3H), 1.82-1.74 (m, 4H).

Compound 90. 4-(3-chlorobenzyl)-1-(1H-pyrazol-4-yl)piperidine

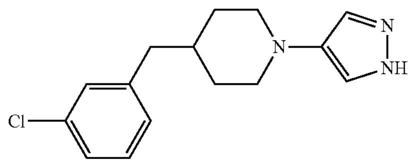 [SMILES: Clc1cccc(CC2CCN(c3cn[nH]c3)CC2)c1]

Compound was prepared from THP-protected 4-iodopyrazole and 4-(3-chlorobenzyl)piperidine according to general procedure 6. The THP-protected intermediate was purified with silica gel column chromatography and 0-100% EtOAc in hexanes gradient. The desired product, 4-(3-chlorobenzyl)-1-(1H-pyrazol-4-yl)piperidine, was isolated after purification of the crude THP deprotection product with 0-100% EtOAc in $CH_2Cl_2$ gradient to afford the product as a white/off-white solid (17% yield). $^1$HNMR (600 MHz, DMSO-$d_6$) δ 12.21 (s, 1H), 7.34-7.31 (m, 1H), 7.28-7.25 (m, 2H), 7.20-7.16 (m, 3H), 3.29-3.27 (m, 2H), 2.54 (d, J=7.2 Hz, 2H), 2.37-2.34 (m, 2H), 1.59-1.57 (m, 3H), 1.34-1.27 (m, 2H).

Compound 91. 4-(3-Chlorobenzyl)-1-(1H-pyrazol-5-yl)piperidine

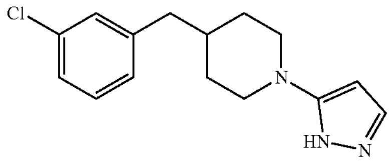 [SMILES: Clc1cccc(CC2CCN(c3ccn[nH]3)CC2)c1]

Compound was prepared from THP-protected 3-iodopyrazole and 4-(3-chlorobenzyl)piperidine according to general procedure 6. The THP-protected intermediate was purified with silica gel column chromatography and 0-100% EtOAc in hexanes gradient. The desired product, 4-(3-chlorobenzyl)-1-(1H-pyrazol-5-yl)piperidine, was isolated after purification of the crude THP deprotection product with 0-100% EtOAc in $CH_2Cl_2$ gradient as a white solid (15% yield). $^1$HNMR (600 MHz, DMSO-$d_6$) δ 12.21 (s, 1H), 7.34-7.31 (m, 1H), 7.28-7.25 (m, 2H), 7.20-7.16 (m, 3H), 3.29-3.27 (m, 2H), 2.54 (d, J=7.2 Hz, 2H), 2.37-2.34 (m, 2H), 1.59-1.57 (m, 3H), 1.34-1.27 (m, 2H).

Compound 92. 4-((2-Fluorophenyl)thio)-1-(1H-pyrazol-4-yl)piperidine

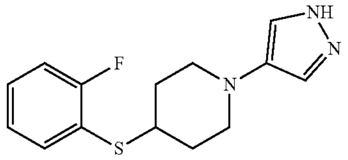 [SMILES: Fc1ccccc1SC1CCN(c2cn[nH]c2)CC1]

Compound was prepared from THP-protected 4-iodopyrazole and 4-((2-fluorophenyl)thio)piperidine according to general procedure 6. The THP-protected intermediate was purified with silica gel column chromatography and 0-100% EtOAc in hexanes. The desired compound, 4-((2-fluorophenyl)thio)-1-(1H-pyrazol-4-yl)piperidine was isolated as an off-white solid after purification of the THP deprotection product with 0-9% MeOH in $CH_2Cl_2$ (18% yield). $^1$H NMR (500 MHz, DMSO-d6) δ 1.55-1.64 (m, 2H), 1.90-1.94 (m, 2H), 2.58 (apparent td, J=13.0, 2.5 Hz, 2H), 3.25 (apparent dt, J=12.5, 3.0 Hz, 2H), 7.18-7.29 (m, 4H), 7.32-7.39 (m, 1H), 7.54 (td, J=7.5, 1.5 Hz, 1H), 12.25 (bs, 1H).

Compound 93. 4-(4-Chlorobenzyl)-1-(1H-pyrazol-4-yl)piperidine

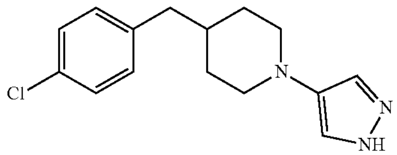 [SMILES: Clc1ccc(CC2CCN(c3cn[nH]c3)CC2)cc1]

Compound was prepared from THP-protected 4-iodopyrazole and 4-(4-chlorobenzyl)piperidine according to general procedure 6. The THP-protected intermediate was purified with silica gel column chromatography and 0-100%

EtOAc in hexanes gradient. The desired product, 4-(4-chlorobenzyl)-1-(1H-pyrazol-4-yl)piperidine, was isolated after purification of the crude THP deprotection product with 0-100% EtOAc in $CH_2Cl_2$ gradient as a white solid (20% yield): $^1$HNMR (400 MHz, DMSO-$d_6$) δ 12.22 (s, 1H), 7.33 (d, J=8.4 Hz, 2H), 7.22-7.19 (m, 4H), 3.28-3.25 (m, 2H), 2.53-2.52 (m, 2H), 2.34 (t, J=10.4 Hz, 2H), 1.59-1.52 (m, 3H), 1.33-1.24 (m, 2H).

Compound 94. 4-(3-Methylbenzyl)-1-(1H-pyrazol-4-yl)piperidine

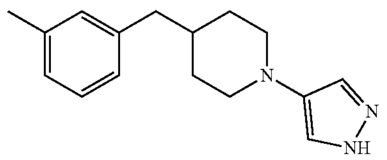 [SMILES: Cc1cccc(CC2CCN(c3cn[nH]c3)CC2)c1]

Compound was prepared from THP-protected 4-iodo-pyrazole and 4-(3-methylbenzyl)piperidine according to general procedure 6. The THP-protected intermediate was purified with silica gel column chromatography and 0-100% EtOAc in hexanes gradient. The desired product, 4-(3-methylbenzyl)-1-(1H-pyrazol-4-yl)piperidine, was isolated as a white solid after purification of the crude THP deprotection product with 0-100% EtOAc in $CH_2Cl_2$ gradient (29% yield). $^1$HNMR (500 MHz, DMSO-$d_6$) δ 12.21 (s, 1H), 7.19-7.15 (m, 3H), 7.00-6.95 (m, 3H), 3.28-3.25 (m, 2H), 2.49-2.48 (m, 2H), 2.34 (td, J=11.5, 2.0 Hz, 2H), 2.28 (s, 3H), 1.61-1.53 (m, 3H), 1.33-1.26 (m, 2H).

Compound 95. 4 3-(1-(1H-Pyrazol-4-yl)piperidin-4-yl)-5-(trifluoromethyl)pyridine

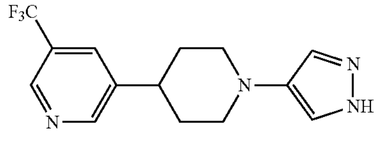 [SMILES: FC(F)(F)c1cncc(C2CCN(c3cn[nH]c3)CC2)c1]

Compound was prepared from THP-protected 4-iodo-pyrazole and 3-(piperidin-4-yl)-5-(trifluoromethyl)pyridine according to general procedure 6. The THP-protected intermediate was purified with silica gel column chromatography and 0-100% EtOAc in hexanes gradient. The desired product, 3-(1-(1H-pyrazol-4-yl)piperidin-4-yl)-5-(trifluoromethyl) pyridine, was isolated as a white solid after purification of the crude THP deprotection product with 0-100% EtOAc in $CH_2Cl_2$ gradient (24% yield). $^1$HNMR (300 MHz, DMSO-d6) δ 12.29 (s, 1-NH), 8.84 (dd, J=8.7, 1.8 Hz, 2H), 8.12 (s, 1H), 7.30-7.26 (m, 2H), 3.47-3.43 (m, 2H), 2.86-2.76 (m, 1H), 2.58-2.53 (m, 2H), 1.95-1.85 (m, 4H).

Compound 96. 1-(1H-Pyrazol-5-yl)-4-(4-(pyrrolidin-1-ylsulfonyl)phenyl)piperidine

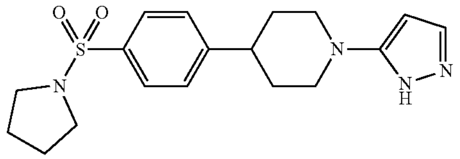 [SMILES: O=S(=O)(c1ccc(C2CCN(c3ccn[nH]3)CC2)cc1)N1CCCC1]

Compound was prepared from THP-protected 3-iodo-pyrazole and 4-(4-(pyrrolidin-1-ylsulfonyl)phenyl)piperidine according to general procedure 6. The THP-protected intermediate was purified with silica gel column chromatography and 0-100% EtOAc in hexanes gradient. The desired product, 1-(1H-pyrazol-5-yl)-4-(4-(pyrrolidin-1-ylsulfonyl)phenyl)piperidine, was isolated as a white solid after purification of the crude THP deprotection product with 0-100% EtOAc in $CH_2Cl_2$ gradient to afford the product as a white solid (10% yield): $^1$HNMR (300 MHz, $CDCl_3$) δ 7.36-7.29 (m, 2H), 7.68 (d, J=8.4 Hz, 3H), 5.71 (d, J=2.4 Hz, 1H), 3.83-3.79 (m, 2H), 3.19-3.14 (m, 4H), 2.80 (td, J=11.7 Hz, 3.6 Hz, 2H), 2.72-2.61 (m, 1H), 1.89-1.78 (m, 4H), 1.71-1.66 (m, 4H).

Compound 97. 4-(3-Methylbenzyl)-1-(1H-pyrazol-5-yl)piperidine

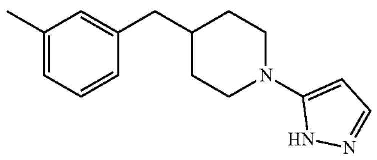 [SMILES: Cc1cccc(CC2CCN(c3ccn[nH]3)CC2)c1]

Compound was prepared from THP-protected 3-iodo-pyrazole and 4-(3-methylbenzyl)piperidine according to general procedure 6. The THP-protected intermediate was purified with silica gel column chromatography and 0-100% EtOAc in hexanes gradient. The desired product 4-(3-methylbenzyl)-1-(1H-pyrazol-5-yl)piperidine, was isolated after purification of the crude THP deprotection product with 0-100% EtOAc in $CH_2Cl_2$ gradient as a white solid (12% yield): $^1$HNMR (300 MHz, DMSO-$d_6$) δ 11.73 (s, 1H), 7.41 (s, 1H), 7.19-7.14 (m, 1H), 7.00-6.95 (m, 3H), 5.64 (br, 1H), 3.61-3.57 (m, 2H), 2.54-2.47 (m, 4H), 2.28 (s, 3H), 1.61-1.57 (m, 3H), 1.30-1.18 (m, 2H).

Compound 98. 4-((1-(1H-Pyrazol-4-yl)piperidin-4-yl)methyl)-2-methoxypyridine

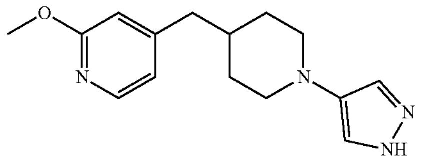 [SMILES: COc1cc(CC2CCN(c3cn[nH]c3)CC2)ccn1]

Compound was prepared from THP-protected 4-iodo-pyrazole and 2-methoxy-4-(piperidin-4-ylmethyl)pyridine according to general procedure 6. The THP-protected intermediate was purified with silica gel column chromatography and 0-100% EtOAc in hexanes gradient. The desired product, 4-((1-(1H-pyrazol-4-yl)piperidin-4-yl)methyl)-2-methoxypyridine, was isolated as a transparent liquid after the purification of the crude THP deprotection product with 0-100% EtOAc in $CH_2Cl_2$ gradient to afford the product as a white solid (36% yield): $^1$HNMR (300 MHz, $CDCl_3$) δ 8.04 (d, J=5.4 Hz, 1H), 7.31 (s, 2H), 6.67 (dd, J=5.1 Hz, 1.2 Hz, 1H), 6.53 (s, 1H), 3.91 (s, 3H), 3.38-3.34 (m, 2H), 2.61-2.51 (m, 4H), 1.75-1.55 (m, 5H).

Compound 99. 4-((1-(1H-Pyrazol-5-yl)piperidin-4-yl)methyl)-2-methoxypyridine

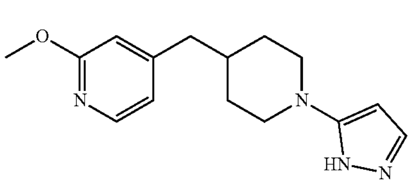 [SMILES: COc1cc(CC2CCN(c3ccn[nH]3)CC2)ccn1]

Compound was prepared from THP-protected 3-iodopyrazole and 2-methoxy-4-(piperidin-4-ylmethyl)pyridine according to general procedure 6. The THP-protected intermediate was purified with silica gel column chromatography and 0-100% EtOAc in hexanes gradient. The desired product, 4-((1-(1H-pyrazol-5-yl)piperidin-4-yl)methyl)-2-methoxypyridine, was isolated as a white solid after the purification of the crude THP deprotection product with 0-100% EtOAc in $CH_2Cl_2$ gradient (10% yield). $^1$HNMR (300 MHz, $CDCl_3$) δ 8.04 (d, J=5.4 Hz, 1H), 7.36 (d, J=2.4 Hz, 1H), 6.68 (dd, J=5.1 Hz, 1.2 Hz, 1H), 6.53 (s, 1H), 5.71 (d, J=2.4 Hz, 1H), 3.91 (s, 3H), 3.70-3.66 (m, 2H), 2.66 (td, J=12.3 Hz, 2.1 Hz, 2H), 2.50 (d, J=6.6 Hz, 2H), 1.74-1.63 (m, 3H), 1.44-1.30 (m, 2H).

Compound 100. 1-(4-(1-(1H-Pyrazol-4-yl)piperidin-4-yl)phenyl)pyrrolidin-2-one

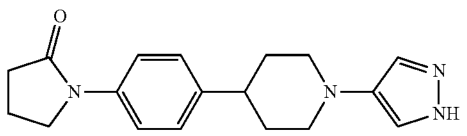 [SMILES: O=C1CCCN1c1ccc(C2CCN(c3cn[nH]c3)CC2)cc1]

Compound was prepared from THP-protected 4-iodopyrazole and 1-(4-(piperidin-4-yl)phenyl)pyrrolidin-2-one according to general procedure 6. The THP-protected intermediate was purified with silica gel column chromatography and 0-100% EtOAc in hexanes gradient. The desired product 1-(4-(1-(1H-pyrazol-4-yl)piperidin-4-yl)phenyl)pyrrolidin-2-one, was isolated as a white solid after the purification of the crude THP deprotection product with 0-15% MeOH in $CH_2Cl_2$ gradient (15% yield): $^1$HNMR (600 MHz, DMSO-$d_6$) δ 12.26 (s, 1-NH), 7.56 (d, J=9.0 Hz, 2H), 7.26 (d, J=8.4 Hz, 4H), 3.81 (t, J=7.2 Hz, 2H), 3.43-3.41 (m, 2H), 3.30-3.28 (m, 1H), 2.58-2.53 (m, 2H), 2.48-2.47 (m, 2H), 2.07-2.02 (m, 2H), 1.78-1.72 (m, 4H).

Compound 101. 1-(4-(1-(1H-Pyrazol-5-yl)piperidin-4-yl)phenyl)pyrrolidin-2-one

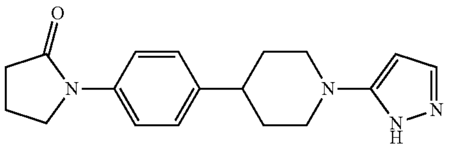 [SMILES: O=C1CCCN1c1ccc(C2CCN(c3ccn[nH]3)CC2)cc1]

Compound was prepared from THP-protected 3-iodopyrazole and 1-(4-(piperidin-4-yl)phenyl)pyrrolidin-2-one according to general procedure 6. The THP-protected intermediate was purified with silica gel column chromatography and 0-100% EtOAc in hexanes gradient. The desired product, 1-(4-(1-(1H-pyrazol-5-yl)piperidin-4-yl)phenyl)pyrrolidin-2-one, was isolated after purification of the crude THP deprotection product with 0-15% MeOH in $CH_2Cl_2$ gradient as a white solid (7% yield). $^1$HNMR (300 MHz, DMSO-$d_6$) δ 11.78 (s, 1-NH), 7.56 (d, J=8.4 Hz, 2H), 7.45 (d, J=1.8 Hz, 1H), 7.26 (d, J=8.7 Hz, 2H), 5.71 (d, J=2.1 Hz, 1H), 3.83-3.73 (m, 4H), 2.72-2.57 (m, 3H), 2.48-2.45 (m, 2H), 2.10-2.00 (m, 2H), 1.81-1.68 (m, 4H).

Compound 102. 5-(1-(1H-Pyrazol-4-yl)piperidin-4-yl)-2,3-dihydrobenzo[b]thiophene 1,1-dioxide

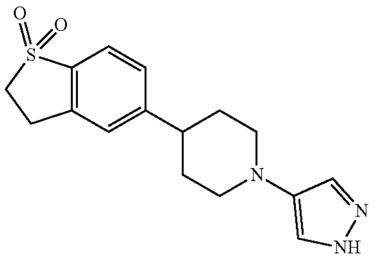 [SMILES: O=S1(=O)CCc2cc(C3CCN(c4cn[nH]c4)CC3)ccc21]

Compound was prepared from THP-protected 4-iodopyrazole and 5-(piperidin-4-yl)-2,3-dihydrobenzo[b]thiophene 1,1-dioxide according to general procedure 6. The THP-protected intermediate was purified with silica gel column chromatography and 0-100% EtOAc in hexanes. The desired product, 1-(4-(1-(1H-pyrazol-3-yl)piperidin-4-yl)phenyl)pyrrolidin-2-one, was isolated after the purification of the crude THP deprotection product with 0-15% MeOH in gradient t as a white solid (13% yield): $^1$HNMR (300 MHz, $CDCl_3$) δ 7.66 (d, J=8.1 Hz, 1H), 7.40 (s, 2H), 7.32 (d, J=8.4 Hz, 1H), 7.24 (s, 1H), 3.55-3.52 (m, 2H), 3.50-3.44 (m, 2H), 3.38-3.32 (m, 2H), 2.83-2.67 (m, 3H), 2.10-2.06 (m, 2H), 1.94-1.90 (m, 2H).

Compound 103. 3-(1-(1H-Pyrazol-5-yl)piperidin-4-yl)-5-(trifluoromethyl)pyridine

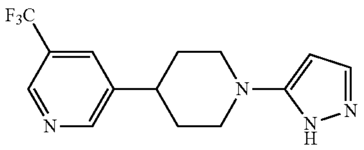 [SMILES: FC(F)(F)c1cncc(C2CCN(c3ccn[nH]3)CC2)c1]

Compound was prepared from THP-protected 3-iodo-pyrazole and 3-(piperidin-4-yl)-5-(trifluoromethyl)pyridine according to general procedure 6. The THP-protected intermediate was purified with silica gel column chromatography and 0-100% EtOAc in hexanes gradient. The desired product, 3-(1-(1H-pyrazol-5-yl)piperidin-4-yl)-5-(trifluoromethyl)pyridine, was isolated after the purification of the crude THP deprotection product using 0-15% MeOH in $CH_2Cl_2$ gradient as a white solid (36% yield). $^1$HNMR (300 MHz, DMSO-$d_6$) δ 11.79 (s, 1-NH), 8.83 (dd, J=6.0 Hz, 1.2 Hz, 2H), 8.10 (s, 1H), 7.47 (s, 1H), 5.74 (s, 1H), 3.80-3.76 (s, 2H), 2.91-2.80 (m, 1H), 2.69 (td, J=11.7 Hz, 3.3 Hz, 2H), 1.88-1.79 (m, 4H).

Compound 104. 4-(1-(1H-Pyrazol-4-yl)piperidin-4-yl)-N-(1,1,1-trifluoropropan-2-yl)aniline

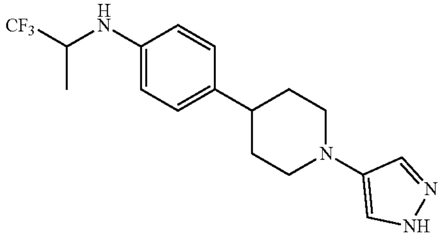 [SMILES: CC(Nc1ccc(C2CCN(c3cn[nH]c3)CC2)cc1)C(F)(F)F]

Compound was prepared from THP-protected 4-iodo-pyrazole and 4-(piperidin-4-yl)-N-(1,1,1-trifluoropropan-2-yl)aniline according to general procedure 6. The THP-protected intermediate was purified with silica gel column chromatography and 0-100% EtOAc in hexanes gradient. The desired product 4-(1-(1H-pyrazol-4-yl)piperidin-4-yl)-N-(1,1,1-trifluoropropan-2-yl)aniline, was isolated after the purification of the crude THP deprotection product using 0-15% MeOH in $CH_2Cl_2$ gradient as a white solid (8% yield): $^1$HNMR (300 MHz, DMSO-$d_6$) δ 12.25 (s, 1-NH), 7.25 (s, 2H), 6.99 (d, J=8.4 Hz, 2H), 6.66 (d, J=8.4 Hz, 2H), 5.76 (d, J=9.0 Hz, 1H), 4.29-4.19 (m, 1H), 3.42-3.38 (m, 2H), 2.48-2.38 (m, 3H), 1.74-1.62 (m, 4H), 1.28 (d, J=6.9 Hz, 3H).

Compound 105. 4-(1-(1H-pyrazol-4-yl)piperidin-4-yl)aniline

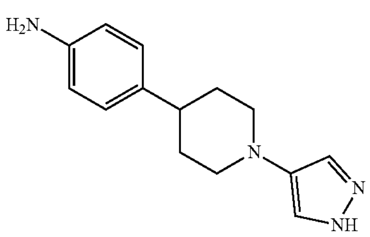

Compound was prepared from THP-protected 4-iodo-pyrazole and commercially available 4-(4-nitrophenyl)piperidine according to general procedure 6. The THP-protected intermediate was purified with silica gel column chromatography and 0-100% EtOAc in hexanes gradient. This intermediate was then hydrogenated at atmospheric pressure using 10% Pd/C (0.1 eq) in ethanol. When starting material deemed consumed by TLC the catalyst was filtered off and washed with 10% MeOH in $CH_2Cl_2$. Combined organic layer was evaporated to afford the crude reduced product that was treated with 4N HCl as described in general procedure 6. The desired product 4-(1-(1H-pyrazol-4-yl)piperidin-4-yl)aniline, was isolated as a white solid after purification of the THP-deprotection product with silica gel column and 0-100% EtOAc in hexanes gradient (10% yield). $^1$HNMR (600 MHz, DMSO-$d_6$) δ 12.22 (s, 1-NH), 7.24 (s, 2H), 6.90 (d, J=8.4 Hz, 2H), 6.50 (d, J=8.4 Hz, 2H), 4.89 (s, 2H), 3.40-3.38 (m, 2H), 2.48-2.46 (m, 2H), 2.37 (tt, J=11.4, 4.2 Hz, 1H), 1.73-1.66 (m, 4H).

Compound 106. 5-(1-(1H-Pyrazol-5-yl)piperidin-4-yl)-2,3-dihydrobenzo[b]thiophene 1,1-dioxide

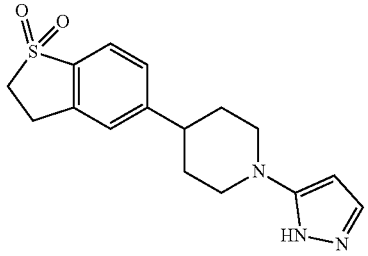 [SMILES: O=S1(=O)CCc2cc(C3CCN(c4ccn[nH]4)CC3)ccc21]

Compound was prepared from THP-protected 3-iodo-pyrazole and 5-(piperidin-4-yl)-2,3-dihydrobenzo[b]thiophene 1,1-dioxide according to general procedure 6. The THP-protected intermediate was purified with silica gel column chromatography and 0-100% EtOAc in hexanes gradient. The desired product 5-(1-(1H-pyrazol-5-yl)piperidin-4-yl)-2,3-dihydrobenzo[b]thiophene 1,1-dioxide, was isolated as a white solid after silica gel column purification of the crude THP deprotection product using 0-15% MeOH in $CH_2Cl_2$ gradient (8% yield). $^1$HNMR (300 MHz, DMSO-$d_6$) δ 11.79 (s, 1-NH), 7.65 (d, J=8.4 Hz, 1H), 7.44-7.42 (m, 3H), 5.73 (s, 1H), 3.79-3.75 (m, 2H), 3.57 (t, J=6.6 Hz, 2H), 3.32 (d, J=6.6 Hz, 2H), 2.77-2.66 (m, 3H), 1.84-1.69 (m, 4H).

Compound 107. 1-(4-((1-(1H-Pyrazol-4-yl)piperidin-4-yl)methyl)phenyl)pyrrolidin-2-one

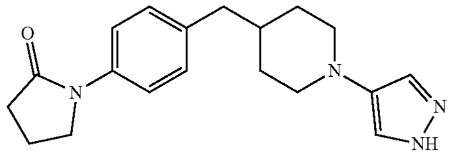 [SMILES: O=C1CCCN1c1ccc(CC2CCN(c3cn[nH]c3)CC2)cc1]

Compound was prepared from THP-protected 4-iodo-pyrazole and 1-(4-(piperidin-4-ylmethyl)phenyl)pyrrolidin-2-one according to general procedure 6. The THP-protected intermediate was purified with silica gel column chromatography and 0-100% EtOAc in hexanes gradient. The desired product, 1-(4-((1-(1H-pyrazol-4-yl)piperidin-4-yl)methyl)phenyl)pyrrolidin-2-one, was isolated as a white solid after silica gel column purification of the crude THP deprotection product using 0-15% MeOH in $CH_2Cl_2$ gradient (5% yield). $^1$HNMR (300 MHz, DMSO-$d_6$) δ 12.21 (s, 1-NH), 7.55 (d, J=8.7 Hz, 2H), 7.17 (d, J=8.4 Hz, 4H), 3.81 (t, J=6.9 Hz, 2H), 3.29-3.25 (m, 2H), 2.49-2.45 (m, 4H), 2.33 (dt, J=11.7 Hz, 2.1 Hz, 2H), 2.10-2.00 (m, 2H), 1.61-1.51 (m, 3H), 1.34-1.23 (m, 2H).

Compound 108. 5-(1-(1H-Pyrazol-4-yl)piperidin-4-yl)-1,3-dihydrobenzo[c]thiophene 2,2-dioxide

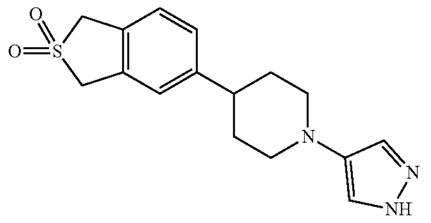 [SMILES: O=S1(=O)Cc2ccc(C3CCN(c4cn[nH]c4)CC3)cc2C1]

Compound was prepared from THP-protected 4-iodo-pyrazole and 5-(piperidin-4-yl)-1,3-dihydrobenzo[c]thiophene 2,2-dioxide according to general procedure 6. The THP-protected intermediate was purified with silica gel column chromatography and 0-100% EtOAc in hexanes gradient. The desired product, 5-(1-(1H-pyrazol-4-yl)piperidin-4-yl)-1,3-dihydrobenzo[c]thiophene 2,2-dioxide, was isolated as a white solid after silica gel column purification of the crude THP deprotection product using a 0-15% MeOH in $CH_2Cl_2$ gradient (6% yield). $^1$HNMR (300 MHz, DMSO-$d_6$) δ 12.21 (s, 1-NH), 7.26-7.20 (m, 5H), 4.38 (d, J=6.0 Hz, 4H), 3.38-3.35 (m, 2H), 2.56-2.47 (m, 3H), 1.75-1.64 (m, 4H).

Compound 109. 1-(4-(1-(1H-Pyrazol-4-yl)piperidin-4-yl)-2-fluorobenzyl)pyrrolidin-2-one

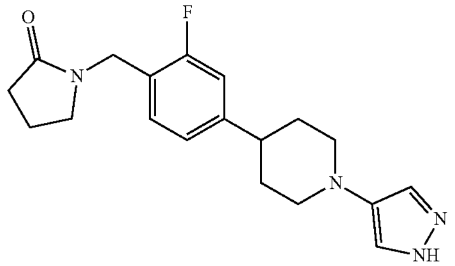 [SMILES: O=C1CCCN1Cc1ccc(C2CCN(c3cn[nH]c3)CC2)cc1F]

Compound was prepared from THP-protected 4-iodo-pyrazole and 1-(2-fluoro-4-(piperidin-4-yl)benzyl)pyrrolidin-2-one according to general procedure 6. The THP-protected intermediate was purified with silica gel column chromatography and 0-100% EtOAc in hexanes gradient. The desired product, 1-(4-(1-(1H-pyrazol-4-yl)piperidin-4-yl)-2-fluorobenzyl)pyrrolidin-2-one, was isolated as a white solid after silica gel column purification of the crude THP deprotection product using a 0-15% MeOH in $CH_2Cl_2$ gradient (10% yield) $^1$HNMR (300 MHz, $CDCl_3$) δ 7.31 (s, 2H), 7.19-7.17 (m, 1H), 6.98-6.88 (m, 2H), 4.45 (s, 2H), 3.49-3.44 (m, 2H), 3.29 (t, J=6.9 Hz, 3H), 2.74-2.54 (m, 3H), 2.38 (t, J=8.1 Hz, 2H), 2.01-1.88 (m, 6H).

Compound 110. 1-(4-(1-(1H-Pyrazol-5-yl)piperidin-4-yl)-2-fluorobenzyl)pyrrolidin-2-one

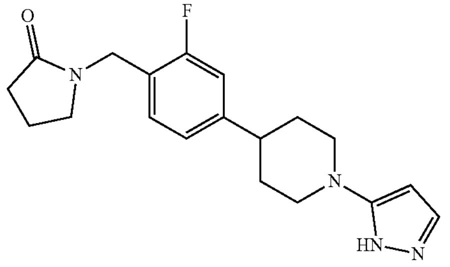 [SMILES: O=C1CCCN1Cc1ccc(C2CCN(c3ccn[nH]3)CC2)cc1F]

Compound was prepared from THP-protected 3-iodo-pyrazole and 1-(2-fluoro-4-(piperidin-4-yl)benzyl)pyrrolidin-2-one according to general procedure 6. The THP-protected intermediate was purified with silica gel column chromatography and 0-100% EtOAc in hexanes gradient. The desired product, 1-(4-(1-(1H-pyrazol-3-yl)piperidin-4-yl)-2-fluorobenzyl)pyrrolidin-2-one, was isolated as a white solid after silica gel column purification of the crude THP deprotection product using 0-15% MeOH in $CH_2Cl_2$ gradient (12% yield): $^1$HNMR (300 MHz, $CDCl_3$) δ 7.40 (s, 1H), 7.22-7.17 (m, 1H), 6.98-6.88 (m, 2H), 5.76 (s, 1H), 4.46 (s, 2H), 3.86-3.82 (m, 2H), 3.29 (t, J=6.9 Hz, 2H), 2.87-2.79 (m, 2H), 2.62 (tt, J=11.7, 4.2 Hz, 1H), 2.42-2.37 (m, 2H), 2.0-1.77 9m, 6H).

Compound 111. 4-(4-Nitrophenyl)-1-(1H-pyrazol-4-yl)piperidine

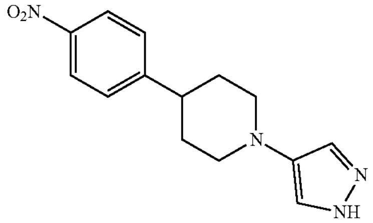 [SMILES: O=[N+]([O-])c1ccc(C2CCN(c3cn[nH]c3)CC2)cc1]

Compound was prepared from THP-protected 4-iodo-pyrazole and commercially available 4-(4-nitrophenyl)piperidine according to general procedure 6. The THP-protected intermediate was purified with silica gel column chromatography and 0-100% EtOAc in hexanes gradient. The desired product, 4-(4-nitrophenyl)-1-(1H-pyrazol-4-yl) piperidine, was isolated as a white solid after the purification of the crude THP deprotection product with silica gel column using 0-15% MeOH in $CH_2Cl_2$ gradient (16% yield): $^1$HNMR (300 MHz, DMSO-$d_6$) δ 12.19 (s, 1-NH), 8.10 (d, J=8.7 Hz, 2H), 7.51 (d, J=7.2 Hz, 2H), 7.21 (s, 2H), 3.40-3.36 (m, 2H), 2.73-2.66 (m, 1H), 2.53-2.45 (m, 2H), 1.79-1.68 (m, 4H).

Compound 112. 4-(4-Nitrophenyl)-1-(1H-pyrazol-5-yl)piperidine

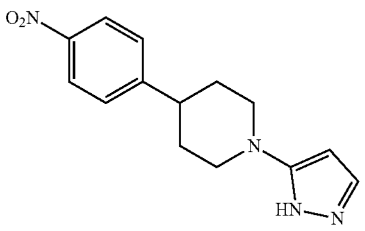 [SMILES: O=[N+]([O-])c1ccc(C2CCN(c3ccn[nH]3)CC2)cc1]

Compound was prepared from THP-protected 3-iodo-pyrazole and commercially available 4-(4-nitrophenyl)piperidine according to general procedure 6. The THP-protected intermediate was purified with silica gel column chromatography and 0-100% EtOAc in hexanes gradient. The desired product 4-(4-nitrophenyl)-1-(1H-pyrazol-5-yl) piperidine, was isolated as a white solid after silica gel column purification of the crude THP deprotection product using 0-15% MeOH in $CH_2Cl_2$ gradient (17% yield): $^1$HNMR (300 MHz, DMSO-$d_6$) δ 11.70 (s, 1-NH), 8.12-8.08 (m, 2H), 7.50 (d, J=8.7 Hz, 2H), 7.42 (s, 1H), 5.69 (s, 1H), 3.74-3.70 (m, 2H), 2.77-2.59 (m, 3H), 1.78-1.61 (m, 4H).

Compound 113. N-(4-(1-(1H-pyrazol-4-yl)piperidin-4-yl)phenyl)methanesulfonamide

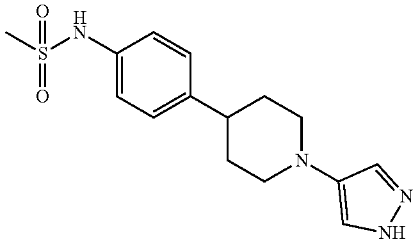 [SMILES: CS(=O)(=O)Nc1ccc(C2CCN(c3cn[nH]c3)CC2)cc1]

THP-protected 4-iodo-pyrazole and commercially available 4-(4-nitrophenyl)piperidine were coupled according to general procedure 6. The resulting THP-protected coupling intermediate was purified with silica gel column chromatography and 0-100% EtOAc in hexanes gradient. This THP protected intermediate was then reduced using 10% Pd/C (0.1 eq) in ethanol and hydrogen gas at atmospheric pressure. When reduction deemed complete by TLC the catalyst was removed and washed with 10% MeOH in DCM and the combined organic layer was concentrated. The residue was sulfonylated in DCM with $CH_3SO_2Cl$ (1.2 eq) in the presence of $Et_3N$ as base (1.2 eq). Upon consumption of the starting material the reaction mixture was partitioned between DCM and water. The organic layer was dried over $Na_2SO_4$ filtered and concentrated and the reside was purified with silica gel column using EtOAc in hexanes as eluent. This intermediate obtained from this purification was then stirred with 50% KOH aq. solution in THF/$H_2O$ (1:1) overnight. Then the mixture was neutralized with 1N HCl aq. to pH 6. Water was added and the mixture extracted with 10% MeOH in DCM. Organic layer was dried over $Na_2SO_4$, filtered and concentrated to a residue that was treated with 4N HCl in dioxane as described in general procedure 6. The desired product, N-(4-(1-(1H-pyrazol-4-yl)piperidin-4-yl) phenyl)methanesulfonamide, was isolated as a white solid after silica gel column purification of the crude THP deprotection product with 0-15% MeOH in $CH_2Cl_2$ gradient (7% yield). $^1$HNMR (300 MHz, DMSO-$d_6$) δ 12.18 (s, 1-NH), 9.52 (s, 1-NH), 7.18-7.06 (m, 4H), 7.08-7. 06 (m, 2H), 3.36-3.32 (m, 2H), 2.87 (s, 3H), 2.52-2.44 (m, 3H), 1.72-1.60 (m, 4H).

Compound 114. N-(4-(1-(1H-pyrazol-4-yl)piperidin-4-yl)phenyl)cyclopropanesulfonamide

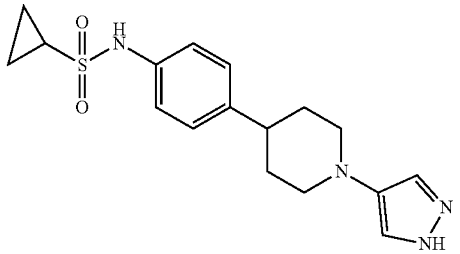 [SMILES: O=S(=O)(Nc1ccc(C2CCN(c3cn[nH]c3)CC2)cc1)C1CC1]

THP-protected 4-iodo-pyrazole and commercially available 4-(4-nitrophenyl)piperidine were coupled according to general procedure 6. The THP-protected intermediate was purified with silica gel column chromatography and 0-100% EtOAc in hexanes gradient. This intermediate was then reduced using ethanol, 10% Pd/C (0.1 eq) and $H_2$ gas at atm pressure. When reaction deemed complete by TLC the catalyst was removed, washed with 10% MeOH in DCM and the combined organic layer was evaporated to a residue that was sulfonylated with cyclopropanesulfonyl chloride (1.1 eq) in $CH_2Cl_2$ and in the presence of $Et_3N$ (1.1 eq) as base. When sulfonylation deemed complete by TLC the mixture was diluted with water and extracted with $CH_2Cl_2$. Combined organic layer was dried over $Na_2SO_4$ filtered and concentrated and the residue was treated with 4 N HCl in dioxane as described in general procedure 6. The desired product N-(4-(1-(1H-pyrazol-4-yl)piperidin-4-yl)phenyl) methanesulfonamide, was isolated as a white solid after purification of the crude THP deprotection product with silica gel column and 0-15% MeOH in $CH_2Cl_2$ gradient (18% yield). $^1$H NMR (300 MHz, DMSO-$d_6$) δ 12.19 (s, 1-NH), 9.51 (s, 1-NH), 7.20-7.08 (m, 6H), 3.36-3.32 (m, 2H), 2.54-2.47 (m, 4H), 1.72-1.61 (m, 4H), 0.84 (d, J=6.3 Hz, 4H).

Compound 115. 4-(4-Chlorobenzyl)-1-(1H-pyrazol-4-yl)piperidine hydrochloride

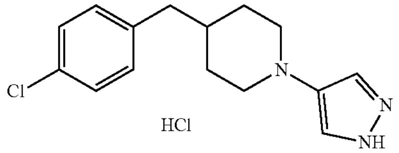 [SMILES: Clc1ccc(CC2CCN(c3cn[nH]c3)CC2)cc1 ; Cl]

4-(4-Chlorobenzyl)-1-(1H-pyrazol-4-yl)piperidine (prepared from THP-protected 4-iodopyrazole and 4-(4-chlorobenzyl)piperidine according to general procedure 6, 1 eq) in dioxane was treated with 1.2 eq of 4N HCl in dioxane and stirred overnight. The volatiles were then evaporated and the resulting solid residue was washed with $CH_2Cl_2$ and dried to afford the product as a white solid (46% yield). $^1H$ NMR (300 MHz, $CD_3OD$) δ 8.04 (s, 2H), 7.32 (dd, J=6.8 Hz, 2.1 Hz, 2H), 7.23 (dd, J=4.8 Hz, 2.1 Hz, 2H), 3.82-3.78 (m, 2H), 3.51 (dt, J=12.6 Hz, 2.7 Hz, 2H), 2.69 (d, J=6.9 Hz, 2H), 2.08-1.99 (m, 3H), 1.80-1.67 (m, 2H).

Compound 116. 4-(4-Methylbenzyl)-1-(1H-pyrazol-4-yl)piperidine

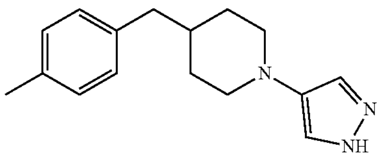 [SMILES: Cc1ccc(CC2CCN(c3cn[nH]c3)CC2)cc1]

Compound was prepared from THP-protected 4-iodopyrazole and 4-(4-methylbenzyl)piperidine according to general procedure 6. The THP-protected intermediate was purified with silica gel column chromatography and 0-100% EtOAc in hexanes gradient. The desired product 4-(4-methylbenzyl)-1-(1H-pyrazol-4-yl)piperidine, was isolated as a white solid after silica gel column purification of the crude THP deprotection product using 0-15% MeOH in $CH_2Cl_2$ gradient (12% yield). $^1$HNMR (300 MHz, DMSO-$d_6$) δ 12.20 (s, 1-NH), 7.18 (s, 2H), 7.10-7.04 (m, 4H), 3.28-3.24 (m, 2H), 2.49-2.47 (m, 2H), 2.37-2.26 (m, 5H), 1.56-1.47 (m, 3H), 1.34-1.21 (m, 2H).

Compound 117. 1-(4-(1-(1H-Pyrazol-4-yl)piperidin-4-yl)-2-chlorobenzyl)pyrrolidin-2-one

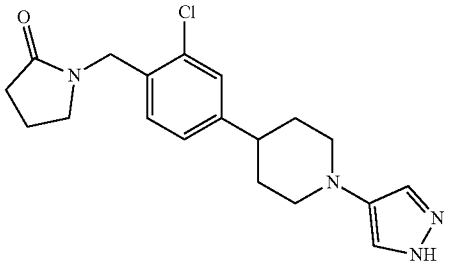 [SMILES: O=C1CCCN1Cc1ccc(C2CCN(c3cn[nH]c3)CC2)cc1Cl]

Compound was prepared from THP-protected 4-iodopyrazole and 1-(2-chloro-4-(piperidin-4-yl)benzyl)pyrrolidin-2-one according to general procedure 6. The THP-protected intermediate was purified with silica gel column chromatography and 0-100% EtOAc in hexanes gradient. The desired product 1-(4-(1-(1H-pyrazol-4-yl)piperidin-4-yl)-2-chlorobenzyl)pyrrolidin-2-one, was isolated as a white solid after silica gel column purification of the crude THP deprotection product using 0-15% MeOH in $CH_2Cl_2$ gradient (3% yield). $^1$HNMR (300 MHz, DMSO-$d_6$) δ 12.27 (s, 1H), 7.36 (d, J=1.5 Hz, 1H), 7.28-7.25 (m, 3H), 7.19 (d, J=7.8 Hz, 1H), 4.42 (s, 2H), 3.44-3.40 (m, 2H), 3.26 (t, J=6.2 Hz, 2H), 2.66-2.54 (m, 3H), 2.30 (t, J=7.8 Hz, 2H), 2.00-1.90 (m, 2H), 1.81-1.73 (m, 4H).

Compound 118. 1-(4-(1-(1H-Pyrazol-4-yl)piperidin-4-yl)-3-fluorobenzyl)pyrrolidin-2-one

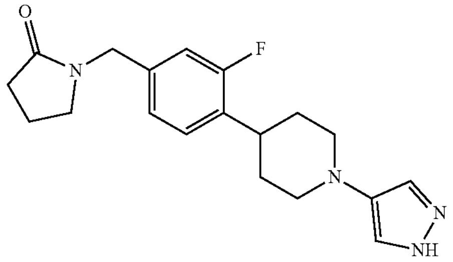 [SMILES: O=C1CCCN1Cc1ccc(C2CCN(c3cn[nH]c3)CC2)c(F)c1]

Compound was prepared from THP-protected 4-iodopyrazole and 1-(3-fluoro-4-(piperidin-4-yl)benzyl)pyrrolidin-2-one according to general procedure 6. The THP-protected intermediate was purified with silica gel column chromatography and 0-100% EtOAc in hexanes gradient. The desired product 1-(4-(1-(1H-pyrazol-4-yl)piperidin-4-yl)-3-fluorobenzyl)pyrrolidin-2-one, was isolated as a white solid after silica gel column purification of the crude THP deprotection product using 0-15% MeOH in $CH_2Cl_2$ (18% yield): $^1$HNMR (400 MHz, $CD_3OD$) δ 7.27 (s, 2H), 7.22 (t, J=7.6 Hz, 1H), 6.96 (dd, J=8.0 Hz, 1.2 Hz, 1H), 6.87 (d, $J_{H-F}$=11.2 Hz, 1H), 4.33 (s, 2H), 3.43-3.40 (m, 2H), 3.26 (d, J=6.8 Hz, 2H), 2.86 (tt, J=12.0, 4.0 Hz, 1H), 2.59 (td, J=11.6, 3.2 Hz, 2H), 2.35 (t, J=7.6 Hz, 2H), 1.96-1.77 (m, 6H).

Compound 119. 1-(4-(1-(1H-Pyrazol-4-yl)piperidin-4-yl)phenyl)pyrrolidin-2-one hydrochloride

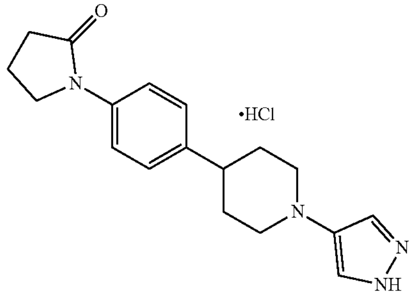 [SMILES: O=C1CCCN1c1ccc(C2CCN(c3cn[nH]c3)CC2)cc1 ; Cl]

1-(4-(1-(1H-Pyrazol-4-yl)piperidin-4-yl)phenyl)pyrrolidin-2-one (prepared from THP protected 4-iodopyrazole and 1-(4-(piperidin-4-yl)phenyl)pyrrolidin-2-one according to general procedure 6, 1 eq) in dioxane was treated with 4N HCl in dioxane (1.2 eq) and the mixture was stirred overnight. The volatiles were then evaporated and the residue was washed with $CH_2Cl_2$ several times and then dried to afford the product as a white solid. $^1$HNMR (300 MHz, DMSO-$d_6$) δ 8.09 (s, 2H), 7.62 (t, J=8.7 Hz, 2H), 7.27 (t, J=8.7 Hz, 2H), 3.85-3.72 (m, 4H), 3.55-3.48 (m, 2H), 2.97-2.89 (m, 1H), 2.49-2.46 (m, 2H), 2.26-2.22 (m, 2H), 2.11-2.01 (m, 4H).

Compound 120. 4-(4-(1-(1H-Pyrazol-4-yl)piperidin-4-yl)phenyl)morpholine

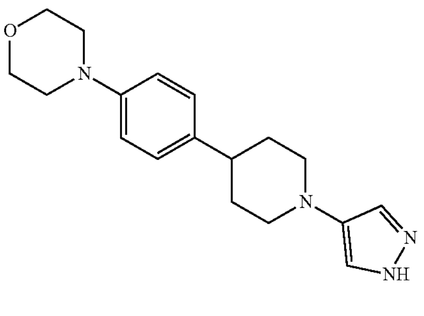 [SMILES: c1cc(N2CCOCC2)ccc1C1CCN(c2cn[nH]c2)CC1]

Compound was prepared from THP-protected 4-iodopyrazole and 4-(4-(piperidin-4-yl)phenyl)morpholine according to general procedure 6. The THP-protected intermediate was purified with silica gel column chromatography and 0-100% EtOAc in hexanes gradient. The desired product 4-(4-(1-(1H-pyrazol-4-yl)piperidin-4-yl)phenyl)morpholine, was isolated as a white solid after silica gel column purification of the crude THP deprotection product using 0-15% MeOH in $CH_2Cl_2$ gradient (5% yield): $^1$HNMR (300 MHz, DMSO-$d_6$) δ 12.25 (s, 1-NH), 7.25 (s, 2H), 7.12 (t, J=8.4 Hz, 2H), 6.87 (t, J=8.7 Hz, 2H), 3.73 (t, J=4.5 Hz, 4H), 3.43-3.39 (m, 2H), 3.05 (t, J=4.8 Hz, 4H), 2.55-2.43 (m, 3H), 1.78-1.65 (m, 4H).

Compound 121. 4-(4-(1-(1H-Pyrazol-4-yl)piperidin-4-yl)benzyl)morpholine

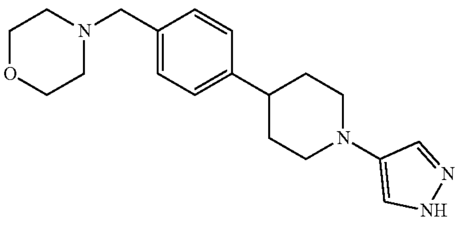 [SMILES: c1cc(C2CCN(c3cn[nH]c3)CC2)ccc1CN1CCOCC1]

Compound was prepared from THP-protected 4-iodopyrazole and 4-(4-(piperidin-4-yl)benzyl)morpholine according to general procedure 6. The THP-protected intermediate was purified with silica gel column chromatography and 0-100% EtOAc in hexanes gradient. The desired product 4-(4-(1-(1H-pyrazol-4-yl)piperidin-4-yl)benzyl)morpholine, was isolated as a white solid after silica gel column purification of the crude THP deprotection product using 0-15% MeOH in $CH_2Cl_2$ gradient (6% yield): $^1$H NMR (300 MHz, DMSO-$d_6$) δ 12.26 (s, 1H), 7.27-7.23 (m, 6H), 3.56 (t, J=9 Hz, 4H), 3.44-3.42 (m, 4H), 2.56-2.53 (m, 3H), 2.33 (t, J=8.4 Hz, 4H), 1.80-1.67 (m, 4H).

Compound 122. 4-(4-(1-(1H-Pyrazol-4-yl)piperidin-4-yl)phenyl)morpholin-3-one

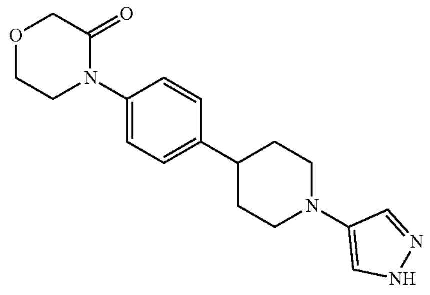 [SMILES: O=C1COCCN1c1ccc(C2CCN(c3cn[nH]c3)CC2)cc1]

Compound was prepared from THP-protected 4-iodopyrazole and 4-(4-(piperidin-4-yl)phenyl)morpholin-3-one according to general procedure 6. The THP-protected intermediate was purified with silica gel column chromatography and 0-100% EtOAc in hexanes gradient. The desired product 4-(4-(1-(1H-pyrazol-4-yl)piperidin-4-yl)phenyl)morpholin-3-one, was isolated as a white solid after silica gel column purification of the crude THP deprotection product using 0-15% MeOH in $CH_2Cl_2$ gradient (4% yield) $^1$H NMR (300 MHz, DMSO-$d_6$) δ 12.19 (s, 1H), 7.24-7.19 (m, 6H), 4.12 (s, 2H), 3.91-3.87 (m, 2H), 3.65-3.62 (m, 2H), 3.38-3.34 (m, 2H), 2.58-2.46 (m, 3H), 1.76-1.65 (m, 4H).

Compound 123. 4-(4-(1-(1H-Pyrazol-4-yl)piperidin-4-yl)-2-fluorophenyl)morpholine

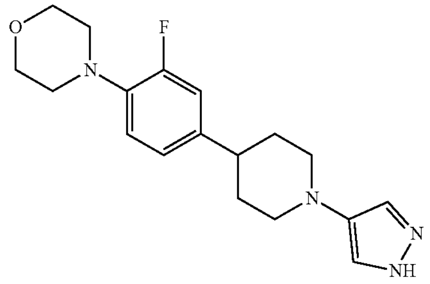 [SMILES: Fc1cc(C2CCN(c3cn[nH]c3)CC2)ccc1N1CCOCC1]

Compound was prepared from THP-protected 4-iodopyrazole and 4-(2-fluoro-4-(piperidin-4-yl)phenyl)morpholine according to general procedure 6. The THP-protected intermediate was purified with silica gel column chromatography and 0-100% EtOAc in hexanes gradient. The desired product 4-(4-(1-(1H-pyrazol-4-yl)piperidin-4-yl)-2-fluorophenyl)morpholine, was isolated as a white solid after silica gel column purification of the crude THP deprotection product using 0-15% MeOH in $CH_2Cl_2$ gradient (8% yield). $^1$H NMR (600 MHz, $CDCl_3$) δ 7.29 (bs, 2H), 6.94-6.90 (m, 2H), 6.86 (t, J=4.2 Hz, 1H), 3.84 (t, J=4.2 Hz, 4H), 3.47-3.45 (m, 2H), 3.03 (t, J=4.8 Hz, 4H), 2.69-2.66 (m, 2H), 2.55-2.51 (m, 1H), 1.93-1.88 (m, 4H).

Compound 124. 4-(4-(1-(1H-Pyrazol-4-yl)piperidin-4-yl)-3-fluorophenyl)morpholine

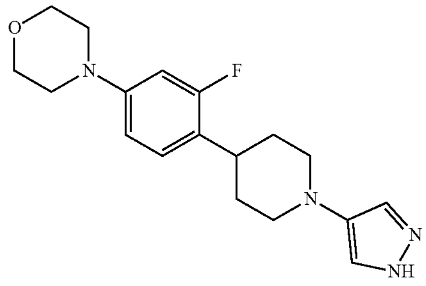 [SMILES: Fc1cc(N2CCOCC2)ccc1C1CCN(c2cn[nH]c2)CC1]

Compound was prepared from THP-protected 4-iodopyrazole and 4-(3-fluoro-4-(piperidin-4-yl)phenyl)morpholine according to general procedure 6. The THP-protected intermediate was purified with silica gel column chromatography and 0-100% EtOAc in hexanes gradient. The desired product, 4-(4-(1-(1H-pyrazol-4-yl)piperidin-4-yl)-3-fluorophenyl)morpholine, was isolated as a white solid after silica gel column purification of the crude THP deprotection product using 0-15% MeOH in $CH_2Cl_2$ gradient (4% yield): $^1H$ NMR (400 MHz, DMSO-$d_6$) δ 12.26 (s, 1H), 7.26 (d, J=9.2 Hz, 2H), 7.17 (t, J=8.8 Hz, 1H), 6.74-6.70 (m, 2H), 3.72 (t, J=4.4 Hz, 4H), 3.43-3.40 (m, 2H), 3.09 (t, J=4.8 Hz, 4H), 2.77-2.71 (m, 1H), 2.55-2.54 (m, 2H), 1.83-1.71 (m, 4H).

Compound 125. (R)-1-(1-(4-(1-(1H-pyrazol-4-yl)piperidin-4-yl)phenyl)ethyl)pyrrolidin-2-one

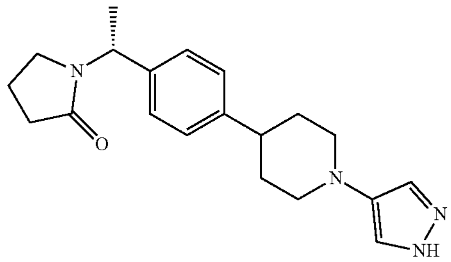 [SMILES: C[C@H](c1ccc(C2CCN(c3cn[nH]c3)CC2)cc1)N1CCCC1=O]

Compound was prepared from THP-protected 4-iodopyrazole and (R)-1-(1-(4-(piperidin-4-yl)phenyl)ethyl)pyrrolidin-2-one according to general procedure 6. The THP-protected intermediate was purified with silica gel column chromatography and 0-100% EtOAc in hexanes gradient. The desired product (R)-1-(1-(4-(1-(1H-pyrazol-4-yl)piperidin-4-yl)phenyl)ethyl)pyrrolidin-2-one, was isolated as a white solid after silica gel column purification of the crude THP deprotection product using 0-15% MeOH in $CH_2Cl_2$ gradient (16% yield). $^1H$ NMR (300 MHz, DMSO-d6): δ 12.18 (bs, 1H), 7.19-7.11 (m, 6H), 5.13 (q, J=7.5 Hz, 1H), 3.37-3.28 (m, 3H), 2.93-2.85 (m, 2H), 2.55-2.47 (m, 2H), 2.21-2.16 (m, 2H), 1.86-1.77 (m, 2H), 1.74-1.66 (m, 4H), 1.36 (d, J=7.2 Hz, 3H).

Compound 126. (S)-1-(1-(4-(1-(1H-pyrazol-4-yl)piperidin-4-yl)phenyl)ethyl)pyrrolidin-2-one

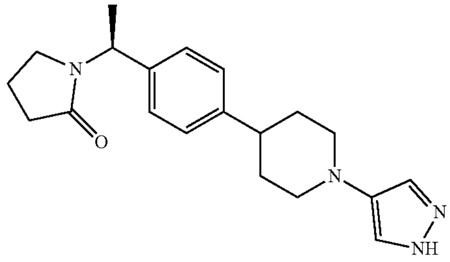 [SMILES: C[C@@H](c1ccc(C2CCN(c3cn[nH]c3)CC2)cc1)N1CCCC1=O]

Compound was prepared from THP-protected 4-iodopyrazole and (S)-1-(1-(4-(piperidin-4-yl)phenyl)ethyl)pyrrolidin-2-one according to general procedure 6. The THP-protected intermediate was purified with silica gel column chromatography and 0-100% EtOAc in hexanes gradient. The desired product (S)-1-(1-(4-(1-(1H-pyrazol-4-yl)piperidin-4-yl)phenyl)ethyl)pyrrolidin-2-one, was isolated as a white solid after silica gel column purification of the crude THP deprotection product using 0-15% MeOH in $CH_2Cl_2$ gradient (26% yield): $^1H$ NMR (300 MHz, DMSO-$d_6$): δ 12.26 (bs, 1H), 7.26-7.19 (m, 6H), 5.21 (q, J=7.2 Hz, 1H), 3.44-3.35 (m, 3H), 3.00-2.93 (m, 1H), 2.59-2.55 (m, 3H), 2.29-2.23 (m, 2H), 1.92-1.85 (m, 2H), 1.85-1.73 (m, 4H), 1.44 (d, J=7.2 Hz, 3H).

Compound 127. 4-[(4-Methoxyphenyl)methyl]-1-(1H-pyrazol-4-yl)piperidine

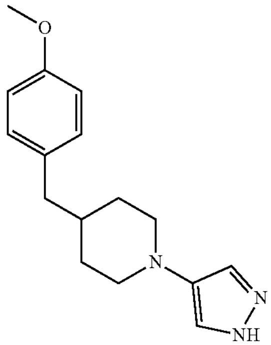 [SMILES: COc1ccc(CC2CCN(c3cn[nH]c3)CC2)cc1]

Synthesized according to general procedure 6 from THP-protected 4-iodopyrazole and commercially available 4-(4-methoxybenzyl)piperidine. The crude THP protected coupling intermediate was chromatographed with 0-80% EtOAc in hexanes. The product 4-[(4-methoxyphenyl)methyl]-1-(1H-pyrazol-4-yl)piperidine was isolated as an off-white solid after silica gel column purification of the crude THP-deprotected product with 0-10% MeOH in EtOAc gradient and a precipitation out of $CH_2Cl_2$ with excess of hexanes (24% yield). $^1H$ NMR (600 MHz, $CD_3OD$) δ 1.40 (qd, J=12.6, 3.6 Hz, 2H), 1.54-1.65 (m, 1H), 1.72 (apparent d, J=13.2 Hz, 2H), 2.49 (td, J=12.0, 1.8 Hz, 2H), 2.52 (d, J=7.2 Hz, 2H), 3.36 (apparent d, J=11.4 Hz, 2H), 3.78 (s, 3H), 6.84 (d, J=8.4 Hz, 2H), 7.87 (d, J=8.4 Hz, 2H), 7.32 (s, 2H).

Compound 128. 1-(4-(1-(1H-pyrazol-4-yl)piperidin-4-yl)-3-fluorophenyl)pyrrolidin-2-one

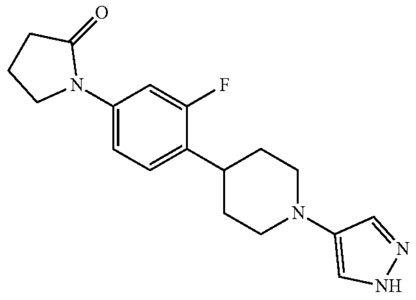 [SMILES: O=C1CCCN1c1ccc(C2CCN(c3cn[nH]c3)CC2)c(F)c1]

Compound was prepared from THP-protected 4-iodo-pyrazole and 1-(3-fluoro-4-(piperidin-4-yl)phenyl)pyrrolidin-2-one according to general procedure 6. The THP-protected intermediate was purified with silica gel column chromatography and 0-100% EtOAc in hexanes gradient. The desired product 1-(4-(1-(1H-pyrazol-4-yl)piperidin-4-yl)-3-fluorophenyl)pyrrolidin-2-one, was isolated as a white solid after silica gel column purification of the crude THP deprotection product with 0-15% MeOH in $CH_2Cl_2$ gradient (13% yield): $^1$H NMR (300 MHz, DMSO-$d_6$) δ 12.27 (s, 1-NH), 7.64-7.59 (m, 1H), 7.37-7.32 (m, 2H), 7.26 (d, $J_{C-F}$=9.9 Hz, 2H), 3.82 (t, J=6.9 Hz, 2H), 3.45-3.41 (m, 2H), 2.87-2.80 (m, 1H), 2.58-2.48 (m, 4H), 2.10-2.00 (m, 2H), 1.89-1.74 (m, 4H).

Compound 129. 4-(4-(1-(1H-Pyrazol-4-yl)piperidin-4-yl)phenyl)thiomorpholine 1,1-dioxide

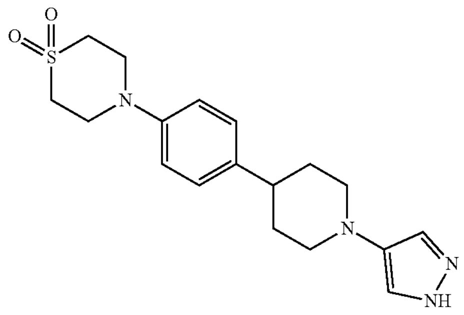 [SMILES: O=S1(=O)CCN(c2ccc(C3CCN(c4cn[nH]c4)CC3)cc2)CC1]

Compound was prepared from THP-protected 4-iodo-pyrazole and 4-(4-(piperidin-4-yl)phenyl)thiomorpholine 1,1-dioxide according to general procedure 6. The THP-protected intermediate was purified with silica gel column chromatography and 0-100% EtOAc in hexanes gradient. The desired product 4-(4-(1-(1H-pyrazol-4-yl)piperidin-4-yl)phenyl)thiomorpholine 1,1-dioxide, was isolated as a white solid after silica gel column purification of the crude THP deprotection product with 0-15% MeOH in $CH_2Cl_2$ gradient (13% yield). $^1$HNMR (300 MHz, DMSO-$d_6$) δ 12.25 (s, 1-NH), 7.25 (d, J=5.7 Hz, 2H), 7.15 (t, J=8.1 Hz, 2H), 6.96 (t, J=8.4 Hz, 2H), 3.72 (bs, 4H), 3.43-3.39 (m, 2H), 3.11 (bs, 4H), 2.50 (m, 3H), 1.76-1.71 (m, 4H).

Example 2: Determination of Compound Inhibition and Selectivity Against 20-HETE Formation Inhibition of 20-HETE Formation Determination at 250 or 500 nM To screen the inhibitory effects against 20-HETE formation, compounds were screened in HLM, RLM, RKM and rCYP4F2 microsomal incubations. Compounds dissolved in either 100% methanol or 100% DMSO to yield 10 mM stock solution. Microsomal incubations containing HLM, RLM, RKM (300 μg/ml) or rCYP4F2 (25 pmol/mL), AA (100 μM), NADPH (1 mM) treated with test compounds at various concentrations (500 nM or 250 nM) in a 1 ml total volume in incubation buffer (0.12 M potassium phosphate buffer containing 5 mM magnesium chloride). Reaction was started by adding NADPH to the incubates and was carried out at 37° C. in a shaking water bath for 20 min. Reaction was stopped by placing tubes on ice, followed by adding 125 μl 20-HETE-$d_6$ as internal standard to each sample. Microsomal incubations were extracted with 3 ml ethyl ether twice, dried down under nitrogen gas and reconstituted in 125 μl 80:20 methanol:deionized $H_2O$ for analysis. 20-HETE formation was quantified using a validated UPLC-MS/MS assay and normalized by vehicle group. Each compound had three replications (n=3). Vehicle group was used as control to calculate percentage of 20-HETE formation rate. HET0016 (250 nM) was used as positive control. Incubates without NADPH group served as the negative control. An Acquity ultra performance LC autosampler (Waters, Milford, MA) was used to isolate 20-HETE on an UPLC BEH C18, 1.7 μm (2.1×100 mm) reversed-phase column (Waters, Milford, MA) protected by a guard column (2.1×5 mm; Waters, Milford, MA) of the same packing material. Column temperature was maintained at 55° C. Mobile phases consisted of 0.005% acetic acid, 5% acetonitrile in deionized water (A) and 0.005% acetic acid in acetonitrile (B). The flow rate for mobile phases is 0.5 ml/min. The initial mixture of mobile phase was 65:35 of A and B. Mobile phase B increased at 0.4 minutes after injection from 35% to 70% in a linear gradient over 4 minutes, and again increased to 95% over 0.5 minutes where it remained for 0.3 minutes. This was followed by a linear return to initial conditions over 0.1 minutes with a 1.5 minute pre-equilibration period prior to the next sample run. Total run time was 6.4 minutes for each injection. Injection volumes were 7.5 μl. Mass spectrometric analysis was carried out using a TSQ Quantum Ultra (Thermo Fisher Scientific, San Jose, CA) triple quadrupole mass spectrometer using heated electrospray ionization (HESI). Mass spectrometer was operated in negative selective reaction monitoring (SRM) mode with unit resolutions at both Q1 and Q3 set at 0.70 Da full width at half maximum. Scan time was set at 0.01 s and collision gas pressure was 1.3 mTorr. Quantitation of 20-HETE by SRM was performed by monitoring the m/z. Analytical data was acquired and analyzed using Xcaliber 3.0 data system (ThermoFinnigan, San Jose, CA).

$IC_{50}$ Determinations

Microsomal incubations contained HLM, RLM (300 μg/ml), AA (100 μM), NADPH (1 mM) and test compounds at 12 concentrations (0.1 nM-50 μM) in a 1 ml total volume in microsomal incubation buffer (0.12 M potassium phosphate buffer containing 5 mM magnesium chloride). Reaction was started by adding NADPH to the incubates and was carried out at 37° C. in a shaking water bath for 20 min. Reaction was stopped by placing tubes on ice, followed by adding 12.5 μl 20-HETE-$d_6$ as internal standard to each sample. Microsomal incubations were extracted with 3 ml ethyl ether twice, dried down under nitrogen gas and reconstituted in 125 μl 80:20 methanol:deionized $H_2O$ for analysis. 20-HETE formation was quantified using the validated UPLC-MS/MS assay described above and normalized by vehicle group. HET0016 (250 nM) was used as positive control. Incubates without NADPH group served as the negative control. $IC_{50}$ was determined by fitting the dose-response curve using Graphpad Prism nonlinear regression.

Determination of Selectivity of Compounds for 20-HETE Formation Inhibition Vs EETs and DiHETs Selectivity of compounds for inhibition of 20-HETE formation vs inhibition of formation of 8,9-, 11,12-, 14,15-EET and 5,6-, 8,9-, 11,12-, 14,15-DiHETs was assessed via the simultaneous monitor of formation of 20-HETE and those metabolites under the UPLC-MS/MS assay conditions described above using HLM incubations and the same 12 test compound concentrations (0.1 nM-50 mM) used for the $IC_{50}$ determination experiments. At each of the 12 concentrations, the selectivity of 20-HETE inhibition over the other metabolites was compared. Epoxygenase activity was assessed by the sum of EETs and DiHETEs as percentage of control.

Example 3: Determination of Blood Brain Barrier Penetration Potential

BBB penetration potential assessment data in Table 1 was obtained as follows. MDR1-MDCK cell monolayers were grown to confluence on collagen-coated, microporous membranes in 12-well assay plates. Atenolol, propranolol and digoxin were used as control to assess plate quality. The permeability assay buffer was Hanks' balanced salt solution containing 10 mM HEPES and 15 mM glucose at a pH of 7.4. The buffer in the receiver chamber also contained 1% bovine serum albumin. The dosing solution concentration was 5 μM of test article in the assay buffer. Cell monolayers were dosed on the apical side (A-to-B) or basolateral side (B-to-A) and incubated at 37° C. with 5% $CO_2$ in a humidified incubator. Samples were taken from the donor and receiver chambers at 120 minutes. Each determination was performed in duplicate the flux of lucifer yellow was also measured post-experimentally for each monolayer to ensure no damage was inflicted to the cell monolayers during the flux period. All samples were assayed by LC-MS/MS using electrospray ionization using a PE SCIEX API 4000 spectrometer and total run time of 1 min. Analytical method/conditions were: Liquid Chromatography Column: Waters ACQUITY UPLC BEH Phenyl 30×2.1 mm, 1.7 m; M.P. Buffer: 25 mM ammonium formate buffer, pH 3.5; Aqueous Reservoir (A): 90% water, 10% buffer; Organic Reservoir (B): 90% acetonitrile, 10% buffer; Flow Rate: 0.7 mL/minute; gradient program: 99% A (t=0 min), 1% A (t=0.65 min), 1% A (t=0.75 min), 99% A (t=0.8 min), 99% A (t=1 min); 5 μL injection volume The apparent permeability ($P_{app}$) and percent recovery were calculated as follows:

$$P_{app}=(dC_r/dt)\times V_r/(A\times C_A) \quad (1)$$

$$\text{Percent Recovery}=100\times((V_r\times C_r^{final})+(V_d\times C_d^{final}))/(V_d\times C_N) \quad (2)$$

wherein:

$dC_r/dt$ is the slope of the cumulative concentration in the receiver compartment versus time in $\mu Ms^{-1}$;

$V_r$ is the volume of the receiver compartment in $cm^3$;

$V_d$ is the volume of the donor compartment in $cm^3$;

A is the area of the insert (1.13 $cm^2$ for 12-well);

$C_A$ is the average of the nominal dosing concentration and the measured 120 minute donor concentration in μM;

$C_N$ is the nominal concentration of the dosing solution in μM;

$C_r^{final}$ is the cumulative receiver concentration in μM at the end of the incubation period;

$C_d^{final}$ is the concentration of the donor in μM at the end of the incubation period.

Efflux ratio (ER) is defined as $P_{app}$ (B-to-A)/$P_{app}$ (A-to-B)

Interpretation

Brain Penetration Potential Classification:

$P_{app}$ (A-to-B)≥3.0 and ER<3.0: High $P_{app}$ (A-to-B)≥3.0 and 10>ER≥3.0: Moderate $P_{app}$ (A-to-B)≥3.0 and ER≥10, or $P_{app}$ (A-to-B)<3.0 Low

Example 4 HLM Stability Determinations

HLM stability determinations shown in Table 3 were obtained as follows. Microsomal incubates contained HLM (500 μg/ml), test compounds (1 μM) and NADPH (1.3 mM) in a 1 ml total volume of microsomal incubation buffer (0.12 M potassium phosphate buffer containing 5 mM magnesium chloride). Reaction was started by adding NADPH to the incubates and was carried out at 37° C. in a shaking water bath for 60 min. At 0, 15, 30, 45, 60 min, a 50 μl aliquot of incubates was taken out and reaction was stopped by adding aliquot into 200 μl ice-cold acetonitrile. After centrifugation at 14000×g for 5 min, 200 μl supernatant was taken out for UPLC-MS/MS analysis as described above. Values at 0 min were used as corresponding control for test compounds. Varapamil, metoprolol, and warfarin, categorized as fast, moderate and slow metabolism, were used as positive control. Incubates without NADPH group served as negative control.

Example 5 Solubility Determination

Solubility determinations shown in Table 3 were obtained turbidometrically and in a manner similar to the one described in Perez et al., *J. Biomol. Screen,* 2015, 20(2), 254-64. The method requires small volumes of 100× stock concentration drug solution to be prepared in DMSO 0, 0.23, 0.47, 0.94, 1.88, 3.75, 7.5, 15.0, 30.0 and 50.0 mM. The stock drug concentrations are then diluted 1:100 added into triplicate wells containing PBS in a clear bottom 384 well microtiter to achieve final testing concentrations of 0, 2.3, 4.7, 9.4, 18.8, 37.5, 75, 150, 300, 600 μM in 1% DMSO. The plate is allowed to equilibrate with constant shaking for 2 hours at room temperature. The plate is then placed in a SpectroMax V plate reader to measure absorbance at 620 nm. Increase in absorbance is evident in test wells which precipitation of the compound is evident. The plot of $OD_{620}$ vs. drug concentration is used to calculate the maximum solubility limit as determined by a statistically significant increase in absorbance above the background levels.

TABLE 3

| | | | | | | | | BBB penetration potential | |
|---|---|---|---|---|---|---|---|---|---|
| | Human Potency Data | | | | | | Stability | MDCK | MDCK |
| Compound # | HLM % inh. @ 250 nM | HLM % inh. @ 500 nM | IC50 (uM) HLM | rCYP4F2 % inh. @ 250 nM | rCYP4F2 % inh. @ 500 nM | EETs Inhibition (nM) | HLM % @ 30 min | A-B 10−6 cm/s | B-A 10−6 cm/s |
| 1 | 64.29 | 78.80 | 0.19 | 78.50 | | >10,000 | 100 | | |
| 2 | | 59.90 | 0.15 | | 47.60 | >50,000 | 61 | | |
| 3 | | 77.30 | 0.05 | | 77.00 | >25,000 | 85 | 62.00 | 60.00 |
| 4 | | 0.00 | | | 0.00 | | | | |
| 5 | | 24.50 | | | 2.60 | | | | |
| 6 | | 31.80 | | | 6.10 | | | | |
| 7 | | 51.70 | 0.19 | | 6.50 | 2.6% @ 50,000 | | | |
| 8 | | 62.70 | 0.17 | | 48.90 | >50,000 | | | |
| 9 | | 0.00 | | | 0.00 | | | | |
| 10 | | 0.00 | | | 0.00 | | | | |
| 11 | | 0.00 | | | 66.50 | | | | |
| 12 | | 0.00 | | | 63.70 | | | | |
| 13 | | 29.00 | | | 1.00 | | | | |
| 14 | | 53.00 | 0.22 | | 60.00 | | 97 | | |
| 15 | | 39.00 | | | 54.00 | | | | |
| 16 | | 27.00 | | | 28.00 | | | | |
| 17 | | 80.00 | | | 83.00 | | | | |
| 18 | | 66.00 | | | 70.00 | | | | |
| 19 | | 72.30 | 0.14 | | 41.40 | >25,000 | 89 | | |
| 20 | | 73.10 | 0.07 | | 67.70 | 3.1%@ 50,000 | 92 | 32.00 | 25.70 |
| 21 | | 8.80 | | | 2.00 | | | | |
| 22 | | 0.00 | | | 0.00 | | | | |
| 23 | | 67.40 | 0.11 | | 70.80 | | 61 | | |
| 24 | | 73.80 | 0.08 | | 79.90 | | 92 | | |
| 25 | | 56.40 | 0.28 | | 67.80 | | 100 | | |
| 26 | | 71.70 | 0.20 | | 81.70 | | 100 | | |
| 27 | | 20.00 | | | 14.00 | | | | |
| 28 | | 75.00 | 0.10 | | 58.00 | | | 18.40 | 40.20 |
| 29 | | 60.00 | 0.17 | | 55.00 | | | | |
| 30 | | 86.00 | 0.05 | | 95.00 | | 0 | | |
| 31 | | 35.00 | | | 44.00 | | | | |
| 32 | | 59.00 | 0.13 | | 67.00 | | | | |
| 33 | | 72.00 | 0.18 | | 69.00 | | | | |
| 34 | | 80.00 | 0.11 | | 86.00 | | | 60.10 | 48.60 |
| 35 | | 20.00 | | | 20.00 | | | | |
| 36 | | 46.00 | 0.65 | | 61.00 | | | | |
| 37 | | 0.00 | | | 31.90 | | | | |
| 38 | | 0.00 | | | 22.30 | | | | |
| 39 | | 6.00 | | | 22.70 | | | | |
| 40 | | 65.80 | 0.10 | | 75.90 | | 82 | | |
| 41 | | 32.00 | | | 0.00 | | | | |
| 42 | | 5.00 | | | 28.00 | | | | |
| 43 | | 82.00 | | | 79.00 | | | | |
| 44 | | 85.00 | 0.05 | | 86.00 | | 100 | | |
| 45 | | 71.00 | | | 73.00 | | | | |
| 46 | | 78.00 | | | 88.00 | | | | |
| 47 | | 82.00 | 0.08 | | 88.00 | | 100 | | |
| 48 | | 67.00 | | | 63.00 | | | | |
| 49 | | 80.00 | | | 90.00 | | | | |
| 50 | | 47.00 | | | 69.00 | | | | |
| 51 | | 77.00 | | | 94.00 | | | | |
| 52 | | 84.10 | 0.08 | | 74.80 | | 100 | | |
| 53 | 14.90 | | | 3.90 | | | | | |
| 54 | 31.60 | 47.40 | 0.44 | 53.60 | | >50,000 | 91 | | |
| 55 | 12.11 | | | 0.00 | | | | | |
| 56 | | 0.00 | | | 11.40 | | | | |
| 57 | | 0.00 | | | 41.20 | | | | |
| 58 | | 67.40 | 0.11 | | 70.60 | | 97 | | |
| 59 | | 63.30 | 0.19 | | 73.70 | | 98 | | |
| 60 | | 3.70 | | | 38.40 | | 100 | | |
| 61 | | 77.5 | | | 81.3 | | | | |
| 62 | | 60.0 | | | 45 | | | | |
| 63 | | 74.3 | | | 73.8 | | | | |
| 64 | | 88 | | | 72 | | | 46.4 | 34.8 |
| 65 | | 57.00 | | | 35 | | | | |
| 66 | | 36 | | | 58 | | | | |
| 67 | | 83.2 | | | 90.86 | | | | |
| 68 | | 48 | | | 70.9 | | | | |
| 69 | | 85.6 | | | 57.9 | | | 22.3 | 44.4 |
| 70 | | 84.8 | | | 80.5 | | | | |
| 71 | | 82 | | | 52.2 | | | | |

TABLE 3-continued

| | Human Potency Data | | | | | | Stability | BBB penetration potential | |
|---|---|---|---|---|---|---|---|---|---|
| | | | | | | | | MDCK | MDCK |
| Compound # | HLM % inh. @ 250 nM | HLM % inh. @ 500 nM | IC50 (uM) HLM | rCYP4F2 % inh. @ 250 nM | rCYP4F2 % inh. @ 500 nM | EETs Inhibition (nM) | HLM % @ 30 min | A-B 10−6 cm/s | B-A 10−6 cm/s |
| 72 | | 77 | | | 77 | | | | |
| 73 | | 61 | | | 54.7 | | | | |
| 74 | | 55 | | | 32 | | | | |
| 75 | | 61.10 | | | 74.50 | | | | |
| 76 | | 84 | | | 71 | | | | |
| 77 | | 84.4 | | | 55 | | | | |
| 78 | | 83.6 | | | 31 | | | | |
| 79 | | 60 | | | 62 | | | | |
| 80 | | 86 | | | 90 | | | | |
| 81 | | 83.1 | 0.0474 | | 66 | | | | |
| 82 | | 75 | | | 36 | | | | |
| 83 | | 91.6 | 0.0542 | | 96.2 | >50 | 91 | 5.16 | 41.6 |
| 84 | | 79.4 | | | 80.3 | | | | |
| 85 | | 81.3 | | | 64 | | | | |
| 86 | | 37.9 | | | 49.4 | | | | |
| 87 | | 15.6 | | | 7.4 | | | | |
| 88 | | 39.8 | | | 26.4 | | | | |
| 89 | | 34.8 | | | 72.9 | | | | |
| 90 | | 67 | | | 70.3 | | | | |
| 91 | | 40.4 | | | 39.1 | | | | |
| 92 | | 77.3 | | | 87.1 | | | | |
| 93 | | 93.03 | 0.017 | | 97.02 | 50% @ 10 μM | 85 | 44.3 | 40 |
| 94 | | 61.3 | | | 60.3 | | | | |
| 95 | | 42.8 | | | 26.3 | | | | |
| 96 | | 63.10 | | | 16.40 | | | | |
| 97 | | 35.30 | | | 22.90 | | | | |
| 98 | | 37.20 | | | 25.00 | | | | |
| 99 | | 17.70 | | | 0.00 | | | | |
| 100 | | 76.1 | 0.054 | | 81.2 | >50 | 95 | 22.20 | 46.90 |
| 101 | | 79.00 | | | 80.00 | | | 33.80 | 46.70 |
| 102 | | 36.50 | | | 27.90 | | | | |
| 103 | | 0.00 | | | 0.00 | | | | |
| 104 | | 86.1 | | | 78.00 | | | 50.40 | 48.90 |
| 105 | | 77.30 | | | 78.00 | | | | |
| 106 | | 0.00 | | | 0.00 | | | | |
| 107 | | 78.90 | | | 82.30 | | | | |
| 108 | | 90.00 | | | 83.00 | | | | |
| 109 | | 90.30 | | | 86.00 | | | 10.80 | 77.50 |
| 110 | | 80.4 | | | 84.1 | | | | |
| 111 | | 43.5 | | | 60.10 | | | | |
| 112 | | 21.90 | | | 41.30 | | | | |
| 113 | | 30.5 | | | 67.6 | | | | |
| 114 | | 68.7 | | | 87.4 | | | | |
| 115 | | 85.50 | | | 84.20 | | | | |
| 116 | | 86.40 | | | 89.30 | | | 77.40 | 70.30 |
| 117 | | | | | | | | | |
| 118 | | | | | | | | | |
| 119 | | | | | | | | | |
| 120 | | | | | | | | | |
| 121 | | | | | | | | | |
| 122 | | | | | | | | | |
| 123 | | | | | | | | | |
| 124 | | | | | | | | | |
| 125 | | | | | | | | | |
| 126 | | | | | | | | | |
| 127 | | | | | | | | | |
| 128 | | | | | | | | | |
| 129 | | | | | | | | | |

TABLE 4

| | Rat Potency Data | | | | | | |
|---|---|---|---|---|---|---|---|
| Compound # | RKM % inh. @ 250 nM | RKM % inh. @ 500 nM | RLM % inh. @ 250 nM | RLM % inh. @ 500 nM | RLM IC50 (uM) | Solubility_ug/mL | Max Solub (uM) |
| 1 | 18.00 | | 27.40 | | | 28.00 | 121 |
| 2 | | 0.00 | | 0.00 | | | oil |
| 3 | | 0.00 | | 2.40 | | 122.00 | 505 |
| 4 | | 0.00 | | 0.00 | | | |
| 5 | | 0.00 | | 0.00 | | | |
| 6 | | 1.20 | | 0.00 | | | |
| 7 | | 0.00 | | 42.30 | | 127.00 | 494 |
| 8 | | 0.00 | | 45.50 | | 29.00 | 111 |
| 9 | | 0.00 | | 0.00 | | | |
| 10 | | 0.00 | | 0.00 | | | |
| 11 | | 1.60 | | 3.60 | | | |
| 12 | | 6.40 | | 18.30 | | | |
| 13 | | 27.00 | | 3.00 | | | |
| 14 | | | | 0.00 | | | |
| 15 | | 27.00 | | 16.00 | | | |
| 16 | | 0.00 | | 29.00 | | | |
| 17 | | 25.00 | | 57.00 | | | |
| 18 | | 0.00 | | 41.00 | | | |
| 19 | | 0.00 | | 31.80 | | 27.30 | 106 |
| 20 | | 4.90 | | 25.90 | | 9.00 | 35 |
| 21 | | | | 0.00 | | | |
| 22 | | | | 0.00 | | | |
| 23 | | | | 0.00 | | 40.10 | 166.2 |
| 24 | | | | 16.30 | | 20.60 | 85.4 |
| 25 | | | | 21.30 | | 63.90 | 235.3 |
| 26 | | | | 27.80 | | 99.40 | 366.4 |
| 27 | | 0.00 | | 8.00 | | 179.00 | >600 |
| 28 | | 43.00 | | 52.00 | | 179.00 | >600 |
| 29 | | 7.00 | | 38.00 | | 170.60 | >600 |
| 30 | | 40.00 | | 37.00 | | 137.00 | 481.8 |
| 31 | | 9.00 | | 0.00 | | 155.00 | >600 |
| 32 | | 25.00 | | 0.00 | | 101.00 | 391 |
| 33 | | 16.00 | | 12.00 | | | oil |
| 34 | | 36.00 | | 44.00 | | 144.80 | >600 |
| 35 | | 4.00 | | 0.00 | | | oil |
| 36 | | 4.00 | | 0.00 | | | 752 |
| 37 | | | | 0.00 | | | |
| 38 | | | | 0.00 | | | |
| 39 | | | | 0.00 | | | |
| 40 | | | | 7.80 | | 24.80 | 95.5 |
| 41 | | 0.00 | | 0.00 | | 107.60 | 369.2 |
| 42 | | 0.00 | | 0.00 | | | |
| 43 | | 31.00 | | 17.00 | | | |
| 44 | | 21.00 | | 42.00 | 0.34 | | |
| 45 | | 0.00 | | 24.00 | | | |
| 46 | | 0.00 | | 47.00 | | | |
| 47 | | 0.00 | | 63.00 | | | |
| 48 | | 8.00 | | 0.00 | | | |
| 49 | | 28.00 | | 31.00 | | | |
| 50 | | 18.00 | | 16.00 | | | |
| 51 | | 26.00 | | 53.00 | | | |
| 52 | | | | 13.40 | | 78.00 | 244.1 |
| 53 | 8.20 | | 4.30 | | | | |
| 54 | 0.00 | | 12.00 | | | 137.00 | >600 |
| 55 | 0.00 | | 0.00 | | | | |
| 56 | | | | 0.00 | | | |
| 57 | | | | 43.10 | | | |
| 58 | | | | 0.00 | | 125.70 | 393.6 |
| 59 | | | | 64.40 | | 155.00 | >600 |
| 60 | | | | 0.00 | | | |
| 61 | | | | 61.00 | | | 121 |
| 62 | | | | 0.00 | | | 42.4 |
| 63 | | | | 10.30 | | | 13.3 |
| 64 | | | | 49.00 | | | 19.5 |
| 65 | | | | 0.00 | | | 18.7 |
| 66 | | | | 0.00 | | | 133 |
| 67 | | | | 30.20 | | | 204.9 |
| 68 | | | | 0 | | | |
| 69 | | | | 27.70 | | | 304 |
| 70 | | | | 35.70 | | | 109 |
| 71 | | | | 25.00 | | | >600 |
| 72 | | | | 11.00 | | | 234 |
| 73 | | | | 0.00 | | | 164 |
| 74 | | | | 0.00 | | | 201 |

TABLE 4-continued

| Compound # | Rat Potency Data RKM % inh. @ 250 nM | RKM % inh. @ 500 nM | RLM % inh. @ 250 nM | RLM % inh. @ 500 nM | RLM IC50 (uM) | Solubility_ug/mL | Max Solub (uM) |
|---|---|---|---|---|---|---|---|
| 75 | | | | 0.00 | | | 127 |
| 76 | | | | 0.00 | | | |
| 77 | | | | 13.80 | | | |
| 78 | | | | 0.00 | | | |
| 79 | | | | 4.00 | | | |
| 80 | | | | 42.00 | | | 89 |
| 81 | | | | 19.30 | | | 353 |
| 82 | | | | 2.00 | | | |
| 83 | | | | 49.60 | 0.72 | | >600 |
| 84 | | | | 42.70 | | | >600 |
| 85 | | | | 0.00 | | | |
| 86 | | | | 18.10 | | | |
| 87 | | | | 2.70 | | | |
| 88 | | | | 0.00 | | | |
| 89 | | | | 0.00 | | | 324.3 |
| 90 | | | | 20.80 | | | |
| 91 | | | | 0.00 | | | |
| 92 | | | | 0.00 | | | |
| 93 | | | | 64.30 | 0.12 | | 117 |
| 94 | | | | 13.50 | | | |
| 95 | | | | 15.40 | | | |
| 96 | | | | 0.00 | | | |
| 97 | | | | 0.00 | | | |
| 98 | | | | 5.00 | | | |
| 99 | | | | 0.00 | | | |
| 100 | | | | 42.90 | 0.57 | | 74 |
| 101 | | | | 48.70 | | | 158 |
| 102 | | | | 0.00 | | | |
| 103 | | | | 0.00 | | | |
| 104 | | | | 36.00 | | | 31 |
| 105 | | | | 17.00 | | | |
| 106 | | | | 0.00 | | | |
| 107 | | | | 63.60 | | | 216 |
| 108 | | | | 41.70 | | | 187 |
| 109 | | | | 62.70 | | | >600 |
| 110 | | | | 63.60 | | | 421 |
| 111 | | | | 22.30 | | | |
| 112 | | | | 20.30 | | | |
| 113 | | | | 14.30 | | | |
| 114 | | | | 36.70 | | | 74 |
| 115 | | | | 74.30 | | | 74 |
| 116 | | | | 59.60 | | | 71 |
| 117 | | | | | | | |
| 118 | | | | | | | 443 |
| 119 | | | | | | | 63 |
| 120 | | | | | | | |
| 121 | | | | | | | 122.3 |
| 122 | | | | | | | 247.2 |
| 123 | | | | | | | 85.5 |
| 124 | | | | | | | 26.6 |
| 125 | | | | | | | >600 |
| 126 | | | | | | | >600 |
| 127 | | | | | | | 151 |
| 128 | | | | | | | |
| 129 | | | | | | | |

* * *

In one embodiment, one or more compounds ofany disclosure of Table 3, or a pharmaceutically acceptable salt or solvate thereof, is excluded from the compound of formula I.

The entire disclosure of each disclosure tabulated in Table 4 is hereby incorporated by reference.

TABLE 5

| |
|---|
| Hoechst Schering Agrevo Gmbh; JP 07-506347 A 1995 |
| Hoechst Schering Agrevo Gmbh; U.S. Pat. No. 5,571,815 A1 1995 |
| Hoechst Schering Agrevo Gmbh; WO 9319050 A1 1995 |

TABLE 5-continued

| | |
|---|---|
| Hoechst Schering Agrevo Gmbh; JP 05-502446 A 1997 | |
| Hoechst Schering Agrevo Gmbh; U.S. Pat. No. 5,723,450 A 1997 | |
| Hoechst Schering Agrevo Gmbh; WO 9507891 A1 1997 | |
| Nippon Soda Co Ltd; WO 20050953801 A1 2005 | |
| Abdelhamid, I; Heterocycles 2007, 71, 2627 | Abdelhamid, I; Synthesis 2010, 1107 |
| Abdelhamid, I; Synlett 2008, 10, 625 | Abdelhamid, I; Synthesis (Stuttg) 2010, 1107 |
| Abdelhamid, I; Synlett 2009, 625 | Abdelhamid, I; Tetrahedron 2009, 65, 10069 |
| Agrawal, A; Chem Mater 1993, 5, 633 | Al-Mousawi, S; Current 2011, 3503 |
| Andriushchenko, A; J Heterocycl Chem 2011, 48, 365 | |
| Anwar, H; ARKIVOC 2009, 1, 198 | |
| ASTRAZENECA AB; WO 2009081197 A1 2009 | |
| Behbehani, H; ARKIVOC 2010, 2, 267 | Bhaskar, G; Eur J Med Chem 2012, 51, 79 |
| BRADBURY ROBERT HUGH; WO 2009081197 A1 2009 | |
| Burgi, H; Structure Correlation 1994, 2, 730 | |
| Chebanov, V; Azaheterocycles Based on a, b-Unsaturated Carhonyls 2008 | |
| Chebanov, V; Chem Heterocycl Compd 2004, 40, 475 | |
| Chebanov, V; J Comb Chem 2006, 8, 427 | Chebanov, V; Org Lett 2007, 9, 1691 |
| Chebanov, V; J Org Chem 2008, 73, 5110 | Chebanov, V; Tetrahedron 2007, 63, 1229 |
| Chebanov, V; Top Heterocycl Chem 2010, 23, 41 | |
| Chebanov, V; Ultrason Sonochem 2012, 19, 707 | |
| Chen, H; J Comb Chem 2010, 12, 571 | Chung, H; J Nat Prod 2001, 64, 1579 |
| Chen, Y; J Med Chem 2001, 44, 2374 | Debnath, K; RSC Adv 2015, 5, 31866 |
| Desenko, S; Chem Heterocycl Compd 1990, 26, 839 | |
| Desenko, S; Chem Heterocycl Compd 1993, 29, 406 | |
| Drizin, I; Bioorg Med Chem Lett 2002, 12, 1481 | |
| D?mling, A; Chem Rev 2012, 112, 3083 | El Ella, D; Bioorg Med Chem 2008, 16, 2391 |
| El-Sayed, O; Boll Chim Farm 2003, 143, 227 | Elnagdi, M; Adv Heterocycl Chem 2009, 97, 1 |
| El-Sayed, O; Boll Chim Farm 2004, 143, 227 | Elguero, J; Targets Heterocycl Syst 2002, 6, 52 |
| Elmaati, T; J Heterocycl Chem 2004, 41, 109 | |
| Elnagdi, M; Comprehensive Heterocyclic Chemistry II 1996, 7, 431 | |
| Eloff, J; Planta Med 1998, 64, 711 | Gakhar, G; Drug Dev Res 2008, 69, 526 |
| Galliford, C; Angew Chem Int Ed 2007, 46, 8748 | |
| Genin Michael James; WO 2009012125 A1 2009 | |
| Ghotekar, B; J Heterocycl Chem 2009, 46, 708 | Ghozlan, S; J Heterocycl Chem 2005, 42, 1185 |
| Ghozlan, S; Arch Pharm 2015, 348, 113 | Ghozlan, S; J Heterocycl Chem 2007, 44, 105 |
| Ghozlan, S; J Chem Res 2004, 789 | Ghozlan, S; Tetrahedron 2015, 71, 1413 |
| Ghorab, M; Arzneimittelforschung 2008, 58, 35 | |
| Ghorab, M; Med Chem Res 2010, 20, 388 | |
| Ghorab, M; Phosphorus Sulfur Silicon Relat Elem 2007, 183, 90 | |
| Ghorab, M; Phosphorus Sulfur Silicon Relat Elem 2008, 183, 2891 | |
| Ghorab, M; Phosphorus Sulfur Silicon Relat Elem 2008, 183, 2906 | |
| Ghorab, M; Phosphorus Sulfur Silicon Relat Elem 2008, 183, 2918 | |
| Ghorab, M; Phosphorus Sulfur Silicon Relat Elem 2008, 183, 2929 | |
| Ghozlan, S; Arch Pharm (Weinheim) 2015, 348, 113 | |
| Ghozlan, S; Arkivoc 2009, 2009, 302 | Ghozlan, S; J Heterocycl Chem 2005, 42, 1185 |
| Ghozlan, S; Curr Org Chem 2011, 15, 3098 | Ghozlan, S; J Heterocycl Chem 2007, 44, 105 |
| Ghozlan, S; J Heterocycl Chem, 10.1002/jhet.2341. 2015 | |
| Ghozlan, S; Tetrahedron 2015, 71, 1413 | |
| Giuseppe, D; Trends Heterocycl Chem 1991, 2, 97 | |
| Hennig, L; J Prakt Chem 1990, 332, 351 | IRM LLC; WO 2012087520 A1 2012 |
| Henry, R; J Am Chem Soc 1954, 76, 923 | IRM LLC; WO 2012087521 A1 2012 |
| Ho, J; Helv Chim Acta 2008, 91, 958 | Hao, W; ACS CatA1 2013, 3, 2501 |
| Hoepping, A; Bioorg Med Chem 2008, 16, 1184 | |
| Jadidi, K; Tetrahedron 2009, 65, 2005 | |
| Jegou, G; Macromolecules 2001, 34, 7926 | Joshi, K; J Fluorine Chem 1989, 42, 149 |
| Jenekhe, S; Macromolecules 2001, 34, 7315 | Kang, S; Synthesis 2013, 45, 2593 |
| Jenekhe, S; Science 1998, 279, 1903 | Kinzel Olaf; WO 2013007387 A1 2013 |
| Jenekhe, S; Science 1999, 283, 372 | Kumar, M; Tetrahedron Lett 2012, 53, 4604 |
| Jiang, B; Eur J Org Chem 2011, 3026 | Li, X; J Org Chem 2015, 80, 1841 |
| Maguire, M; J Med Chem 1994, 37, 2129 | Lilly Co., Eli; WO 2009012125 A1 2009 |
| Lipson, V; Chem Heterocycl Compd 2003, 39, 1041 | |
| Lipson, V; Russ J Org Chem 2005, 41, 114 | Miyaoka, H; Tetrahedron Lett 1998, 39, 6503 |
| Maguire, M; J Med Chem 1994, 37, 2129 | Mondal, A; ACS Comb Sci 2015, 17, 404 |
| Moukha-chafiq, O; Nucleosides Nucleotides 2003, 22, 967 | |
| Muravyova, E; Synthesis 2009, 1375 | Muravyova, E; Tetrahedron 2011, 67, 9389 |
| Mustazza, C; J Heterocycl Chem 2001, 38, 1119 | |
| Nagahara, K; J Heterocycl Chem 1994, 31, 239 | |
| Neurogen Corp; WO 0248152 A2 2002 | Neurogen Corp; EP 1347982 A2 2002 |
| Neurogen Corp; US 2003036652 A1 2002 | |
| Phenex Pharmaceuticals AG; WO 2013007387 A1 2013 | |
| Radl, S; J Heterocycl Chem 2010, 47, 276 | |
| Reddy, K; Indian J Chem Sect B: Org Chem Incl Med Chem 1992, 31, 163 | |
| Reddy, K; Indian J Chem Sect B: Org Chem Incl Med Chem 1993, 32, 586 | |
| Riyadh, S; Heterocycles 2008, 75, 1849 | Sadek, K; Beilstein J Org Chem 2012, 8, 18 |
| Roma, G; Eur J Med Chem 2000, 35, 1021 | Sakhno, Y; Mol Diversity 2010, 14, 5231 |
| Sedash, Y; RSC Adv 2012, 2, 6719 | |
| Sheldrick, G; Acta Crystallogr, Sect A 2008, 64, 112 | |
| Singh, S; Bioorg Med Chem Lett 2004, 14, 499 | |
| Terrett, N; Bioorg Med Chem Lett 1996, 6, 1819 | |

TABLE 5-continued

| | | |
|---|---|---|
| Tian, Y; PloS One 2012, 7, e49306 | | Woodward, R; J Am Chem Soc 1951, 73, 4057 |
| Tully David C; WO 2012087520 A1 2012 | | Zefirov, N; J Phys Org Chem 1990, 3, 147 |
| Tully David C; WO 2012087521 A1 2012 | | Zhu, S; Synth Commun 2009, 39, 1355 |
| Vinogradov, V; Khim-Farm Zh 1994, 28, 37 | | Bayer Ag; JP 02-111773 A 1990 |
| Wang, S; Tetrahedron 2011, 67, 9417 | | Bayer Ag; EP 0355599 A1 1990 |
| Wawer, I; J Pharm Biomed Anal 2005, 38, 865 | | Bayer Ag; U.S. Pat. No. 4,985,063 A 1990 |
| Glaxo Group Ltd; WO 2005014578 A1 2005 | | |
| Hoechst Schering Agrevo Gmbh; JP 07-506347 A 1995 | | |
| Hoechst Schering Agrevo Gmbh; U.S. Pat. No. 5,571,815 A1 1995 | | |
| Hoechst Schering Agrevo Gmbh; WO 9319050 A1 1995 | | |
| Hoechst Schering Agrevo Gmbh; JP 05-502446 A 1997 | | |
| Hoechst Schering Agrevo Gmbh; U.S. Pat. No. 5,723,450 A 1997 | | |
| Hoechst Schering Agrevo Gmbh; WO 9507891 A1 1997 | | |
| Nippon Soda Co Ltd; WO 2005095380 A1 2005 | | |
| Nippon Soda Co Ltd; WO 2005095380 A1 2005 | | |
| Richter Gedeon Vegyeszeti Gyar Rt; GB 2102801 A 1983 | | |
| Richter Gedeon Vegyeszeti Gyar Rt; DE 3226921 A1 1983 | | |
| Richter Gedeon Vegyeszeti Gyar Rt; U.S. Pat. No. 4,451,473 A 1983 | | |
| Richter Gedeon Vegyeszeti Gyar Rt; JP 58-049383 A 1983 | | |
| Zenaca Ltd; WO 1998022462 A1 2001 | | Zenaca Ltd; JP 2001506989 A 2001 |
| Zenaca Ltd; WO 1998025924 A1 2001 | | Zenaca Ltd; U.S. Pat. No. 5,912,254 A 2001 |
| Zenaca Ltd; JP 2001504476 A 2001 | | Zenaca Ltd; U.S. Pat. No. 5,968,947 A 2001 |
| Haque, T; Bioorganic & Medicinal Chemistry Letters, 10.1016/J.BMCL.2009.08.077 2009, 19, 5872 | | |
| Novartis Ag; WO 2008110611 A1 2008 | | Pfizer; WO 2009144555 A1 2009 |
| Pfizer; OA 13029 A 2006 | | Pfizer Ltd; WO 2004037809 A1 2004 |
| Yu, G; Journal of Medicinal Chemistry, 10.1021/JM070035A 2007, 50, 1078 | | |
| U.S. Pat. No. 4,178,449 A | | U.S. Pat. No. 4,281,000 A |
| Hoechst Schering Agrevo Gmbh; JP 07-506347 A 1995 | | |
| Hoechst Schering Agrevo Gmbh; U.S. Pat. No. 5,571,815 A1 1995 | | |
| Hoechst Schering Agrevo Gmbh; WO 9319050 A1 1995 | | |
| Hoechst Schering Agrevo Gmbh; JP 05-502446 A 1997 | | |
| Hoechst Schering Agrevo Gmbh; U.S. Pat. No. 5,723,450 A 1997 | | |
| Hoechst Schering Agrevo Gmbh; WO 9507891 A1 1997 | | |
| Nippon Soda Co Ltd; WO 2005095380 A1 2005 | | |
| Abdulmalik, O; Acta Cryst 2011, D67, 920 | | Ackermann; US 20050096337 A1 2005 |
| Abraham; US 20010046997 A1 2001 | | Adhikary, P; Experientia 1978, 34, 804 |
| Ackermann; U.S. Pat. No. 6,242,644 B1 2001 | | Ahlem; US 20030060425 A1 2003 |
| DE 2238628 1973 | U.S. Pat. No. 3,926,999 A | WO 2005087766 2005 |
| DE 2238734 1973 | U.S. Pat. No. 3,944,551 A | WO 2005096337 2005 |
| FR 2217016 1974 | U.S. Pat. No. 3,988,348 A | WO 2006003923 2006 |
| GB 1409865 1975 | U.S. Pat. No. 4,421,753 A | WO 2006011469 2006 |
| EP 10063 1980 | WO 199611902 1996 | WO 2006065204 2006 |
| DE 2853765 1980 | DE 4442050 1996 | WO 2006088173 2006 |
| DE 2904829 1980 | WO 199744306 1997 | WO 2006103463 2006 |
| GB 1593417 1981 | WO 0078748 A1 | WO 2006106711 2006 |
| EP 0054924 1982 | WO 0107432 A2 | WO 2006116764 2006 |
| JP 57145844 1982 | WO 2004011436 A1 | JP 2006342115 2006 |
| JP 59029667 1984 | WO 2004035569 A2 | WO 2007003962 2007 |
| DE 226590 1985 | WO 2004089947 A2 | WO 2007009389 2007 |
| DE 3503435 1985 | WO 2005070430 A1 | WO 2007017267 2007 |
| IL 64573 1985 | WO 9506047 A1 | WO 2007047204 2007 |
| DE 3431004 1986 | WO 199808818 1998 | WO 2007049675 2007 |
| JP 61040236 1986 | WO 199821199 1998 | WO 2007061923 2007 |
| EP 236140 1987 | WO 199943672 1999 | WO 2007084914 2007 |
| DE 3704223 1987 | WO 199947529 1999 | WO 2007117180 2007 |
| EP 0268989 1988 | WO 199959978 1999 | CN 101113148 2008 |
| EP 0637586 1988 | WO 199962908 1999 | WO 2008013414 2008 |
| DE 258226 1988 | WO 9929694 1999 | WO 2008016132 2008 |
| EP 278686 1988 | WO 9948490 1999 | WO 2008029200 2008 |
| EP 291916 1988 | WO 0012121 2000 | WO 2008041118 2008 |
| JP 63230687 1988 | WO 0026202 2000 | WO 2008051532 2008 |
| JP 63258463 1988 | WO 2000035858 2000 | WO 2008066145 2008 |
| JP 01190688 1989 | WO 2000040564 2000 | WO 2008080391 2008 |
| EP 0348155 1989 | WO 2000075145 2000 | WO 2008081096 2008 |
| EP 303465 1989 | WO 200071123 A1 2000 | WO 2008101682 2008 |
| EP 336369 1989 | WO 0132596 2001 | WO 2008116620 2008 |
| EP 0365328 1990 | WO 2001000612 2001 | WO 2009001214 2008 |
| EP 0401517 1990 | WO 2001019823 2001 | FR 2909379 2008 |
| DE 276479 1990 | WO 2001023383 2001 | WO 2009050183 2009 |
| DE 276480 1990 | WO 2001036375 2001 | WO 2009125606 2009 |
| DE 3931954 1990 | WO 2001057006 2001 | WO 2009128537 2009 |
| WO 199119697 1991 | WO 2001057044 2001 | WO 2009130560 2009 |
| EP 453210 1991 | WO 2001062705 2001 | WO 2009136889 2009 |
| EP 462800 1991 | WO 2001070663 2001 | WO 2009146555 2009 |
| WO 199202503 1992 | WO 2002000622 2002 | JP 2009203230 2009 |
| EP 481802 1992 | WO 2002012235 2002 | EP 2123637 2009 |
| EP 0352944 A1 1990 | WO 2002024635 2002 | CA 2720096 2009 |
| EP 0659745 A1 1995 | WO 2002024679 2002 | WO 2010031589 2010 |
| WO 2006061147 2006 | WO 2002051849 2002 | WO 2010056631 2010 |
| EP 498380 1992 | WO 2002053547 2002 | WO 2010129055 2010 |

TABLE 5-continued

| | | |
|---|---|---|
| EP 0528337 1993 | JP 2002523469 2002 | EP 2149545 2010 |
| EP 0542372 1993 | JP 2002528537 2002 | CN 102116772 2011 |
| WO 199317013 1993 | WO 2003051366 2003 | WO 2011033045 2011 |
| EP 567133 1993 | WO 2003053368 2003 | WO 2011136459 2011 |
| JP 06041118 1994 | JP 2003075970 2003 | EP 2305625 2011 |
| WO 199401406 1994 | WO 2003101959 2003 | WO 2012138981 2012 |
| DE 4318550 1994 | JP 2003513060 2003 | WO 2012141228 2012 |
| DE 2261351 A1 | WO 2004014899 2004 | WO 2013052803 2013 |
| EP 0632036 1995 | WO 2004018430 2004 | WO 2013102142 2013 |
| EP 0640609 1995 | WO 2004024705 2004 | WO 2013102145 2013 |
| JP 07025882 1995 | WO 2004050030 2004 | WO 2013102145 2013 |
| WO 199514015 1995 | WO 2004056727 2004 | WO 2013102145 2013 |
| WO 199521854 1995 | WO 2004058790 2004 | WO 2014150256 2014 |
| EP 0747393 1996 | WO 2004087075 2004 | WO 2014150258 2014 |
| U.S. Pat. No. 4,178,449 A | WO 2004111031 2004 | WO 2014150261 2014 |
| U.S. Pat. No. 4,281,000 A | WO 2005047249 2005 | WO 2014150268 2014 |
| U.S. Pat. No. 3,534,058 A | WO 2005074513 2005 | WO 2014150276 2014 |
| U.S. Pat. No. 3,839,336 A | WO 2005077932 2005 | WO 2014150289 2014 |
| U.S. Pat. No. 3,920,693 A | WO 2005086951 2005 | WO 2015031284 2015 |
| WO 2015031285 2015 | | |

Abdulmalik et al, “Sickle cell disease: current therapeutic approaches,” Expert Opinion Ther Patents, 15(11): 1497-1506 (2005) 2005

Abraham et al, “Vanillin, a potential agent for the treatment of sickle cell anemia,” Blood, 77(6): 1334-1341 (1991) 1991

Adhikary et al, “A new antisickling agent: In vitro studies of its effect on S/S erythrocytes and on hemoglobin S,” Experientia, 34(6): 804-806 (1978) 1978

Babu, et al. Regioselective synthesis and structural elucidation of 1,4-disubstituted 1,2,3-triazole derivatives using 1D and 2D NMR spectral techniques. Magn. Reson. Chem., 49: 824-829. doi: 10.1002/mrc.2820

Bacsa et al, “Novel products from Baylis-Hillman reactions of salicylaldehydes,” South African Journal of Chemistry, 51(1): 47-54 (1998) 1998

Ballerini et al, High pressure Diels-Alder approach to hydroxy-substituted 6a-cyano-tetahydro-6Hbenzo[c]chromen-6-ones: A route to D6-Cis-Cannabidiol, J Org Chem, 74(11): 4511-4317 (2009) 2009

Ballet et al, “Novel selective human melanocortin-3 receptor ligands: Use of the 4-amino-1,2,4,5-tetrahydro-2-benzazepin-3-one (Aba) scaffold,” Bioorganic & Medicinal Chemistry Letters, 17(9): 2492-2498 (2007) 2007

Barnes “COPD: is there light at the end of the tunnel?” Current Opinion in Pharmacology, 2004, 4: 263-272 2004

Barnes, et al, “Prospects for new drugs for chronic obstructive pulmonary disease.” The Lancet, 2004, 364, 985-996 2004

Baxter et al, “Reductive aminations of carbonyl compounds with borohydride and borane reducing agents,” Organic Reactions (Hoboken, NJ, United States), 59, including pp 1-57 and 660-727, 125 pages (2002) 2002

Beaumont et al, Design of ester prodrugs to enhance oral absorption of poorly permeable compounds: challenges to the discovery scientist Curr Drug Metab 2003, 4: 461-85 2003

Beddell, “Substituted benzaldehydes designed to increase the oxygen affinity of human haemoglobin and inhibit the sickling of sickle erythrocytes,” Br J Pharmac, 82: 397-407 (1984)1984

Beena et al, “Synthesis and antibacterial activity evaluation of metronidazole-triazole conjugates,” Bioorg Med Chem Lett, 19(5): 1396-1398 (2009) 2009

Berge et al, “Pharmaceutical Salts,” Journal of Pharmaceutical Science, 66: 1-19 (1977) 1977

Bernstein Crystals in Supramolecular Chemistry ACA Transactions 2004; 39: 1-14 2004

Bernstein Polymorphism in Molecular Crystals Clarendon Press, Oxford 2002 115-118, 272 2002

Bode et al, “Novel synthesis and x-ray crystal structure of a coumarin derivative,” South African Journal of Chemistry, 45(1): 25-27 (1992) 1992

Bonaventura, et al, “Molecular Controls of the Oxygenation and Redox Reactions of Hemoglobin.” Antioxidants & Redox Signaling, 18(17), 2013, 2298-2313 2013

Bradbury et al, “New nonpeptide angiotensin II receptor antagonists”, Journal of Medicinal Chemistry, 1993, vol 36, pp 1245-1254 1993

Braga, et al Making crystals from crystals: a green route to crystal engineering and polymorphism Chem Commun (Camb) Aug. 7, 2005; (29): 3635-45 Epub Jun. 15, 2005 2005

Britton et al, “Structure-activity relationships of a series of benzothiophene-derived NPY Y1 antagonists: optimization of the C-2 side chain.” Bioorganic & Medicinal Chemistry Letters 9(3): 475-480 (1999) 1999

Brown et al, “1,2-Dihydroisoquinolines-III Dimerization,” Tetrahedron, 22(8): 2437-2443 (1966) 1966

CAS Registry No 1039841-20-7; entry dated Aug. 10, 2008 2008

CAS Registry No 1096911-11-3; entry dated Jan. 28, 2009 2009

CAS Registry 1153166-41-6; entry dated Jun. 7, 2009 2009

CAS Registry No 1153961-01-3; entry dated Jun. 8, 2009 2009

CAS Registry No 1184809-65-1; entry dated Sep. 15, 2009 2009

CAS Registry No 1303782-57-1; entry dated Jun. 1, 2011 2011

CAS Registry No 1306264-96-9; entry dated Jun. 5, 2011 2011

CAS Registry No 631858-40-7; entry dated Dec. 29, 2003 2003

CMU Pharmaceutical polymorphism, internet p 1-3 (2002) printout Apr. 3, 2008 2002

Caira Crystalline Polymorphism of Organic Compounds Topics in Current Chemistry, Springer, Berlin, DE 1998; 198: 163-208 1998

Chemical Abstract Registry No <collkey context = “embedded” form = “n-2-1” fkey = “y”

TABLE 5-continued coll = "registry"> 1142191-55-6, Indexed in the Registry File on STN CAS Online May 4, 2009, 1 page (2009) 2009
Cherian et al, "Structure-activity relationships of antitubercula nitro imidazoles 3, exploration of the linker and lipophilic tail of ((S)-2-nitro-6,7-dihydro-5H-imidazol[2,1b] [1,3]oxazin-6-yl)-(4-trifluoromethoxy-benzyl)amine (6-Amino PA-824)," J Med Ch 2011
Ciganek, "The catalyzed alpha-hydroxyalkylation and alpha-aminoalkylation of activated olefins (the Morita- Baylis-Hillman reaction," Organic Reactions (Hoboken, NJ, United States), 51: 201-267 and 342-350, 76 pages (1997) 1997
Concise Encyclopedia Chemistry, NY: Walter de Gruyter, 1993, 872-873 1993
Congreve et al Application of Fragment Screening by X-ray Crstallography to the Discovery of Aminopyridimes as Inhibitors of Beta-Secretase J Med Chem 50: 1124-1132 (2007) 2007
Cos et al, "Structure-activity relationship and classification of flavonoids as inhibitors of xanthineoxidease and superoxide scavengers." J Nat Prod. 61: 71-76 (1998) 1998
Database Espacenet, Bibliographic data: CN102952062 (A), Li et al, "Substituted-benzoheterocycle derivatives, preparation, and application for preparation of antiviral or antineoplastic drugs," XP002726578 retrieved from STN Database accession No 2013: 36677 2013
Database Pubchem Compound Dec. 4, 2011 XP 003033770 (11 pages) 2011
DATABASE PUBCHEM 4 Dec. 2011 Database accession no. 54009805
DATABASE PUBCHEM 19 Aug. 2012 Database accession no. 58443281
Davidovich, et al Detection of polymorphism by powder x-ray diffraction: interference by preferred orientation Am Pharm Rev 2004; 10, 12, 14, 16, 100 2004
Dean Analytical Chemistry Handbook University of Tennesse, Knoxville McGraw-Hill, Inc 1995; 10.24-10.26 1995
Deem "Red Blood Cells and Hemoglobin in Hypoxic Pulmonary Vasoconstriction" Advances in experimental medicine and biology, (2006) 588, 217-231 2006
Desai et al Preparation of N-[ro-(4-aryl-1-piperazinyl)ethyl/propyl]-3-hydroxyphthalimidines Indian Journal of Chemistry 39: 455-457 (2000) 2000
Desideri et al, "Guanylhydrazones of 3-substituted 2-pyridinecarboxaldehyde and of (2-substituted 3-pyridinyloxy) acetaldehyde as prostanoid biosynthesis and platelet aggregation inhibitors", European Journal of Medicinal Chemistry, Editions Scientifique E 1991
Di Stilo, et al New 1,4-dihydropyridines conjugated to furoxanyl moieties, endowed with both nitric oxide-like and calcium channel antagonist vasodilator activities J Med Chem 41: 5393-5401 (1998) 1998
Ding et al, "Crystal structure of bis(m3-oxo)-bis[m2-2-(2-formylphenoxy)acetato-O,O']-bis[m2-2-(2-formylphenoxy)acetato-O,O']-octakis(n-butyl)tetratin(IV), Sn4O2(C9H7O4)4(C4H9)8," Zeitschrift fuer Kristallographie-New Crystal Structures, 226(1): 31-32 (2011 2011
Doelker English translation of Ann Pharm Fr, 2002, 60: 161-176, pp 1-39 2002
Doelker, English translation of S.T.P, Pratiques (1999), 9(5), 399-409, pp 1033 1999
Einfalt, et al Methods of amorphization and investigation of the amorphous state Acta Pharm 2013; 63: 305-334 2013
Elwahy, "Synthesis of new benzo-substituted macrocyclic ligands containing quinoxaline subunits," Tetrahedron, 56(6): 897-907 (2000) 2000
Epsztajn et al, "Application of organolithium", Tetrahedron, Elsevier Science Publishers, Amsterdam, NL, 1991, vol 47, No 9, pp 1697-1706 1991
Gadaginamath et al, "Synthesis and antibacterial activity of novel 1-butyl-2-phenoxy/2-phenylthio/2-aminomethyl-5-methoxyindole derivatives," Polish Journal of Chemistry, 71(7): 923-928 (1997) 1997
Gao et al, "A novel one-pot three-step synthesis of 2-(1-benzofuran-2-yl)quinoline-3-carboxylic acid derivatives," Journal of the Brazilian Chemical Society, 21(5): 806-812 (2010) 2010
Ghate et al, "Synthesis of vanillin ethers from 4-(bromomethyl) coumarins as anti-inflammatory agents," European Journal of Medicinal Chemistry, 38(3): 297-302 (2003) 2003
Gibson et al, "Novel small molecule bradykinin B2 receptor antagonists", Journal of Medicinal Chemistry, 2009, vol 52, pp 4370-4379 2009
Glasson et al Metal Template Synthesis of a Tripodal Tris(bipyridyl) Receptor that Encapsulates a Proton and an Iron (ii) Centre in a Pseudo Cage Aust J Chem 65: 1371-1376 (2 2012
Grashey, "The nitro group as a 1,3-dipole in cycloadditions," Angewandte Chemie, 74: 155 (1962) 1962
Guillaumel, et al. Synthetic routes to 2-(2-benzofuranyl)benzoic acids and their cyclization into benz[6]indeno[2,1-d]furan-10-ones. Journal of Heterocyclic Chemistry, 1990; 27: 1047-1051. doi: 10.1002/jhet.5570270444 1990
Guillory (in Brittain ed.) Polymorphism in Pharmaceutical Solids NY, Marcel Dekker, Inc 1999; 1-2: 183-226 1999
Gunter et al, "Structural control of co-receptor binding in porphyrin-bipyridinium supramolecular assemblies," Journal of the Chemical Society, Perkin Transactions 1: Organic and Bio-Organic Chemistry, (1: 1945-1958 (1998) 1998
Hanmantgad et al, "Synthesis and pharmacological properties of some 4-(2'-benzo[b]furanyl)coumarins," Indian Journal of Chemistry, Section B: Organic Chemistry Including Medicinal Chemistry, 25B(7): 779-781 (1986) 1986
He et al, "Prodrugs of phosphonates, phosphinates, and phosphates", Prodrugs: Challenges and Rewards, Part 2, edited by Stella et al, pp 223-264 (2007) 2007
Heimbach et al, "2.2.1: Over-coming poor aqueous solubility of drugs for oral delivery," from Prodrugs: Challenges and Rewards, Part I, New York NY, Singer: AAPS Press, pp 157-215 (2 2007
Heimbach et al, "Enzyme-mediated precipitation of parent drugs from their phosphate prodrugs," International Journal of Pharmaceutics 261: 81-92 (2002) 2002
Heimgartner et al, "Stereoselective synthesis of swainsonines from pyridines", Tetrahedron, Elsevier Science Publishers, Amsterdam, NL, 2005, vol 61, No 3, pp 643-655 2005

TABLE 5-continued

| |
|---|
| Hoffman, et al 3-Hydroxy-3-methyglutaryl-coenzyme A Reductase Inhibitors, 2 Structural Modification of 7-(Substituted aryl)-3,5-dihydroxy-6-heptenoic Acids and Their Lactone Derivatives Journal of Medical Chemistry 29(2): 159-169 (1986) 1986 |
| Hong et al, "Potential Anticancer Agents VI: 5-Substituted Pyrimidine-6-Carboxaldehydes", Journal of Pharmaceutical Sciences, American Pharmaceutical Association, Washington, US, 1970, vol 59, No 11, pp 1637-1645 1970 |
| Huckauf, et al, "Oxygen Affinity of Haemoglobin and Red Cell Acid-Base Status in Patients with Severe Chronic Obstructive Lung Disease" Bull Europe Physiopath Resp, 1976, 12, 129-142 1976 |
| Ito et at, "A medium-term rat liver bioassay for rapid in vivo detection of carcinogenic potential of chemicals," Cancer Science, 94(1): 3-8 (2003) 2003 non; Ivanisevic, et al Uses of x-ray powder diffraction in the pharmaceutical industry Pharm Sci Encycl 2010; 1-42 2010 |
| Jain, et al, "Polymorphism in Pharmacy", Indian Drugs, 1986, 23(6) 315-329 1986 |
| Jarvest et al, "Discovery and optimisation of potent, selective, ethanolamine inhibitors of bacterial phenylalanyl tRNA synthetase," Bioorganic & Medicinal Chemistry Letters, 15(9): 2305-2309 (2005) 2005 |
| Karche et al, "Electronic effects in migratory groups [1,4]- versus [1,2]-rearrangement in rhodium carbenoid generated bicyclic oxonium ylides," Journal of Organic Chemistry, 66(19): 6323-6332 (2001) 2001 |
| Katritzky et al, "Synthesis of 3-hydroxymethyl-2,3-dihydrobenzofurans and 3-hydroxymethylbenzofurans," ARKIVOC (Gainesville, FL, United States), (6): 49-61 (2003) 2003 |
| Kaye et al "DABCO-catalyzed reactions of salicylaldehydes with acrylate derivatives," Synthetic Communications: An International Journal for Rapid Communication of Synthetic Organic Chemistry, 26(11): 2085-97 (1996) 1996 |
| Kaye et al, "Does the DABCO-catalysed reaction of 2-hydroxybenzaldehydes with methyl acrylate follow a Baylis-Hillman pathway?," Organic & Biomolecular Chemistry, 1(7): 1133-1138 (2003) 2003 |
| Keidan, et al Effect of BW12C on oxygen affinity of hemogoblin in sickle-cell disease The Lancet 1986; 327(8485): 831-834 1986 |
| Kessar et al, "An interesting application of photocyclisation in aporhoeadane alkaloid synthesis", Tetrahedron Letters, 28(44): 5323-5326 (1987) 1987 |
| Kessar et al, "Synthesis of isoindolobenzazepines via photocyclization of N-(2-formylphenethyl)phthalimide derivatives," Indian Journal of Chemistry, 30B(11): 999-1005 (1991) 1991 |
| Kirk-Othermer Encyclopedia of Chemical Technology 2002; 8: 95-147 2002 |
| Kise et al, "Electroreductive intramolecular coupling of phthalimides with aromatic aldehydes: application to the synthesis of lennoxamine," Journal of Organic Chemistry, 76(23): 9856-9860 (2011) 2011 |
| Klis, et al Halogen-lithium exchange versus deprotonation: synthesis of diboromic acids derived from arylbenzyl ethers Tetrahedron Letters, 48(7): 1169-1173 (2007) 2007 |
| Kratochvil Chapter 8 Solid Forms of Pharmaceutical Molecues J Sestak et al (eds.), Glassy, Amorphous and Nano-Crystalline Materials Hot Topics in Thermal Analysis and Calorimetry 8, 2011, pp 129-140 2011 |
| Krow, Grant R, "Chapter 3, The Baeyer-Villiger oxidation of ketones and aldehydes," Organic Reactions, 43: 251-353 and 775-808 (1993) 1993 |
| Lakkannavar et al, "4-[2'-Benzylideneanilino aryloxymethyl] coumarins E and Z isomers," Indian Journal of Heterocyclic Chemistry, 4(4): 303-304 (1995) 1995 |
| Lin et al Synthesis and anticancer activity of benzyloxybenzaldehyde derivatives against HL-60 cells Bioorganic & Medicinal Chemistry 13(5), 1537-1544 (2005) 2005 |
| Lin et al, "Potential Antitumor Agents.8 Derivatives of 3- and 5-Benzyloxy-2-formylpyridine Thiosemicarbazone", Journal of Medicinal Chemistry, American Chemical Society, US, 1972, vol 15, No 6, pp 615-618 1972 |
| Liu et al, "Synthesis of Double-Armed Benzo-15-crown-5 and Their Complexation Thermodynamics with A1kali Cations," Journal of Inclusion Phenomena and Macrocyclic Chemistry. 52(3-4): 229-235 (2005) 2005 |
| Luan, et al OPS-Mode model of multiplexing neuroprotective effects of drugs and experimental-theoretic study of new 1,3-rasagiline derivatives potentially useful in neurodegenerative diseases Bioorganic & Medicinal Chemistry 2013; 21: 1870-1879 2013 |
| Mahoney et al, "Functionalization of Csp3-H bond-Sc(OTf)3-catalyzed domino 1,5-hydride shift/cyclization/Friedel-Crafts acylation reaction of benzylidene Meldrum's acids," Tetrahedron Letters, 50(33): 4706-4709 (2009) 2009 |
| Majhi et al, "An efficient synthesis of novel dibenzo-fused nine-membered oxacycles using a sequential Baylis-Hillman reaction and radical cyclization," Synthesis, (1): 94-100 (2008) 2008 |
| Manna et al, Synthesis and beta-adrenoreceptor blocking activity of [[3-(alkylamine)-2-hydroxypropyl]oximino]pyridines and 0[3-(alkylamine)-2-hydroxypropyl]methylpyridine ketone oximes derivatives, IL FARMACO, 1996, vol 51, No 8, 9, pp 579-587 1996 |
| Mantyla et al, Synthesis, in vitro evaluation and antileishmanial activity of water-soluble prodrugs of buparvaquone J Med Chem 2004, 47: 188-195 2004 |
| Marchetti et al, "Synthesis and biological evaluation of 5-substituted O4-alkylpyrimidines as CDK2 inhibitors," Org Biomol Chem, 8: 2397-2407 (2010) 2010 |
| McKay et al, "7,11,15,28-Tetrakis[(2-formylphenoxy)-methyl]-1,21,23,25-tetramethyl-resorcin[4]arene cavitand ethyl acetate clathrate at 173 K," Acta Crystallographica, Section E: Structure Reports Online, E65(4): o692-o693 (2009) 2009 |
| McKay et al, "Microwave-assisted synthesis of a new series of resorcin[4]arene cavitand-capped porphyrin capsules," Organic & Biomolecular Chemistry, 7(19): 3958-3968 (2009) 2009 |
| Merlino et al, "Development of second generation amidinohydrazones, thio- and semicarbazones as Trypanosoma cruzi-inhibitors bearing benzofuroxan and benzimidazole |

TABLE 5-continued 1,3-dioxide core scaffolds," Med Chem Commun, 1(3): 216-228 (2010) 2010
Mesguiche et al, "4-Alkoxy-2,6-diaminopyrimidine derivatives: inhibitors of cyclin dependent kinases 1 and 2," Bioorganic & Medicinal Chemistry Letters, 13: 217-222 (2003) 2003
Mitra et al, "Synthesis and biological evaluation of dibenz[b,f][1,5]oxazocine derivatives for agonist activity at k-opioid receptor," European Journal of Medicinal Chemistry, 46(5): 1713-1720 (2011) 2011
Mulwad et al, "Synthesis and antimicrobial activity of [6'-methyl-4'-methoxy-2-oxo-2H-[1]-benzopyran)-2",4"-dihydro-[1",2",4"]-triazol-3"-one and 3"-phenylthiazolidin-4"-one-phenoxymethyl derivatives of dipyranoquinoline," Pharmaceutical Chemistry 2011
Muzaffar, et al, "Polymorphism and Drug Availability: a Review" J of Pharm (Lahore), 1979, 1(1), 59-66 1979
Nagy et al, Selective coupling of methotrexate to peptide hormone carriers through a y-carboxamide linkage of its glutamic acid moiety: Benzotriazol-1-yloxytris(dimethylamino)phosphonium hexafluorophosphate activation in salt coupling Proc Natl AcadSci USA 1993
Neelima et al, "A novel annelation reaction: synthesis of 6H-[1]benzopyrano[4,3-b]quinolines," Chemistry & Industry (London, United Kingdom), (4): 141-2 (1986) 1986
Nnamani et al, "Pyridyl derivatives of benzaldehyde as potential antisickling agents", Chemistry & Biodiversity, 5: 1762-1769 (2008) 2008
Nogrady, Medicinal Chemistry A BioChemical Approach, Oxford University Press, New York, pp 388-392 (1985) 1985
Nonoyama et al, "Cyclometallation of 2-(2-pyridyl)benzo[b]furan and 1-(2-pyridyl and 2-pyrimidyl)indole with palladium(II) and rhodium(III) Structures of unexpectedly formed nitro palladium(II) complexes," Polyhedron, 18: 533-543 (1999) 1999
Notice of Allowance dated Dec. 19, 2014 for U.S Appl No 13/730,730 11 pages 2014
Nyerges et al, "Synthesis of indazole N-oxides via the 1,7-electrocyclization of azomethine ylides." Tetrahedron Letters, 42(30): 5081-5083 (2001) 2001
Nyerges et al, "Synthesis of indazole-N-oxides via the 1,7-electrocyclization of azomethine ylides," Tetrahedron, 60(44): 9937-9944 (2004) 2004
OECD SIDS, "Potassium Hydroxide, SIDS Initial Assessment Report for SIAM 13, CAS No 1310-58-3," UNEP Publications, pp 1-96 (2 2002
Otsuka, et al, "Effect of Polymorphic Forms of Bulk Powders on Pharmaceutical Properties of Carbamazepine Granules." Chem Pharm Bull, 47(6) 852-856 (1999) 1999
O'Reilly et al, "Metal-phenoxyalkanoic acid interactions XXV The crystal structures of (2-formyl-6-methoxyphenoxy)acetic acid and its zinc(II) complex and the lithium, zinc(II) and cadmium(II) complexes of (2-chlorophenoxy)acetic acid," Australian Journal 1987
Patani, et al Bioisosterism: A Rational Approach in Drug Design J Chem Rev 1996, 96(8), pp 3147-3176 1996
Perez et al, "Preparation of new 1,2-disubstituted ferrocenyl stibine derivatives containing ether/thioether pendant arm from a quaternary ferrocenyl ammonium salt," Polyhedron, 28(14): 3115-3119 (2009) 2009
Perkins et al, "Manganese(II), iron(II), cobalt(II), and copper(II) complexes of an extended inherently chiral trisbipyridyl cage," Proceedings of the national Academy of Sciences of the United States of America, 103(3): 532-537 (2006) 2006
Potapov, et al A convenient synthesis of heterocyclic compounds containing 11-oxo-6,11,12,13-tetrahydrodibenzo[b,g][1,5]oxazonine fragment Mendeleev Communications 2009; 19: 287-289 2009
Prohens, et al Polymorphism in pharmaceutical industry The Pharmacist Apr. 1, 2007; 373: 58-68 (in Spanish with English abstract) 2007
Pubchem CID 54009805, create date: Dec. 4, 2011, 3 pages, (2011) 2011
Pubchem CID 54883281, create date: Jan. 24, 2012, 3 pages, (2012) 2012
Remington's Pharmaceutical Sciences, 17th Edition, A Gennaro editor, Easton Pennsylvania Table of Contents (1985) 1985
Rodriguez-Spong, et al General principles of pharmaceutical solid polymorphism: a supramolecular perspective Adv Drug Deliv Rev Feb. 23, 2004; 56(3): 241-74 2004
Rolan et al, "The pharmacokinetics, tolerability and pharmacodynamics of tucaresol (589C80; 4[2-formyl-3-hydroxyphenoxymethyl] benzoic acid), a potential anti-sickling agent, following oral administration to healthy subjects", Br J Clin Pharmacol, 35(4): 41 1993
Rooseboom et al, Enzyme-catalyzed activation of anticancer prodrugs Pharmacol Rev 2004, 56: 53-102 2004
Ruchirawat et al, "A novel synthesis of aporhoeadanes," Tetrahedron Letters, 25(32): 3485-3488 (1984) 1984
Safo, et al structural basis for the potent antisickling effect of a novel class of five-membered heterocyclic aldehydic compounds J Med Chem Sep. 9, 2004; 47(19): 4665-76 2004
Sahakitpichan et al, "A practical and highly efficient synthesis of lennoxamine and related isoindolobenzazepines," Tetrahedron, 60(19): 4169-4172 (2004) 2004
Sahm et al, "Synthesis of 2-arylbenzofurans," Justus Liebigs Annalen der Chemie, (4): 523-38, includes English language abstract, (1974) 1974
Sainsbury et al, "1,2-Dihydroisoquinolines IV Acylation," Tetrahedron, 22(8): 2445-2452 (1966) 1966
Sarodnick et al, "Quinoxalines XV Convenient synthesis and structural study of pyrazolo[1,5-a]quinoxalines," Journal of Organic Chemistry, 74(3): 1282-1287 (2009) 2009
Schudel, et al Uber die Chemie des Vitamins E Helvatica Chimica Acta 1963; 66: 636-649 1963
Seddon Pseudopolymorph: A Polemic The QUILL Centre, The Queen's University of Belfast, United Kingdom Jul. 26, 2004 2 pages 2004
Shetty et al Palladium catalyzed alpha-arylation of methyl isobutyrate and isobutyronitrile: an efficient synthesis of 2,5-disubstituted benzyl alcohol and amine intermediates Tetrahedron Letters, 47: 8021-8024 (2006) 2006

TABLE 5-continued

Siddiqui et al, "The presence of substitutents on the aryl moiety of the aryl phosphoramidate derivatives of d4T enhances anti-HIV efficacy in cell culture: a structure-activity relationship," J Med Chem, 42: 393-399 (1999) 1999
Silva et al, "Advances in proddrug design," Mini-Rev Med Chem, 5(10): 893-914, 2005 2005
Singh et al, "Reductive-cyclization-mediated synthesis of fused polycyclic quinolines from Baylis-Hillman adducts of acrylonitrile: scope and limitations," European Journal of Organic Chemistry, (20): 3454-3466 (2009) 2009
Singhal, et al, "Drug Polymorphism and Dosage Form Design: a Practical Perspective" Advanced Drug Delivery reviews 56, p 335-347 (2004) 2004
Sobolev et al, Effect of acyl chain length and branching on the enantioselectivity of Candida rugosa lipase in the kinetic resolution of 4-(2-difluoromethoxyphenyl)-substituted 1,4-dihydropyridine 3,5-diesters J Org Chem 2002, 67: 401-410 2002
Srivastava et al, "Synthesis and biological evaluation of 4-substituted tetrazolo[4,5-a]quinolines and 2,3- disubstituted quinoline derivatives," Indian Journal of Chemistry, Section B: Organic Chemistry Including Medicinal Chemistry, 28B(7): 562-573 (1989) 1989
Starke et al, "Quinoxalines Part 13: Synthesis and mass spectrometric study of aryloxymethylquinoxalines and benzo[b]furylquinoxalines," Tetrahedron, 60(29): 6063-6078 (2 2004
Stetinova, et al Synthesis and Properties of 4-Alkylamino methyl and 4-Alkoxymethyl Derivatives of 5-Methyl-2-Furancarboxylic Acid Collection Czechosloval Chem Commun 1986; 51: 2186-2192 1986
Swann et al, "Rates of reductive elimination of substituted nitrophenols from the (indo1-3-yl)methyl position of indolequinones," Journal of the Chemical Society, Perkin Transactions 2, (8): 1340-1345 (2001) 2001
Table of Compounds, each of which can be found either in Table 1 of U.S. Pat. No. 9,018,210 or Table 1 of U.S. Pat. No. 9,012,450
Taday, et al, "Using Terahertz Pulse Spectroscopy to Study the Crystalline Structure of a Drug: A Case Study of the Polymorphs of Ranitidine Hydrochloride." J of Pharm Sci, 92(4), 2003, 831-838 2003
Testa et al, Hydrolysis in Drug and Prodrug Metabolism, June 2003, Wiley-VCH, Zurich, 419-534 2003
Tome, A.C, "13.13, Product class 13: 1,2,3-triazoles," Science of Synthesis: Houben-Weyl Methods of Molecular Transformations, Georg Thieme Verlag publishers, Stuttgart, Germany, pp 415-601, (2003) 2003
U.S Appl No 13/815,735, filed Mar. 15, 2013, Xu 2013
U.S Appl No 13/815,776, filed Mar. 15, 2103, Xu
U.S Appl No 13/815,810, filed Mar. 15, 2013, Metcalf 2013
U.S Appl No 13/815,810, filed Mar. 15, 2013, Metcalf et al 2013
U.S Appl No 13/815,872, filed Mar. 15, 2013, Metcalf 2013
U.S Appl No 13/815,874, filed Mar. 15, 2013, Harris 2013
U.S Appl No 14/010,455, filed Aug. 26, 2013, Harris 2013
U.S Appl No 14/207,289, filed Mar. 12, 2014, Li 2014
U.S Appl No 61/581,053, filed Dec. 28, 2011, Metcalf et al 2011
U.S Appl No 61/661,320, filed Jun. 18, 2012, Metcalf et al 2012
U.S Pharmacopia #23, national Formulary #18, 1995, 1843-1844 1995
Van Rompaey et al, "A versatile synthesis of 2-substituted 4-amino-1,2,4,5-tetrahydro-2-benzazepine-3-ones," Tetrahedron, 59(24): 4421-4432 (2003) 2003
Van Rompaey et al, "Synthesis and evaluation of the b-turn properties of 4-amino-1,2,4,5-tetrahydro-2-benzazepin-3-ones and of their spirocyclic derivative," European Journal of Organic Chemistry, (13): 2899-2911 (2006) 2006
Vicente et al, "Carbopalladation of maleate and fumarate esters and 1,1-dimethylallene with ortho-substituted aryl palladium complexes," Organometallics, 29(2): 409-416 (2010) 2010
Vichinsky "Emerging 'A' therapies in hemoglobinopathies: agonists, antagonists, antioxidants, and arginine." Hematology 2012, 271-275 2012
Vippagunta, et al Crystalline Solids Advanced Drug Delivery Reviews 2001; 48: 3-26 2001
Wang et al, "Studies of benzothiophene template as potent factor IXa (FIXa) inhibitors in thrombosis," Journal of Medicinal Chemistry, 53(4): 1465-1472 (2010) 2010
Warshawsky et al, "The synthesis of aminobenzazepinones as anti-phenylalanine dipeptide mimics and their use in NEP inhibition," Bioorganic & Medicinal Chemistry Letters, 6(8): 957-962 (1 1996
Wendt et al, "Synthesis and SAR of 2-aryl pyrido[2,3-d]pyrimidines as potent mGlu5 receptor antagonists," Bioorganic & Medicinal Chemistry Letters, 17: 5396-5399 (2007) 2007
Wermuth, Camille G, "Molecular Variations Based on Isosteric Replacements", The Practice of Medicinal Chemistry, 1996, pp 203-232 1996
Yan et al, "Synthesis, crystal structure and antibacterial activity of di-n-butyltin carboxylate," Huaxue Tongbao, 70(4): 313-316, includes English language abstract, (2007) 2007
Yan et al, "Synthesis, crystal structure and antibacterial activity of di-n-butyltin di-2-(2-formylphenoxy)acetic ester," Yingyong Huaxue, 24(6): 660-664, includes English language abstract, (2007) 2007
Yang, et al structural requirement of chalcones for the inhibitory activity of interleukin-5 Bioorg Med Chem 2007, 15(1), 99 104-111 2007
Yoon et al, "The chirality conversion reagent for amino acids based on salicyl aldehyde," Bull Korean Chem Soc, 33(5): 1715-18 (2012) 2012
Zhang et al, "DFT study on RuII-catalyzed cyclization of terminal alkynals to cycloalkenes," International Journal of Quantum Chemistry, 109(4): 679-687 (2009) 2009
Zhang, et al Current prodrug strategies for improving oral absorption of nucleoside analogues Asian Journal of Pharmaceutical Sciences April 2014; 9(2): 65-74 2014
Zhu et al, "Isoquinoline-pyridine-based protein kinase B/Akt antagonists: SAR and in vivo antitumor activity", Bioorganic & Medicinal Chemistry Letters, Pergamon, Amsterdam, NL, 2006, vol 16, No 12, pp 3150-3155 2006

TABLE 5-continued

| | |
|---|---|
| Zwaagstra et at, "Synthesis and structure-activity relationships of carboxylated chalcones: a novel series of Cys-LT1 (LTD4) Receptor Antagonists", Journal of Medicinal Chemistry, 40(7): 1075-1089 (1997) 1997 | |
| ASTRAZENECA AB; US 20100311748 A1 2010 | |
| Abdel-Rahman, R; Pharmazie 1994, 49, 729 | Bakale; U.S. Pat. No. 6,627,646 B2 2003 |
| Aggarwal, V; Synthesis 1982, 214 | Binder; U.S. Pat. No. 5,679,678 A 1997 |
| Ansel, J; Tetrahedron Lett 2002, 43, 8319 | Blout; U.S. Pat. No. 3,236,893 A 1966 |
| Atlan, V; Synlett 2000, 489 | Breault; U.S. Pat. No. 5,994,353 A 1999 |
| Baiani; U.S. Pat No. 5,202,243 A 1993 | Bridger; US 20040209921 A1 2004 |
| Buettelmann; US 20090143371 A1 2009 | |
| BUETTELMANN, B; US 20090143371 A1 2009 | |
| BUETTELMANN BERND; US 20090143371 A1 2009 | |
| Braibante, M; Synthesis 2003, 1160 | Dakin; US 20100311748 A1 2010 |
| Castro; US 20080114167 A1 2008 | DAKIN, L; US 20100311748 A1 2010 |
| Cen; US 20130045251 A1 2013 | Dodd, D; Tetrahedron Lett 2004, 45, 4265 |
| Chauhan, S; Synthesis 1975, 798 | Dodd, D; Tetrahedron Lett 2004, 45, 4265 |
| Coispeau, G; Bull Soc Chim Fr 1970, 2717 | Diakur; US 20040186077 A1 2004 |
| Cooper, C; PCT WO 18346 A1 2002 | Dufu; US 20160303099 A1 2016 |
| 39Chen; U.S. Pat. No. 5,185,251 A 1993 | Dunkel; US 20130190375 A1 2013 |
| Chen; U.S. Pat. No. 5,760,232 A 1998 | Embury; US 20040072796 A1 2004 |
| Chen; US 20090163512 A1 2009 | Endo; US 20120245344 A1 2012 |
| Elguero, J; Bull Soc Chim Fr 1973, 3401 | |
| Elguero, J; Comprehensive Heterocyclic Chemistry 1984, 5, 167 | |
| Elguero, J; Comprehensive Heterocyclic Chemistry II 1996, 3, 1 | |
| Ellis; U.S. Pat. No. 5,965,572 A 1999 | Greenwald; U.S. Pat. No. 6,608,076 B1 2003 |
| Firestone; US 20020147138 A1 2002 | Hague; US 20060094761 A1 2006 |
| Gapalasamy; U.S. Pat. No. 7,411,083 B2 2008 | Harris; US 20140275181 A1 2014 |
| Gillespie; US 20090023709 A1 2009 | Harris; US 20150057251 A1 2015 |
| Gless; US 20130072472 A1 2013 | Harris; US 20160024127 A1 2016 |
| Greenwald; U.S. Pat. No. 5,840,900 A 1998 | Harris; U.S. Pat. No. 9,604,999 B2 2017 |
| Greenwald; U.S. Pat. No. 5,880,131 A 1999 | Hernandez; US 20100210651 A1 2010 |
| Greenwald; U.S. Pat. No. 5,965,566 A 1999 | Hoehn; U.S. Pat. No. 4,062,858 A 1977 |
| Greenwald; U.S. Pat. No. 6,011,042 A 2000 | Hoffmann; U.S. Pat. No. 6,593,472 B2 2003 |
| Greenwald; U.S. Pat. No. 6,111,107 A 2000 | HOFFMANN, T; U.S. Pat. No. 6,593,472 B2 2003 |
| Greenwald; U.S. Pat. No. 6,127,355 A 2000 | Huang, Y; Org Lett 2000, 2, 2833 |
| Greenwald; U.S. pat. No. 6,194,580 B1 2001 | Ila, H; J Organomet Chem 2001, 624, 34 |
| Ila, H; Progress in Heterocyclic Chemistry, Chapter 1 2001, 13, 1 | |
| Imogai; US 20070213323 A1 2007 | Junjappa, H; Tetrahedron 1990, 46, 5423 |
| Jensen-Korte; U.S. Pat. No. 4,803,215 A 1989 | Kashima, C; Synthesis 1994, |
| Kost, A; Advances in Heterocyclic Chemistry 1966, 6, 347 | |
| Kumar, A; Synthesis 1980, 748 | |
| Kneen; U.S. Pat. No. 4,410,537 A 1983 | Kneen; U.S. Pat. No. 4,535,183 A 1985 |
| KOBAYASHI HIDEKI; WO 2013187462 A1 2013 | |
| Lai; U.S. Pat. No. 6,355,661 B1 2002 | Metcalf; US 20130190316 A1 2013 |
| Lai; US 20030022923 A1 2003 | Metcalf; US 20140274961 A1 2014 |
| Lee; US 20030165714 A1 2003 | 44Metcalf; US 20140275152 A1 2014 |
| Lee, K; Tetrahedron Lett 2003, 44, 6737 | Metcalf; US 20150344472 A1 2015 |
| Li; US 20030187026 A1 2003 | Metcalf; US 20150344483 A1 2015 |
| Li; US 20030199511 A1 2003 | Metcalf; U.S. Pat. No. 9,012,450 B2 2015 |
| Li; US 20150259296 A1 2015 | Metcalf; U.S. Pat. No. 9,018,210 B2 2015 |
| Li; US 20160031865 A1 2016 | Metcalf; US 20160039801 A1 2016 |
| Li; US 20160031904 A1 2016 | Metcalf; US 20160206604 A1 2016 |
| Li; US 20160207904 A1 2016 | Metcalf; US 20160206614 A1 2016 |
| Li; US 20160346263 A1 2016 | Metcalf; US 20160332984 A1 2016 |
| Li; U.S. Pat. No. 9,447,071 B2 2016 | Metcalf; U.S. Pat. No. 9,248,199 B2 2016 |
| Lizos; US 20100204235 A1 2010 | Metcalf; U.S. Pat. No. 9,422,279 B2 2016 |
| Mahata, P; J Org Chem 2003, 68, 3966 | Metcalf; US 20170107199 A1 2017 |
| Martinez; U.S. Pat. No. 5,681,567 A 1997 | Metcalf; US 20170174654 A1 2017 |
| Martinez; U.S. Pat. No. 6,153,655 A 2000 | Michael, A; WO 2004002490 A 2004 |
| Martinez; U.S. Pat. No. 6,395,266 B1 2002 | Mitchell; US 20050085484 A1 2005 |
| Metcalf; US 20130190315 A1 2013 | Mossman; US 20030190333 A1 2003 |
| Moreno-Manas, M; Synthesis 1999, 157 | |
| Moutouh-de Parseval; US 20050143420 A1 2005 | |
| Murray, W; Synthesis 1991, 18 | Nudelman; U.S. Pat. No. 6,239,176 B1 2001 |
| Nandi, S; Tetrahedron 2004, 60, 3663 | Ohashi; US 20120220569 A1 2012 |
| Nicolau; US 20020142995 A1 2002 | Palacios, F; Tetrahedron 1996, 52, 4123 |
| Panda, K; J Org Chem 2003, 68, 3498 | |
| Peruncheralathan, S; Tetrahedron 2004, 60, 3457 | |
| Purkayastha, M; Synthesis 1989, 21 | Shroff; U.S. Pat. No. 4,478,834 A 1984 |
| Quick; US 20070293698 A1 2007 | Sinha; US 20140271591 A1 2014 |
| Ramos; US 20170157101 A1 2017 | Sinha; US 20160038474 A1 2016 |
| Rahman, A; Synthesis 1984, 247 | Spivey, A; J Org Chem 2000, 65, 5253 |
| Robinson, M; Tetrahedron 1987, 43, 4043 | Stewart; U.S. Pat. No. 6,232,320 B1 2001 |
| Riley; U.S. Pat. No. 6,214,817 B1 2001 | Tang, J; Bioorg Med Chem Lett 2003, 13, 2985 |
| Sakya, S; Tetrahedron Lett 2003, 44, 7629 | Takabe; U.S. Pat. No. 5,403,816 A 1995 |
| Safo; U.S. Pat. No. 7,160,910 B2 2007 | Tarur; US 20050159605 A1 2005 |
| Satyanarayana, J; Synthesis 1991, 889 | Thomas, D; WO 02056882 A 2002 |
| Schenone, S; Il Farmaco 1995, 50, 179 | Voiante; U.S. Pat. No. 5,290,941 A 1994 |
| Seehra; U.S. Pat. No. 6,630,496 B1 2003 | van Gestel, J; WO 2004011436 A 2004 |
| Schroth, W; Synthesis 1982, 199 | Wang; US 20030073712 A1 2003 |

TABLE 5-continued

| | | |
|---|---|---|
| Schiemann kai; wo 2012028243 a1 2012 | | Warshawsky; US 20020095035 A1 2002 |
| Wommack, J; Journal OF Medicinal CHEMISTRY 1971, 12, 1218 | | |
| Xu; US 20140275176 A1 2014 | | EP 0659745 A1 1995 |
| Xu; US 20150133430 A1 2015 | | WO 2006061147 2006 |
| Xu; U.S. Pat. No. 8,952,171 B2 2015 | | Jensen-Korte; U.S. Pat. No. 4,803,215 A 1989 |
| Xu; US 20160083343 A1 2016 | | Neurogen Corp; WO 0248152 A2 2002 |
| Xu; US 20160152602 A1 2016 | | Neurogen Corp; EP 1347982 A2 2002 |
| Xu; U.S. Pat. No. 9,458,139 B2 2016 | | Neurogen Corp; US 2003036652 A1 2002 |
| Xu; U.S. Pat. No. 9,776,960 B2 2017 | | Abbaszade, I; J Biol Chem 1999, 274, 23443 |
| Yamaguchi; US 20090312315 A1 2009 | | Adams; U.S. Pat. No. 5,559,137 A 1996 |
| Yee; US 20150141465 A1 2015 | | Adams; U.S. Pat. No. 5,658,903 A 1997 |
| EP 0352944 A1 1990 | | Adams; U.S. Pat. No. 5,739,143 A 1998 |
| Adams; U.S. Pat. No. 5,998,425 A 1999 | | |
| Adams, J; Bioorganic & Medicinal Chemistry Letters 1998, 8, 3111 | | |
| Addex Pharm S A; EP 1765795 A2 2005 | | Addex Pharm S A; JP 2008502674 A 2005 |
| Addex Pharm S A; WO 2005123703 A2 2005 | | Addex Pharm S A; US 20090124625 A1 2005 |
| Aggarwal, R; Beilstein J Org Chem 2011, 7, 179 | | |
| Aggarwal, V; Synthesis 1982, 214 | | |
| Allen; US Patent Appl No 10/254,445 2002 | | Anantanarayan; U.S. Pat. No. 6,514,977 B1 2003 |
| Allen; US Patent Appl No 10/406,150 2003 | | Anantanarayan; U.S. Pat. No. 6,525,059 B1 2003 |
| Anantanarayan; U.S. Pat. No. 6,423,713 B1 2002 | | Anantanarayan; US Appl No 09/083,670 2000 |
| Anatanarayan; US Patent Appl No 09/512,696 2001 | | |
| Anantanarayan, A; WO 9852937 A 1998 | | Anantanarayan, A; WO 9852940 A 1998 |
| Anderson, E; J Med Chem 1964, 7, 259 | | |
| EP 0115640 A2 1983 | WO 9725048 A1 1997 | WO 0018758 A1 |
| WO 8300330 1983 | WO 9732583 A1 1997 | WO 0170729 A1 |
| EP 0352944 A1 1990 | WO 9735855 A1 1997 | WO 03037888 A1 |
| EP 0418845 A1 1991 | WO 9735856 A1 1997 | EP 0319817 A2 |
| DE 295374 A5 1991 | WO 9747618 A1 1997 | EP 1052252 A1 |
| JP 04-145081 1992 | EP 0846686 A1 1998 | EP 1136483 A1 |
| EP 0515041 A2 1992 | EP 0846687 A1 1998 | EP 1454908 A1 |
| WO 9219615 1992 | WO 9807425 A1 1998 | DE 19927072 A1 |
| JP 05-17470 1993 | WO 9816230 A1 1998 | DE 19930927 A1 |
| JP 05-345772 1993 | WO 9825619 A1 1998 | DE 2261351 A1 |
| EP 0531901 A2 1993 | WO 9852937 A3 1998 | U.S. Pat. No. 3,534,058 A |
| WO 9323384 1993 | WO 9852937 A2 1998 | U.S. Pat. No. 3,647,351 A |
| WO 9419350 1994 | WO 9852940 A1 1998 | U.S. Pat. No. 3,839,336 A |
| EP 0659745 A1 1995 | WO 9852941 A1 1998 | U.S. Pat. No. 3,920,693 A |
| WO 9506036 1995 | WO 9857966 A1 1998 | U.S. Pat. No. 3,926,999 A |
| WO 9507271 1995 | WO 9857968 A1 1998 | U.S. Pat. No. 3,944,551 A |
| WO 9514684 1995 | WO 9901130 A1 1999 | U.S. Pat. No. 3,988,348 A |
| WO 9522545 A1 1995 | WO 9901131 A1 1999 | DE 4008049 A1 |
| WO 9531451 1995 | WO 9901136 A1 1999 | U.S. Pat. No. 4,178,449 A |
| JP 08-183787 1996 | WO 9901452 A1 1999 | U.S. Pat. No. 4,281,000 A |
| WO 9603385 A1 1996 | WO 9917776 A1 1999 | U.S. Pat. No. 4,421,753 A |
| WO 9621452 A1 1996 | WO 9932121 A1 1999 | U.S. Pat. No. 4,745,652 A |
| WO 9621654 A1 1996 | WO 9958523 1999 | U.S. Pat. No. 5,344,464 A |
| WO 9640143 A1 1996 | WO 9961426 A1 1999 | U.S. Pat. No. 5,430,159 A |
| WO 9701551 1997 | WO 0031072 2000 | U.S. Pat. No. 5,865,855 A |
| WO 9723479 A1 1997 | WO 2006061147 2006 | WO 9323384 A1 |
| WO 9725046 A1 1997 | EP 0008079 A1 | WO 9514684 A1 |
| WO 9725047 A1 1997 | EP 0011843 A2 | WO 9801434 A1 |
| WO 9838175 A1 | | WO 2004085408 A1 |
| Chemical Abstracts, 13th Chemical Substance Index, Book 51 1992-1996, 546 | | |
| Anwar, H; ARKIVOC 2009, 1, 198 | | Augustin, M; J Prakt Chem 1979, 321, 205 |
| Badger, A; Arthritis & Rheumatism 2000, 43, 175 | | |
| Bakhite, E; Phosphorus Sulfur Silicon Rel Elem 2000, 157, 107 | | |
| Barbachyn; WO 9507271 1995 | | Beiler; U.S. Pat. No. 4,000,281 A 1976 |
| Barun, O; Tetrahedron Lett 1999, 40, 3797 | | Benson; U S Patent Appl No 10/456,933 2003 |
| Bauer, V; J Med Chem 1968, 11, 981 | | Bhat, L; Tetrahedron 1992, 48, 10377 |
| Bayer A-G; U.S. Pat. No. 4,803,215 A 1989 | | Boehm, J; Exp Opin Ther Patents 2000, 10, 25 |
| Bayer A-G; EP 0659745 A 1995 | | Brickner; U.S. Pat. No. 5,652,238 1997 |
| Brickner, S; Journal of Medicinal Chemistry 1996, 39, 673 | | |
| Bristol-Myers Squibb Co; EP 0918051 A 1999 | | Brittelli; U.S. Pat. No. 4,977,173 1990 |
| Bursavich, M; Bioorg Med Chem Lett, in press 2007, 17 | | |
| Carlson; U.S. Pat. No. 4,948,801 1990 | | Carlson; U.S. Pat. No. 5,254,577 1993 |
| Carotti, A; J Med Chem 2007, 50, 5364 | | |
| Carty, T; Curr Opin Anti-Inflamm Immunomod Invest Drugs 1999, 1, 89 | | |
| Catalan, J; J Am Chem Soc 1992, 114, 5039 | | Chauhan, S; Synthesis 1975, 798 |
| Cativiela, C; J Heterocycl Chem 1988, 25, 851 | | Chauhan, S; Tetrahedron 1976, 32, 1779 |
| Chauhan, S; Synthesis 1974, 880 | | Chebanov, V; J Org Chem 2008, 73, 5110 |
| Cheng, H; PCT Int Appl 2001 | | |
| Cherney, R; Bioorg Med Chem Lett 2003, 13, 1297 | | |
| Dannhardt, G; Arch Pharm 1988, 321, 17 | | Deng, X; Org Lett 2008, 10, 1307 |
| Dannhardt, G; Curr Med Chem 2000, 7, 1101 | | Dickore, K; Ger Offen 1986 |
| Das, J; Bioorg Med Chem Lett 2010, 20, 6886 | | Dodd, D; Tetrahedron Lett 2004, 45, 4265 |
| Deng, X; J Org Chem 2008, 73, 2412 | | Dolzhenko, A; Heterocycles 2008, 75, 1575 |
| Dorlars, A; Angew Chem 1975, 87, 693 | | |
| Dorlars, A; Angew Chem Int Ed Engl 1975, 14, 665 | | |
| Elguero, J; Comprehensive Heterocyclic Chemistry II 1996, 3, 1 | | |

TABLE 5-continued

| | |
|---|---|
| Elguero, J; Targets in Heterocyclic Systems 2002, 52 | |
| Elmaati, T; J Heterocycl Chem 2004, 41, 109 | |
| Elnagdi, M; Comprehensive Heterocyclic Chemistry II 1996, 7, 431 | |
| Elnagdi, M; Comprehensive Heterocyclic Chemistry III 2008, 10, 599 | |
| Ewen, J; J Am Chem Soc 2001, 123, 4763 | Flores, M; U.S. Pat. No. 2,989,538 1961 |
| Fischer, U; Helv Chim Acta 1980, 63, 1719 | Fossa, P; Bioorg Med Chem 2003, 11, 4749 |
| Fujisawa Pharmaceutical Co; EP 0531901 A 1993 | |
| Fustero, S; J Org Chem 2008, 73, 3523 | |
| Gallagher, T; Bioorganic & Medicinal Chemistry 1997, 5, 49 | |
| Gehring, R; Ger Offen 1986 | Goto; U.S. Pat. No. 5,589,439 A 1996 |
| Gerstenberger, B; Org Lett 2009, 11, 2097 | Graneto, M; J Med Chem 2007, 50, 5712 |
| Glasson, S; Arthritis Rheum 2004, 50, 2547 | Gueremy; U.S. Pat. No. 3,984,431 A 1976 |
| Hans Schwarzkopf Gmbh; WO 9801418 A 1998 | |
| Hans Schwarzkopf Gmbh; WO 9801434 A 1998 | |
| Hansen, M; Tetrahedron: Asymmetry 1996, 7, 2515 | |
| Hanson, G; Exp Opin Ther Patents 1997, 7, 729 | |
| Heinrich Timo; US 20070099933 A1 2007 | |
| Heller, S; Org Lett 2006, 8, 2675 | Henkel Kgaa; EP 0195363 A 1986 |
| Henkel Kgaa; EP 0008079 A 1980 | Henkel Kgaa; EP 0256468 A 1988 |
| Henkel Kgaa; DE 2934329 A 1981 | Henry, J; Drugs of the Future 1999, 24, 1345 |
| Hoepping, A; Bioorg Med Chem 2008, 16, 1184 | |
| Hoffmann la Roche & Co Ag F; EP 1349839 A1 2002 | |
| Hoffmann la Roche & Co Ag F; EP 1349839 B1 2002 | |
| Hoffmann la Roche & Co Ag F; EP 1349839 B8 2002 | |
| Hoffmann la Roche & Co Ag F; US 20020128263 A1 2002 | |
| Hoffmann la Roche & Co Ag F; WO 2002046166 A1 2002 | |
| Hoffmann la Roche & Co Ag F; US 20030208082 A1 2002 | |
| Hoffmann la Roche & Co Ag F; US 20030225070 A1 2002 | |
| Hoffmann la Roche & Co Ag F; JP 2004520292 A 2002 | |
| Hoffmann la Roche & Co Ag F; US 20050131043 A1 2002 | |
| Hoffmann la Roche & Co Ag F; JP 2008169206 A 2002 | |
| Hoffmann la Roche & Co Ag F; JP 4077317 B2 2002 | |
| Hoffmann la Roche & Co Ag F; U.S. Pat. No. 6,706,707 B2 2002 | |
| Hoffmann la Roche & Co Ag F; U.S. Pat. No. 6,927,232 B2 2002 | |
| Hoffmann la Roche & Co Ag F; U.S. Pat. No. 6,972,299 B2 2002 | |
| Hoffmann la Roche & Co Ag F; US 20090054490 A1 2009 | |
| Hoffmann la Roche & Co Ag F; WO 2009024491 A1 2009 | |
| Hoffmann la Roche & Co Ag F; TW 200924764 A 2009 | |
| Huisgen; U.S. Pat. No. 3,254,093 A 1966 | Hutchinson; U.S. Pat. No. 5,547,950 1996 |
| Ila, H; Progress in Heterocyclic Chemistry 2001, 1 | |
| Isakson; U.S. Pat. No. 5,756,529 A 1998 | Kawano, T; Tetrahedron Lett 2005, 46, 1233 |
| Jachak, M; J Heterocycl Chem 2008, 45, 1221 | Khan, M; J Heterocyclic Chem 1983, 20, 277 |
| Jensen-Korte; U.S. Pat. No. 4,803,215 A 1989 | Kuettel. S; J Med Chem 2007, 50, 5833 |
| Junjappa, H; Tetrahedron 1990, 46, 5423 | Kumar, A; Synthesis 1980, 748 |
| Karatsu, T; Bull Chem Soc Jpn 2003, 76, 1227 | Kumar, S; Tetrahedron 2007, 63, 10067 |
| Lamberth, C; Heterocycles 2007, 71, 1467 | |
| Laszlo, S; Bioorganic & Medicinal Chemistry Letters 1998, 8, 2689 | |
| Lau, C; Bioorg Med Chem Lett 1999, 9, 3187 | |
| Leblanc, Y; Bioorg Med Chem Lett 1999, 9, 2207 | |
| Lee; U.S. Pat. No. 5,486,534 A 1996 | Lee, L; J Heterocycl Chem 1990, 27, 243 |
| Lee, K; Tetrahedron Lett 2003, 44, 6737 | Lee, L; J Heterocyclic Chem 1990, 27, 243 |
| Levy, R; Antiepileptic Drugs, Third Ed 1989 | |
| Levy, R; Pharmac Weekblad, Sc Ed 1992, 14, 132 | |
| Li, C; Bioorg Med Chem Lett 1999, 9, 3181 | Liebscher, J; J Prakt Chem 1983, 325, 689 |
| Li, Z; Heteroatom, Chem 1998, 9, 317 | Lilly Co Eli; EP 0846687 A 1998 |
| Liu, R; Curr Med Chem - Anti-Inflam Anti-Allergy Agents 2005, 4, 251 | |
| Liverton, N; J Med Chem 1999, 42, 2180 | Maeda, H; Chem Commun 2007, 1136 |
| Loev, B; U.S. Pat. No. 2,969,374 1961 | Mahata, P; J Org Chem 2003, 68, 3966 |
| Mandal, S; J Chem Soc Perkin Trans 1 1999, 2639 | |
| Martin, R; Angew Chem 2006, 118, 7237 | Masa, S; WO 9855454 A2 1998 |
| Martin, R; Angew Chem Int Ed 2006, 45, 7079 | Mashraqui, S; J Chem Res Synop 1999, 492 |
| Matasi, J; Bioorg Med Chem Lett 2005, 15, 1333 | |
| Matsuo; U.S. Pat. No. 5,134,142 A 1992 | May And Baker Ltd; EP 0352944 A 1990 |
| McDonald, E; Curr Top Med Chem 2006, 6, 1193 | |
| Merz Pharma Gmbh & Co Kgaa de; WO 20100063487 A1 2010 | |
| Mihelich; U.S. Pat. No. 5,972,972 A 1999 | Mishra, N; J Org Chem 2007, 72, 1246 |
| Moerck, R; J Chem Soc, Chem Commun 1974, 782 | |
| Molina, P; J Org Chem 1988, 53, 4654 | |
| Mukherjee, R; Coord Chem Rev 2000, 203, 151 | |
| Murray; U.S. Pat. No. 5,051,518 A 1991 | Nugiel, D; J Med Chem 2001, 44, 1334 |
| Nandi, G; J Org Chem 2010, 75, 7785 | Nugiel, D; J Med Chem 2002, 45, 5224 |
| Nandi, G; J Org Chem 2011, 76, 8009 | Oku Teruo; WO 9419350 A 1994 |
| Naraian; U.S. Pat. No. 6,617,324 B1 2003 | Panda, K; Synlett 2004, 449 |
| Neunhoeffer, H; Ger Offen 1994 | Penning, T; J Med Chem 1997, 40, 1347 |
| Penning, T; J Med Chem 1997, 40, 1347 | |
| Peruncheralathan, S; J Org Chem 2005, 70, 10030 | |
| Peruncheralathan, S; J Org Chem 2005, 70, 9644 | |
| Pfizer Ltd; EP 0846686 A 1998 | Potts, K; J Am Chem Soc 1981, 103, 3585 |
| Popova, A; Chemical Abstracts 1983 | Purkayastha, M; Synthesis 1989, 20 |
| Rastogi, R; J Chem Soc, Perkin Trans 1 1978, 549 | |

TABLE 5-continued

| | |
|---|---|
| Reddy, G; Org Prep Proced Int 2004, 36, 494 | Ried, W; Chem Ber 1988, 121, 805 |
| Rose, D; U.S. Pat. No. 4,314,809 A 1982 | Rose, D; U.S. Pat. No. 4,629,466 A 1986 |
| Rose, D; U.S. Pat. No. 4,371,370 A 1983 | Roy, A; Org Lett 2001, 3, 229 |
| Rundfeldt, C; to be published in Epilepsy Res 1998 | |
| Ryckebusch, A; J Med Chem 2008, 51, 3617 | Sachse, A; Synthesis 2008, 800 |
| Sakya, S; Bioorg Med Chem Lett 2007, 17, 1067 | |
| Salituro, F; Current Medicinal Chemistry 1999, 807 | |
| Samuel, R; Tetrahedron Lett 2007, 48, 8376 | |
| Sanol Arznei Schwarz Gmbh; WO 2006072430 A1 2006 | |
| Searle & Co; WO 9603385 A 1996 | Singh, G; Synthesis 1982, 693 |
| Searle & Co; WO 9852941 A 1998 | Singh, O; J Org Chemd 2009, 74, 3141 |
| Singh, P; J Org Chem 2009, 74, 5496 | |
| Smithkline Beecham Corp; WO 9531451 A 1995 | |
| Stanovnik, B; Chem Rev 2004, 104, 2433 | Sterling Drug Inc; DD 295374 A 1991 |
| Stanton, H; Nature 2005, 434, 648 | Surmont, R; J Org Chem 2011, 76, 4105 |
| Sutharchanadevi, M; Comprehensive Heterocyclic Chemistry II 1996, 6, 221 | |
| Svenstrup, N; J Org Chem 1999, 64, 2814 | |
| Takeda Chemical Industries Ltd; EP 1136477 A1 2001 | |
| Takeda Chemical Industries Ltd; EP 1411052 A1 2004 | |
| Takeda Chemical Industries Ltd; EP 1481679 A1 2004 | |
| Tao, Z; Bioorg Med Chem Lett 2007, 17, 5944 | |
| Tao, Z; Tetrahedron Lett 2005, 46, 7615 | |
| Tang, J; Bioorg Med Chem Lett 2003, 13, 2985 | |
| Teng, M; J Med Chem 2007, 50, 5253 | |
| Terrett, N; Bioorg Med Chem Lett 1996, 6, 1819 | |
| The Cambridge Crystallographic Data Centre; www.ccdc.cam.au.uk/data_request/cif | |
| Thomas, A; Tetrahedron Lett 1989, 30, 3093 | |
| Tominaga, Y; Chem Pharm Bull 1984, 32, 2910 | |
| Tominaga, Y; Chem Pharm Bull 1985, 33, 962 | |
| Tominaga, Y; Yakugaku Zasshi 1980, 100, 699 | |
| Tominaga, Y; Yakugaku Zasshi 1984, 104, 127 | |
| Trofimenko, S; Polyhedron 2004, 23, 197 | |
| Tseng, C; Bioorg Med Chem 2008, 16, 3153 | |
| Uehara, F; WO 03027080 A 2003 | Ward, M; Coord Chem Rev 2001, 222, 251 |
| Uehara, F; WO 03037888 A 2003 | Warjeet, S; Steroids 2002, 67, 203 |
| Unangst, P; J Med Chem 1994, 37, 322 | Weinges, A; Ger Offen 1996 |
| Unverferth, K; J Med Chem 1998, 41, 63 | Wella Ag; EP 1052252 A 2000 |
| Usui, T; Bioorg Med Chem Lett 2008, 18, 285 | Wieland, H; Nat Rev Drug Disc 2005, 4, 331 |
| Verma, R; Tetrahedron 2011, 67, 584 | Willy, B; Org Lett 2011, 13, 2082 |
| Vishwakarma, J; Ind J Chem 1985, 24B, 466 | Wu, X; Chem Eur J 2010, 16, 12104 |
| Vishwakarma, J; Ind J Chem 1985, 24B, 472 | Wu, Y; J Heterocycl Chem 2005, 42, 609 |
| Walworth, B; DE 2260485 1973 | Xiang, J; Bioorg Med Chem Lett 2006, 16, 311 |
| Wang; U.S. Pat. No. 4,801,600 1989 | Yadav, A; Synlett 2008, 2674 |
| Wang; U.S. Pat. No. 4,921,869 1990 | Yao, W; Bioorg Med Chem Lett 2001, 12, 101 |
| Wang, K; Org Lett 2008, 10, 1691 | Yao, W; J Med Chem 2001, 44, 3347 |
| Yet, L; Comprehensive Heterocyclic Chemistry III 2008, 4, 1 | |
| Yue, E; Biorg Med Chem Lett 2004, 14, 343 | |
| Yue, E; J Med Chem 2002, 45, 5233 | |
| Zheng-Nian, H; Chemical Abstracts 1996, 546 | |
| Zheng-Nian, H; Chinese Chemical Letters 1994, 5, 31 | |
| Albert; US 20090215801 A9 2009 | |
| DATABASE REGISTRY [Online] Chemical ABSTRACTS SERVICE, COLUMBUS, OHIO, US; "3-Pyridinccarbonitrile, 6-[4-[1-(1,1-dimethylethyl)-4,5-dihydro-4-oxo-1H-pyrazolo[3,4-d]pyrimidin-6-yl]-1-piperazin yl]-",XP002698968, Database accession no. 1293654-00-8 | |
| DATABASE REGISTRY [Online] CHEMICAL ABSTRACTS SERVICE, COLUMBUS, OHIO, US; 17 Apr. 2011(2011 Apr. 17), "4H-Pyrazolo[3,4-d]pyrimidin-4-one,1,5-dihydro-1-methyl-6-[4-(4-methyl-2-thiazolyl)-1-piperazinyl]", XP002698965, Database accession no. 1280926-39-3 | |
| DATABASE REGISTRY [Online] CHEMICAL ABSTRACTS SERVICE, COLUMBUS, OHIO, US; 20 May 2011(2011 May 20), "4H-Pyrazolo[3,4-d]pyrimidin-4-one,1-(1,1-dimethylethyl)-1,5-dihydro-6-(4-phenyl-1-piperidinyl)-", XP002698966, Database accession no. 1297853-78-1 | |
| DATABASE REGISTRY [Online] CHEMICAL ABSTRACTS SERVICE, COLUMBUS, OHIO, US; 22 May 2011(2011 May 22), "4H-Pyrazolo[3,4-d]pyrimidin-4-one,1-(1,1-dimethylethyl)-6-[4-(4-fluorophenyl)-1-piperazinyl]-1,5-dihydro-", XP002698967, Database accession no. 1298294-CELL PATHWAYS INC; U.S. Pat. No. 6,200,980 B1 2001 | |
| Cao; US 20050038010 A1 2005 | |
| CELL PATHWAYS INC; U.S. Pat. No. 6,200,980 B1 2001 | |
| Chiang; WO 2010068863 A2 2010 | Glasky; US 20020040031 A1 2002 |
| Karlberg, T; Journal Of Medicinal Chemistry, 10.1021/jm100249w 2010, 53, 5352 | |
| Li; PNAS 2002, 99, 5567 | Spohr; U.S. Pat. No. 6,096,753 A 2000 |
| Liu; U.S. Pat. No. 7,429,594 B2 2008 | Spohr; U.S. Pat. No. 6,420,385 B1 2002 |
| Shua-Haim; US 20090192142 A1 2009 | Spohr; U.S. Pat. No. 6,649,604 B2 2003 |
| Spohr; U.S. Pat. No. 6,649,604 B2 2003 | |
| Tan theresa may, C; Journal Of Combinatorial Chemistry, 10.1021/CC060084T 2007, 9, 210 | |
| Wahlberg, E; Nature Biotechnology, DOI: 10.1038/NBT.2121 2012, 30, 283 | |
| Walker; WO 8900423 A1 1989 | Walker; U.S. Pat. No. 4,910,204 A 1990 |
| Wang; Current Topics in Medicinal Chemistry 2009, 9, 724 | |
| American Cyanamid Co; EP 1021413 A1 1999 | |

TABLE 5-continued

| | |
|---|---|
| American Cyanamid Co; NO 2000001755 A 1999 | |
| American Cyanamid Co; CA 2303449 A 1999 | |
| American Cyanamid Co; BR 9812727 A 1999 | |
| American Cyanamid Co; AU 9869685 A 1999 | |
| American Cyanamid Co; WO 9918076 A1 1999 | |
| American Cyanamid Co; US 20010025047 A 2001 | |
| American Cyanamid Co; US 20010046989 A 2001 | |
| American Cyanamid Co; U.S. Pat. No. 6,228,869 B1 2001 | |
| American Cyanamid Co; U.S. Pat. No. 6,498,167 B2 2001 | |
| American Cyanamid Co; U.S. Pat. No. 6,548,524 B2 2001 | |
| Aventis Pharmaceuticals Products Inc; WO 0190101 A1 2001 | |
| Aventis Pharmaceuticals Products Inc; EP 1296972 A1 2001 | |
| Aventis Pharmaceuticals Products Inc; BR 2001011206 A 2001 | |
| Aventis Pharmaceuticals Products Inc; NO 2002005601 A 2001 | |
| Bartroli, J; Journal of Medicinal Chemistry 1998, 41, 1855 | |
| Bayer CropScience A-G; CN 101663261 A 2008 | |
| Bayer CropScience A-G; WO 2008128711 A1 2008 | |
| Bayer CropScience A-G; JP 2008266230 A 2008 | |
| Bayer CropScience A-G; KR 20100016562 A 2008 | |
| Bayer CropScience A-G; EP 2148853 A1 2008 | |
| Beecham Group Ltd; CA 1093551 A 1980 | Beecham Group Ltd; AU 508264 B 1980 |
| Beecham Group Ltd; PL 110458 B1 1980 | Beecham Group Ltd; JP 52-077081 A 1980 |
| Beecham Group Ltd; PL 110478 B1 1980 | Beecham Group Ltd; JP 53-121789 A 1980 |
| Beecham Group Ltd; GB 1568962 A 1980 | Beecham Group Ltd; CH 629209 A 1980 |
| Beecham Group Ltd; GB 1579362 A 1980 | Beecham Group Ltd; AU 7419164 A 1980 |
| Beecham Group Ltd; FR 2329279 A1 1980 | Beecham Group Ltd; FI 7603112 A 1980 |
| Beecham Group Ltd; FR 2383950 A1 1980 | Beecham Group Ltd; NO 7603695 A 1980 |
| Beecham Group Ltd; DE 2811483 A1 1980 | Beecham Group Ltd; DK 7604927 A 1980 |
| Beecham Group Ltd; AT 350725 B 1980 | Beecham Group Ltd; AT 7608009 A 1980 |
| Beecham Group Ltd; AT 356813 B 1980 | Beecham Group Ltd; NL 7612073 A 1980 |
| Beecham Group Ltd; U.S. Pat. No. 4,166,817 A 1980 | Beecham Group Ltd; SE 7612082 A 1980 |
| Beecham Group Ltd; ES 462782 A1 1980 | Beecham Group Ltd; AT 7802859 A 1980 |
| Beecham Group Ltd; IL 50797 A 1980 | Beecham Group Ltd; BE 847698 A1 1980 |
| Checchi, S; Gazzetta Chimica Italiana 1956, 86, 631 | |
| Checchi, S; Gazzetta Chimica Italiana 1957, 87, 597 | |
| Du Pont Merck Pharmaceutical Co; JP 2002503207 A 1997 | |
| Du Pont Merck Pharmaceutical Co; EP 960104 A1 1997 | |
| Du Pont Merck Pharmaceutical Co; WO 9738984 A1 1997 | |
| E I du Pont de Nemours and Co; CN 101426769 A 2007 | |
| E I du Pont de Nemours and Co; WO 2007123853 A2 2007 | |
| Elworthy, T; Journal of Medicinal Chemistry 1997, 40, 2674 | |
| F Hoffmann-La Roche A-G; JP 2001514163 A 1999 | |
| F Hoffmann-La Roche A-G; U.S. Pat. No. 6,455,50 B1 1999 | |
| F Hoffmann-La Roche A-G; BR 9811988 A 1999 | |
| F Hoffmann-La Roche A-G; WO 9910313 A1 1999 | |
| F Hoffmann-La Roche A-G; EP 1005445 A1 2001 | |
| F Hoffmann-La Roche A-G; NO 2000000841 A 2001 | |
| F Hoffmann-La Roche A-G; JP 2001514162 A 2001 | |
| F Hoffmann-La Roche A-G; CA 2301377 A 2001 | |
| F Hoffmann-La Roche A-G; NZ 502813 A 2001 | |
| F Hoffmann-La Roche A-G; U.S. Pat. No. 6,229,011 B1 2001 | |
| F Hoffmann-La Roche A-G; AU 739511 B 2001 | |
| F Hoffmann-La Roche A-G; BR 9811730 A 2001 | |
| F Hoffmann-La Roche A-G; AU 9892620 A 2001 | |
| F Hoffmann-La Roche A-G; WO 9910312 A1 2001 | |
| Glaxo Group Ltd; EP 1802307 A1 2006 | J Uriach & Cia S A; ES 2112774 A1 1999 |
| Glaxo Group Ltd; WO 2006040192 A1 2006 | J Uriach & Cia S A; ES 2112774 Bl 1999 |
| Glaxo Group Ltd; US 20080045506 A1 2006 | J Uriach & Cia S A; CA 2201478 A 1999 |
| Glaxo Group Ltd; JP 2008516922 A 2006 | J Uriach & Cia S A; U.S. Pat. No. 5,888,941 A 1999 |
| Heinrich Timo; US 20070099933 A1 2007 | J Uriach & Cia S A; EP 783502 A1 1999 |
| J Uriach & Cia S A; JP 10-507205 A 1999 | J Uriach & Cia S A; BR 9606546 A 1999 |
| J Uriach & Cia S A; ES 2107376 A1 1999 | J Uriach & Cia S A; AU 9667889 A 1999 |
| J Uriach & Cia S A; ES 2107376 B1 1999 | J Uriach & Cia S A; NO 9701471 A 1999 |
| J Uriach & Cia S A; WO 9705131 A1 1999 | |
| Janssen Pharmaceutica N V; CN 1036569 A 1990 | |
| Janssen Pharmaceutica N V; JP 23678 A 1990 | |
| Janssen Pharmaceutica N V; EP 331232 A2 1990 | |
| Janssen Pharmaceutica N V; U.S. Pat. No. 4,931,444 A 1990 | |
| Lederle Japan Ltd; JP 07-267960 A 1995 | Merck Patent Gmbh; WO 0228820 A1 2002 |
| Levin. J; US 20020132826 A 2002 | Merck Patent Gmbh; AU 2001089891 A 2002 |
| Masa, S; WO 9855454 A2 1998 | Merck Patent Gmbh; FR 2815030A1 2002 |
| Millennium Pharmaceuticals Inc; WO 200753498 A1 2007 | |
| Mustazza, C; Journal of Heterocyclic Chemistry 2001, 38, 1119 | |
| Nissan Chemical Industries Ltd; JP 2001302666 A 2001 | |
| Novinson, T; Journal of Medicinal Chemistry 1977, 20, 296 | |
| Pfizer Products Inc; WO 02024613 A2 2002 | Pfizer Products Inc; US 20020137961 A 2002 |
| Pfizer Products Inc; WO 02024613 A3 2002 | Pfizer Products Inc; U.S. Pat. No. 6,541,473 B2 2002 |
| Pola Chemical Industries Inc; JP 02-275882 A 1991 | |
| Pola Chemical Industries Inc; CN 1041943 A 1991 | |
| Pola Chemical Industries Inc; CA 1330079 A 1991 | |

TABLE 5-continued

| | | |
|---|---|---|
| Pola Chemical Industries Inc; ES 2088882 T3 1991 | | |
| Pola Chemical Industries Inc; EP 369145 A2 1991 | | |
| Pola Chemical Industries Inc; U.S. Pat. No. 4,992,442 A 1991 | | |
| Sanol Arznei Schwarz Gmbh; WO 2006072430 A1 2006 | | |
| Smithkline Beecham Corp; EP 1067894 A2 1999 | | |
| Smithkline Beecham Corp; JP 2002515411 A 1999 | | |
| Smithkline Beecham Corp; CA 2332531 A 1999 | | |
| Smithkline Beecham Corp; U.S. Pat. No. 6,518,267 B1 1999 | | |
| Smithkline Beecham Corp; WO 9959526 A2 1999 | | |
| Smithkline Beecham Corp; WO 9959526 A3 1999 | | |
| Takamizawa, A; Chemical & Pharmaceutical Bulletin 1968, 16, 2195 | | |
| Takeda Chemical Industries Ltd; EP 1136477 A1 2001 | | |
| Takeda Chemical Industries Ltd; EP 1411052 A1 2004 | | |
| Takeda Chemical Industries Ltd; EP 1481679 A1 2004 | | |
| TorreyPines Therapeutics Inc; WO 2008137102 A2 2008 | | |
| Yoshitomi Pharmaceutical Industries Ltd; U.S. Pat. No. 4,918,074 A 1990 | | |
| Yoshitomi Pharmaceutical Industries Ltd; JP 60-193990 A 1990 | | |
| Yoshitomi Pharmaceutical Industries Ltd; JP 60-246387 A 1990 | | |
| Yoshitomi Pharmaceutical Industries Ltd; JP 62-077387 A 1990 | | |
| Yoshitomi Pharmaceutical Industries Ltd; JP 62-270584 A 1990 | | |
| Yoshitomi Pharmaceutical Industries Ltd; JP 05-194401 A 1995 | | |
| Yoshitomi Pharmaceutical Industries Ltd; JP 06-041080 A 1995 | | |
| Yoshitomi Pharmaceutical Industries Ltd; CA 2117096 C 1995 | | |
| Yoshitomi Pharmaceutical Industries Ltd; ES 2148179 T3 1995 | | |
| Yoshitomi Pharmaceutical Industries Ltd; U.S. Pat. No. 5,478,838 A 1995 | | |
| Yoshitomi Pharmaceutical Industries Ltd; EP 641781 A1 1995 | | |
| Yoshitomi Pharmaceutical Industries Ltd; WO 9305021 A1 1995 | | |
| Abbaszade, I; J Biol Chem 1999. 274, 23443 | | EP 0659745 A1 1995 |
| EP 0352944 A1 1990 | | WO 2006061147 2006 |
| Bursavich, M; Bioorg Med Chem Lett, in press 2007, 17 | | |
| Cherney, R; Bioorg Med Chem Lett 2003, 13, 1297 | | |
| Glasson, S; Arthritis Rheum 2004, 50, 2547 | | |
| Hansen, M; Tetrahedron: Asymmetry 1996, 7, 2515 | | |
| Jensen-Korte; U.S. Pat. No. 4,803,215 A 1989 | | Lee, L; J Heterocycl Chem 1990, 27, 243 |
| Liu, R; Curr Med Chem - Anti-Inflam Anti-Allergy Agents 2005, 4, 251 | | |
| Stanton, H; Nature 2005, 434, 648 | | Xiang, J; Bioorg Med Chem Lett 2006, 16, 311 |
| Unangst, P; J Med Chem 1994, 37, 322 | | Yao, W; Bioorg Med Chem Lett 2001, 12, 101 |
| Wieland, H; Nat Rev Drug Disc 2005, 4, 331 | | Yao, W; J Med Chem 2001, 44, 3347 |
| U.S. Pat. No. 4,562,189 1985 | WO970981 | WO2011139107 |
| U.S. Pat. No. 4,576,943 1986 | U.S. Pat. No. 9,981,939 | WO201200110 |
| U.S. Pat. No. 4,826,866A | WO2007040280 | WO2012015024 |
| U.S. Pat. No. 54,576,943 | WO2010104194 | WO2013102145 |
| U.S. Pat. No. 5,736,545 | WO2011016559 | US20140275152 |
| WO2014150276 | | WO2018053588 |
| Indian J. Chem. Section B Vol 34B(6), Pages 521-4 1995 | | |
| WO0132164A1 | WO0236108A2 | JP2001354656A |
| WO0168610A1 | WO03022821A1 | JP2004010513A |
| WO0196309A1 | WO201714927Al | WO2004024677A1 |
| WO02088071A1 | JP2001354658A | JP2004143099A |
| JP2004262890A-2 | | |
| Masakazu Sato Biorg Med Chem Lett 2001 | | |
| Toshio Nakamura 2004 Biorg Med Chem Lett 3 | | |
| Toshio Nakamura J Med Cehm 2003 | | |
| Toshio Nakamura 2004 Biorg Med Chem Lett-2 | | |
| Toshio Nakamura 2004 Bior Med Chem Lett | | |

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as “up to,” “at least,” “greater than,” “less than,” and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A compound of formula I:

(I)

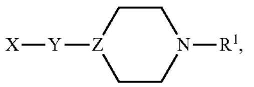

or a pharmaceutically acceptable salt or solvate thereof, wherein:

X is

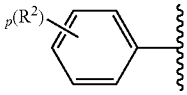
,
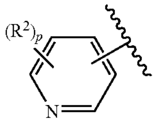
,
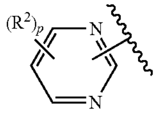
,
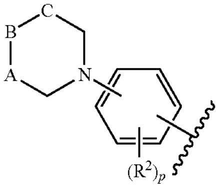
, or
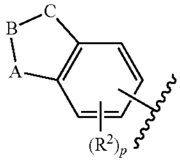

wherein each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, $—SR^3$, $—S(O)R^3$, $—CH_2OR^3$, $—(CH_2)nS(O)R^3$, $—(CH_2)_nS(O)_2R^3$, $—SO_2R^3$, $—CO_2R^3$, $—SO_2NHR^4$, $—(CH_2)_n—OR^4$, $—OR^4$, $—CO_2R^4$, $—NR^5R^6$, $—NR^5C(O)R^6$, $—(CH_2)_n—NR^5C(O)R^6$, $—CH(CH_3)—NR^5C(O)R^6$, $—CONR^5R^6$, $—N(R^5)S(O)_2R^6$, $—N(R^5)(CH_2)_nS(O)R^6$, $—N(R^5)(CH_2)_nS(O)_2R^6$, $—SO_2NR^5R^6$, and $—NR^4C(O)R^3$, $R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent, $R^4$ is H, optionally substituted $C_1$-$C_6$ alkyl, optionally substituted $C_3$-$C_6$ cycloalkyl, optionally substituted tetrahydrofuranyl, optionally substituted piperidinyl, optionally substituted pyrrolidinyl, optionally substituted azetidinyl, or optionally substituted oxetanyl, $R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring, and n and p are each independently 1, 2, or 3, wherein when X is

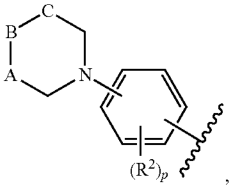
,

A, B and C are selected from $—(C(R^{2'})_2)_{1-2}—$, O, or $SO_2$, wherein one of A, B and C is O or $SO_2$, and wherein $R^{2'}$ is H or F, and wherein when X is

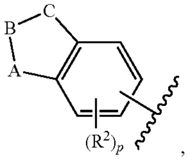
,

A, B and C are selected from $—(C(R^{2'})_2)_{1-2}—$ or $SO_2$, wherein one of A, B and C is $SO_2$, and wherein $R^{2'}$ is H or F;

Y is a bond, O, S, S═O, $SO_2$, or an optionally substituted methylene;

Z is CH; and $R^1$ is

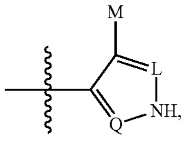, 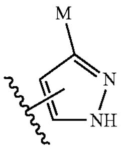 or 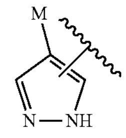, wherein

Q is N or CH;

L is N, CH or $CCH_3$, provided that L is not N when Q is N, and L is not CH or $CCH_3$ when Q is CH; and M is H or $CH_3$.

2. The compound of claim 1 or a pharmaceutically acceptable salt or solvate thereof, wherein Y is a bond.

3. The compound of claim 1 or a pharmaceutically acceptable salt or solvate thereof, wherein X is

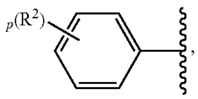, 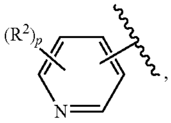, or

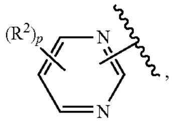, and wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, —$SR^3$, —$S(O)R^3$, —$CH_2OR^3$, —$(CH_2)_nS(O)R^3$, —$(CH_2)_nS(O)_2R^3$, —$SO_2R^3$, —$CO_2R^3$, —$SO_2NR^4$, —$(CH_2)_n$—$OR^4$, —$OR^4$, —$CO_2R^4$, —$NR^5R^6$, —$NR^5C(O)R^6$, —$(CH_2)_n$—$NR^5C(O)R^6$, —$CH(CH_3)$—$NR_5C(O)R^6$, —$CONR^5R^6$, —$N(R^5)S(O)_2R^6$, —$N(R^5)(CH_2)_nS(O)R^6$, —$N(R^5)(CH_2)_nS(O)_2R^6$, —$SO_2NR^5R^6$, and —$NR^4C(O)R^3$, $R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent, $R^4$ is H, optionally substituted $C_1$-$C_6$ alkyl, optionally substituted $C_3$-$C_6$ cycloalkyl, optionally substituted tetrahydrofuranyl, optionally substituted piperidinyl, optionally substituted pyrrolidinyl, optionally substituted azetidinyl, or optionally substituted oxetanyl, $R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring, and n and p are each independently 1, 2, or 3.

4. The compound of claim 1, or a pharmaceutically acceptable salt or solvate thereof, wherein X is

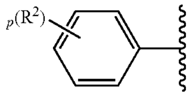

and $R^1$ is

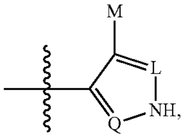, and wherein:

each $R^2$ is independently selected from a group consisting of H, F, Cl, optionally substituted $C_1$-$C_6$ alkyl, optionally substituted $C_3$-$C_6$ cycloalkyl, optionally substituted heterocyclyl, —$SR^3$, —$S(O)R^3$, —$SO_2R^3$, —$SO_2NHR^4$, —$OR^4$, —$(CH_2)_n$—$OR^4$, —$CO_2R^4$, —$NR^5R^6$, —$NR^5C(O)R^6$, —$CONR^5R^6$, —$N(R^5)SO_2R^6$, and —$SO_2NR^5R^6$;

$R^3$ is optionally substituted $C_1$-$C_6$ alkyl or optionally substituted $C_3$-$C_6$ cycloalkyl;

$R^4$ is H, optionally substituted $C_1$-$C_6$ alkyl, optionally substituted $C_3$-$C_6$ cycloalkyl, optionally substituted tetrahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is O;

Z is CH;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

5. The compound of claim 1 or a pharmaceutically acceptable salt or solvate thereof, wherein:

X is

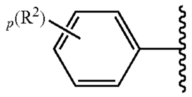

and $R^1$ is

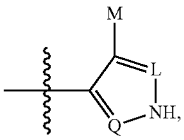, and wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, —$SR^3$, —$S(O)R^3$, $—CH_2OR^3$, $—(CH_2)_nS(O)R^3$, $—(CH_2)_nS(O)_2R^3$, $—SO_2R^3$, $—CO_2R^3$, $—SO_2NR^4$, $—(CH_2)_n—OR^4$, $—OR^4$, $—CO_2R^4$, $—NR^5R^6$, $—NR^5C(O)R^6$, $—(CH_2)_n—NR_5C(O)R^6$, $—CH(CH_3)—NR_5C(O)R^6$, $—CONR^5R^6$, $—N(R^5)S(O)_2R^6$, $—N(R^5)(CH_2)_nS(O)R^6$, $—N(R^5)(CH_2)_nS(O)_2R^6$, $—SO_2NR^5R^6$, and $—NR^4C(O)R^3$;

$R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent;

$R^4$ is H, optionally substituted $C_1$-$C_6$ alkyl, optionally substituted $C_3$-$C_6$ cycloalkyl, optionally substituted tetrahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is S, S═O, or $SO_2$;

Z is CH;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

6. The compound of claim 1, or a pharmaceutically acceptable salt or solvate thereof, wherein:

X is

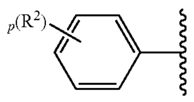

and $R^1$ is

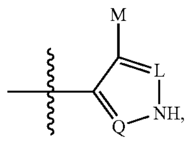

and wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, $—SR^3$, $—S(O)R^3$, $—CH_2OR^3$, $—(CH_2)_nS(O)R^3$, $—(CH_2)_nS(O)_2R^3$, $—SO_2R^3$, $—CO_2R^3$, $—SO_2NR^4$, $—(CH_2)_n—OR^4$, $—OR^4$, $—CO_2R^4$, $—NR^5R^6$, $—NR^5C(O)R^6$, $—(CH_2)_n—NR_5C(O)R^6$, $—CH(CH_3)—NR_5C(O)R^6$, $—CONR^5R^6$, $—N(R^5)S(O)_2R^6$, $—N(R^5)(CH_2)_nS(O)R^6$, $—N(R^5)(CH_2)_nS(O)_2R^6$, $—SO_2NR^5R^6$, and $—NR^4C(O)R^3$;

$R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent;

$R^4$ is H, optionally substituted $C_1$-$C_6$ alkyl, optionally substituted $C_3$-$C_6$ cycloalkyl, optionally substituted tetrahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is $CH_2$;

Z is CH;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

7. The compound of claim 1, or a pharmaceutically acceptable salt or solvate thereof, wherein:

X is

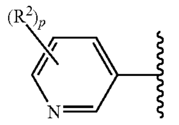

and $R^1$ is

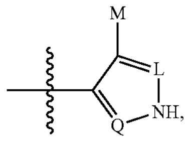

and wherein:

$R^2$ is selected from a group consisting of H, F, Cl, optionally substituted $C_1$-$C_6$ alkyl, optionally substituted $C_3$-$C_6$ cycloalkyl, optionally substituted heterocyclyl, $—OR^4$, $—(CH_2)_n—OR^4$, $—CO_2R^4$, $—NR^5R^6$, $—NR_5C(O)R^6$, $—CONR^5R^6$, and $—N(R^5)SO_2R^6$;

$R^4$ is H, optionally substituted $C_1$-$C_6$ alkyl, optionally substituted $C_3$-$C_6$ cycloalkyl, optionally substituted tetrahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is a bond or $CH_2$;

Z is CH;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

8. The compound of claim 1, or a pharmaceutically acceptable salt or solvate thereof, wherein:

X is

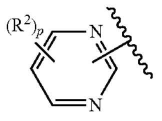

or

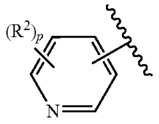

and $R^1$ is

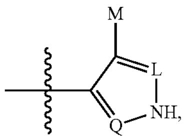

and wherein:

$R^2$ is selected from a group consisting of H, F, Cl, optionally substituted $C_1$-$C_6$ alkyl, optionally substituted $C_3$-$C_6$ cycloalkyl, optionally substituted heterocyclyl, $-OR^4$, $-(CH_2)_n-OR^4$, $-CO_2R^4$, $-NR^5R^6$, $-NR^5C(O)R^6$, and $-CONR^5R^6$;

$R^4$ is H, optionally substituted $C_1$-$C_6$ alkyl, optionally substituted $C_3$-$C_6$ cycloalkyl, optionally substituted tetrahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is a bond or $CH_2$;

Z is CH;

Q is N or CH;

L is N, CH or $CCH_3$, provided that L is not N when Q is N, and L is not CH or $CCH_3$ when Q is CH;

M is H or $CH_3$; and n and p are each independently is 1, 2, or 3.

9. The compound of claim 1 or a pharmaceutically acceptable salt or solvate thereof, wherein:

X is

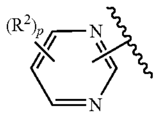

or

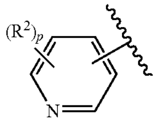

and $R^1$ is

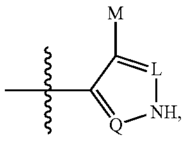

and wherein:

each $R^2$ is independently selected from a group consisting of H, optionally substituted $C_1$-$C_6$ alkyl, optionally substituted $C_3$-$C_6$ cycloalkyl, optionally substituted heterocyclyl, $C_1$-$C_6$ alkoxy, halo, $-SR^3$, $-S(O)R^3$, $-CH_2OR^3$, $-(CH_2)_nS(O)R^3$, $-(CH_2)_nS(O)_2R^3$, $-SO_2R^3$, $-CO_2R^3$, $-SO_2NR^4$, $-(CH_2)_n-OR^4$, $-OR^4$, $-CO_2R^4$, $-NR^5R^6$, $-NR^5C(O)R^6$, $-(CH_2)_n-NR_5C(O)R^6$, $-CH(CH_3)-NR_5C(O)R^6$, $-CONR^5R^6$, $-N(R^5)S(O)_2R^6$, $-N(R^5)(CH_2)_nS(O)R^6$, $-N(R^5)(CH_2)_nS(O)_2R^6$, $-SO_2NR^5R^6$, and $-NR^4C(O)R^3$;

$R^3$ is an optionally substituted $C_1$-$C_6$ alkyl or an optionally substituted $C_3$-$C_6$ cycloalkyl or an optionally substituted alkylene forming a 4, 5 or 6-member ring with the aromatic carbon atom adjacent to the location of the $R^2$ substituent;

$R^4$ is H, optionally substituted $C_1$-$C_6$ alkyl, optionally substituted $C_3$-$C_6$ cycloalkyl, optionally substituted tetrahydrofuranyl, optionally substituted piperidinyl, optionally substituted pyrrolidinyl, optionally substituted azetidinyl, or optionally substituted oxetanyl;

$R^5$ and $R^6$ are each independently H, optionally substituted $C_1$-$C_6$ alkyl, or optionally substituted $C_3$-$C_6$ cycloalkyl; or $R^5$ and $R^6$ and the atoms to which they are attached, together form an optionally substituted 4 to 6 membered ring;

Y is S;

Z is CH;

Q is N or CH;

L is N, CH or $CCH_3$, provided that L is not N when Q is N, and L is not CH or $CCH_3$ when Q is CH;

M is H or $CH_3$; and n and p are each independently 1, 2, or 3.

10. A compound selected from a group consisting of:

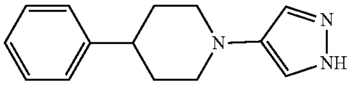

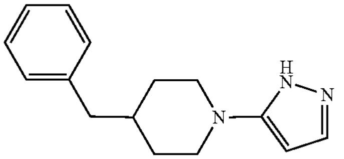

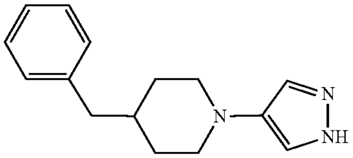

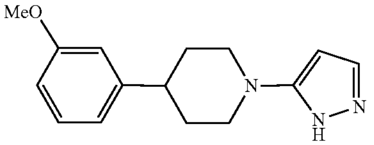

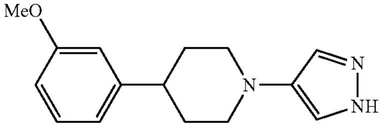

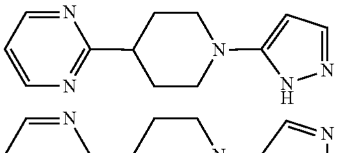

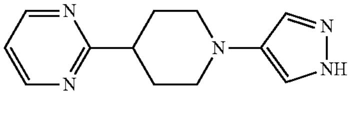

-continued
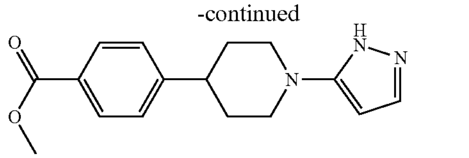
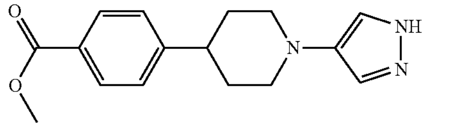
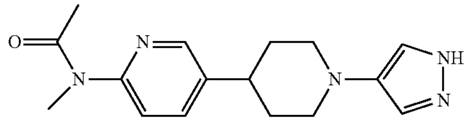
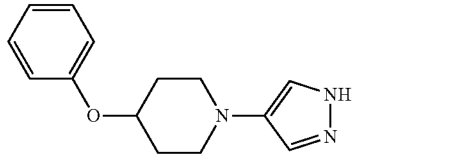
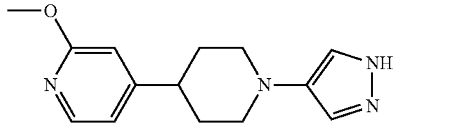
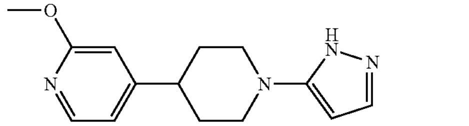
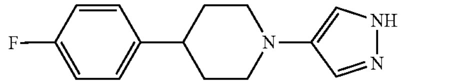
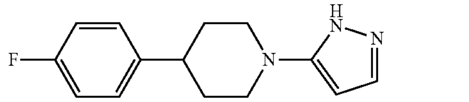
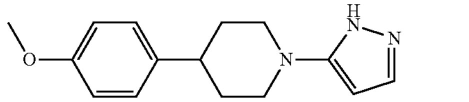
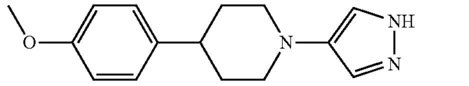
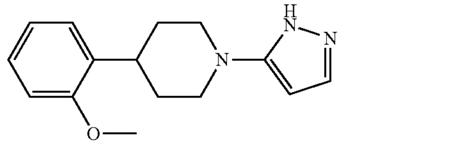
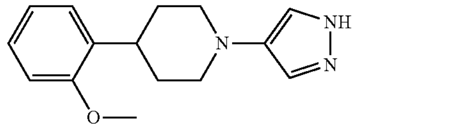
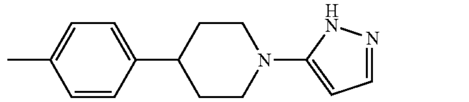
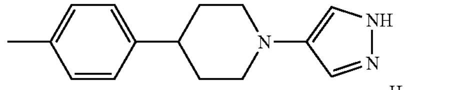
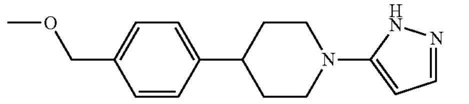
-continued
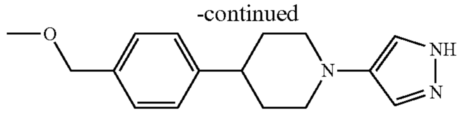
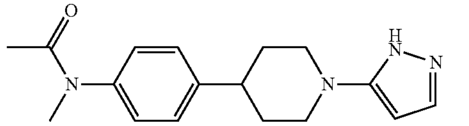
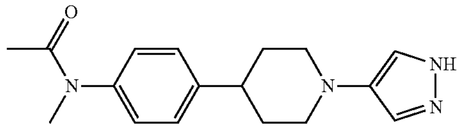
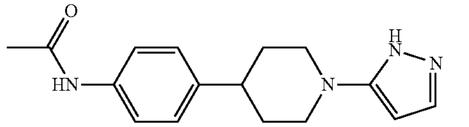
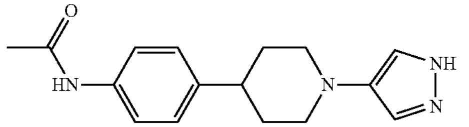
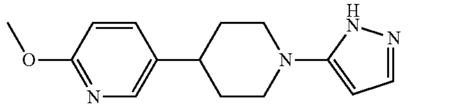
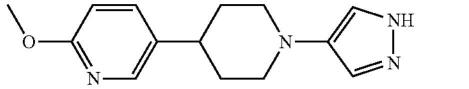
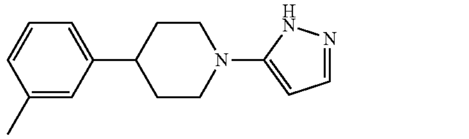
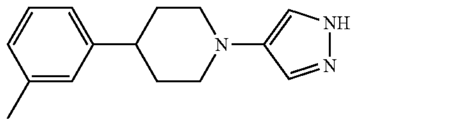
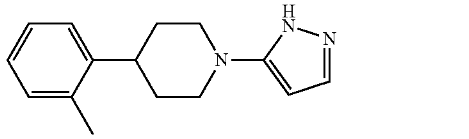
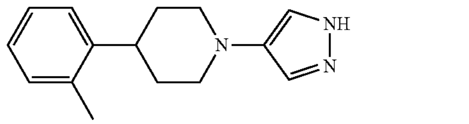
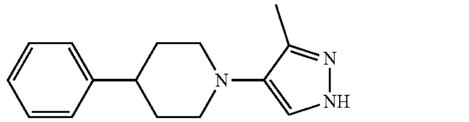
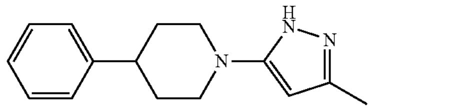
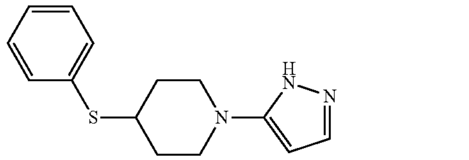

-continued
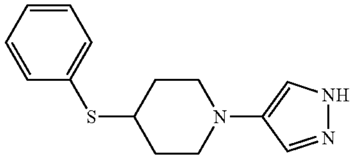
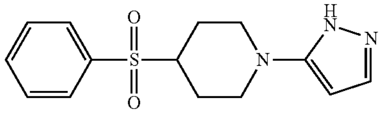
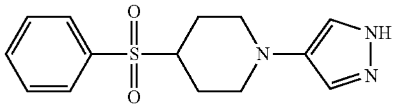
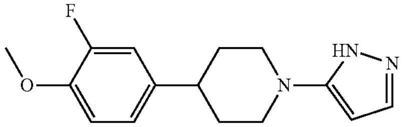
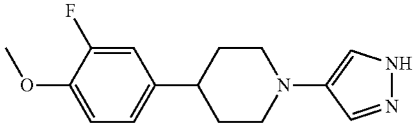
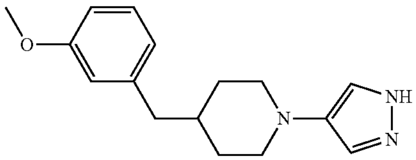
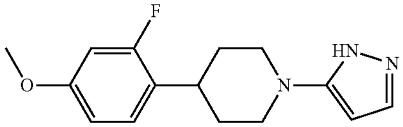
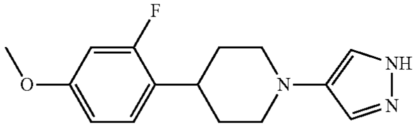
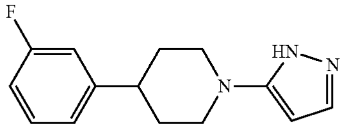
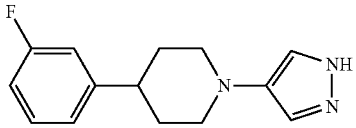
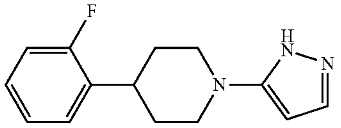
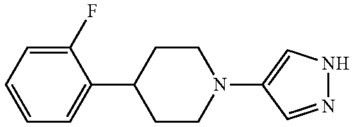
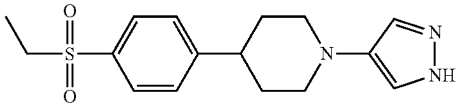
-continued
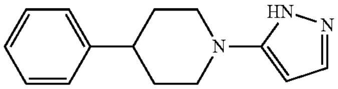
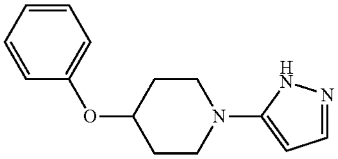
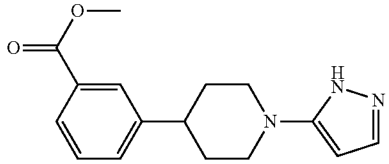
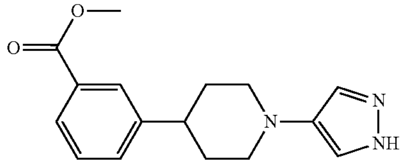
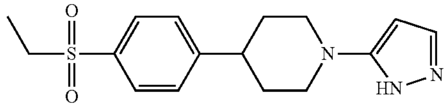
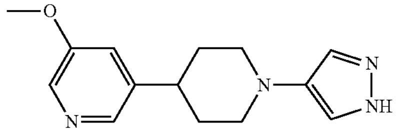
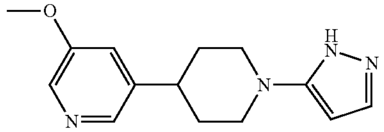
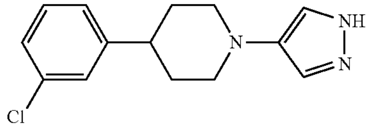
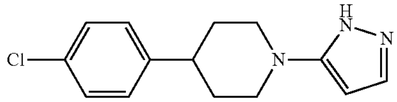
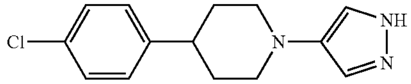
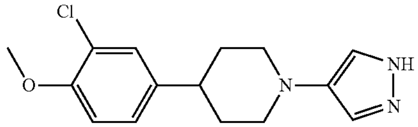
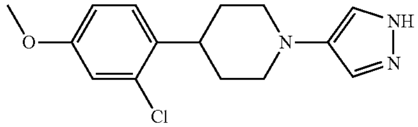
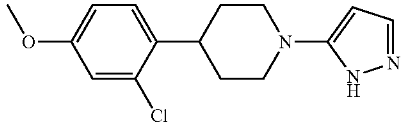

-continued
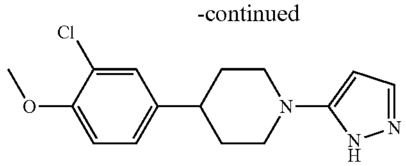
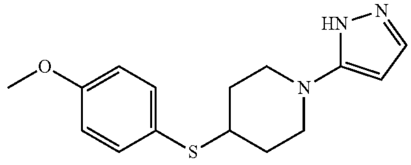
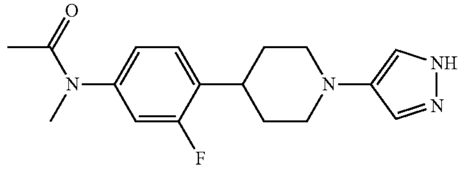
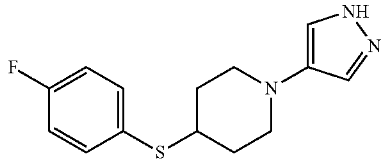
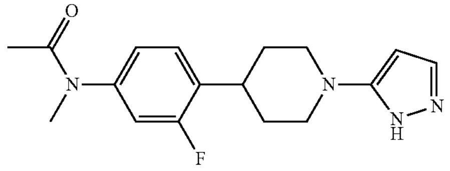
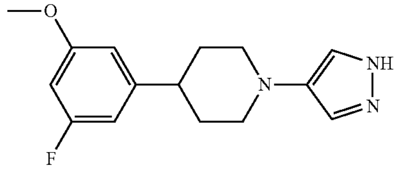
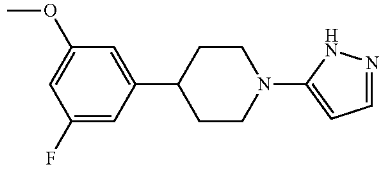
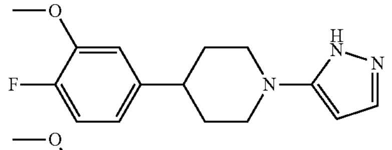
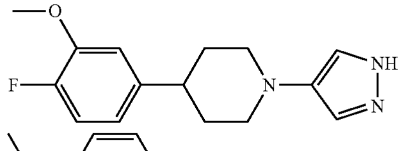
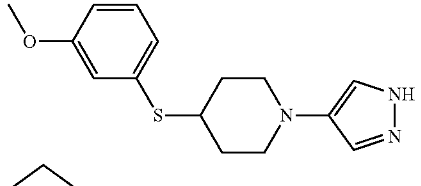
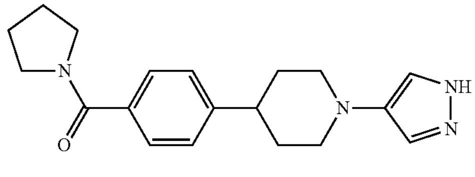
-continued
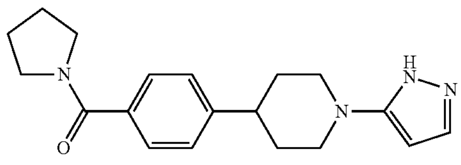
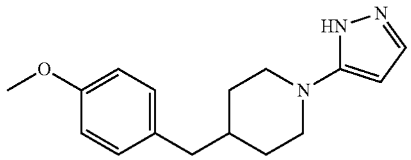
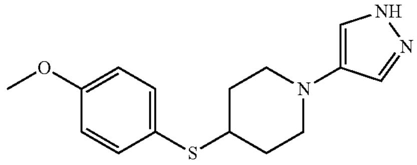
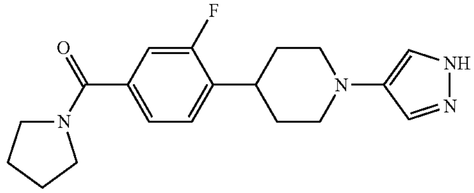
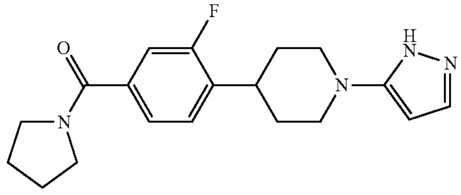
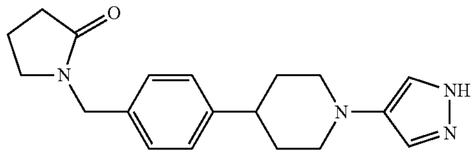
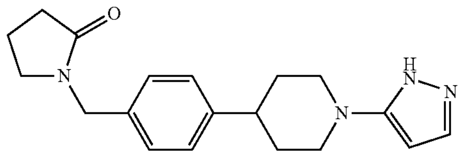
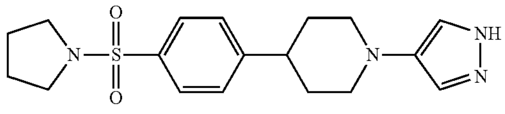
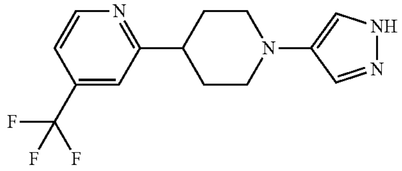
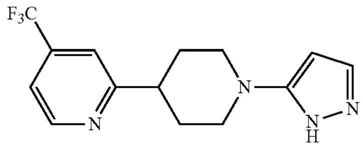

-continued
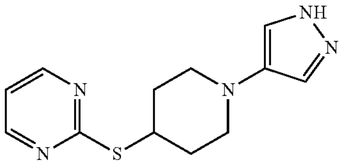
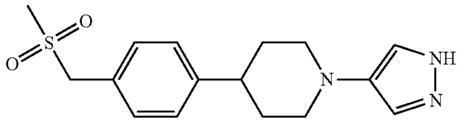
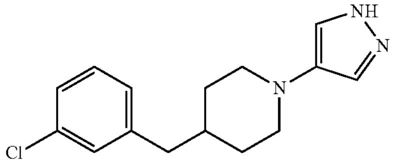
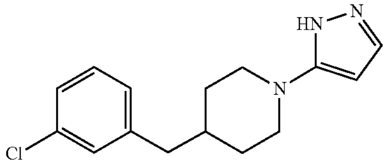
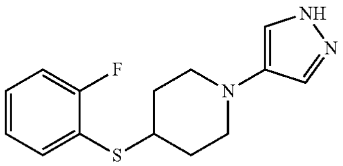
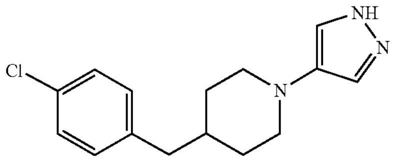
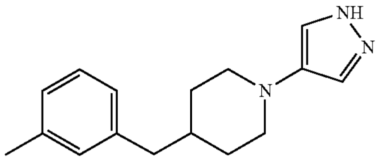
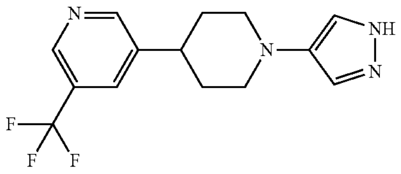
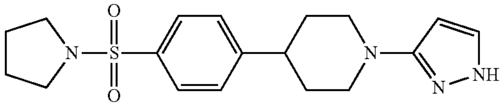
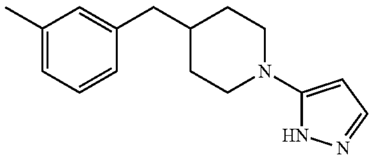
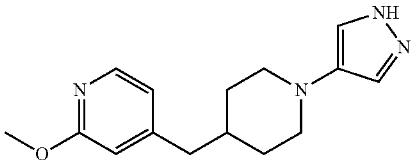
-continued
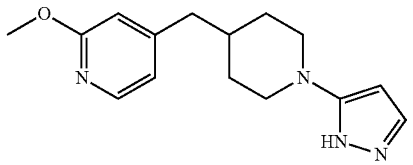
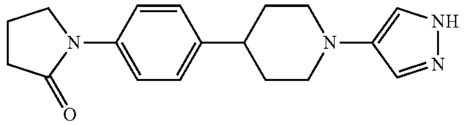
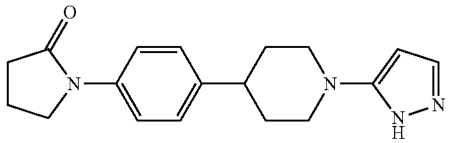
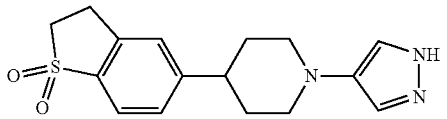
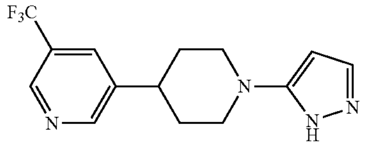
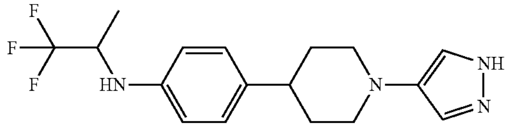
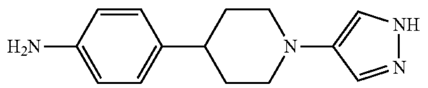
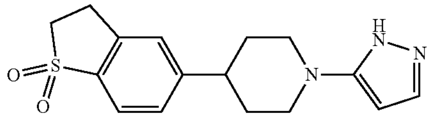
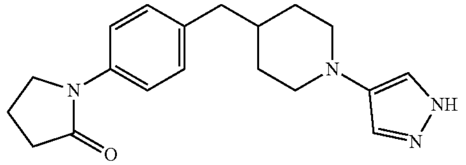
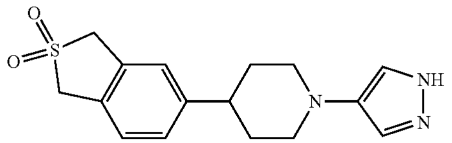
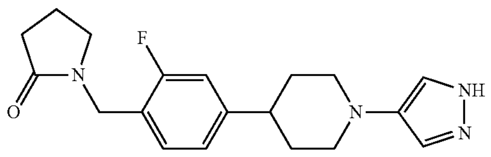
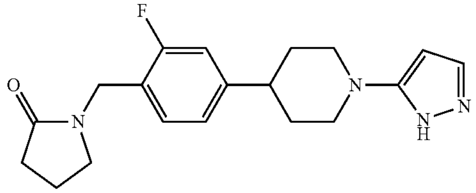

-continued

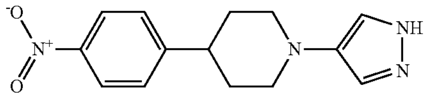

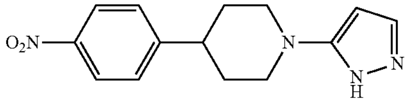

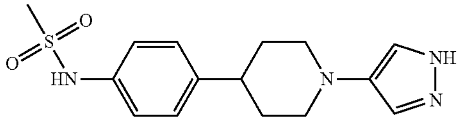

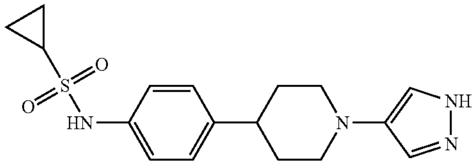

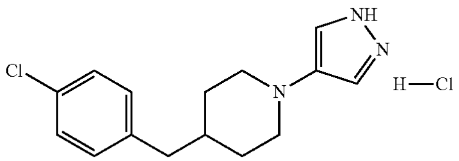

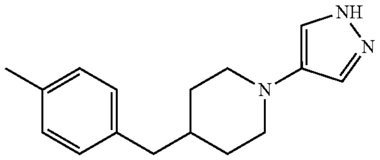

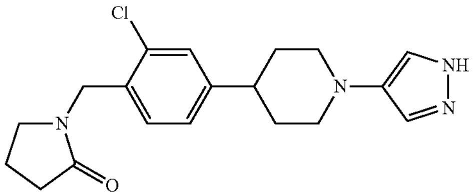

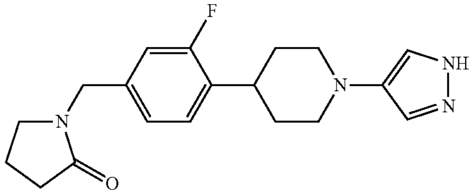

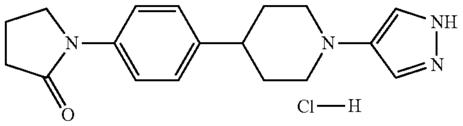

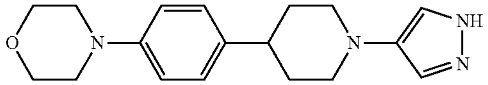

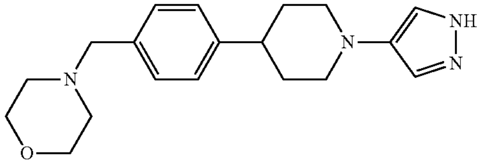

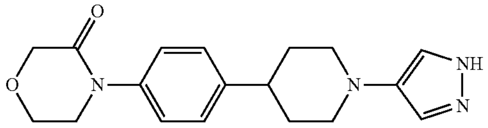

-continued

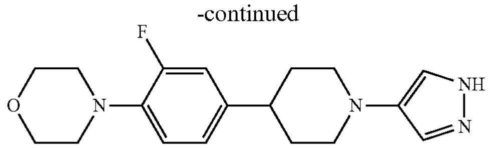

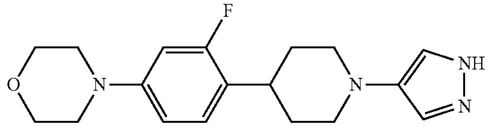

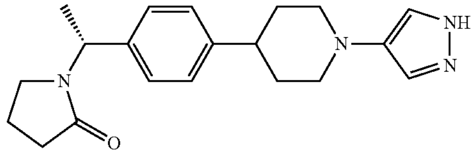

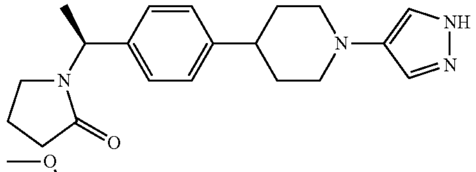

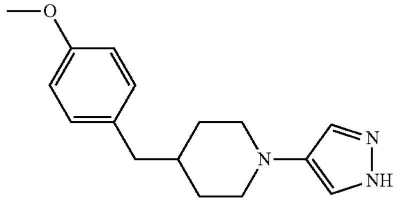

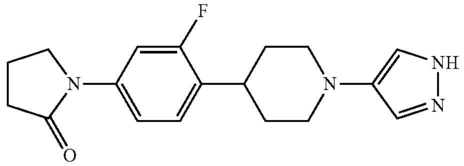

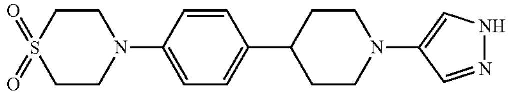

and a pharmaceutically acceptable salt or solvate thereof.

11. A method of inhibiting the biosynthesis of 20-hydroxyeicosatetraenoic acid (20-HETE) in a subject in need thereof, comprising administering to the subject a therapeutically effective amount of the compound of claim 1, or a pharmaceutically acceptable salt or solvate thereof.

12. A method of inhibiting CYP4, comprising contacting CYP4 with a compound of claim 1, or a pharmaceutically acceptable salt or solvate thereof.

13. The method of claim 12, wherein the contacting is in vitro.

14. The method of claim 12, wherein the contacting is in vivo in a subject in need.

15. A method of producing neuroprotection and decreased brain damage by preventing cerebral microvascular blood flow impairment and anti-oxidant mechanisms in a subject experiencing or having experienced an ischemic event, comprising administering to the subject a therapeutically effective amount of the compound of claim 1, or a pharmaceutically acceptable salt or solvate thereof.

16. The method of claim 15, wherein the ischemic event comprises trauma, focal ischemia (TFI), subarachnoid hemorrhage (SAH), vasoconstriction, thrombosis, embolism, cardiac arrest, stroke, aneurysm, hypertension, sickle cell disease, application of g-forces, arteriovenous malformation, peripheral artery occlusive disease, central nervous system (CNS) depressant overdose, or a combination thereof.

17. A method of reducing the size or slowing the growth of kidney cysts by preventing 20-HETE formation and/or 20-HETE driven renal epithelial cell proliferation in a subject suffering from polycystic kidney disease, comprising administering a pharmacologically effective amount of a compound of claim 1, or pharmaceutically acceptable salt thereof.

18. The method of claim 17, wherein PKD is of the autosomal dominant or recessive type.

19. The method of claim 11, wherein the subject is a human.

* * * * *